(12) United States Patent
Khvorova et al.

(10) Patent No.: US 7,674,896 B2
(45) Date of Patent: Mar. 9, 2010

(54) SIRNA TARGETING BCL2L1

(75) Inventors: Anastasia Khvorova, Boulder, CO (US); Angela Reynolds, Littleton, CO (US); Devin Leake, Denver, CO (US); William Marshall, Boulder, CO (US); Stephen Scaringe, Lafayette, CO (US); Steven Read, Denver, CO (US)

(73) Assignee: Dharmacon, Inc., Lafayette, CO (US)

( * ) Notice: Subject to any disclaimer, the term of this patent is extended or adjusted under 35 U.S.C. 154(b) by 138 days.

(21) Appl. No.: 11/635,329

(22) Filed: Dec. 7, 2006

(65) Prior Publication Data

US 2007/0088153 A1    Apr. 19, 2007

Related U.S. Application Data

(63) Continuation of application No. 10/714,333, filed on Nov. 14, 2003.

(60) Provisional application No. 60/502,050, filed on Sep. 10, 2003, provisional application No. 60/426,137, filed on Nov. 14, 2002.

(51) Int. Cl.
  *A61K 31/70* (2006.01)
  *C07H 21/04* (2006.01)

(52) U.S. Cl. .................. 536/24.5; 536/23.1; 514/44

(58) Field of Classification Search .................. None
    See application file for complete search history.

(56) References Cited

U.S. PATENT DOCUMENTS 6,001,992 A    12/1999  Ackermann
6,172,216 B1 *  1/2001  Bennett et al. ............ 536/24.5
6,506,559 B1    1/2003  Fire
2002/0150945 A1  10/2002  Finney et al.
2003/0105051 A1   6/2003  McSwiggen
2004/0054155 A1   3/2004  Woolf et al.
2004/0180357 A1   9/2004  Reich et al.
2004/0248299 A1  12/2004  Jayasena et al.
2005/0130181 A1   6/2005  McSwiggen
2005/0176025 A1   8/2005  McSwiggen
2005/0181382 A1   8/2005  Zamore et al.
2005/0186586 A1   8/2005  Zamore et al.
2005/0239731 A1  10/2005  McSwiggen et al.
2006/0286575 A1  12/2006  Farrell
2007/0031844 A1   2/2007  Khvorova et al.

FOREIGN PATENT DOCUMENTS

WO    WO/0076497    12/2000
WO    WO/0244321     6/2002
WO    WO/2005001043  1/2005
WO    WO/2006015389  2/2006

OTHER PUBLICATIONS

Bass, B.L. (2001) The Short Answer. Nature, V.411:428-9.*

(Continued)

*Primary Examiner*—J D Schultz
*Assistant Examiner*—Jennifer Pitrak
(74) *Attorney, Agent, or Firm*—Kalow & Springut, LLP; Scott D. Locke, Esq.

(57) ABSTRACT

Efficient sequence specific gene silencing is possible through the use of siRNA technology. By selecting particular siRNAs by rationale design, one can maximize the generation of an effective gene silencing reagent, as well as methods for silencing genes.

20 Claims, 31 Drawing Sheets

OTHER PUBLICATIONS

Elbashir, et al. (2001) Duplexes of 21-Nucleotide RNAS Mediate RNA Interference in Cultured Mammalian Cells. Nature, v.411:494-8.*

Genbank Accession No. NM_138578 [online]. [retrieved on Aug. 11, 2008]. Retrieved from the Internet: <http://www.ncbi.nlm.nih.gov/entrez/viewer.fcgi?db=nuccore&id=20336334>.*

Khvorova et al., Functional siRNAs and miRNAs Exhibit Strand Bias, Cell, vol. 115, 209-216, Oct. 17, 2003, Cell Press.

Reynolds et al., Rational siRNA Design for RNA Interference, vol. 22, No. 3, Mar. 2004, Nature Biotechnology.

Kasif et al., A Computational Framework for Optimal Masking in the Synthesis of Oligonucleotide Microarrays; Nucleic Acids Research, 2002, vol. 30, No. 20 e106, c2002 Oxford University Press.

Amarzguioui et al., Secondary Structure Prediction and in Vitro Accessibility of mRNA as Tools in the Selection of Target Sites for Ribozymes, Nucleic Acids Research, 2000, vol. 28, No. 21 4113-4124, c2000 Oxford University Press.

Chinault et al, Overlap Hybridization Screening: Isolation and Characterization of Overlapping DNA Fragments Surrounding the leu2 Gene on Yeasr Chromosome III.

Vickers, et al., Efficient Reduction of Target RNAs by Small Interfering RNA and RNase H-dependent Antisense Agents, Feb. 2003, The Journal of Biological Chemistry, vol. 278, pp. 7108-7118.

Zhang et al., Physical and Functional Interaction between Myeloid Cell Leukemia 1 Protein (MCL1) and Fortilin, 2002, The Journal of Biological Chemistry, vol. 277, pp. 37340-37438.

"siRNA Target Finder." results for the entry of the nucleotide sequence of GeneBank Accession No. NM_021960. http://www.ambion.com/techlib/misc/siRNA_finder.html, accessed on Mar. 6, 2008 in U.S. Appl. No. 11/633,404.

Ui-Tei, et al., Guidelines for the selection of highly effective siRNA sequences for mammalian and chick RNA interference, Nucleic Acids Research, Feb. 2004, vol. 32, No. 3, pp. 936-948.

Tusterman, et al., Dicers at RISC: The Mechanism of RNAi, Cell, Apr. 2004, vol. 117, pp. 1-4.

Brusca, John S. PCT International Search Report, USPTO, Sep. 24, 2007.

Epps-Ford, Janet L., PCT International Search Report, USPTO, Feb. 25, 2005.

Elbashir, et al., Analysis of Gene Function in Somatic mammalian cells using small interfering RNAs,Methods 26 (2002), vol. 26, pp. 199-213.

Elbashir et al., Functional Anatomy of siRNAs for Mediating Efficient RNAi in Dropshophila Melangoaster Embryo Lysate European Molecular Biology Organization, 2001, pp. 6877-6888.

Betrand et al., Comparison of Antisense Oligonucleotides and siRNAs in cell culture and in vivo, 2002 Biotechnical and Biophysical Research Communication, 296 1000-1004.

Tuschl et al., Expanding RNA Interference, (May 2002) Nature Biotechnology, vol. 20, pp. 446-448.

Futami, et al. (2002) Induction of Apoptosis in Hela Cells with siRNA Expression Vector Targeted Against BCL-2. Nucleic Acids Research Supplement No. 2:251-252.

Promega (2003) siRNA Target Designer-Version 1.1, SilentGene U6 Cassette RNA Interference System. http:///www.promega.com/siRNADesigner/program.

Marathi et al. RAD1, A Human Structural Homolog of the Schizosaccharomyces pombe RAD1 Cell Cycle Checkpoint Gene, 1998, Genomics, vol. 54, pp. 344-347.

Kalra, et al., Central Administration of Antisense oligodeoxynucleotides to neuropeptide Y (NPY) mRNA reveals the critical role of newly synthesized NPY in regulation of LHRH release, 1995, Regulatory Peptides, vol. 59, pp. 215-220.

Boutla et al., Short 5'-phosporylated double-stranded RNAs induce RNA interference in Drosophila, 2001, Current Biology, vol. 11, pp. 1776-1780.

NCBI Sequence Viewer v2.0 for NM-000905, http://www.ncbi.nlm.nih.gov/entrez/viewer, accessed on Mar. 18, 2008.

Chinault et al, Overlap Hybridization Screening: Isolation and Characterization of Overlapping DNA Fragments Surrounding the leu2 Gene on Yeast Chromosome III, 1979, 5(2): 111-26.

* cited by examiner

Sequences of top Bcl2

| | | |
|---|---|---|
| siRNA 1 | GGGAGAUAGUGAUGAAGUA | (SEQ ID NO:302) |
| siRNA 2 | GAAGUACAUCCAUUAUAAG | (SEQ ID NO:303) |
| siRNA 3 | GUACGACAACCGGGAGAUA | (SEQ ID NO:304) |
| siRNA 4 | AGAUAGUGAUGAAGUACAU | (SEQ ID NO:305) |
| siRNA 5 | UGAAGACUCUGCUCAGUUU | (SEQ ID NO:306) |
| siRNA 6 | GCAUGCGGCCUCUGUUUGA | (SEQ ID NO:307) |
| siRNA 7 | UGCGGCCUCUGUUUGAUUU | (SEQ ID NO:308) |
| siRNA 8 | GAGAUAGUGAUGAAGUACA | (SEQ ID NO:309) |
| siRNA 9 | GGGAGAUAGUGAUGAAGUAC | (SEQ ID NO:310) |
| siRNA 10 | GAAGACUCUGCUCAGUUUG | (SEQ ID NO:311) |

FIGURE 13

SIRNA TARGETING BCL2L1

This application is a continuation of U.S. Ser. No. 10/714,333, filed Nov. 14, 2003, which is a nonprovisional of the following two provisional applications: U.S. Provisional Application Ser. No. 60/426,137, filed Nov. 14, 2002, entitled "Combinatorial Pooling Approach for siRNA Induced Gene Silencing and Methods for Selecting siRNA" and U.S. Provisional Application Ser. No. 60/502,050, filed Sep. 10, 2003, entitled "Methods for Selecting siRNA." The entire disclosures of Ser. Nos. 10/714,333, 60/426,137, and 60/502,050, including the tables filed in electronic format and sequence listings, are herein incorporated by reference.

SEQUENCE LISTING

The sequence listing for this application has been submitted in accordance with 37 CFR §1.52(e) and 37 CFR §1.821 on CD-ROM in lieu of paper on a disk containing the sequence listing file entitled "DHARMA_0100-US12_CRF.txt" created Dec. 7, 2006, 89 kb. Applicants hereby incorporate by reference the sequence listing provided on CD-ROM in lieu of paper into the instant specification.

FIELD OF INVENTION

The present invention relates to RNA interference ("RNAi").

BACKGROUND OF THE INVENTION

Relatively recently, researchers observed that double stranded RNA ("dsRNA") could be used to inhibit protein expression. This ability to silence a gene has broad potential for treating human diseases, and many researchers and commercial entities are currently investing considerable resources in developing therapies based on this technology.

Double stranded RNA induced gene silencing can occur on at least three different levels: (i) transcription inactivation, which refers to RNA guided DNA or histone methylation; (ii) siRNA induced mRNA degradation; and (iii) mRNA induced transcriptional attenuation.

It is generally considered that the major mechanism of RNA induced silencing (RNA interference, or RNAi) in mammalian cells is mRNA degradation. Initial attempts to use RNAi in mammalian cells focused on the use of long strands of dsRNA. However, these attempts to induce RNAi met with limited success, due in part to the induction of the interferon response, which results in a general, as opposed to a target-specific, inhibition of protein synthesis. Thus, long dsRNA is not a viable option for RNAi in mammalian systems.

More recently it has been shown that when short (18-30 bp) RNA duplexes are introduced into mammalian cells in culture, sequence-specific inhibition of target mRNA can be realized without inducing an interferon response. Certain of these short dsRNAs, referred to as small inhibitory RNAs ("siRNAs"), can act catalytically at sub-molar concentrations to cleave greater than 95% of the target mRNA in the cell. A description of the mechanisms for siRNA activity, as well as some of its applications are described in Provost et al. (2002) Ribonuclease Activity and RNA Binding of Recombinant Human Dicer, EMBO J., 21(21): 5864-5874; Tabara et al. (2002) The dsRNA Binding Protein RDE-4 Interacts with RDE-1, DCR-1 and a DexH-box Helicase to Direct RNAi in *C. elegans,* Cell 109(7):861-71; Ketting et al., Dicer Functions in RNA Interference and in Synthesis of Small RNA Involved in Developmental Timing in *C. elegans*; Martinez et al. (2002) Single-Stranded Antisense siRNAs Guide Target RNA Cleavage in RNAi, Cell 110(5):563; Hutvagner & Zamore (2002) A microRNA in a multiple-turnover RNAi enzyme complex, Science 297:2056.

From a mechanistic perspective, introduction of long double stranded RNA into plants and invertebrate cells is broken down into siRNA by a Type III endonuclease known as Dicer. Sharp (2001) RNA interference—2001, Genes Dev. 15:485. Dicer, a ribonuclease-III-like enzyme, processes the dsRNA into 19-23 base pair short interfering RNAs with characteristic two base 3' overhangs. Bernstein, Caudy, Hammond, & Hannon (2001) Role for a bidentate ribonuclease in the initiation step of RNA interference, Nature 409:363. The siRNAs are then incorporated into an RNA-induced silencing complex (RISC) where one or more helicases unwind the siRNA duplex, enabling the complementary antisense strand to guide target recognition. Nykanen, Haley, & Zamore (2001) ATP requirements and small interfering RNA structure in the RNA interference pathway, Cell 107:309. Upon binding to the appropriate target mRNA, one or more endonucleases within the RISC cleaves the target to induce silencing. Elbashir, Lendeckel, & Tuschl (2001) RNA interference is mediated by 21- and 22-nucleotide RNAs, Genes Dev. 15:188, FIG. 1.

The interference effect can be long lasting and may be detectable after many cell divisions. Moreover, RNAi exhibits sequence specificity. Kisielow, M. et al. (2002) Isoform-specific knockdown and expression of adaptor protein ShcA using small interfering RNA, J. of Biochemistry 363: 1-5. Thus, the RNAi machinery can specifically knock down one type of transcript, while not affecting closely related mRNA. These properties make siRNA a potentially valuable tool for inhibiting gene expression and studying gene function and drug target validation. Moreover, siRNAs are potentially useful as therapeutic agents against: (1) diseases that are caused by over-expression or misexpression of genes; and (2) diseases brought about by expression of genes that contain mutations.

Successful siRNA-dependent gene silencing depends on a number of factors. One of the most contentious issues in RNAi is the question of the necessity of siRNA design, i.e., considering the sequence of the siRNA used. Early work in *C. elegans* and plants circumvented the issue of design by introducing long dsRNA (see, for instance, Fire, A. et al. (1998) Nature 391:806-811). In this primitive organism, long dsRNA molecules are cleaved into siRNA by Dicer, thus generating a diverse population of duplexes that can potentially cover the entire transcript. While some fraction of these molecules are non-functional (i.e. induce little or no silencing) one or more have the potential to be highly functional, thereby silencing the gene of interest and alleviating the need for siRNA design. Unfortunately, due to the interferon response, this same approach is unavailable for mammalian systems. While this effect can be circumvented by bypassing the Dicer cleavage step and directly introducing siRNA, this tactic carries with it the risk that the chosen siRNA sequence may be non-functional or semi-functional.

A number of researches have expressed the view that siRNA design is not a crucial element of RNAi. On the other hand, others in the field have begun to explore the possibility that RNAi can be made more efficient by paying attention to the design of the siRNA. Unfortunately, none of the reported methods have provided a satisfactory scheme for reliably selecting siRNA with acceptable levels of functionality. Accordingly, there is a need to develop rational criteria by which to select siRNA with an acceptable level of functionality, and to identify siRNA that have this improved level of functionality, as well as to identify siRNAs that are hyper-functional.

SUMMARY OF THE INVENTION

The present invention is directed to increasing the efficiency of RNAi, particularly in mammalian systems. Accordingly, the present invention provides kits, siRNAs and methods for increasing siRNA efficacy.

According to one embodiment, the present invention provides a kit for gene silencing, wherein said kit is comprised of a pool of at least two siRNA duplexes, each of which is comprised of a sequence that is complementary to a portion of the sequence of one or more target messenger RNA.

According to a second embodiment, the present invention provides a method for optimizing RNA interference by using one or more siRNAs that are optimized according to a formula (or algorithm) selected from:

$$\text{Relative functionality of siRNA} = -(GC/3) + (AU_{15-19}) - (Tm_{20°C.})*3 - (G_{13})*3 - (C_{19}) + (A_{19})*2 + (A_3) + (U_{10}) + (A_{14}) - (U_5) - (A_{11}) \quad \text{Formula I}$$

$$\text{Relative functionality of siRNA} = -(GC/3) - (AU_{15-19})*3 - (G_{13})*3 - (C_{19}) + (A_{19})*2 + (A_3) \quad \text{Formula II}$$

$$\text{Relative functionality of siRNA} = -(GC/3) + (AU_{15-19}) - (Tm_{20°C.})*3 \quad \text{Formula III}$$

$$\text{Relative functionality of siRNA} = -GC/2 + (AU_{15-19})/2 - (Tm_{20°C.})*2 - (G_{13})*3 - (C_{19}) + (A_{19})*2 + (A_3) + (U_{10}) + (A_{14}) - (U_5) - (A_{11}) \quad \text{Formula IV}$$

$$\text{Relative functionality of siRNA} = -(G_{13})*3 - (C_{19}) + (A_{19})*2 + (A_3) + (U_{10}) + (A_{14}) - (U_5) - (A_{11}) \quad \text{Formula V}$$

$$\text{Relative functionality of siRNA} = -(G_{13})*3 - (C_{19}) + (A_{19})*2 + (A_3) \quad \text{Formula VI}$$

$$\text{Relative functionality of siRNA} = -(GC/2) + (AU_{15-19})/2 - (Tm_{20°C.})*1 - (G_{13})*3 - (C_{19}) + (A_{19})*3 + (A_3)*3 + (U_{10})/2 + (A_{14})/2 - (U_5)/2 - (A_{11})/2 \quad \text{Formula VII}$$

wherein in Formulas I-VII:

$Tm_{20°C.}=1$ if the Tm is greater than 20° C.;

$A_{19}=1$ if A is the base at position 19 on the sense strand, otherwise its value is 0;

$AU_{15-19}=0-5$ depending on the number of A or U bases on the sense strand at positions 15-19;

$G_{13}=1$ if G is the base at position 13 on the sense strand, otherwise its value is 0;

$C_{19}=1$ if C is the base at position 19 of the sense strand, otherwise its value is 0;

GC=the number of G and C bases in the entire sense strand;

$A_3=1$ if A is the base at position 3 on the sense strand, otherwise its value is 0;

$A_{11}=1$ if A is the base at position 11 on the sense strand, otherwise its value is 0;

$A_{14}=1$ if A is the base at position 14 on the sense strand, otherwise its value is 0;

$U_{10}=1$ if U is the base at position 10 on the sense strand, otherwise its value is 0;

$U_5=1$ if U is the base at position 5 on the sense strand, otherwise its value is 0;

or $$\begin{aligned}\text{Relative functionality of siRNA} = &(-14)*G_{13} - 13*A_1 - 12*U_7 - 11*U_2 - 10*A_{11} - 10*U_4 - 10*C_3 - 10*C_5 - 10*C_6 - 9*A_{10} + 9*U_9 - 9*C_{18} - 8*G_{10} - 7*U_1 - 7*U_{16} - 7*C_{17} - 7*C_{19} + 7*U_{17} + 8*A_2 + 8*A_4 + 8*A_5 + 8*C_4 + 9*G_8 + 10*A_7 + 10*U_{18} + 11*A_{19} + 11*C_9 + 15*G_1 + 18*A_3 + 19*U_{10} - Tm - 3*(GC_{total}) - 6*(GC_{15-19}) - 30*X;\end{aligned} \quad \text{Formula VIII}$$

and $$\begin{aligned}\text{Relative functionality of siRNA} = &(14.1)*A_3 + (14.9)*A_6 + (17.6)*A_{13} + (24.7)*A_{19} + (14.2)*U_{10} + (10.5)*C_9 + (23.9)*G_1 + (16.3)*G_2 + (-12.3)*A_{11} + (-19.3)*U_1 + (-12.1)*U_2 + (-11)*U_3 + (-15.2)*U_{15} + (-11.3)*U_{16} + (-11.8)*C_3 + (-17.4)*C_6 + (-10.5)*C_7 + (-13.7)*G_{13} + (-25.9)*G_{19} - Tm - 3*(GC_{total}) - 6*(GC_{15-19}) - 30*X\end{aligned} \quad \text{Formula IX}$$

wherein $A_1=1$ if A is the base at position 1 of the sense strand, otherwise its value is 0;

$A_2=1$ if A is the base at position 2 of the sense strand, otherwise its value is 0;

$A_3=1$ if A is the base at position 3 of the sense strand, otherwise its value is 0;

$A_4=1$ if A is the base at position 4 of the sense strand, otherwise its value is 0;

$A_5=1$ if A is the base at position 5 of the sense strand, otherwise its value is 0;

$A_6=1$ if A is the base at position 6 of the sense strand, otherwise its value is 0;

$A_7=1$ if A is the base at position 7 of the sense strand, otherwise its value is 0;

$A_{10}=1$ if A is the base at position 10 of the sense strand, otherwise its value is 0;

$A_{11}=1$ if A is the base at position 11 of the sense strand, otherwise its value is 0;

$A_{13}=1$ if A is the base at position 13 of the sense strand, otherwise its value is 0;

$A_{19}=1$ if A is the base at position 19 of the sense strand, otherwise if another base is present or the sense strand is only 18 base pairs in length, its value is 0;

$C_3=1$ if C is the base at position 3 of the sense strand, otherwise its value is 0;

$C_4=1$ if C is the base at position 4 of the sense strand, otherwise its value is 0;

$C_5=1$ if C is the base at position 5 of the sense strand, otherwise its value is 0;

$C_6=1$ if C is the base at position 6 of the sense strand, otherwise its value is 0;

$C_7=1$ if C is the base at position 7 of the sense strand, otherwise its value is 0;

$C_9=1$ if C is the base at position 9 of the sense strand, otherwise its value is 0;

$C_{17}=1$ if C is the base at position 17 of the sense strand, otherwise its value is 0;

$C_{18}=1$ if C is the base at position 18 of the sense strand, otherwise its value is 0;

$C_{19}=1$ if C is the base at position 19 of the sense strand, otherwise if another base is present or the sense strand is only 18 base pairs in length, its value is 0;

$G_1=1$ if G is the base at position 1 on the sense strand, otherwise its value is 0;

$G_2=1$ if G is the base at position 2 of the sense strand, otherwise its value is 0;

$G_8=1$ if G is the base at position 8 on the sense strand, otherwise its value is 0;

$G_{10}=1$ if G is the base at position 10 on the sense strand, otherwise its value is 0;

$G_{13}=1$ if G is the base at position 13 on the sense strand, otherwise its value is 0;

$G_{19}=1$ if G is the base at position 19 of the sense strand, otherwise if another base is present or the sense strand is only 18 base pairs in length, its value is 0;

$U_1=1$ if U is the base at position 1 on the sense strand, otherwise its value is 0;

$U_2=1$ if U is the base at position 2 on the sense strand, otherwise its value is 0;

$U_3=1$ if U is the base at position 3 on the sense strand, otherwise its value is 0;

$U_4=1$ if U is the base at position 4 on the sense strand, otherwise its value is 0;

$U_7=1$ if U is the base at position 7 on the sense strand, otherwise its value is 0;

$U_9=1$ if U is the base at position 9 on the sense strand, otherwise its value is 0;

$U_{10}=1$ if U is the base at position 10 on the sense strand, otherwise its value is 0;

$U_{15}=1$ if U is the base at position 15 on the sense strand, otherwise its value is 0;

$U_{16}=1$ if U is the base at position 16 on the sense strand, otherwise its value is 0;

$U_{17}=1$ if U is the base at position 17 on the sense strand, otherwise its value is 0;

$U_{18}=1$ if U is the base at position 18 on the sense strand, otherwise its value is 0;

$GC_{15-19}$=the number of G and C bases within positions 15-19 of the sense strand or within positions 15-18 if the sense strand is only 18 base pairs in length;

$GC_{total}$=the number of G and C bases in the sense strand;

Tm=100 if the targeting site contains an inverted repeat longer than 4 base pairs, otherwise its value is 0; and X=the number of times that the same nucleotide repeats four or more times in a row.

According to a third embodiment, the present invention is directed to a kit comprised of at least one siRNA that contains a sequence that is optimized according to one of the formulas above. Preferably the kit contains at least two optimized siRNA, each of which comprises a duplex, wherein one strand of each duplex comprises at least eighteen contiguous bases that are complementary to a region of a target messenger RNA. For mammalian systems, the siRNA preferably comprises between 18 and 30 nucleotide base pairs.

The ability to use the above algorithms, which are not sequence or species specific, allows for the cost-effective selection of optimized siRNAs for specific target sequences. Accordingly, there will be both greater efficiency and reliability in the use of siRNA technologies.

According to a fourth embodiment, the present invention provides a method for developing an siRNA algorithm for selecting functional and hyperfunctional siRNAs for a given sequence. The method comprises:

(a) selecting a set of siRNAs;

(b) measuring the gene silencing ability of each siRNA from said set;

(c) determining the relative functionality of each siRNA;

(d) determining the amount of improved functionality by the presence or absence of at least one variable selected from the group consisting of the total GC content, melting temperature of the siRNA, GC content at positions 15-19, the presence or absence of a particular nucleotide at a particular position and the number of times that the same nucleotide repeats within a given sequence; and (e) developing an algorithm using the information of step (d).

According to this embodiment, preferably the set of siRNAs comprises at least 90 siRNAs from at least one gene, more preferably at least 180 siRNAs from at least two different genes, and most preferably at least 270 and 360 siRNAs from at least three and four different genes, respectively. Additionally, in step (d) the determination is made with preferably at least two, more preferably at least three, even more preferably at least four, and most preferably all of the variables. The resulting algorithm is not target sequence specific.

In a fifth embodiment, the present invention provides rationally designed siRNAs identified using the formulas above.

In a sixth embodiment, the present invention is directed to hyperfunctional siRNA.

For a better understanding of the present invention together with other and further advantages and embodiments, reference is made to the following description taken in conjunction with the examples, the scope of which is set forth in the appended claims.

BRIEF DESCRIPTION OF THE FIGURES

FIG. 13 is the sequence of the top ten Bcl2 siRNAs as determined by Formula VIII. Sequences are listed 5' to 3'.

DETAILED DESCRIPTION

Definitions

Figure 1:
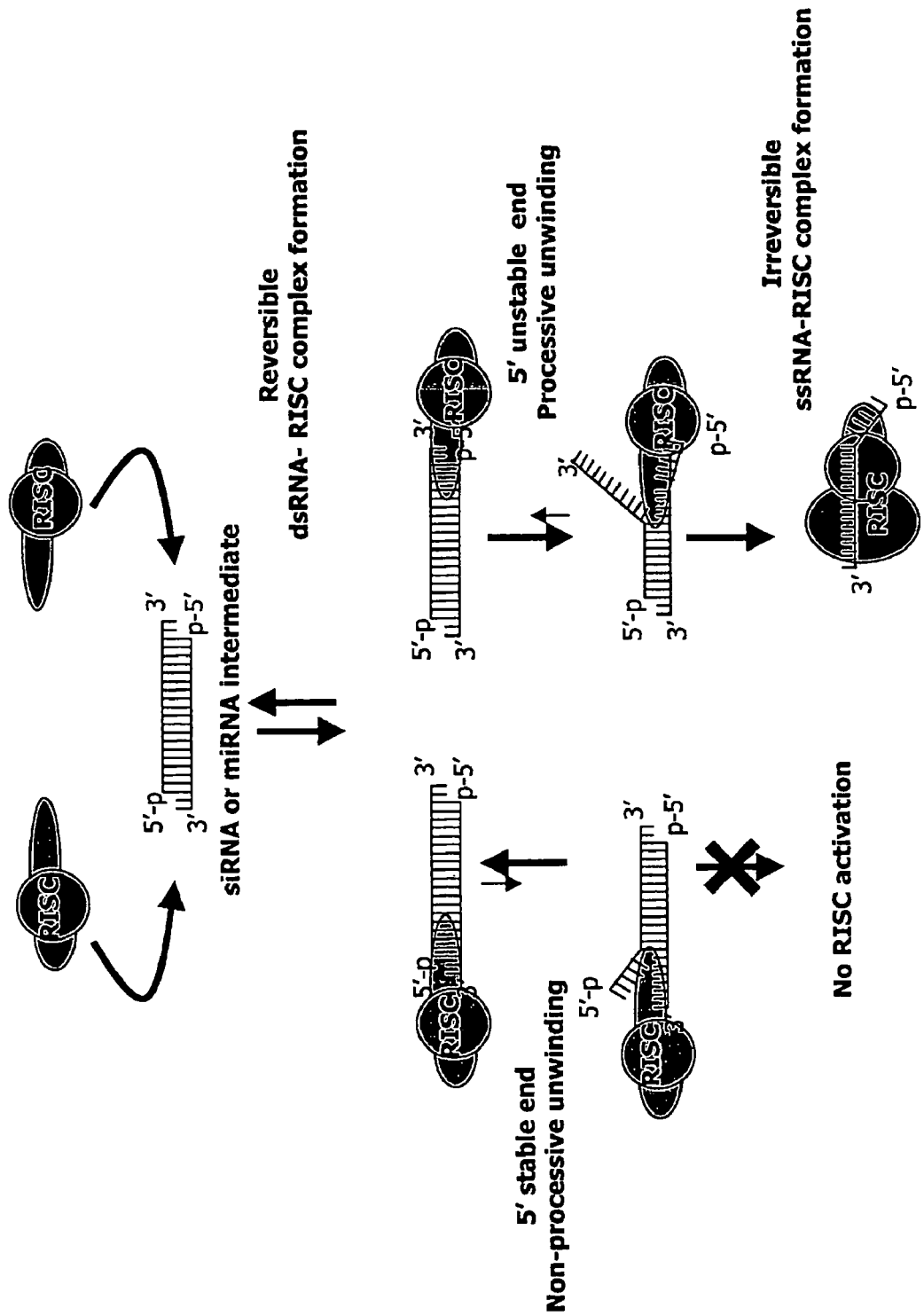
FIG. 1 shows a model for siRNA-RISC interactions. RISC has the ability to interact with either end of the siRNA or miRNA molecule. Following binding, the duplex is unwound, and the relevant target is identified, cleaved, and released.

Unless stated otherwise, the following terms and phrases have the meanings provided below:

Complementary

The term "complementary" refers to the ability of polynucleotides to form base pairs with one another. Base pairs are typically formed by hydrogen bonds between nucleotide units in antiparallel polynucleotide strands. Complementary polynucleotide strands can base pair in the Watson-Crick manner (e.g., A to T, A to U, C to G), or in any other manner that allows for the formation of duplexes. As persons skilled in the art are aware, when using RNA as opposed to DNA, uracil rather than thymine is the base that is considered to be complementary to adenosine. However, when a U is denoted in the context of the present invention, the ability to substitute a T is implied, unless otherwise stated.

Perfect complementarity or 100% complementarity refers to the situation in which each nucleotide unit of one polynucleotide strand can hydrogen bond with a nucleotide unit of a second polynucleotide strand. Less than perfect complementarity refers to the situation in which some, but not all, nucleotide units of two strands can hydrogen bond with each other. For example, for two 20-mers, if only two base pairs on each strand can hydrogen bond with each other, the polynucleotide strands exhibit 10% complementarity. In the same example, if 18 base pairs on each strand can hydrogen bond with each other, the polynucleotide strands exhibit 90% complementarity.

Deoxynucleotide

The term "deoxynucleotide" refers to a nucleotide or polynucleotide lacking a hydroxyl group (OH group) at the 2' and/or 3' position of a sugar moiety. Instead, it has a hydrogen bonded to the 2' and/or 3' carbon. Within an RNA molecule that comprises one or more deoxynucleotides, "deoxynucleotide" refers to the lack of an OH group at the 2' position of the sugar moiety, having instead a hydrogen bonded directly to the 2' carbon.

Deoxyribonucleotide

The terms "deoxyribonucleotide" and "DNA" refer to a nucleotide or polynucleotide comprising at least one sugar moiety that has an H, rather than an OH, at its 2' and/or 3' position.

Duplex Region

The phrase "duplex region" refers to the region in two complementary or substantially complementary polynucleotides that form base pairs with one another, either by Watson-Crick base pairing or any other manner that allows for a stabilized duplex between polynucleotide strands that are complementary or substantially complementary. For example, a polynucleotide strand having 21 nucleotide units can base pair with another polynucleotide of 21 nucleotide units, yet only 19 bases on each strand are complementary or substantially complementary, such that the "duplex region" has 19 base pairs. The remaining bases may, for example, exist as 5' and 3' overhangs. Further, within the duplex region, 100% complementarity is not required; substantial complementarity is allowable within a duplex region. Substantial complementarity refers to 79% or greater complementarity. For example, a mismatch in a duplex region consisting of 19 base pairs results in 94.7% complementarity, rendering the duplex region substantially complementary.

Gene Silencing

The phrase "gene silencing" refers to a process by which the expression of a specific gene product is lessened or attenuated. Gene silencing can take place by a variety of pathways. Unless specified otherwise, as used herein, gene silencing refers to decreases in gene product expression that results from RNA interference (RNAi), a defined, though partially characterized pathway whereby small inhibitory RNA (siRNA) act in concert with host proteins (e.g. the RNA induced silencing complex, RISC) to degrade messenger RNA (mRNA) in a sequence-dependent fashion. The level of gene silencing can be measured by a variety of means, including, but not limited to, measurement of transcript levels by Northern Blot Analysis, B-DNA techniques, transcription-sensitive reporter constructs, expression profiling (e.g. DNA chips), and related technologies. Alternatively, the level of silencing can be measured by assessing the level of the protein encoded by a specific gene. This can be accomplished by performing a number of studies including Western Analysis, measuring the levels of expression of a reporter protein that has e.g. fluorescent properties (e.g. GFP) or enzymatic activity (e.g. alkaline phosphatases), or several other procedures.

miRNA

The term "miRNA" refers to microRNA.

Nucleotide

The term "nucleotide" refers to a ribonucleotide or a deoxyribonucleotide or modified form thereof, as well as an analog thereof. Nucleotides include species that comprise purines, e.g., adenine, hypoxanthine, guanine, and their derivatives and analogs, as well as pyrimidines, e.g., cytosine, uracil, thymine, and their derivatives and analogs.

Nucleotide analogs include nucleotides having modifications in the chemical structure of the base, sugar and/or phosphate, including, but not limited to, 5-position pyrimidine modifications, 8-position purine modifications, modifications at cytosine exocyclic amines, and substitution of 5-bromo-uracil; and 2'-position sugar modifications, including but not limited to, sugar-modified ribonucleotides in which the 2'-OH is replaced by a group such as an H, OR, R, halo, SH, SR, $NH_2$, NHR, $NR_2$, or CN, wherein R is an alkyl moiety. Nucleotide analogs are also meant to include nucleotides with bases such as inosine, queuosine, xanthine, sugars such as 2'-methyl ribose, non-natural phosphodiester linkages such as methylphosphonates, phosphorothioates and peptides.

Modified bases refer to nucleotide bases such as, for example, adenine, guanine, cytosine, thymine, uracil, xanthine, inosine, and queuosine that have been modified by the replacement or addition of one or more atoms or groups. Some examples of types of modifications that can comprise nucleotides that are modified with respect to the base moieties include but are not limited to, alkylated, halogenated, thiolated, aminated, amidated, or acetylated bases, individually or in combination. More specific examples include, for example, 5-propynyluridine, 5-propynylcytidine, 6-methyladenine, 6-methylguanine, N,N,-dimethyladenine, 2-propyladenine, 2-propylguanine, 2-aminoadenine, 1-methylinosine, 3-methyluridine, 5-methylcytidine, 5-methyluridine and other nucleotides having a modification at the 5 position, 5-(2-amino)propyl uridine, 5-halocytidine, 5-halouridine, 4-acetylcytidine, 1-methyladenosine, 2-methyladenosine, 3-methylcytidine, 6-methyluridine, 2-methylguanosine, 7-methylguanosine, 2,2-dimethylguanosine, 5-methylaminoethyluridine, 5-methyloxyuridine, deazanucleotides such as 7-deaza-adenosine, 6-azouridine, 6-azocytidine, 6-azothymidine, 5-methyl-2-thiouridine, other thio bases such as 2-thiouridine and 4-thiouridine and 2-thiocytidine, dihydrouridine, pseudouridine, queuosine, archaeosine, naphthyl and substituted naphthyl groups, any O- and N-alkylated purines and pyrimidines such as N6-methyladenosine, 5-methylcarbonylmethyluridine, uridine 5-oxyacetic acid, pyridine-4-one, pyridine-2-one, phenyl and modified phenyl groups such as aminophenol or 2,4,6-trimethoxy benzene, modified cytosines that act as G-clamp nucleotides, 8-substituted adenines and guanines, 5-substituted uracils and thymines, azapyrimidines, carboxyhydroxyalkyl nucleotides, carboxyalkylaminoalkyl nucleotides, and alkylcarbonylalkylated nucleotides. Modified nucleotides also include those nucleotides that are modified with respect to the sugar moiety, as well as nucleotides having sugars or analogs thereof that are not ribosyl. For example, the sugar moieties may be, or be based on, mannoses, arabinoses, glucopyranoses, galactopyranoses, 4'-thioribose, and other sugars, heterocycles, or carbocycles.

The term nucleotide is also meant to include what are known in the art as universal bases. By way of example, universal bases include but are not limited to 3-nitropyrrole, 5-nitroindole, or nebularine. The term "nucleotide" is also meant to include the N3' to P5' phosphoramidate, resulting from the substitution of a ribosyl 3' oxygen with an amine group.

Further, the term nucleotide also includes those species that have a detectable label, such as for example a radioactive or fluorescent moiety, or mass label attached to the nucleotide.

Off-Target Silencing and Off-Target Interference

The phrases "off-target silencing" and "off-target interference" are defined as degradation of mRNA other than the intended target mRNA due to overlapping and/or partial homology with secondary mRNA messages.

Polynucleotide

The term "polynucleotide" refers to polymers of nucleotides, and includes but is not limited to DNA, RNA, DNA/RNA hybrids including polynucleotide chains of regularly and/or irregularly alternating deoxyribosyl moieties and ribosyl moieties (i.e., wherein alternate nucleotide units have an —OH, then and —H, then an —OH, then an —H, and so on at the 2' position of a sugar moiety), and modifications of these kinds of polynucleotides, wherein the attachment of various entities or moieties to the nucleotide units at any position are included.

Polyribonucleotide

The term "polyribonucleotide" refers to a polynucleotide comprising two or more modified or unmodified ribonucleotides and/or their analogs. The term "polyribonucleotide" is used interchangeably with the term "oligoribonucleotide."

Ribonucleotide and Ribonucleic Acid

The term "ribonucleotide" and the phrase "ribonucleic acid" (RNA), refer to a modified or unmodified nucleotide or polynucleotide comprising at least one ribonucleotide unit. A ribonucleotide unit comprises an hydroxyl group attached to the 2' position of a ribosyl moiety that has a nitrogenous base attached in N-glycosidic linkage at the 1' position of a ribosyl moiety, and a moiety that either allows for linkage to another nucleotide or precludes linkage.

siRNA

The term "siRNA" refers to small inhibitory RNA duplexes that induce the RNA interference (RNAi) pathway. These molecules can vary in length (generally between 18-30 basepairS) and contain varying degrees of complementarity to their target mRNA in the antisense strand. Some, but not all, siRNA have unpaired overhanging bases on the 5' or 3' end of the sense strand and/or the antisense strand. The term "siRNA" includes duplexes of two separate strands, as well as single strands that can form hairpin structures comprising a duplex region.

siRNA may be divided into five (5) groups (non-functional, semi-functional, functional, highly functional, and hyperfunctional) based on the level or degree of silencing that they induce in cultured cell lines. As used herein, these definitions are based on a set of conditions where the siRNA is transfected into said cell line at a concentration of 100 nM and the level of silencing is tested at a time of roughly 24 hours after transfection, and not exceeding 72 hours after transfection. In this context, "non-functional siRNA" are defined as those siRNA that induce less than 50% (<50%) target silencing. "Semi-functional siRNA" induce 50-79% target silencing. "Functional siRNA" are molecules that induce 80-95% gene silencing. "Highly-functional siRNA" are molecules that induce greater than 95% gene silencing. "Hyperfunctional siRNA" are a special class of molecules. For purposes of this document, hyperfunctional siRNA are defined as those molecules that: (1) induce greater than 95% silencing of a specific target when they are transfected at subnanomolar concentrations (i.e., less than one nanomolar); and/or (2) induce functional (or better) levels of silencing for greater than 96 hours. These relative functionalities (though not intended to be absolutes) may be used to compare siRNAs to a particular target for applications such as functional genomics, target identification and therapeutics.

SMARTSCORE™, or siRNA Rank

The term "SMARTSCORE™", or siRNA rank, refers to a number determined by applying any of the Formulas I-Formula IX to a given siRNA sequence. The term "SMART-selected" or "rationally selected" or "rational selection" refers to siRNA that have been selected on the basis of their SMARTSCORES™, or siRNA ranking.

Substantially Similar

The phrase "substantially similar" refers to a similarity of at least 90% with respect to the identity of the bases of the sequence.

Target

The term "target" is used in a variety of different forms throughout this document and is defined by the context in which it is used. "Target mRNA" refers to a messenger RNA to which a given siRNA can be directed against. "Target sequence" and "target site" refer to a sequence within the mRNA to which the sense strand of an siRNA shows varying degrees of homology and the antisense strand exhibits varying degrees of complementarity. The term "siRNA target" can refer to the gene, mRNA, or protein against which an siRNA is directed. Similarly "target silencing" can refer to the state of a gene, or the corresponding mRNA or protein.

Transfection

The term "transfection" refers to a process by which agents are introduced into a cell. The list of agents that can be transfected is large and includes, but is not limited to, siRNA, sense and/or anti-sense sequences, DNA encoding one or more genes and organized into an expression plasmid, proteins, protein fragments, and more. There are multiple methods for transfecting agents into a cell including, but not limited to, electroporation, calcium phosphate-based transfections, DEAE-dextran-based transfections, lipid-based transfections, molecular conjugate-based transfections (e.g. polylysine-DNA conjugates), microinjection and others.

The present invention is directed to improving the efficiency of gene silencing by siRNA. Through the inclusion of multiple siRNA sequences that are targeted to a particular gene and/or selecting an siRNA sequence based on certain defined criteria, improved efficiency may be achieved.

The present invention will now be described in connection with preferred embodiments. These embodiments are presented in order to aid in an understanding of the present invention and are not intended, and should not be construed, to limit the invention in any way. All alternatives, modifications and equivalents that may become apparent to those of ordinary skill upon reading this disclosure are included within the spirit and scope of the present invention.

Furthermore, this disclosure is not a primer on RNA interference. Basic concepts known to persons skilled in the art have not been set forth in detail.

Optimizing siRNA

According to one embodiment, the present invention provides a method for improving the effectiveness of gene silencing for use to silence a particular gene through the selection of an optimal siRNA. An siRNA selected according to this method may be used individually, or in conjunction with the first embodiment, i.e., with one or more other siRNAs, each of which may or may not be selected by this criteria in order to maximize their efficiency.

The degree to which it is possible to select an siRNA for a given mRNA that maximizes these criteria will depend on the sequence of the mRNA itself. However, the selection criteria will be independent of the target sequence. According to this method, an siRNA is selected for a given gene by using a rational design. That said, rational design can be described in a variety of ways. Rational design is, in simplest terms, the application of a proven set of criteria that enhance the probability of identifying a functional or hyperfunctional siRNA. In one method, rationally designed siRNA can be identified by maximizing one or more of the following criteria:

(1) A low GC content, preferably between about 30-52%.
(2) At least 2, preferably at least 3 A or U bases at positions 15-19 of the siRNA on the sense strand.
(3) An A base at position 19 of the sense strand.
(4) An A base at position 3 of the sense strand.
(5) A U base at position 10 of the sense strand.
(6) An A base at position 14 of the sense strand.
(7) A base other than C at position 19 of the sense strand.
(8) A base other than G at position 13 of the sense strand.
(9) A Tm, which refers to the character of the internal repeat that results in inter- or intramolecular structures for one strand of the duplex, that is preferably not stable at greater than 50° C., more preferably not stable at greater than 37° C., even more preferably not stable at greater than 30° C. and most preferably not stable at greater than 20° C.
(10) A base other than U at position 5 of the sense strand.
(11) A base other than A at position 11 of the sense strand.

Criteria 5, 6, 10 and 11 are minor criteria, but are nonetheless desirable. Accordingly, preferably an siRNA will satisfy as many of the aforementioned criteria as possible, more preferably at least 1-4 and 7-9, and most preferably all of the criteria With respect to the criteria, GC content, as well as a high number of AU in positions 15-19, may be important for easement of the unwinding of double stranded siRNA duplex. Duplex unwinding has been shown to be crucial for siRNA functionality in vivo.

With respect to criterion 9, the internal structure is measured in terms of the melting temperature of the single strand of siRNA, which is the temperature at which 50% of the molecules will become denatured. With respect to criteria 2-8 and 10-11, the positions refer to sequence positions on the sense strand, which is the strand that is identical to the mRNA.

In one preferred embodiment, at least criteria 1 and 8 are satisfied. In another preferred embodiment, at least criteria 7 and 8 are satisfied. In still another preferred embodiment, at least criteria 1, 8 and 9 are satisfied.

It should be noted that all of the aforementioned criteria regarding sequence position specifics are with respect to the 5' end of the sense strand. Reference is made to the sense strand, because most databases contain information that describes the information of the mRNA. Because according to the present invention a chain can be from 18 to 30 bases in length, and the aforementioned criteria assumes a chain 19 base pairs in length, it is important to keep the aforementioned criteria applicable to the correct bases.

When there are only 18 bases, the base pair that is not present is the base pair that is located at the 3' of the sense strand. When there are twenty to thirty bases present, then additional bases are added at the 5' end of the sense chain and occupy positions $-1$ to $-11$. Accordingly, with respect to SEQ ID NO 001. NNANANNNNUCNAANNNNA and SEQ ID NO 028. GUCNNANANNNNUCNAANNNNA, both would have A at position 3, A at position 5, U at position 10, C at position 11, A and position 13, A and position 14 and A at position 19. However, SEQ ID NO 028 would also have C at position $-1$, U at position $-2$ and G at position $-3$.

For a 19 base pair siRNA, an optimal sequence of one of the strands may be represented below, where N is any base, A, C, G, or U:

```
SEQ ID NO 001.     NNANANNNNUCNAANNNNA
SEQ ID NO 002.     NNANANNNNUGNAANNNNA
SEQ ID NO 003.     NNANANNNNUUNAANNNNA
SEQ ID NO 004.     NNANANNNNUCNCANNNNA
SEQ ID NO 005.     NNANANNNNUGNCANNNNA
SEQ ID NO 006.     NNANANNNNUUNCANNNNA
SEQ ID NO 007.     NNANANNNNUCNUANNNNA
SEQ ID NO 008.     NNANANNNNUGNUANNNNA
SEQ ID NO 009.     NNANANNNNUUNUANNNNA
SEQ ID NO 010.     NNANCNNNNUCNAANNNNA
SEQ ID NO 011.     NNANCNNNNUGNAANNNNA
SEQ ID NO 012.     NNANCNNNNUUNAANNNNA
SEQ ID NO 013.     NNANCNNNNUCNCANNNNA
SEQ ID NO 014.     NNANCNNNNUGNCANNNNA
SEQ ID NO 015.     NNANCNNNNUUNCANNNNA
SEQ ID NO 016.     NANCNNNNUCNUANNNNA
SEQ ID NO 017.     NNANCNNNNUGNUANNNNA
SEQ ID NO 018.     NNANCNNNNUUNUANNNNA
SEQ ID NO 019.     NNANGNNNNUCNAANNNNA
SEQ ID NO 020.     NNANGNNNNUGNAANNNNA
SEQ ID NO 021.     NNANGNNNNUUNAANNNNA
SEQ ID NO 022.     NNANGNNNNUCNCANNNNA
SEQ ID NO 023.     NNANGNNNNUGNCANNNNA
SEQ ID NO 024.     NNANGNNNNUUNCANNNNA
```

-continued
```
SEQ ID NO 025.     NNANGNNNNUCNUANNNNA
SEQ ID NO 026.     NNANGNNNNUGNUANNNNA
SEQ ID NO 027.     NNANGNNNNUNUANNNNA
```

In one embodiment, the sequence used as an siRNA is selected by choosing the siRNA that score highest according to one of the following seven algorithms that are represented by Formulas I-VII:

$$\text{Relative functionality of siRNA} = -(GC/3) + (AU_{15-19}) - (Tm_{20°C.})*3 - (G_{13})*3 - (C_{19}) + (A_{19})*2 + (A_3) + (U_{10}) + (A_{14}) - (U_5) - (A_{11}) \quad \text{Formula I}$$

$$\text{Relative functionality of siRNA} = -(GC/3) - (AU_{15-19})*3 - (G_{13})*3 - (C_{19}) + (A_{19})*2 + (A_3) \quad \text{Formula II}$$

$$\text{Relative functionality of siRNA} = -(GC/3) + (AU_{15-19}) - (Tm_{20°C.})*3 \quad \text{Formula III}$$

$$\text{Relative functionality of siRNA} = -GC/2 + (AU_{15-19})/2 - (Tm_{20°C.})*2 - (G_{13})*3 - (C_{19}) + (A_{19})*2 + (A_3) + (U_{10}) + (A_{14}) - (U_5) - (A_{11}) \quad \text{Formula IV}$$

$$\text{Relative functionality of siRNA} = -(G_{13})*3 - (C_{19}) + (A_{19})*2 + (A_3) + (U_{10}) + (A_{14}) - (U_5) - (A_{11}) \quad \text{Formula V}$$

$$\text{Relative functionality of siRNA} = -(G_{13})*3 - (C_{19}) + (A_{19})*2 + (A_3) \quad \text{Formula VI}$$

$$\text{Relative functionality of siRNA} = -(GC/2) + (AU_{15-19})/2 - (Tm_{20°C.})*1 - (G_{13})*3 - (C_{19}) + (A_{19})*3 + (A_3)*3 + (U_{10})/2 + (A_{14})/2 - (U_5)/2 - (A_{11})/2 \quad \text{Formula VII}$$

In Formulas I-VII:

wherein $A_{19}=1$ if A is the base at position 19 on the sense strand, otherwise its value is 0, $AU_{15-19}=0\text{-}5$ depending on the number of A or U bases on the sense strand at positions 15-19;

$G_{13}=1$ if G is the base at position 13 on the sense strand, otherwise its value is 0;

$C_{19}=1$ if C is the base at position 19 of the sense strand, otherwise its value is 0;

GC=the number of G and C bases in the entire sense strand;

$Tm_{20°C.}=1$ if the Tm is greater than 20° C.;

$A_3=1$ if A is the base at position 3 on the sense strand, otherwise its value is 0;

$U_{10}=1$ if U is the base at position 10 on the sense strand, otherwise its value is 0;

$A_{14}=1$ if A is the base at position 14 on the sense strand, otherwise its value is 0;

$U_5=1$ if U is the base at position 5 on the sense strand, otherwise its value is 0; and $A_{11}=1$ if A is the base at position 11 of the sense strand, otherwise its value is 0.

Formulas I-VII provide relative information regarding functionality. When the values for two sequences are compared for a given formula, the relative functionality is ascertained; a higher positive number indicates a greater functionality. For example, in many applications a value of 5 or greater is beneficial.

Additionally, in many applications, more than one of these formulas would provide useful information as to the relative functionality of potential siRNA sequences. However, it is beneficial to have more than one type of formula, because not every formula will be able to help to differentiate among potential siRNA sequences. For example, in particularly high GC mRNAs, formulas that take that parameter into account would not be useful and application of formulas that lack GC elements (e.g., formulas V and VI) might provide greater insights into duplex functionality. Similarly, formula II might by used in situations where hairpin structures are not observed in duplexes, and formula IV might be applicable for sequences that have higher AU content. Thus, one may consider a particular sequence in light of more than one or even all of these algorithms to obtain the best differentiation among sequences. In some instances, application of a given algorithm may identify an unusually large number of potential siRNA sequences, and in those cases, it may be appropriate to re-analyze that sequence with a second algorithm that is, for instance, more stringent. Alternatively, it is conceivable that analysis of a sequence with a given formula yields no acceptable siRNA sequences (i.e. low SMARTSCORES™, or siRNA ranking). In this instance, it may be appropriate to re-analyze that sequences with a second algorithm that is, for instance, less stringent. In still other instances, analysis of a single sequence with two separate formulas may give rise to conflicting results (i.e. one formula generates a set of siRNA with high SMARTSCORES™, or siRNA ranking, while the other formula identifies a set of siRNA with low SMART-SCORES™, or siRNA ranking). In these instances, it may be necessary to determine which weighted factor(s) (e.g. GC content) are contributing to the discrepancy and assessing the sequence to decide whether these factors should or should not be included. Alternatively, the sequence could be analyzed by a third, fourth, or fifth algorithm to identify a set of rationally designed siRNA.

The above-referenced criteria are particularly advantageous when used in combination with pooling techniques as depicted in Table I:

TABLE I

| CRITERIA | FUNCTIONAL PROBABILITY | | | | | |
|---|---|---|---|---|---|---|
| | OLIGOS | | | POOLS | | |
| | >95% | >80% | <70% | >95% | >80% | <70% |
| CURRENT | 33.0 | 50.0 | 23.0 | 79.5 | 97.3 | 0.3 |
| NEW | 50.0 | 88.5 | 8.0 | 93.8 | 99.98 | 0.005 |
| (GC) | 28.0 | 58.9 | 36.0 | 72.8 | 97.1 | 1.6 |

The term "current" refers to Tuschl's conventional siRNA parameters (Elbashir, S. M. et al. (2002) "Analysis of gene function in somatic mammalian cells using small interfering RNAs" *Methods* 26: 199-213). "New" refers to the design parameters described in Formulas I-VII. "GC" refers to criteria that select siRNA solely on the basis of GC content.

As Table I indicates, when more functional siRNA duplexes are chosen, siRNAs that produce <70% silencing drops from 23% to 8% and the number of siRNA duplexes that produce >80% silencing rises from 50% to 88.5%. Further, of the siRNA duplexes with >80% silencing, a larger portion of these siRNAs actually silence >95% of the target expression (the new criteria increases the portion from 33% to 50%). Using this new criteria in pooled siRNAs, shows that, with pooling, the amount of silencing >95% increases from 79.5% to 93.8% and essentially eliminates any siRNA pool from silencing less than 70%.

Table II similarly shows the particularly beneficial results of pooling in combination with the aforementioned criteria. However, Table II, which takes into account each of the aforementioned variables, demonstrates even a greater degree of improvement in functionality.

TABLE II

| | FUNCTIONAL PROBABILITY | | | | | |
|---|---|---|---|---|---|---|
| | OLIGOS | | | POOLS | | |
| | FUNCTIONAL | AVERAGE | NON-FUNCTIONAL | FUNCTIONAL | AVERAGE | NON-FUNCTIONAL |
| RANDOM | 20 | 40 | 50 | 67 | 97 | 3 |
| CRITERIA 1 | 52 | 99 | 0.1 | 97 | 93 | 0.0040 |
| CRITERIA 4 | 89 | 99 | 0.1 | 99 | 99 | 0.0000 |

The terms "functional," "Average," and "Non-functional" refer to siRNA that exhibit >80%, >50%, and <50% functionality, respectively. Criteria 1 and 4 refer to specific criteria described above.

The above-described algorithms may be used with or without a computer program that allows for the inputting of the sequence of the mRNA and automatically outputs the optimal siRNA. The computer program may, for example, be accessible from a local terminal or personal computer, over an internal network or over the Internet.

In addition to the formulas above, more detailed algorithms may be used for selecting siRNA. Preferably, at least one RNA duplex of between 18 and 30 base pairs is selected such that it is optimized according a formula selected from:

$$(-14)*G_{13}-13*A_1-12*U_7-11*U_2-10*A_{11}-10*U_4- 10*C_3-10*C_5-10*C_6-9*A_{10}-+9*U_9-9*C_{18}- 8*G_{10}-7*U_1-7*U_{16}-7*C_{17}-7*C_{19}+7*U_{17}+ 8*A_2+8*A_4+8*A_5+8*C_4+9*G_8+10*A_7+ 10*U_{18}+11*A_{19}+11*C_9+15*G_1+18*A_3+ 19*U_{10}-Tm-3*(GC_{total})-6*(GC_{15-19})-30*X;\; \text{and}$$

Formula VIII $$(14.1)*A_3+(14.9)*A_6+(17.6)*A_{13}+(24.7)*A_{19}+ (14.2)*U_{10}+(10.5)*C_9+(23.9)*G_1+(16.3)*G_2+ (-12.3)*A_{11}+(-19.3)*U_1+(-12.1)*U_2+ (-11)*U_3+(-15.2)*U_{15}+(-11.3)*U_{16}+ (-11.8)*C_3+(-17.4)*C_6+(-10.5)*C_7+ (-13.7)*G_{13}+(-25.9)*G_{19}-Tm-3*(GC_{total})- 6*(GC_{15-19})-30*X$$

Formula IX wherein $A_1=1$ if A is the base at position 1 of the sense strand, otherwise its value is 0;

$A_2=1$ if A is the base at position 2 of the sense strand, otherwise its value is 0;

$A_3=1$ if A is the base at position 3 of the sense strand, otherwise its value is 0;

$A_4=1$ if A is the base at position 4 of the sense strand, otherwise its value is 0;

$A_5=1$ if A is the base at position 5 of the sense strand, otherwise its value is 0;

$A_6=1$ if A is the base at position 6 of the sense strand, otherwise its value is 0;

$A_7=1$ if A is the base at position 7 of the sense strand, otherwise its value is 0;

$A_{10}=1$ if A is the base at position 10 of the sense strand, otherwise its value is 0;

$A_{11}=1$ if A is the base at position 11 of the sense strand, otherwise its value is 0;

$A_{13}=1$ if A is the base at position 13 of the sense strand, otherwise its value is 0;

$A_{19}=1$ if A is the base at position 19 of the sense strand, otherwise if another base is present or the sense strand is only 18 base pairs in length, its value is 0;

$C_3=1$ if C is the base at position 3 of the sense strand, otherwise its value is 0;

$C_4=1$ if C is the base at position 4 of the sense strand, otherwise its value is 0;

$C_5=1$ if C is the base at position 5 of the sense strand, otherwise its value is 0;

$C_6=1$ if C is the base at position 6 of the sense strand, otherwise its value is 0;

$C_7=1$ if C is the base at position 7 of the sense strand, otherwise its value is 0;

$C_9=1$ if C is the base at position 9 of the sense strand, otherwise its value is 0;

$C_{17}=1$ if C is the base at position 17 of the sense strand, otherwise its value is 0;

$C_{18}=1$ if C is the base at position 18 of the sense strand, otherwise its value is 0;

$C_{19}=1$ if C is the base at position 19 of the sense strand, otherwise if another base is present or the sense strand is only 18 base pairs in length, its value is 0;

$G_1=1$ if G is the base at position 1 on the sense strand, otherwise its value is 0;

$G_2=1$ if G is the base at position 2 of the sense strand, otherwise its value is 0;

$G_8=1$ if G is the base at position 8 on the sense strand, otherwise its value is 0;

$G_{10}=1$ if G is the base at position 10 on the sense strand, otherwise its value is 0;

$G_{13}=1$ if G is the base at position 13 on the sense strand, otherwise its value is 0;

$G_{19}=1$ if G is the base at position 19 of the sense strand, otherwise if another base is present or the sense strand is only 18 base pairs in length, its value is 0;

$U_1=1$ if U is the base at position 1 on the sense strand, otherwise its value is 0;

$U_2=1$ if U is the base at position 2 on the sense strand, otherwise its value is 0;

$U_3=1$ if U is the base at position 3 on the sense strand, otherwise its value is 0;

$U_4=1$ if U is the base at position 4 on the sense strand, otherwise its value is 0;

$U_7=1$ if U is the base at position 7 on the sense strand, otherwise its value is 0;

$U_9=1$ if U is the base at position 9 on the sense strand, otherwise its value is 0;

$U_{10}=1$ if U is the base at position 10 on the sense strand, otherwise its value is 0;

$U_{15}=1$ if U is the base at position 15 on the sense strand, otherwise its value is 0;

$U_{16}=1$ if U is the base at position 16 on the sense strand, otherwise its value is 0;

$U_{17}=1$ if U is the base at position 17 on the sense strand, otherwise its value is 0;

$U_{18}=1$ if U is the base at position 18 on the sense strand, otherwise its value is 0;

$GC_{15-19}$=the number of G and C bases within positions 15-19 of the sense strand, or within positions 15-18 if the sense strand is only 18 base pairs in length;

$GC_{total}$=the number of G and C bases in the sense strand;

Tm=100 if the siRNA oligo has the internal repeat longer then 4 base pairs, otherwise its value is 0; and X=the number of times that the same nucleotide repeats four or more times in a row.

The above formulas VIII and IX, as well as formulas I-VII, provide methods for selecting siRNA in order to increase the efficiency of gene silencing. A subset of variables of any of the formulas may be used, though when fewer variables are used, the optimization hierarchy becomes less reliable.

With respect to the variables of the above-referenced formulas, a single letter of A or C or G or U followed by a subscript refers to a binary condition. The binary condition is that either the particular base is present at that particular position (wherein the value is "1") or the base is not present (wherein the value is "0"). Because position 19 is optional, i.e. there might be only 18 base pairs, when there are only 18 base pairs, any base with a subscript of 19 in the formulas above would have a zero value for that parameter. Before or after each variable is a number followed by *, which indicates that the value of the variable is to be multiplied or weighed by that number.

The numbers preceding the variables A, or G, or C, or U in Formulas VIII and IX (or after the variables in Formula I-VII) were determined by comparing the difference in the frequency of individual bases at different positions in functional siRNA and total siRNA. Specifically, the frequency in which a given base was observed at a particular position in functional groups was compared with the frequency that that same base was observed in the total, randomly selected siRNA set. If the absolute value of the difference between the functional and total values was found to be greater than 6%, that parameter was included in the equation. Thus for instance, if the frequency of finding a "G" at position 13 ($G_{13}$) is found to be 6% in a given functional group, and the frequency of $G_{13}$ in the total population of siRNAs is 20%, the difference between the two values is 6%−20%=−14%. As the absolute value is greater than six (6), this factor (−14) is included in the equation. Thus in Formula VIII, in cases where the siRNA under study has a G in position 13, the accrued value is (−14)*(1)=−14. In contrast, when a base other than G is found at position 13, the accrued value is (−14)*(0)=0.

When developing a means to optimize siRNAs, the inventors observed that a bias toward low internal thermodynamic stability of the duplex at the 5'-antisense (AS) end is characteristic of naturally occurring miRNA precursors. The inventors extended this observation to siRNAs for which functionality had been assessed in tissue culture.

With respect to the parameter $GC_{5-19}$, a value of 0-5 will be ascribed depending on the number of G or C bases at positions 15 to 19. If there are only 18 base pairs, the value is between 0 and 4.

With respect to the criterion $GC_{total}$ content, a number from 0-30 will be ascribed, which correlates to the total number of G and C nucleotides on the sense strand, excluding overhangs. Without wishing to be bound by any one theory, it is postulated that the significance of the GC content (as well as AU content at positions 15-19, which is a parameter for formulas III-VII) relates to the easement of the unwinding of a double-stranded siRNA duplex. Duplex unwinding is believed to be crucial for siRNA functionality in vivo and overall low internal stability, especially low internal stability of the first unwound base pair is believed to be important to maintain sufficient processivity of RISC complex-induced duplex unwinding. If the duplex has 19 base pairs, those at positions 15-19 on the sense strand will unwind first if the molecule exhibits a sufficiently low internal stability at that position. As persons skilled in the art are aware, RISC is a complex of approximately twelve proteins; Dicer is one, but not the only, helicase within this complex. Accordingly, although the GC parameters are believed to relate to activity with Dicer, they are also important for activity with other RISC proteins.

The value of the parameter Tm is 0 when there are no internal repeats longer than (or equal to) four base pairs present in the siRNA duplex; otherwise the value is 1. Thus for example, if the sequence ACGUACGU, or any other four nucleotide (or more) palindrome exists within the structure, the value will be one (1). Alternatively if the structure ACGGACG, or any other 3 nucleotide (or less) palindrome exists, the value will be zero (0).

The variable "X" refers to the number of times that the same nucleotide occurs contiguously in a stretch of four or more units. If there are, for example, four contiguous As in one part of the sequence and elsewhere in the sequence four contiguous Cs, X=2. Further, if there are two separate contiguous stretches of four of the same nucleotides or eight or more of the same nucleotides in a row, then X=2. However, X does not increase for five, six or seven contiguous nucleotides.

Again, when applying Formula VIII or Formula IX to a given mRNA, (the "target RNA" or "target molecule"), one may use a computer program to evaluate the criteria for every sequence of 18-30 base pairs or only sequences of a fixed length, e.g., 19 base pairs. Preferably the computer program is designed such that it provides a report ranking of all of the potential siRNAs between 18 and 30 base pairs, ranked according to which sequences generate the highest value. A higher value refers to a more efficient siRNA for a particular target gene. The computer program that may be used, may be developed in any computer language that is known to be useful for scoring nucleotide sequences, or it may be developed with the assistance of commercially available product such as Microsoft's product .net. Additionally, rather than run every sequence through one and/or another formula, one may compare a subset of the sequences, which may be desirable if for example only a subset are available. For instance, it may be desirable to first perform a BLAST (Basic Local Alignment Search Tool) search and to identify sequences that have no homology to other targets. Alternatively, it may be desirable to scan the sequence and to identify regions of moderate GC context, then perform relevant calculations using one of the above-described formulas on these regions. These calculations can be done manually or with the aid of a computer.

As with Formulas I-VII, either Formula VIII or Formula IX may be used for a given mRNA target sequence. However, it is possible that according to one or the other formula more than one siRNA will have the same value. Accordingly, it is beneficial to have a second formula by which to differentiate sequences. Formula IX was derived in a similar fashion as Formula VIII, yet used a larger data set and thus yields sequences with higher statistical correlations to highly functional duplexes. The sequence that has the highest value ascribed to it may be referred to as a "first optimized duplex." The sequence that has the second highest value ascribed to it may be referred to as a "second optimized duplex." Similarly, the sequences that have the third and fourth highest values ascribed to them may be referred to as a third optimized duplex and a fourth optimized duplex, respectively. When more than one sequence has the same value, each of them may, for example, be referred to as first optimized duplex sequences or co-first optimized duplexes.

siRNA sequences identified using Formula VIII are contained within the compact disks provided in parent application Ser. No. 10/714,333. The data included on the compact disks is described more fully below. The sequences identified by Formula VIII that are disclosed in the compacts disks may be used in gene silencing applications.

It should be noted that for Formulas VIII and IX all of the aforementioned criteria are identified as positions on the sense strand when oriented in the 5' to 3' direction as they are identified in connection with Formulas I-VII unless otherwise specified.

Formulas I-IX, may be used to select or to evaluate one, or more than one, siRNA in order to optimize silencing. Preferably, at least two optimized siRNAs that have been selected according to at least one of these formulas are used to silence a gene, more preferably at least three and most preferably at least four. The siRNAs may be used individually or together in a pool or kit. Further, they may be applied to a cell simultaneously or separately. Preferably, the at least two siRNAs are applied simultaneously. Pools are particularly beneficial for many research applications. However, for therapeutics, it may be more desirable to employ a single hyperfunctional siRNA as described elsewhere in this application.

When planning to conduct gene silencing, and it is necessary to choose between two or more siRNAs, one should do so by comparing the relative values when the siRNA are subjected to one of the formulas above. In general a higher scored siRNA should be used.

Useful applications include, but are not limited to, target validation, gene functional analysis, research and drug discovery, gene therapy and therapeutics. Methods for using siRNA in these applications are well known to persons of skill in the art.

Because the ability of siRNA to function is dependent on the sequence of the RNA and not the species into which it is introduced, the present invention is applicable across a broad range of species, including but not limited to all mammalian species, such as humans, dogs, horses, cats, cows, mice, hamsters, chimpanzees and gorillas, as well as other species and organisms such as bacteria, viruses, insects, plants and *C. elegans*.

The present invention is also applicable for use for silencing a broad range of genes, including but not limited to the roughly 45,000 genes of a human genome, and has particular relevance in cases where those genes are associated with diseases such as diabetes, Alzheimer's, cancer, as well as all genes in the genomes of the aforementioned organisms.

The siRNA selected according to the aforementioned criteria or one of the aforementioned algorithms are also, for example, useful in the simultaneous screening and functional analysis of multiple genes and gene families using high throughput strategies, as well as in direct gene suppression or silencing.

Development of the Algorithms

To identify siRNA sequence features that promote functionality and to quantify the importance of certain currently accepted conventional factors—such as G/C content and target site accessibility—the inventors synthesized an siRNA panel consisting of 270 siRNAs targeting three genes, Human Cyclophilin, Firefly Luciferase, and Human DBI. In all three cases, siRNAs were directed against specific regions of each gene. For Human Cyclophilin and Firefly Luciferase, ninety siRNAs were directed against a 199 bp segment of each respective mRNA. For DBI, 90 siRNAs were directed against a smaller, 109 base pair region of the mRNA. The sequences to which the siRNAs were directed are provided below.

It should be noted that in certain sequences, "t" is present. This is because many databases contain information in this manner. However, the t denotes a uracil residue in mRNA and siRNA. Any algorithm will, unless otherwise specified, process a t in a sequence as a u.

```
HUMAN CYCLOPHILIN: 193-390, M60857
SEQ ID NO 029:
gttccaaaaa cagtggataa ttttgtggcc ttagctacag gagagaaagg atttggctac aaaaacagca aattccatcg tgtaatcaag gacttcatga tccagggcgg agacttcacc aggggagatg gcacaggagg aaagagcatc tacggtgagc gcttccccga tgagaacttc aaactgaagc actacgggcc tggctggg FIREFLY LUCIFERASE: 1434-1631, U47298 (PGL3,
PROMEGA)
SEQ ID NO 030:
tgaacttccc gccgccgttg ttgttttgga gcacggaaag acgatgacgg aaaaagagat cgtggattac gtcgccagtc aagtaacaac cgcgaaaaag ttgcgcggag gagttgtgtt tgtggacgaa gtaccgaaag gtcttaccgg aaaactcgac gcaagaaaaa tcagagagat cctcataaag gccaagaagg DBI, NM_020548 (202-310) (EVERY POSITION)
SEQ ID NO NO. 031:
acgggcaagg ccaagtggga tgcctggaat gagctgaaag ggacttccaa ggaagatgcc atgaaagctt acatcaacaa agtagaagag ctaaagaaaa aatacggg
```

A list of the siRNAs appears in Table IV (see Examples Section, Example I).

The set of duplexes was analyzed to identify correlations between siRNA functionality and other biophysical or thermodynamic properties. When the siRNA panel was analyzed in functional and non-functional subgroups, certain nucleotides were much more abundant at certain positions in functional or non-functional groups. More specifically, the frequency of each nucleotide at each position in highly functional siRNA duplexes was compared with that of non-functional duplexes in order to assess the preference for or against any given nucleotide at every position. These analyses were used to determine important criteria to be included in the siRNA algorithms (Formulas VIII and IX).

The data set was also analyzed for distinguishing biophysical properties of siRNAs in the functional group, such as optimal percent of GC content, propensity for internal structures and regional thermodynamic stability. Of the presented criteria, several are involved in duplex recognition, RISC activation/duplex unwinding, and target cleavage catalysis.

Figure 2:
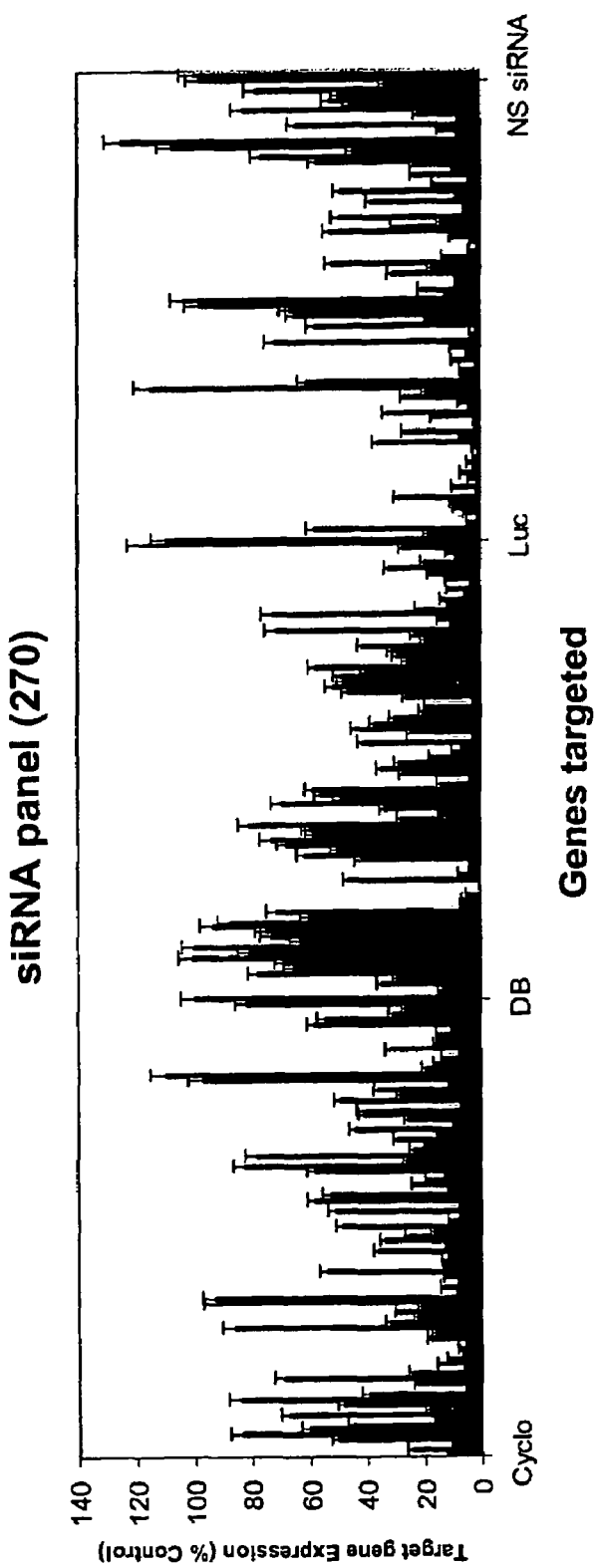
FIG. 2 is a representation of the functionality of two hundred and seventy siRNA duplexes that were generated to target human cyclophilin, human diazepam-binding inhibitor (DB), and firefly luciferase.
Figure 3A:
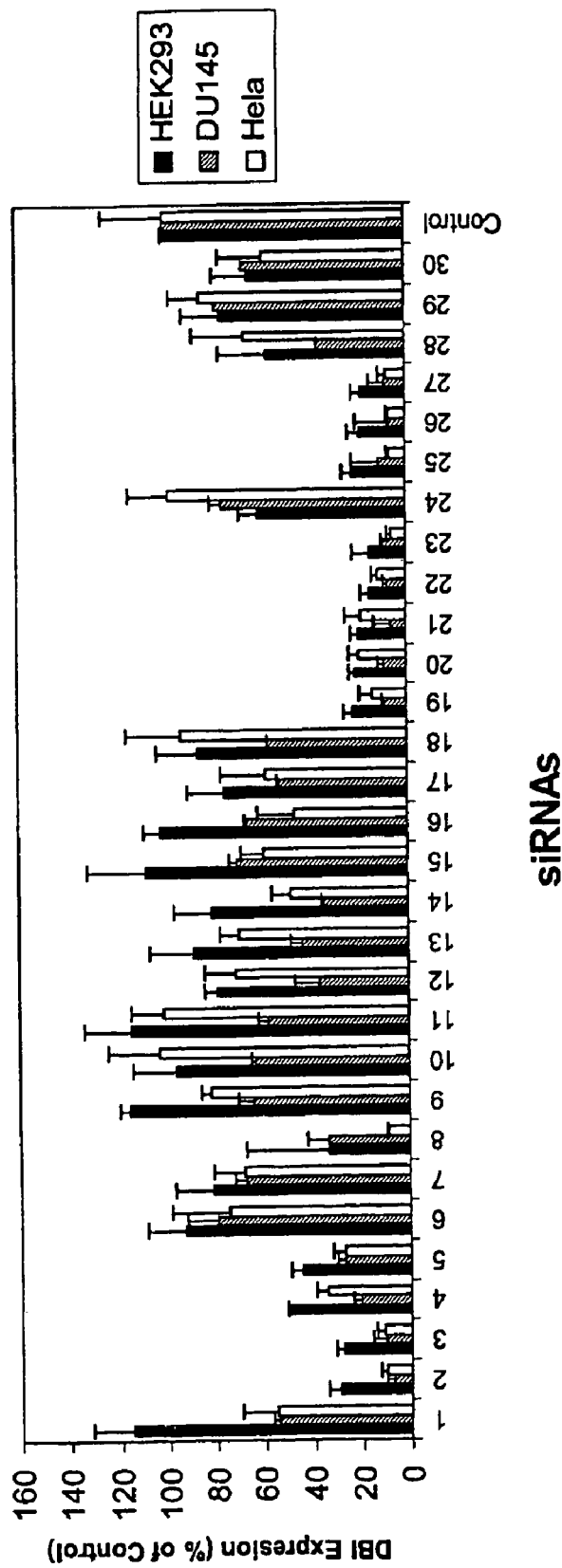
FIG. 3A is a representation of the silencing effect of 30 siRNAs in three different cells lines, HEK293, DU145, and Hela.

The original data set that was the source of the statistically derived criteria is shown in FIG. 2. Additionally, this figure shows that random selection yields siRNA duplexes with unpredictable and widely varying silencing potencies as measured in tissue culture using HEK293 cells. In the figure, duplexes are plotted such that each x-axis tick-mark represents an individual siRNA, with each subsequent siRNA differing in target position by two nucleotides for Human Cyclophilin and Firefly Luciferase, and by one nucleotide for Human DBI. Furthermore, the y-axis denotes the level of target expression remaining after transfection of the duplex into cells and subsequent silencing of the target.

siRNA identified and optimized in this document work equally well in a wide range of cell types. FIG. 3a shows the evaluation of thirty siRNAs targeting the DBI gene in three cell lines derived from different tissues. Each DBI siRNA displays very similar functionality in HEK293 (ATCC, CRL-1573, human embryonic kidney), HeLa (ATCC, CCL-2, cervical epithelial adenocarcinoma) and DU145 (HTB-81, prostate) cells as determined by the B-DNA assay. Thus, siRNA functionality is determined by the primary sequence of the siRNA and not by the intracellular environment. Additionally, it should be noted that although the present invention provides for a determination of the functionality of siRNA for a given target, the same siRNA may silence more than one gene. For example, the complementary sequence of the silencing siRNA may be present in more than one gene. Accordingly, in these circumstances, it may be desirable not to use the siRNA with highest SMARTSCORE™, or siRNA ranking. In such circumstances, it may be desirable to use the siRNA with the next highest SMARTSCORE™, or siRNA ranking.

Figure 3B:
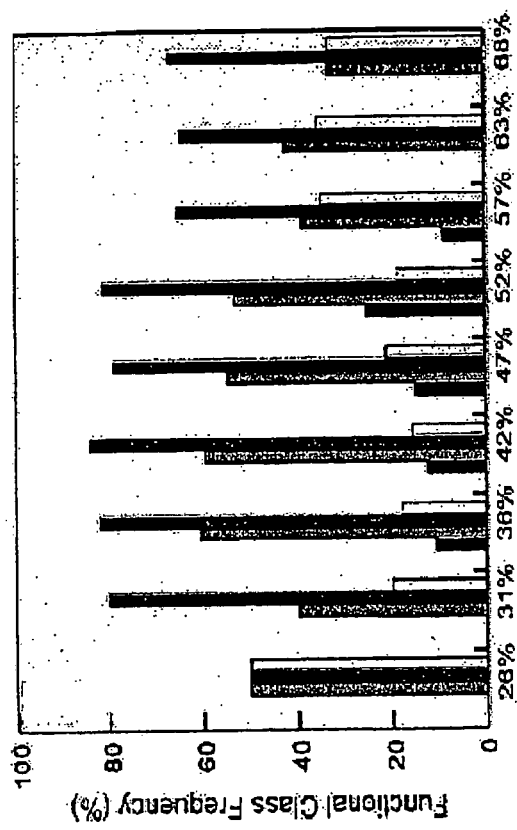
FIG. 3B shows the frequency of different functional groups (>95% silencing (black), >80% silencing (gray), >50% silencing (dark gray), and <50% silencing (white)) based on GC content. In cases where a given bar is absent from a particular GC percentage, no siRNA were identified for that particular group.

To determine the relevance of G/C content in siRNA function, the G/C content of each duplex in the panel was calculated and the functional classes of siRNAs (<F50, ≧F50, ≧F80, ≧F95 where F refers to the percent gene silencing) were sorted accordingly. The majority of the highly-functional siRNAs (≧F95) fell within the G/C content range of 36%-52% (FIG. 3B). Twice as many non-functional (<F50) duplexes fell within the high G/C content groups (>57% GC content) compared to the 36%-52% group. The group with extremely low GC content (26% or less) contained a higher proportion of non-functional siRNAs and no highly-functional siRNAs. The G/C content range of 30%-52% was therefore selected as Criterion I for siRNA functionality, consistent with the observation that a G/C range 30%-70% promotes efficient RNAi targeting. Application of this criterion alone provided only a marginal increase in the probability of selecting functional siRNAs from the panel: selection of F50 and F95 siRNAs was improved by 3.6% and 2.2%, respectively. The siRNA panel presented here permitted a more systematic analysis and quantification of the importance of this criterion than that used previously.

A relative measure of local internal stability is the A/U base pair (bp) content; therefore, the frequency of A/U bp was determined for each of the five terminal positions of the duplex (5' sense (S)/5' antisense (AS)) of all siRNAs in the panel. Duplexes were then categorized by the number of A/U bp in positions 1-5 and 15-19 of the sense strand. The thermodynamic flexibility of the duplex 5'-end (positions 1-5; S) did not appear to correlate appreciably with silencing potency, while that of the 3'-end (positions 15-19; S) correlated with efficient silencing. No duplexes lacking A/U bp in positions 15-19 were functional. The presence of one A/U bp in this region conferred some degree of functionality, but the presence of three or more A/Us was preferable and therefore defined as Criterion II. When applied to the test panel, only a marginal increase in the probability of functional siRNA selection was achieved: a 1.8% and 2.3% increase for F50 and F95 duplexes, respectively (Table III).

Figure 3C:
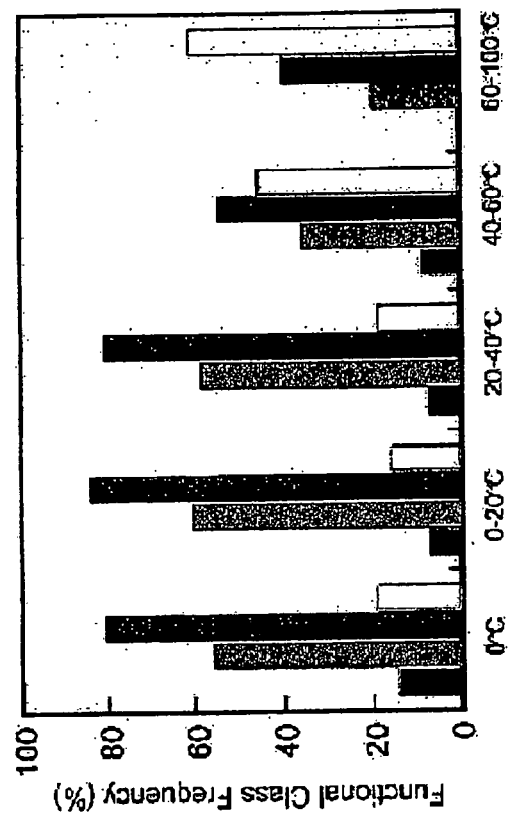
FIG. 3c shows the frequency of different functional groups based on melting temperature (Tm). Again, each group has four different divisions: >95% (black), >80% (gray), >50% (dark gray), and <50% (white) silencing.

The complementary strands of siRNAs that contain internal repeats or palindromes may form internal fold-back structures. These hairpin-like structures exist in equilibrium with the duplexed form effectively reducing the concentration of functional duplexes. The propensity to form internal hairpins and their relative stability can be estimated by predicted melting temperatures. High Tm reflects a tendency to form hairpin structures. Lower Tm values indicate a lesser tendency to form hairpins. When the functional classes of siRNAs were sorted by $T_m$ (FIG. 3C), the following trends were identified: duplexes lacking stable internal repeats were the most potent silencers (no F95 duplex with predicted hairpin structure $T_m > 60°$ C.). In contrast, about 60% of the duplexes in the groups having internal hairpins with calculated $T_m$ values less than 20° C. were F80. Thus, the stability of internal repeats is inversely proportional to the silencing effect and defines Criterion III (predicted hairpin structure $T_m \leq 20°$ C.).

Sequence-Based Determinants of siRNA Functionality

Figure 4:
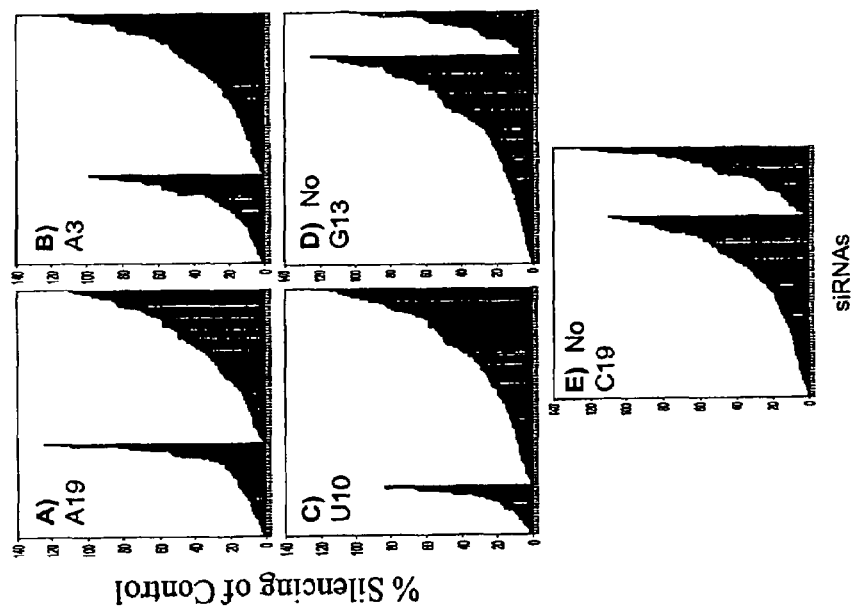
FIG. 4 is a representation of a statistical analysis that revealed correlations between silencing and five sequence-related properties of siRNA: (A) an A at position 19 of the sense strand, (B) an A at position 3 of the sense strand, (C) a U at position 10 of the sense strand, (D) a base other than G at position 13 of the sense strand, and (E) a base other than C at position 19 of the sense strand. All variables were correlated with siRNA silencing of firefly luciferase and human cyclophilin. siRNAs satisfying the criterion are grouped on the left (Selected) while those that do not, are grouped on the right (Eliminated). Y-axis is "% Silencing of Control." Each position on the X-axis represents a unique siRNA.

When the siRNA panel was sorted into functional and non-functional groups, the frequency of a specific nucleotide at each position in a functional siRNA duplex was compared with that of a nonfunctional duplex in order to assess the preference for or against a certain nucleotide. FIG. 4 shows the results of these queries and the subsequent resorting of the data set (from FIG. 2). The data is separated into two sets: those duplexes that meet the criteria, a specific nucleotide in a certain position—grouped on the left (Selected) and those that do not—grouped on the right (Eliminated). The duplexes are further sorted from most functional to least functional with the y-axis of FIGS. 4a-e representing the % expression i.e. the amount of silencing that is elicited by the duplex (Note: each position on the X-axis represents a different duplex). Statistical analysis revealed correlations between silencing and several sequence-related properties of siRNAs. FIG. 4 and Table III show quantitative analysis for the following five sequence-related properties of siRNA: (A) an A at position 19 of the sense strand; (B) an A at position 3 of the sense strand; (C) a U at position 10 of the sense strand; (D) a base other than G at position 13 of the sense strand; and (E) a base other than C at position 19 of the sense strand.

When the siRNAs in the panel were evaluated for the presence of an A at position 19 of the sense strand, the percentage of non-functional duplexes decreased from 20% to 11.8%, and the percentage of F95 duplexes increased from 21.7% to 29.4% (Table III). Thus, the presence of an A in this position defined Criterion IV.

Another sequence-related property correlated with silencing was the presence of an A in position 3 of the sense strand (FIG. 4b). Of the siRNAs with A3, 34.4% were F95, compared with 21.7% randomly selected siRNAs. The presence of a U base in position 10 of the sense strand exhibited an even greater impact (FIG. 4c). Of the duplexes in this group, 41.7% were F95. These properties became criteria V and VI, respectively.

Two negative sequence-related criteria that were identified also appear on FIG. 4. The absence of a G at position 13 of the sense strand, conferred a marginal increase in selecting functional duplexes (FIG. 4d). Similarly, lack of a C at position 19 of the sense strand also correlated with functionality (FIG. 4e). Thus, among functional duplexes, position 19 was most likely occupied by A, and rarely occupied by C. These rules were defined as criteria VII and VIII, respectively.

Application of each criterion individually provided marginal but statistically significant increases in the probability of selecting a potent siRNA. Although the results were informative, the inventors sought to maximize potency and therefore consider multiple criteria or parameters. Optimization is particularly important when developing therapeutics. Interestingly, the probability of selecting a functional siRNA based on each thermodynamic criteria was 2%-4% higher than random, but 4%-8% higher for the sequence-related determinates. Presumably, these sequence-related increases reflect the complexity of the RNAi mechanism and the multitude of protein-RNA interactions that are involved in RNAi-mediated silencing.

TABLE III

| CRITERION | | PERCENT FUNCTIONAL | IMPROVEMENT OVER RANDOM (%) |
|---|---|---|---|
| I. 30%-52% G/C Content | <F50 | 16.4 | −3.6 |
| | ≧F50 | 83.6 | 3.6 |
| | ≧F80 | 60.4 | 4.3 |
| | ≧F95 | 23.9 | 2.2 |
| II. At least 3 A/U bases at positions 15-19 of the sense strand | <F50 | 18.2 | −1.8 |
| | ≧F50 | 81.8 | 1.8 |
| | ≧F80 | 59.7 | 3.6 |
| | ≧F95 | 24.0 | 2.3 |
| III. Absence of internal repeats, as measured by Tm of secondary structure ≦20° C. | <F50 | 16.7 | −3.3 |
| | ≧F50 | 83.3 | 3.3 |
| | ≧F80 | 61.1 | 5.0 |
| | ≧F95 | 24.6 | 2.9 |
| IV. An A base at position 19 of the sense strand | <F50 | 11.8 | −8.2 |
| | ≧F50 | 88.2 | 8.2 |
| | ≧F80 | 75.0 | 18.9 |
| | ≧F95 | 29.4 | 7.7 |
| V. An A base at position 3 of the sense strand | <F50 | 17.2 | −2.8 |
| | ≧F50 | 82.8 | 2.8 |
| | ≧F80 | 62.5 | 6.4 |
| | ≧F95 | 34.4 | 12.7 |
| VI. A U base at position 10 of the sense strand | <F50 | 13.9 | −6.1 |
| | ≧F50 | 86.1 | 6.1 |
| | ≧F80 | 69.4 | 13.3 |
| | ≧F95 | 41.7 | 20 |
| VII. A base other than C at position 19 of the sense strand | <F50 | 18.8 | −1.2 |
| | ≧F50 | 81.2 | 1.2 |
| | ≧F80 | 59.7 | 3.6 |
| | ≧F95 | 24.2 | 2.5 |
| VIII. A base other than G at position 13 of the sense strand | <F50 | 15.2 | −4.8 |
| | ≧F50 | 84.8 | 4.8 |
| | ≧F80 | 61.4 | 5.3 |
| | ≧F95 | 26.5 | 4.8 |

The siRNA Selection Algorithm

Figures 5A, 5B:
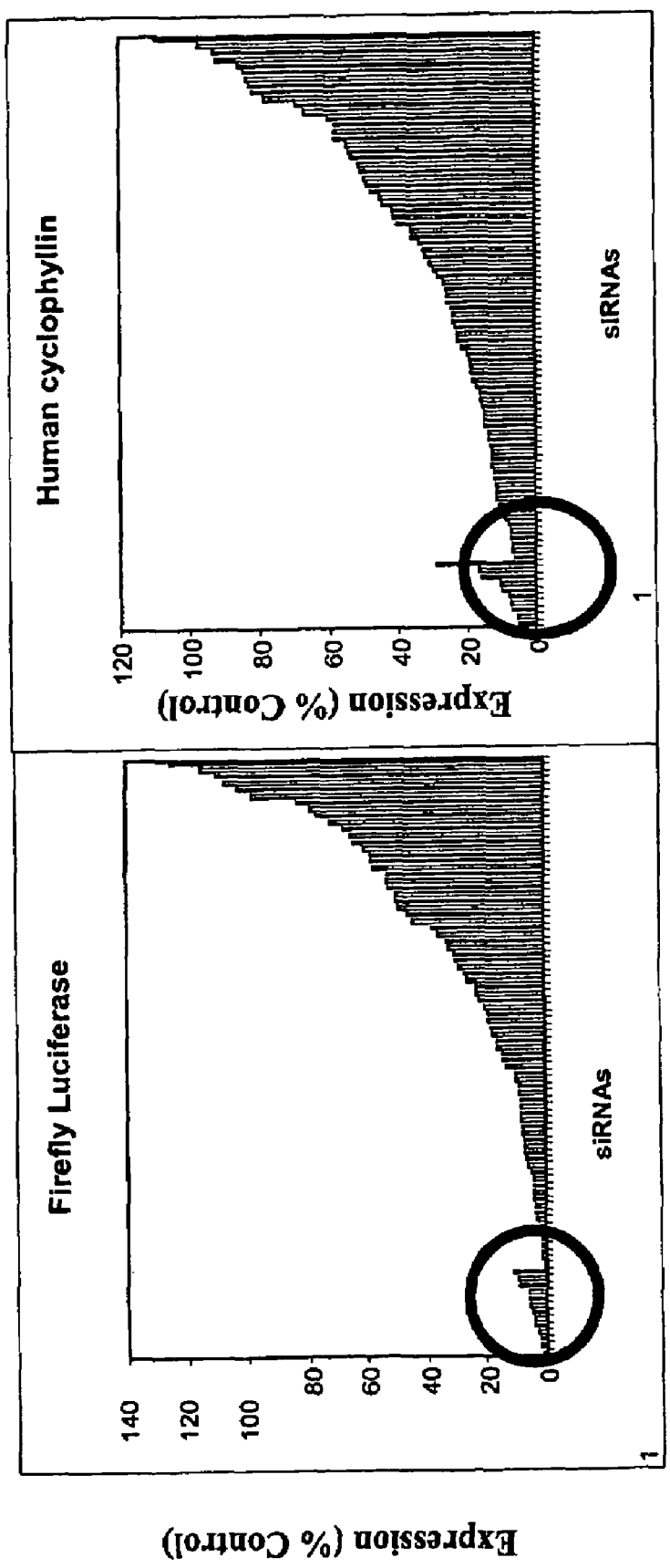
FIGS. 5A and 5B are representations of firefly luciferase and cyclophilin siRNA panels sorted according to functionality and predicted values using Formula VIII. The siRNA found within the circle represent those that have Formula VIII values (SMARTSCORES™, or siRNA rank) above zero. SiRNA outside the indicated area have calculated Formula VIII values that are below zero. Y-axis is "Expression (% Control)." Each position on the X-axis represents a unique siRNA.

In an effort to improve selection further, all identified criteria, including but not limited to those listed in Table III were combined into the algorithms embodied in Formula VIII and Formula IX. Each siRNA was then assigned a score (referred to as a SMARTscore™) according to the values derived from the formulas. Duplexes that scored higher than 0 or 20, for Formulas VIII and IX, respectively, effectively selected a set of functional siRNAs and excluded all non-functional siRNAs. Conversely, all duplexes scoring lower than 0 and 20 according to formulas VIII and IX, respectively, contained some functional siRNAs but included all non-functional siRNAs. A graphical representation of this selection is shown in FIG. 5.

The methods for obtaining the seven criteria embodied in Table III are illustrative of the results of the process used to develop the information for Formulas VIII and IX. Thus similar techniques were used to establish the other variables and their multipliers. As described above, basic statistical methods were use to determine the relative values for these multipliers.

To determine the value for "Improvement over Random" the difference in the frequency of a given attribute (e.g. GC content, base preference) at a particular position is determined between individual functional groups (e.g. <F50) and the total siRNA population studied (e.g. 270 siRNA molecules selected randomly). Thus, for instance, in Criterion I (30%-52% GC content) members of the <F50 group were observed to have GC contents between 30-52% in 16.4% of the cases. In contrast, the total group of 270 siRNAs had GC contents in this range, 20% of the time. Thus for this particular attribute, there is a small negative correlation between 30%-52% GC content and this functional group (i.e. 16.4%-20%=−3.6%). Similarly, for Criterion VI, (a "U" at position 10 of the sense strand), the >F95 group contained a "U" at this position 41.7% of the time. In contrast, the total group of 270 siRNAs had a "U" at this position 21.7% of the time, thus the improvement over random is calculated to be 20% (or 41.7%-21.7%).

Identifying the Average Internal Stability Profile of Strong siRNA

In order to identify an internal stability profile that is characteristic of strong siRNA, 270 different siRNAs derived from the cyclophilin B, the diazepam binding inhibitor (DBI), and the luciferase gene were individually transfected into HEK293 cells and tested for their ability to induce RNAi of the respective gene. Based on their performance in the in vivo assay, the sequences were then subdivided into three groups, (i) >95% silencing; (ii) 80-95% silencing; and (iii) less than 50% silencing. Sequences exhibiting 51-84% silencing were eliminated from further consideration to reduce the difficulties in identifying relevant thermodynamic patterns.

Following the division of siRNA into three groups, a statistical analysis was performed on each member of each group to determine the average internal stability profile (AISP) of the siRNA. To accomplish this the Oligo 5.0 Primer Analysis Software and other related statistical packages (e.g. Excel) were exploited to determine the internal stability of pentamers using the nearest neighbor method described by Freier et al., (1986) Improved free-energy parameters for predictions of RNA duplex stability, *Proc Natl. Acad. Sci. USA* 83(24): 9373-7. Values for each group at each position were then averaged, and the resulting data were graphed on a linear coordinate system with the Y-axis expressing the ΔG (free energy) values in kcal/mole and the X-axis identifying the position of the base relative to the 5' end.

Figure 6A:
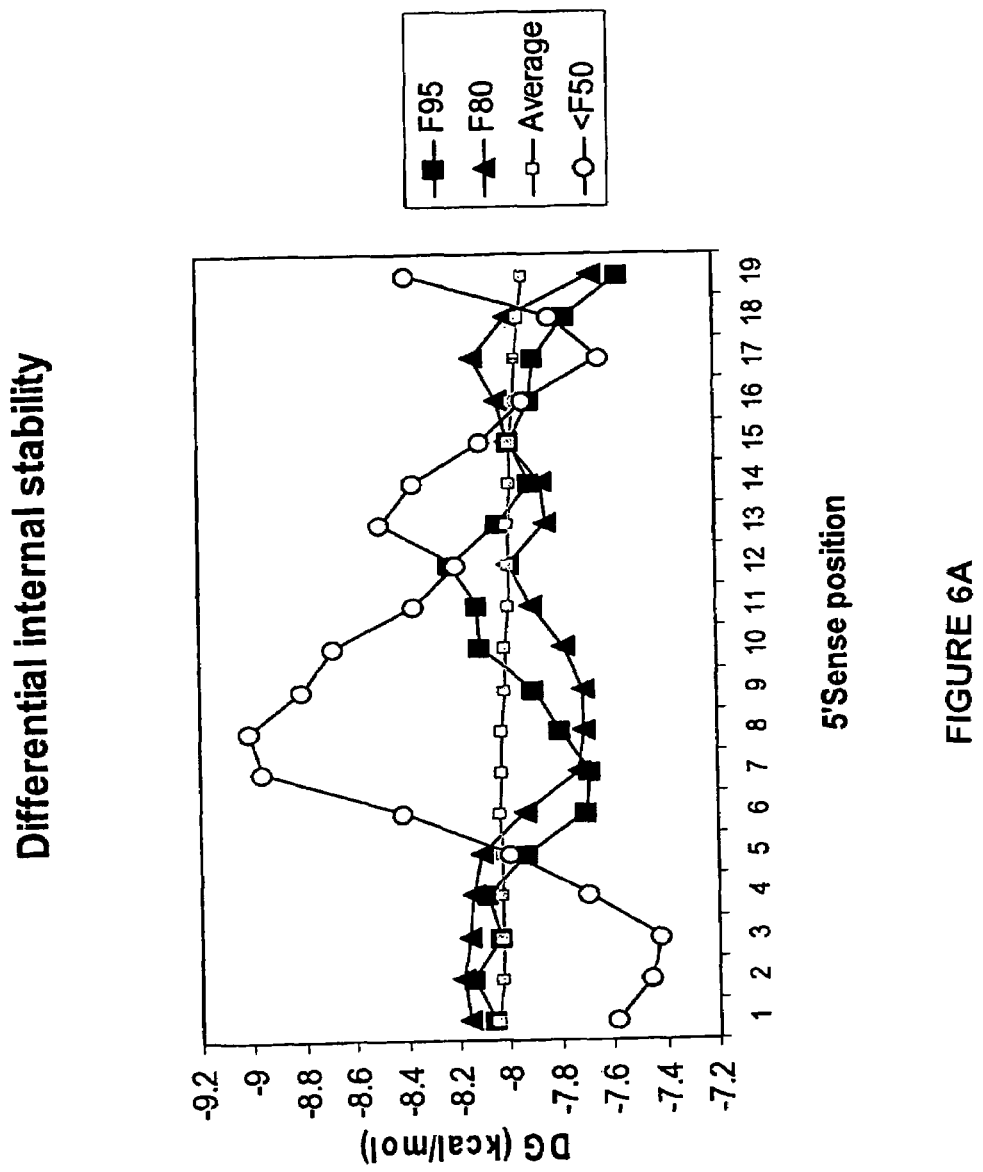
FIG. 6A is a representation of the average internal stability profile (AISP) derived from 270 siRNAs taken from three separate genes (cyclophilin B, DBI and firefly luciferase). Graphs represent AISP values of highly functional, functional, and non-functional siRNA.

The results of the analysis identified multiple key regions in siRNA molecules that were critical for successful gene silencing. At the 3'-most end of the sense strand (5' antisense), highly functional siRNA (>95% gene silencing, see FIG. 6A, >F95) have a low internal stability (AISP of position 19=∼−7.6 kcal/mol). In contrast low-efficiency siRNA (i.e. those exhibiting less than 50% silencing, <F50) display a distinctly different profile, having high ΔG values (∼−8.4 kcal/mol) for the same position. Moving in a 5' (sense strand) direction, the internal stability of highly efficient siRNA rises (position 12=∼−8.3 kcal/mole) and then drops again (position 7=∼−7.7 kcal/mol) before leveling off at a value of approximately −8.1 kcal/mol for the 5' terminus. siRNA with poor silencing capabilities show a distinctly different profile. While the AISP value at position 12 is nearly identical with that of strong siRNAs, the values at positions 7 and 8 rise considerably, peaking at a high of ∼−9.0 kcal/mol. In addition, at the 5' end of the molecule the AISP profile of strong and weak siRNA differ dramatically. Unlike the relatively strong values exhibited by siRNA in the >95% silencing group, siRNAs that exhibit poor silencing activity have weak AISP values (−7.6, −7.5, and −7.5 kcal/mol for positions 1, 2 and 3 respectively).

Overall the profiles of both strong and weak siRNAs form distinct sinusoidal shapes that are roughly 180° out-of-phase with each other. While these thermodynamic descriptions define the archetypal profile of a strong siRNA, it will likely be the case that neither the ΔG values given for key positions in the profile or the absolute position of the profile along the Y-axis (i.e. the ΔG-axis) are absolutes. Profiles that are shifted upward or downward (i.e. having on an average, higher or lower values at every position) but retain the relative shape and position of the profile along the X-axis can be foreseen as being equally effective as the model profile described here. Moreover, it is likely that siRNA that have strong or even stronger gene-specific silencing effects might have exaggerated ΔG values (either higher or lower) at key positions. Thus, for instance, it is possible that the 5'-most position of the sense strand (position 19) could have ΔG values of 7.4 kcal/mol or lower and still be a strong siRNA if, for instance, a G-C→G-T/U mismatch were substituted at position 19 and altered duplex stability. Similarly, position 12 and position 7 could have values above 8.3 kcal/mol and below 7.7 kcal/mole, respectively, without abating the silencing effectiveness of the molecule. Thus, for instance, at position 12, a stabilizing chemical modification (e.g. a chemical modification of the 2' position of the sugar backbone) could be added that increases the average internal stability at that position. Similarly, at position 7, mismatches similar to those described previously could be introduced that would lower the ΔG values at that position.

Lastly, it is important to note that while functional and non-functional siRNA were originally defined as those molecules having specific silencing properties, both broader or more limiting parameters can be used to define these molecules. As used herein, unless otherwise specified, "non-functional siRNA" are defined as those siRNA that induce less than 50% (<50%) target silencing, "semi-functional siRNA" induce 50-79% target silencing, "functional siRNA" are molecules that induce 80-95% gene silencing, and "highly-functional siRNA" are molecules that induce great than 95% gene silencing. These definitions are not intended to be rigid and can vary depending upon the design and needs of the application. For instance, it is possible that a researcher attempting to map a gene to a chromosome using a functional assay, may identify an siRNA that reduces gene activity by only 30%. While this level of gene silencing may be "non-functional" for e.g. therapeutic needs, it is sufficient for gene mapping purposes and is, under these uses and conditions, "functional." For these reasons, functional siRNA can be defined as those molecules having greater than 10%, 20%, 30%, 40%, 50%, 60%, 70%, 80%, or 90% silencing capabilities at 100 nM transfection conditions. Similarly, depending upon the needs of the study and/or application, non-functional and semi-functional siRNA can be defined as having different parameters. For instance, semi-functional siRNA can be defined as being those molecules that induce 20%, 30%, 40%, 50%, 60%, or 70% silencing at 100 nM transfection conditions. Similarly, non-functional siRNA can be defined as being those molecules that silence gene expression by less than 70%, 60%, 50%, 40%, 30%, or less. Nonetheless, unless otherwise stated, the descriptions stated in the "Definitions" section of this text should be applied.

Functional attributes can be assigned to each of the key positions in the AISP of strong siRNA. The low 5' (sense strand) AISP values of strong siRNAs may be necessary for determining which end of the molecule enters the RISC complex. In contrast, the high and low AISP values observed in the central regions of the molecule may be critical for siRNA-target mRNA interactions and product release, respectively.

Figure 6B:
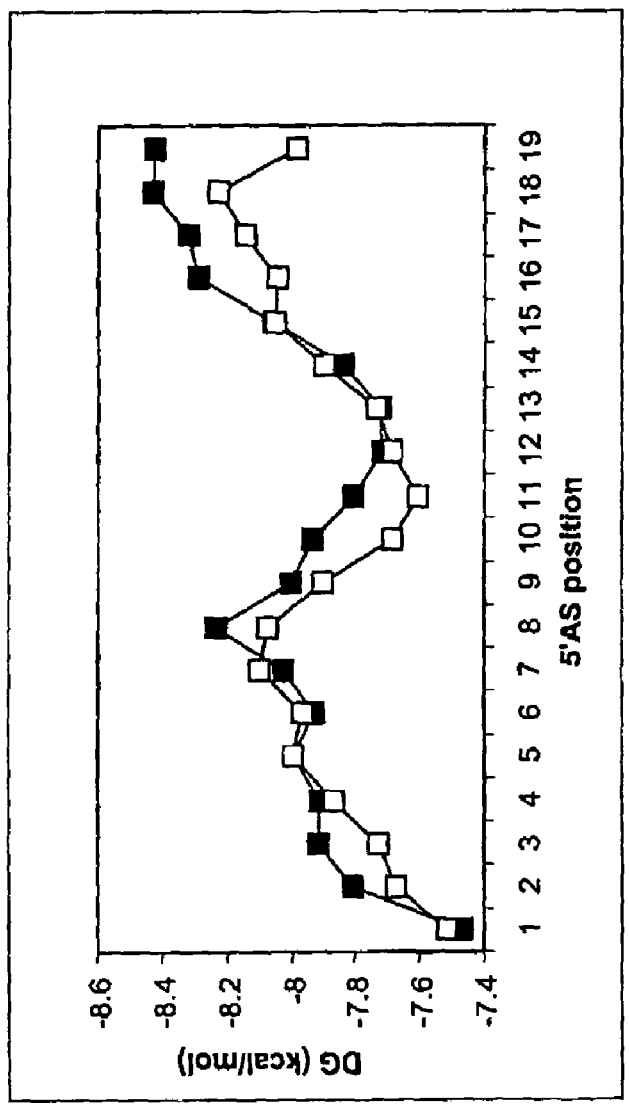
FIG. 6B is a comparison between the AISP of naturally derived GFP siRNA (filled squares) and the AISP of siRNA from cyclophilin B, DBI, and luciferase having >90% silencing properties (no fill) for the antisense strand. "DG" is the symbol for ΔG, free energy.

If the AISP values described above accurately define the thermodynamic parameters of strong siRNA, it would be expected that similar patterns would be observed in strong siRNA isolated from nature. Natural siRNAs exist in a harsh, RNase-rich environment and it can be hypothesized that only those siRNA that exhibit heightened affinity for RISC (i.e. siRNA that exhibit an average internal stability profile similar to those observed in strong siRNA) would survive in an intracellular environment. This hypothesis was tested using GFP-specific siRNA isolated from N. benthamiana. Llave et al. (2002) Endogenous and Silencing-Associated Small RNAs in Plants, The Plant Cell 14, 1605-1619, introduced long double-stranded GFP-encoding RNA into plants and subsequently re-isolated GFP-specific siRNA from the tissues. The AISP of fifty-nine of these GFP-siRNA were determined, averaged, and subsequently plotted alongside the AISP profile obtained from the cyclophilin B/DBI/luciferase siRNA having >90% silencing properties (FIG. 6B). Comparison of the two groups show that profiles are nearly identical. This finding validates the information provided by the internal stability profiles and demonstrates that: (1) the profile identified by analysis of the cyclophilin B/DBI/luciferase siRNAs are not gene specific; and (2) AISP values can be used to search for strong siRNAs in a variety of species.

Figure 7:
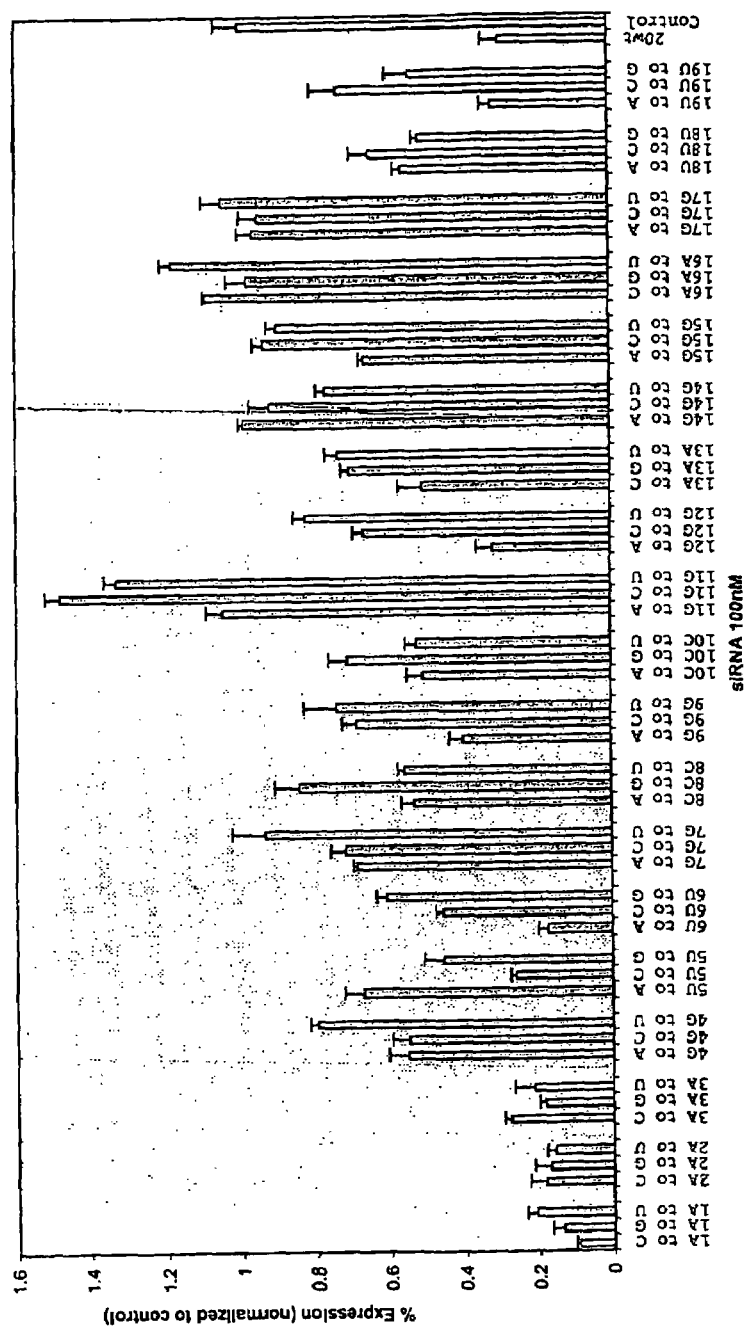
FIG. 7 is a histogram showing the differences in duplex functionality upon introduction of basepair mismatches. The X-axis shows the mismatch introduced into the siRNA and the position it is introduced (e.g., 8C→A reveals that position 8 (which normally has a C) has been changed to an A). The Y-axis is "% Expression (Normalized to Control)."
Figure 8A:
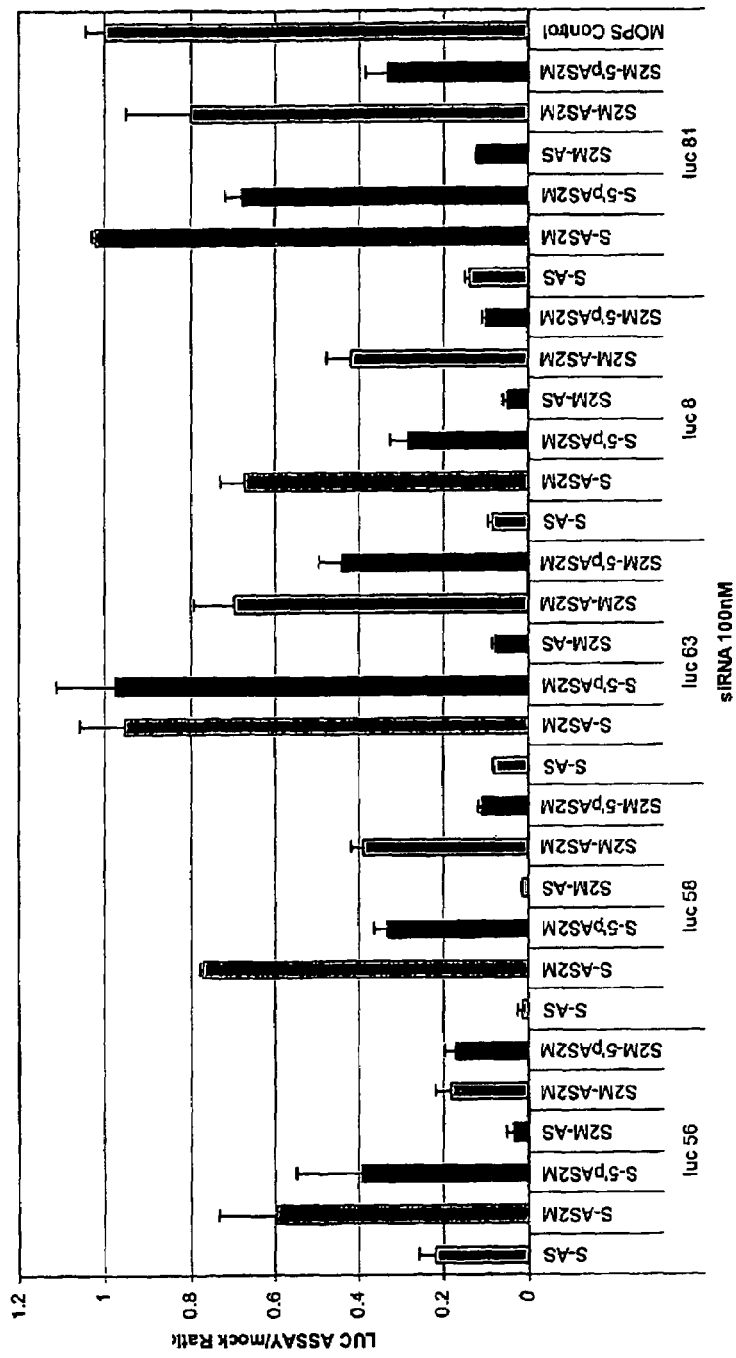
FIG. 8A is histogram that shows the effects of 5'sense and antisense strand modification with 2'-O-methylation on functionality.
Figure 8B:
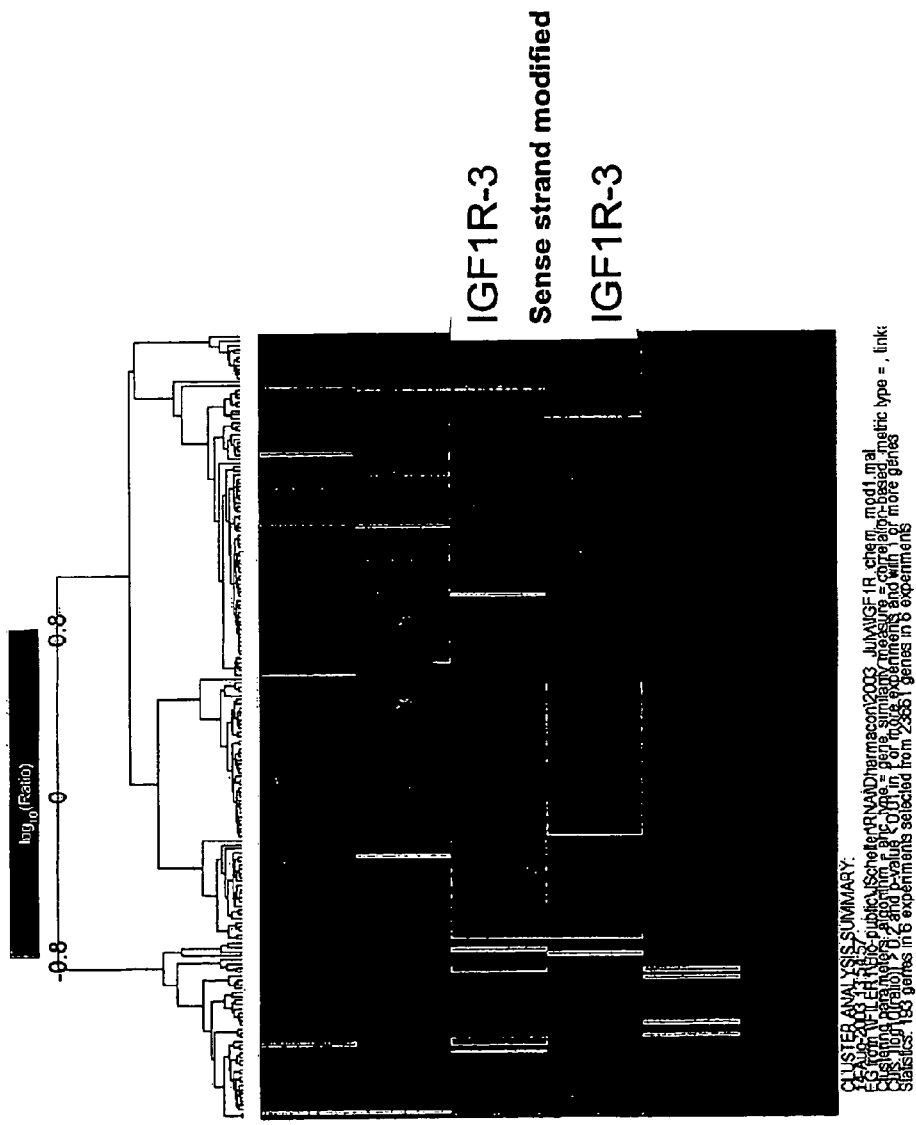
FIG. 8B is an expression profile showing a comparison of sense strand off-target effects for IGF1R-3 and 2'-O-methyl IGF1R-3. Sense strand off-targets (lower white box) are not induced when the 5' end of the sense strand is modified with 2'-O-methyl groups (top white box).

Both chemical modifications and base-pair mismatches can be incorporated into siRNA to alter the duplex's AISP and functionality. For instance, introduction of mismatches at positions 1 or 2 of the sense strand destabilized the 5' end of the sense strand and increases the functionality of the molecule (see Luc, FIG. 7). Similarly, addition of 2'-O-methyl groups to positions 1 and 2 of the sense strand can also alter the AISP and (as a result) increase both the functionality of the molecule and eliminate off-target effects that results from sense strand homology with the unrelated targets (FIGS. 8A, 8B).

Rationale for Criteria in a Biological Content

The fate of siRNA in the RNAi pathway may be described in 5 major steps: (1) duplex recognition and pre-RISC complex formation; (2) ATP-dependent duplex unwinding/strand selection and RISC activation; (3) mRNA target identification; (4) mRNA cleavage, and (5) product release (FIG. 1). Given the level of nucleic acid-protein interactions at each step, siRNA functionality is likely influenced by specific biophysical and molecular properties that promote efficient interactions within the context of the multi-component complexes. Indeed, the systematic analysis of the siRNA test set identified multiple factors that correlate well with functionality. When combined into a single algorithm, they proved to be very effective in selecting active siRNAs.

The factors described here may also be predictive of key functional associations important for each step in RNAi. For example, the potential formation of internal hairpin structures correlated negatively with siRNA functionality. Complementary strands with stable internal repeats are more likely to exist as stable hairpins thus decreasing the effective concentration of the functional duplex form. This suggests that the duplex is the preferred conformation for initial pre-RISC association. Indeed, although single complementary strands can induce gene silencing, the effective concentration required is at least two orders of magnitude higher than that of the duplex form.

siRNA-pre-RISC complex formation is followed by an ATP-dependent duplex unwinding step and "activation" of the RISC. The siRNA functionality was shown to correlate with overall low internal stability of the duplex and low internal stability of the 3' sense end (or differential internal stability of the 3' sense compare to the 5' sense strand), which may reflect strand selection and entry into the RISC. Overall duplex stability and low internal stability at the 3' end of the sense strand were also correlated with siRNA functionality. Interestingly, siRNAs with very high and very low overall stability profiles correlate strongly with non-functional duplexes. One interpretation is that high internal stability prevents efficient unwinding while very low stability reduces siRNA target affinity and subsequent mRNA cleavage by the RISC.

Several criteria describe base preferences at specific positions of the sense strand and are even more intriguing when considering their potential mechanistic roles in target recognition and mRNA cleavage. Base preferences for A at position 19 of the sense strand but not C, are particularly interesting because they reflect the same base preferences observed for naturally occurring miRNA precursors. That is, among the reported miRNA precursor sequences 75% contain a U at position 1 which corresponds to an A in position 19 of the sense strand of siRNAs, while G was under-represented in this same position for miRNA precursors. These observations support the hypothesis that both miRNA precursors and siRNA duplexes are processed by very similar if not identical protein machinery. The functional interpretation of the predominance of a U/A base pair is that it promotes flexibility at the 5' antisense ends of both siRNA duplexes and miRNA precursors and facilitates efficient unwinding and selective strand entrance into an activated RISC.

Among the criteria associated with base preferences that are likely to influence mRNA cleavage or possibly product release, the preference for U at position 10 of the sense strand exhibited the greatest impact, enhancing the probability of selecting an F80 sequence by 13.3%. Activated RISC preferentially cleaves target mRNA between nucleotides 10 and 11 relative to the 5' end of the complementary targeting strand. Therefore, it may be that U, the preferred base for most endoribonucleases, at this position supports more efficient cleavage. Alternatively, a U/A bp between the targeting siRNA strand and its cognate target mRNA may create an optimal conformation for the RISC-associated "slicing" activity.

Pooling

According to another embodiment, the present invention provides a pool of at least two siRNAs, preferably in the form of a kit or therapeutic reagent, wherein one strand of each of the siRNAs, the sense strand comprises a sequence that is substantially similar to a sequence within a target mRNA. The opposite strand, the antisense strand, will preferably comprise a sequence that is substantially complementary to that of the target mRNA. More preferably, one strand of each siRNA will comprise a sequence that is identical to a sequence that is contained in the target mRNA. Most preferably, each siRNA will be 19 base pairs in length, and one strand of each of the siRNAs will be 100% complementary to a portion of the target mRNA.

By increasing the number of siRNAs directed to a particular target using a pool or kit, one is able both to increase the likelihood that at least one siRNA with satisfactory functionality will be included, as well as to benefit from additive or synergistic effects. Further, when two or more siRNAs directed against a single gene do not have satisfactory levels of functionality alone, if combined, they may satisfactorily promote degradation of the target messenger RNA and successfully inhibit translation. By including multiple siRNAs in the system, not only is the probability of silencing increased, but the economics of operation are also improved when compared to adding different siRNAs sequentially. This effect is contrary to the conventional wisdom that the concurrent use of multiple siRNA will negatively impact gene silencing (e.g. Holen, T. et al. (2003) "Similar behavior of single strand and double strand siRNAs suggests they act through a common RNAi pathway." NAR 31: 2401-21407).

In fact, when two siRNAs were pooled together, 54% of the pools of two siRNAs induced more than 95% gene silencing. Thus, a 2.5-fold increase in the percentage of functionality was achieved by randomly combining two siRNAs. Further, over 84% of pools containing two siRNAs induced more than 80% gene silencing.

More preferably, the kit is comprised of at least three siRNAs, wherein one strand of each siRNA comprises a sequence that is substantially similar to a sequence of the target mRNA and the other strand comprises a sequence that is substantially complementary to the region of the target mRNA. As with the kit that comprises at least two siRNAs, more preferably one strand will comprise a sequence that is identical to a sequence that is contained in the mRNA and another strand that is 100% complementary to a sequence that is contained in the mRNA. During experiments, when three siRNAs were combined together, 60% of the pools induced more than 95% gene silencing and 92% of the pools induced more than 80% gene silencing.

Further, even more preferably, the kit is comprised of at least four siRNAs, wherein one strand of each siRNA comprises a sequence that is substantially similar to a region of the sequence of the target mRNA, and the other strand comprises a sequence that is substantially complementary to the region of the target mRNA. As with the kit or pool that comprises at least two siRNAs, more preferably one strand of each of the siRNA duplexes will comprise a sequence that is identical to a sequence that is contained in the mRNA, and another strand that is 100% complementary to a sequence that is contained in the mRNA.

Additionally, kits and pools with at least five, at least six, and at least seven siRNAs may also be useful with the present invention. For example, pools of five siRNA induced 95% gene silencing with 77% probability and 80% silencing with 98.8% probability. Thus, pooling of siRNAs together can result in the creation of a target-specific silencing reagent with almost a 99% probability of being functional. The fact that such high levels of success are achievable using such pools of siRNA, enables one to dispense with costly and time-consuming target-specific validation procedures.

For this embodiment, as well as the other aforementioned embodiments, each of the siRNAs within a pool will preferably comprise between 18 and 30 base pairs, more preferably between 18 and 25 base pairs, and most preferably 19 base pairs. Within each siRNA, preferably at least 18 contiguous bases of the antisense strand will be 100% complementary to the target mRNA. More preferably, at least 19 contiguous bases of the antisense strand will be 100% complementary to the target mRNA. Additionally, there may be overhangs on either the sense strand or the antisense strand, and these overhangs may be at either the 5' end or the 3' end of either of the strands, for example there may be one or more overhangs of 1-6 bases. When overhangs are present, they are not included in the calculation of the number of base pairs. The two nucleotide 3' overhangs mimic natural siRNAs and are commonly used but are not essential. Preferably, the overhangs should consist of two nucleotides, most often dTdT or UU at the 3' end of the sense and antisense strand that are not complementary to the target sequence. The siRNAs may be produced by any method that is now known or that comes to be known for synthesizing double stranded RNA that one skilled in the art would appreciate would be useful in the present invention. Preferably, the siRNAs will be produced by Dharmacon's proprietary ACE® technology. However, other methods for synthesizing siRNAs are well known to persons skilled in the art and include, but are not limited to, any chemical synthesis of RNA oligonucleotides, ligation of shorter oligonucleotides, in vitro transcription of RNA oligonucleotides, the use of vectors for expression within cells, recombinant Dicer products and PCR products.

The siRNA duplexes within the aforementioned pools of siRNAs may correspond to overlapping sequences within a particular mRNA, or non-overlapping sequences of the mRNA. However, preferably they correspond to non-overlapping sequences. Further, each siRNA may be selected randomly, or one or more of the siRNA may be selected according to the criteria discussed above for maximizing the effectiveness of siRNA.

Included in the definition of siRNAs are siRNAs that contain substituted and/or labeled nucleotides that may, for example, be labeled by radioactivity, fluorescence or mass. The most common substitutions are at the 2' position of the ribose sugar, where moieties such as H (hydrogen) F, $NH_3$, $OCH_3$ and other O-alkenyl, alkynyl, and orthoesters, may be substituted, or in the phosphorous backbone, where sulfur, amines or hydrocarbons may be substituted for the bridging of non-bridging atoms in the phosphodiester bond. Examples of modified siRNAs are explained more fully in commonly assigned U.S. patent application Ser. No. 10/613,077, filed Jul. 1, 2003, which is incorporated by reference herein.

Additionally, as noted above, the cell type into which the siRNA is introduced may affect the ability of the siRNA to enter the cell; however, it does not appear to affect the ability of the siRNA to function once it enters the cell. Methods for introducing double-stranded RNA into various cell types are well known to persons skilled in the art.

As persons skilled in the art are aware, in certain species, the presence of proteins such as RdRP, the RNA-dependent RNA polymerase, may catalytically enhance the activity of the siRNA. For example, RdRP propagates the RNAi effect in *C. elegans* and other non-mammalian organisms. In fact, in organisms that contain these proteins, the siRNA may be inherited. Two other proteins that are well studied and known to be a part of the machinery are members of the Argonaute family and Dicer, as well as their homologues. There is also initial evidence that the RISC complex might be associated with the ribosome so the more efficiently translated mRNAs will be more susceptible to silencing than others.

Another very important factor in the efficacy of siRNA is mRNA localization. In general, only cytoplasmic mRNAs are considered to be accessible to RNAi to any appreciable degree. However, appropriately designed siRNAs, for example, siRNAs modified with internucleotide linkages, may be able to cause silencing by acting in the nucleus.

Examples of these types of modifications are described in commonly assigned U.S. patent application Ser. Nos. 10/431,027 and 10/613,077, each of which is incorporated by reference herein.

As described above, even when one selects at least two siRNAs at random, the effectiveness of the two may be greater than one would predict based on the effectiveness of two individual siRNAs. This additive or synergistic effect is particularly noticeable as one increases to at least three siRNAs, and even more noticeable as one moves to at least four siRNAs. Surprisingly, the pooling of the non-functional and semi-functional siRNAs, particularly more than five siRNAs, can lead to a silencing mixture that is as effective if not more effective than any one particular functional siRNA.

Within the kit of the present invention, preferably each siRNA will be present in a concentration of between 0.001 and 200 µM, more preferably between 0.01 and 200 nM, and most preferably between 0.1 and 10 nM.

In addition to preferably comprising at least four or five siRNAs, the kit of the present invention will also preferably comprise a buffer to keep the siRNA duplex stable. Persons skilled in the art are aware of buffers suitable for keeping siRNA stable. For example, the buffer may be comprised of 100 mM KCl, 30 mM HEPES-pH 7.5, and 1 mM $MgCl_2$. Alternatively, kits might contain complementary strands that contain any one of a number of chemical modifications (e.g. a 2'-O-ACE) that protect the agents from degradation by nucleases. In this instance, the user may (or may not) remove the modifying protective group (e.g. deprotect) before annealing the two complementary strands together.

By way of example, the kit may be organized such that pools of siRNA duplexes are provided on an array or microarray of wells or drops for a particular gene set or for unrelated genes. The array may, for example, be in 96 wells, 384 wells or 1284 wells arrayed in a plastic plate or on a glass slide using techniques now known or that come to be known to persons skilled in the art. Within an array, preferably there will be controls such as functional anti-lamin A/C, cyclophilin and two siRNA duplexes that are not specific to the gene of interest.

In order to ensure stability of the siRNA pools prior to usage, they may be retained in lyophilized form at minus twenty degrees (−20° C.) until they are ready for use. Prior to usage, they should be resuspended; however, even once resuspended, for example, in the aforementioned buffer, they should be kept at minus twenty degrees, (−20° C.) until used. The aforementioned buffer, prior to use, may be stored at approximately 4° C. or room temperature. Effective temperatures at which to conduct transfections are well known to persons skilled in the art and include for example, room temperature.

The kit may be applied either in vivo or in vitro. Preferably, the siRNA of the pools or kits is applied to a cell through transfection, employing standard transfection protocols. These methods are well known to persons skilled in the art and include the use of lipid-based carriers, electroporation, cationic carriers, and microinjection. Further, one could apply the present invention by synthesizing equivalent DNA sequences (either as two separate, complementary strands, or as hairpin molecules) instead of siRNA sequences and introducing them into cells through vectors. Once in the cells, the cloned DNA could be transcribed, thereby forcing the cells to generate the siRNA. Examples of vectors suitable for use with the present application include but are not limited to the standard transient expression vectors, adenoviruses, retroviruses, lentivirus-based vectors, as well as other traditional expression vectors. Any vector that has an adequate siRNA expression and procession module may be used. Furthermore, certain chemical modifications to siRNAs, including but not limited to conjugations to other molecules, may be used to facilitate delivery. For certain applications it may be preferable to deliver molecules without transfection by simply formulating in a physiological acceptable solution.

This embodiment may be used in connection with any of the aforementioned embodiments. Accordingly, the sequences within any pool may be selected by rational design.

Multigene Silencing

In addition to developing kits that contain multiple siRNA directed against a single gene, another embodiment includes the use of multiple siRNA targeting multiple genes. Multiple genes may be targeted through the use of high- or hyperfunctional siRNA. High- or hyper-functional siRNA that exhibit increased potency, require lower concentrations to induce desired phenotypic (and thus therapeutic) effects. This circumvents RISC saturation. It therefore reasons that if lower concentrations of a single siRNA are needed for knockout or knockdown expression of one gene, then the remaining (uncomplexed) RISC will be free and available to interact with siRNA directed against two, three, four, or more, genes. Thus in this embodiment, the authors describe the use of highly functional or hyper-functional siRNA to knock out three separate genes. More preferably, such reagents could be combined to knockout four distinct genes. Even more preferably, highly functional or hyperfunctional siRNA could be used to knock out five distinct genes. Most preferably, siRNA of this type could be used to knockout or knockdown the expression of six or more genes.

Hyperfunctional siRNA

The term hyperfunctional siRNA (hf-siRNA) describes a subset of the siRNA population that induces RNAi in cells at low- or sub-nanomolar concentrations for extended periods of time. These traits, heightened potency and extended longevity of the RNAi phenotype, are highly attractive from a therapeutic standpoint. Agents having higher potency require lesser amounts of the molecule to achieve the desired physiological response, thus reducing the probability of side effects due to "off-target" interference. In addition to the potential therapeutic benefits associated with hyperfunctional siRNA, hf-siRNA are also desirable from an economic position. Hyperfunctional siRNA may cost less on a pertreatment basis, thus reducing the overall expenditures to both the manufacturer and the consumer.

Figure 9:
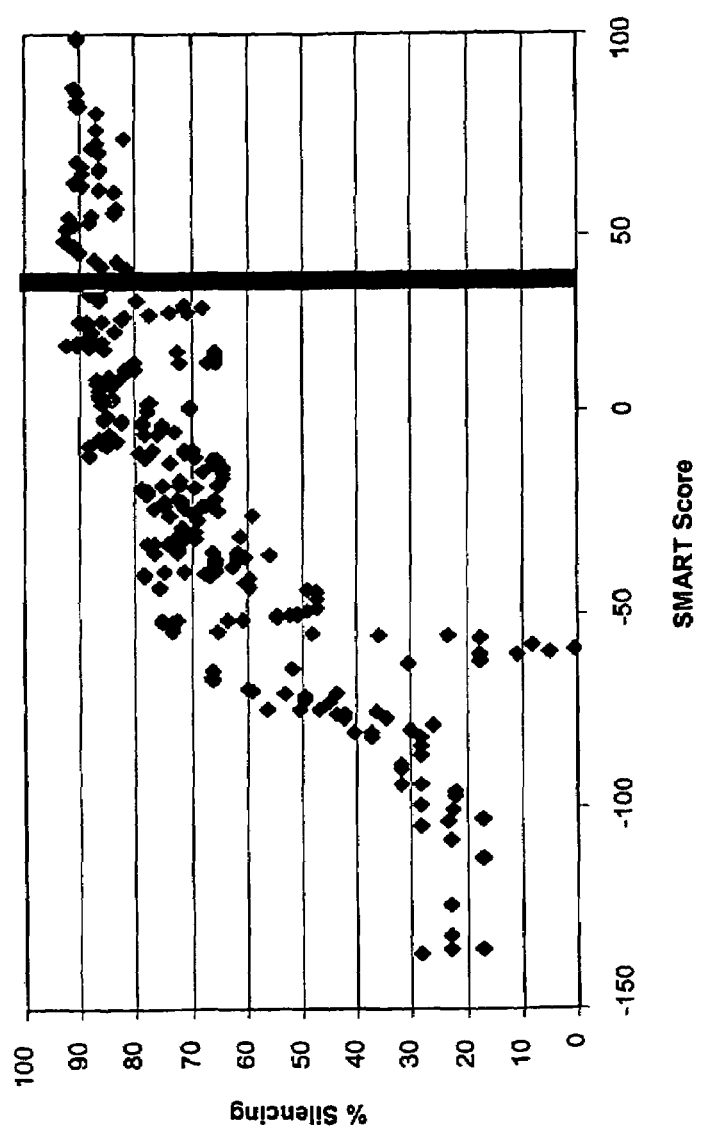
FIG. 9 shows a graph of SMARTSCORES™, or siRNA rank, versus RNAi silencing values for more than 360 siRNA directed against 30 different genes. SiRNA to the right of the vertical bar represent those siRNA that have desirable SMARTSCORES™, or siRNA rank.

Identification of hyperfunctional siRNA involves multiple steps that are designed to examine an individual siRNA agent's concentration- and/or longevity-profiles. In one non-limiting example, a population of siRNA directed against a single gene are first analyzed using the previously described algorithm (Formula VIII). Individual siRNA are then introduced into a test cell line and assessed for the ability to degrade the target mRNA. It is important to note that when performing this step it is not necessary to test all of the siRNA. Instead, it is sufficient to test only those siRNA having the highest SMARTSCORES™, or siRNA ranking (i.e. SMARTSCORE™>−10). Subsequently, the gene silencing data is plotted against the SMARTSCORES™, or siRNA rankings (see FIG. 9). siRNA that (1) induce a high degree of gene silencing (i.e. they induce greater than 80% gene knockdown) and (2) have superior SMARTSCORES™, or siRNA rankings (i.e. a SMARTSCORE™ of >−10, suggesting a desirable average internal stability profile) are selected for further investigations designed to better understand the molecule's potency and longevity. In one, non-limiting study dedicated to understanding a molecule's potency, an siRNA is introduced into one (or more) cell types in increasingly diminishing concentrations (e.g. 3.0→0.3 nM). Subsequently, the level of gene silencing induced by each concentration is examined and siRNA that exhibit hyperfunctional potency (i.e. those that induce 80% silencing or greater at e.g. picomolar concentrations) are identified. In a second study, the longevity profiles of siRNA having high (>−10) SMARTSCORES™, or siRNA rankings, and greater than 80% silencing are examined. In one non-limiting example of how this is achieved, siRNA are introduced into a test cell line and the levels of RNAi are measured over an extended period of time (e.g. 24-168 hrs). siRNAs that exhibit strong RNA interference patterns (i.e. >80% interference) for periods of time greater than, e.g., 120 hours are thus identified. Studies similar to those described above can be performed on any and all of the >$10^6$ siRNA included in this document to further define the most functional molecule for any given gene. Molecules possessing one or both properties (extended longevity and heightened potency) are labeled "hyperfunctional siRNA," and earmarked as candidates for future therapeutic studies.

While the example(s) given above describe one means by which hyperfunctional siRNA can be isolated, neither the assays themselves nor the selection parameters used are rigid and can vary with each family of siRNA. Families of siRNA include siRNAs directed against a single gene, or directed against a related family of genes.

The highest quality siRNA achievable for any given gene may vary considerably. Thus, for example, in the case of one gene (gene X), rigorous studies such as those described above may enable the identification of an siRNA that, at picomolar concentrations, induces 99$^+$% silencing for a period of 10 days. Yet identical studies of a second gene (gene Y) may yield an siRNA that at high nanomolar concentrations (e.g. 100 nM) induces only 75% silencing for a period of 2 days. Both molecules represent the very optimum siRNA for their respective gene targets and therefore are designated "hyperfunctional." Yet due to a variety of factors including but not limited to target concentration, siRNA stability, cell type, off-target interference, and others, equivalent levels of potency and longevity are not achievable. Thus, for these reasons, the parameters described in the before mentioned assays, can vary. While the initial screen selected siRNA that had SMARTSCORES™, or siRNA rankings, above −10 and a gene silencing capability of greater than 80%, selections that have stronger (or weaker) parameters can be implemented. Similarly, in the subsequent studies designed to identify molecules with high potency and longevity, the desired cutoff criteria (i.e. the lowest concentration that induces a desirable level of interference, or the longest period of time that interference can be observed) can vary. The experimentation subsequent to application of the rational criteria of this application is significantly reduced where one is trying to obtain a suitable hyperfunctional siRNA for, for example, therapeutic use. When, for example, the additional experimentation of the type described herein is applied by one skilled in the art with this disclosure in hand, a hyperfunctional siRNA is readily identified.

The siRNA may be introduced into a cell by any method that is now known or that comes to be known and that from reading this disclosure, persons skilled in the art would determine would be useful in connection with the present invention in enabling siRNA to cross the cellular membrane. These methods include, but are not limited to, any manner of transfection, such as for example transfection employing DEAE-Dextran, calcium phosphate, cationic lipids/liposomes, micelles, manipulation of pressure, microinjection, electroporation, immunoporation, use of vectors such as viruses, plasmids, cosmids, bacteriophages, cell fusions, and coupling of the polynucleotides to specific conjugates or ligands such as antibodies, antigens, or receptors, passive introduction, adding moieties to the siRNA that facilitate its uptake, and the like.

Having described the invention with a degree of particularity, examples will now be provided. These examples are not intended to and should not be construed to limit the scope of the claims in any way.

EXAMPLES

General Techniques and Nomenclatures siRNA nomenclature. All siRNA duplexes are referred to by sense strand. The first nucleotide of the 5'-end of the sense strand is position 1, which corresponds to position 19 of the antisense strand for a 19-mer. In most cases, to compare results from different experiments, silencing was determined by measuring specific transcript mRNA levels or enzymatic activity associated with specific transcript levels, 24 hours post-transfection, with siRNA concentrations held constant at 100 nM. For all experiments, unless otherwise specified transfection efficiency was ensured to be over 95%, and no detectable cellular toxicity was observed. The following system of nomenclature was used to compare and report siRNA-silencing functionality: "F" followed by the degree of minimal knockdown. For example, F50 signifies at least 50% knockdown, F80 means at least 80%, and so forth. For this study, all sub-F50 siRNAs were considered non-functional.

Cell culture and transfection. 96-well plates are coated with 50 µl of 50 mg/ml poly-L-lysine (Sigma) for 1 hr, and then washed 3× with distilled water before being dried for 20 min. HEK293 cells or HEK293Lucs or any other cell type of interest are released from their solid support by trypsinization, diluted to 3.5×$10^5$ cells/ml, followed by the addition of 100 µL of cells/well. Plates are then incubated overnight at 37° C., 5% $CO_2$. Transfection procedures can vary widely depending on the cell type and transfection reagents. In one non-limiting example, a transfection mixture consisting of 2 mL Opti-MEM I (Gibco-BRL), 80 µl Lipofectamine 2000 (Invitrogen), 15 µL SUPERNasin at 20 U/µl (Ambion), and 1.5 µl of reporter gene plasmid at 1 µg/µl is prepared in 5-ml polystyrene round bottom tubes. 100 µl of transfection reagent is then combined with 100 µl of siRNAs in polystyrene deep-well titer plates (Beckman) and incubated for 20 to 30 min at room temp. 550 µl of Opti-MEM is then added to each well to bring the final siRNA concentration to 100 nM. Plates are then sealed with parafilm and mixed. Media is removed from HEK293 cells and replaced with 95 µl of transfection mixture. Cells are incubated overnight at 37° C., 5% $CO_2$.

Quantification of gene knockdown. A variety of quantification procedures can be used to measure the level of silencing induced by siRNA or siRNA pools. In one non-limiting example: to measure mRNA levels 24 hrs post-transfection, QuantiGene branched-DNA (bDNA) kits (Bayer) (Wang, et al, *Regulation of insulin preRNA splicing by glucose*. Proc Natl Acad Sci 1997, 94:4360.) are used according to manufacturer instructions. To measure luciferase activity, media is removed from HEK293 cells 24 hrs post-transfection, and 50

Example I

Sequences Used to Develop the Algorithm

Anti-Firefly and anti-Cyclophilin siRNAs panels (FIGS. 5a, b) sorted according to using Formula VIII predicted values. All siRNAs scoring more than 0 (formula VIII) and more then 20 (formula IX) are fully functional. All ninety sequences for each gene (and DBI) appear below in Table IV.

µl of Steady-GLO reagent (Promega) is added. After 5 min, plates are analyzed on a plate reader.

TABLE IV

| Cyclo | 1  | SEQ ID NO 032 | GUUCCAAAAACAGUGGAUA |
| --- | --- | --- | --- |
| Cyclo | 2  | SEQ ID NO 033 | UCCAAAAACAGUGGAUAAU |
| Cyclo | 3  | SEQ ID NO 034 | CAAAAACAGUGGAUAAUUU |
| Cyclo | 4  | SEQ ID NO 035 | AAAACAGUGGAUAAUUUUG |
| Cyclo | 5  | SEQ ID NO 036 | AACAGUGGAUAAUUUUGUG |
| Cyclo | 6  | SEQ ID NO 037 | CAGUGGAUAAUUUUGUGGC |
| Cyclo | 7  | SEQ ID NO 038 | GUGGAUAAUUUUGUGGCCU |
| Cyclo | 8  | SEQ ID NO 039 | GGAUAAUUUUCUGGCCUUA |
| Cyclo | 9  | SEQ ID NO 040 | AUAAUUUUGUGGCCUUAGC |
| Cyclo | 10 | SEQ ID NO 041 | AAUUUUGUGGCCUUAGCUA |
| Cyclo | 11 | SEQ ID NO 042 | UUUUGUGGCCUUAGCUACA |
| Cyclo | 12 | SEQ ID NO 043 | UUCUGGCCUUAGCUACAGG |
| Cyclo | 13 | SEQ ID NO 044 | GUGGCCUUAGCUACAGGAG |
| Cyclo | 14 | SEQ ID NO 045 | GGCCUUAGCUACAGGAGAG |
| Cyclo | 15 | SEQ ID NO 046 | CCUUAGCUACAGGAGAGAA |
| Cyclo | 16 | SEQ ID NO 047 | UUAGCUACAGGAGAGAAAG |
| Cyclo | 17 | SEQ ID NO 048 | AGCUACAGGAGAGAAAGGA |
| Cyclo | 18 | SEQ ID NO 049 | CUACAGGAGAGAAAGGAUU |
| Cyclo | 19 | SEQ ID NO 050 | ACAGGAGAGAAAGGAUUUG |
| Cyclo | 20 | SEQ ID NO 051 | AGGAGAGAAAGGAUUUGGC |
| Cyclo | 21 | SEQ ID NO 052 | GAGAGAAAGGAUUUGGCUA |
| Cyclo | 22 | SEQ ID NO 053 | GAGAAAGGAUUUGGCUACA |
| Cyclo | 23 | SEQ ID NO 054 | GAAAGGAUUUGGCUACAAA |
| Cyclo | 24 | SEQ ID NO 055 | AAGGAUUUGGCUACAAAAA |
| Cyclo | 25 | SEQ ID NO 056 | GGAUUUGGCUACAAAAACA |
| Cyclo | 26 | SEQ ID NO 057 | AUUUGGCUACAAAAACAGC |
| Cyclo | 27 | SEQ ID NO 058 | UUGGCUACAAAAACAGCAA |
| Cyclo | 28 | SEQ ID NO 059 | GGCUACAAAAACAGCAAAU |
| Cyclo | 29 | SEQ ID NO 060 | CUACAAAAACAGCAAAUUC |
| Cyclo | 30 | SEQ ID NO 061 | ACAAAAACAGCAAAUUCCA |
| Cyclo | 31 | SEQ ID NO 062 | AAAAACAGCAAAUUCCAUC |
| Cyclo | 32 | SEQ ID NO 063 | AAACAGCAAAUUCCAUCGU |

TABLE IV-continued

| Cyclo | 33 | SEQ ID NO 064 | ACAGCAAAUUCCAUCGUGU |
| --- | --- | --- | --- |
| Cyclo | 34 | SEQ ID NO 065 | AGCAAAUUCCAUCGUGUAA |
| Cyclo | 35 | SEQ ID NO 066 | CAAAUUCCAUCGUGUAAUC |
| Cyclo | 36 | SEQ ID NO 067 | AAUUCCAUCGUGUAAUCAA |
| Cyclo | 37 | SEQ ID NO 068 | UUCCAUCGUGUAAUCAAGG |
| Cyclo | 38 | SEQ ID NO 069 | CCAUCGUGUAAUCAAGGAC |
| Cyclo | 39 | SEQ ID NO 070 | AUCGUGUAAUCAAGGACUU |
| Cyclo | 40 | SEQ ID NO 071 | CGUGUAAUCAAGGACUUCA |
| Cyclo | 41 | SEQ ID NO 072 | UGUAAUCAAGGACUUCAUG |
| Cyclo | 42 | SEQ ID NO 073 | UAAUCAAGGACUUCAUGAU |
| Cyclo | 43 | SEQ ID NO 074 | AUCAAGGACUUCAUGAUCC |
| Cyclo | 44 | SEQ ID NO 075 | CAAGGACUUCAUGAUCCAG |
| Cyclo | 45 | SEQ ID NO 076 | AGGACUUCAUGAUCCAGGG |
| Cyclo | 46 | SEQ ID NO 077 | GACUUCAUGAUCCAGGGCG |
| Cyclo | 47 | SEQ ID NO 078 | CUUCAUGAUCCAGGGCGGA |
| Cyclo | 48 | SEQ ID NO 079 | UCAUGAUCCAGGGCGGAGA |
| Cyclo | 49 | SEQ ID NO 080 | AUGAUCCAGGGCGGAGACU |
| Cyclo | 50 | SEQ ID NO 081 | GAUCCAGGGCGGAGACUUC |
| Cyclo | 51 | SEQ ID NO 082 | UCCAGGGCGGAGACUUCAC |
| Cyclo | 52 | SEQ ID NO 083 | CAGGGCGGAGACUUCACCA |
| Cyclo | 53 | SEQ ID NO 084 | GGGCGGAGACUUCACCAGG |
| Cyclo | 54 | SEQ 10 NO 085 | GCGGAGACUUCACCAGGGG |
| Cyclo | 55 | SEQ ID NO 086 | GGAGACUUCACCAGGGGAG |
| Cyclo | 56 | SEQ ID NO 087 | AGACUUCACCAGGGGAGAU |
| Cyclo | 57 | SEQ ID NO 088 | ACUUCACCAGGGGAGAUGG |
| Cyclo | 58 | SEQ ID NO 089 | UUCACCAGGGGAGAUGGCA |
| Cyclo | 59 | SEQ ID NO 090 | CACCACGGGAGAUGGCACA |
| Cyclo | 60 | SEQ ID NO 091 | CCAGGGGACAUGGCACAGG |
| Cyclo | 61 | SEQ ID NO 092 | AGGGGAGAUGGCACAGGAG |
| Cyclo | 62 | SEQ ID NO 093 | GGGAGAUGGCACAGGAGGA |
| Cyclo | 63 | SEQ ID NO 094 | GAGAUGGCACAGGAGGAAA |
| Cyclo | 64 | SEQ ID NO 095 | GAUGGCACAGGAGGAAAGA |
| Cyclo | 65 | SEQ ID NO 096 | UGGCACAGGAGGAAAGAGC |
| Cyclo | 66 | SEQ ID NO 097 | GCACAGGAGGAAAGAGCAU |
| Cyclo | 67 | SEQ ID NO 098 | ACAGGAGGAAAGAGCAUCU |
| Cyclo | 68 | SEQ ID NO 099 | AGGAGGAAAGAGCAUCUAC |
| Cyclo | 69 | SEQ ID NO 100 | GAGGAAAGAGCAUCUACGG |
| Cyclo | 70 | SEQ ID NO 101 | GGAAAGAGCAUCUACGGUG |
| Cyclo | 71 | SEQ ID NO 102 | AAAGAGCAUCUACGGUGAG |
| Cyclo | 72 | SEQ ID NO 103 | AGAGCAUCUACGGUGAGCG |

TABLE IV-continued

| | | | |
|---|---|---|---|
| Cyclo | 73 | SEQ ID NO 104 | AGCAUCUACGGUGAGCGCU |
| Cyclo | 74 | SEQ ID NO 105 | CAUCUACGGUGAGCGCUUC |
| Cyclo | 75 | SEQ ID NO 106 | UCUACGGUGAGCGCUUCCC |
| Cyclo | 76 | SEQ ID NO 107 | UACGGUGAGCGCUUCCCCG |
| Cyclo | 77 | SEQ ID NO 108 | CGGUGAGCGCUUCCCCGAU |
| Cyclo | 78 | SEQ ID NO 109 | GUGAGCGCUUCCCCGAUGA |
| Cyclo | 79 | SEQ ID NO 110 | GAGCGCUUCCCCGAUGAGA |
| Cyclo | 80 | SEQ ID NO 111 | GCGCUUCCCCGAUGAGAAC |
| Cyclo | 81 | SEQ ID NO 112 | GCUUCCCCGAUGAGAACUU |
| Cyclo | 82 | SEQ ID NO 113 | UUCCCCGAUGAGAACUUCA |
| Cyclo | 83 | SEQ ID NO 114 | CCCCGAUGAGAACUUCAAA |
| Cyclo | 84 | SEQ ID NO 115 | CCGAUGAGAACUUCAAACU |
| Cyclo | 85 | SEQ ID NO 116 | GAUGAGAACUUCAAACUGA |
| Cyclo | 86 | SEQ ID NO 117 | UGAGAACUUCAAACUGAAG |
| Cyclo | 87 | SEQ ID NO 118 | AGAACUUCAAACUGAAGCA |
| Cyclo | 88 | SEQ ID NO 119 | AACUUCAAACUGAAGCACU |
| Cyclo | 89 | SEQ ID NO 120 | CUUCAAACUGAAGCACUAC |
| Cyclo | 90 | SEQ ID NO 121 | UCAAACUGAAGCACUACGG |
| DB | 1 | SEQ ID NO 122 | ACGGGCAAGCCCAAGUGGG |
| DB | 2 | SEQ ID NO 123 | CGGGCAAGGCCAAGUGGGA |
| DB | 3 | SEQ ID NO 124 | GGGCAAGGCCAAGUGGGAU |
| DB | 4 | SEQ ID NO 125 | GGCAAGGCCAAGUGGGAUG |
| DB | 5 | SEQ ID NO 126 | CCAAGCCCAAGUGGGAUGC |
| DB | 6 | SEQ ID NO 127 | CAAGGCCAAGUGGGAUGCC |
| DB | 7 | SEQ ID NO 128 | AAGGCCAAGUGGGAUGCCU |
| DB | 8 | SEQ ID NO 129 | AGGCCAAGUGGGAUGCCUG |
| DB | 9 | SEQ ID NO 130 | GGCCAAGUGGGAUGCCUGG |
| DB | 10 | SEQ ID NO 131 | GCCAAGUGGGAUGCCUGGA |
| DB | 11 | SEQ ID NO 132 | CCAAGUGGGAUGCCUGGAA |
| DB | 12 | SEQ ID NO 133 | CAAGUGGGAUGCCUGGAAU |
| DB | 13 | SEQ ID NO 134 | AAGUGGGAUGCCUGGAAUG |
| DB | 14 | SEQ ID NO 135 | AGUGGGAUGCCUGGAAUGA |
| DB | 15 | SEQ ID NO 136 | GUGGGAUGCCUGGAAUGAG |
| DB | 16 | SEQ ID NO 137 | UGGGAUGCCUGGAAUGAGC |
| DB | 17 | SEQ ID NO 138 | GGGAUGCCUGGAAUGAGCU |
| DB | 18 | SEQ ID NO 139 | GGAUGCCUGGAAUGAGCUG |
| DB | 19 | SEQ ID NO 140 | GAUGCCUGGAAUGAGCUGA |
| DB | 20 | SEQ ID NO 141 | AUGCCUGGAAUGAGCUGAA |
| DB | 21 | SEQ ID NO 142 | UGCCUGGAAUGAGCUGAAA |
| DB | 22 | SEQ ID NO 143 | GCCUGGAAUGAGCUGAAAG |
| DB | 23 | SEQ ID NO 144 | CCUGGAAUGAGCUGAAAGG |
| DB | 24 | SEQ ID NO 145 | CUGGAAUGAGCUGAAAGGG |
| DB | 25 | SEQ ID NO 146 | UGGAAUGAGCUGAAAGGGA |
| DB | 26 | SEQ ID NO 147 | GGAAUGAGCUGAAAGGGAC |
| DB | 27 | SEQ ID NO 148 | GAAUGAGCUGAAAGGGACU |
| DB | 28 | SEQ ID NO 149 | AAUGAGCUGAAAGGGACUU |
| DB | 29 | SEQ ID NO 150 | AUGAGCUGAAAGGGACUUC |
| DB | 30 | SEQ ID NO 151 | UGAGCUGAAAGGGACUUCC |
| DB | 31 | SEQ ID NO 152 | GAGCUGAAAGGGACUUCCA |
| DB | 32 | SEQ ID NO 153 | AGCUGAAAGGGACUUCCAA |
| DB | 33 | SEQ ID NO 154 | GCUGAAAGGGACUUCCAAG |
| DB | 34 | SEQ ID NO 155 | CUGAAAGGGACUUCCAAGG |
| DB | 35 | SEQ ID NO 156 | UGAAAGGGACUUCCAAGGA |
| DB | 36 | SEQ ID NO 157 | GAAAGGGACUUCCAAGGAA |
| DB | 37 | SEQ ID NO 158 | AAAGGGACUUCCAAGGAAG |
| DB | 38 | SEQ ID NO 159 | AAGGGACUUCCAAGGAAGA |
| DB | 39 | SEQ ID NO 160 | AGGGACUUCCAAGGAAGAU |
| DB | 40 | SEQ ID NO 161 | GGGACUUCCAAGGAAGAUG |
| DB | 41 | SEQ ID NO 162 | GGACUUCCAAGGAAGAUGC |
| DB | 42 | SEQ ID NO 163 | GACUUCCAAGGAAGAUGCC |
| DB | 43 | SEQ ID NO 164 | ACUUCCAAGGAACAUGCCA |
| DB | 44 | SEQ ID NO 165 | CUUCCAAGGAAGAUGCCAU |
| DB | 45 | SEQ ID NO 166 | UUCCAAGGAAGAUGCCAUG |
| DB | 46 | SEQ ID NO 167 | UCCAAGGAAGAUGCCAUGA |
| DB | 47 | SEQ ID NO 168 | CCAAGGAAGAUGCCAUGAA |
| DB | 48 | SEQ ID NO 169 | CAAGGAAGAUGCCAUGAAA |
| DB | 49 | SEQ ID NO 170 | AAGGAAGAUGCCAUGAAAG |
| DB | 50 | SEQ ID NO 171 | AGGAAGAUGCCAUGAAAGC |
| DB | 51 | SEQ ID NO 172 | GGAAGAUGCCAUGAAAGCU |
| DB | 52 | SEQ ID NO 173 | GAAGAUGCCAUGAAAGCUU |
| DB | 53 | SEQ ID NO 174 | AAGAUGCCAUGAAAGCUUA |
| DB | 54 | SEQ ID NO 175 | AGAUGCCAUGAAAGCUUAC |
| DB | 55 | SEQ ID NO 176 | GAUGCCAUGAAAGCUUACA |
| DB | 56 | SEQ ID NO 177 | AUGCCAUGAAAGCUUACAU |
| DB | 57 | SEQ ID NO 178 | UGCCAUGAAAGCUUACAUC |
| DB | 58 | SEQ ID NO 179 | GCCAUGAAAGCUUACAUCA |
| DB | 59 | SEQ ID NO 180 | CCAUGAAAGCUUACAUCAA |
| DB | 60 | SEQ ID NO 181 | CAUGAAAGCUUACAUCAAC |
| DB | 61 | SEQ ID NO 182 | AUGAAAGCUUACAUCAACA |
| DB | 62 | SEQ ID NO 183 | UGAAAGCUUACAUCAACAA |

TABLE IV-continued

| | | | |
|---|---|---|---|
| DB | 63 | SEQ ID NO 184 | GAAAGCUUACAUCAACAAA |
| DB | 64 | SEQ ID NO 185 | AAAGCUUACAUCAACAAAG |
| DB | 65 | SEQ ID NO 186 | AAGCUUACAUCAACAAAGU |
| DB | 66 | SEQ ID NO 187 | AGCUUACAUCAACAAAGUA |
| DB | 67 | SEQ ID NO 188 | GCUUACAUCAACAAAGUAG |
| DB | 68 | SEQ ID NO 189 | CUUACAUCAACAAAGUAGA |
| DB | 69 | SEQ ID NO 190 | UUACAUCAACAAAGUAGAA |
| DB | 70 | SEQ ID NO 191 | UACAUCAACAAAGUAGAAG |
| DB | 71 | SEQ ID NO 192 | ACAUCAACAAAGUAGAAGA |
| DB | 72 | SEQ ID NO 193 | CAUCAACAAAGUAGAAGAG |
| DB | 73 | SEQ ID NO 194 | AUCAACAAAGUAGAAGAGC |
| DB | 74 | SEQ ID NO 195 | UCAACAAAGUAGAAGAGCU |
| DB | 75 | SEQ ID NO 196 | CAACAAAGUAGAAGAGCUA |
| DB | 76 | SEQ ID NO 197 | AACAAAGUAGAAGAGCUAA |
| DB | 77 | SEQ ID NO 198 | ACAAAGUAGAAGAGCUAAA |
| DB | 78 | SEQ ID NO 199 | CAAAGUAGAAGAGCUAAAG |
| DB | 79 | SEQ ID NO 200 | AAAGUAGAAGAGCUAAAGA |
| DB | 80 | SEQ ID NO 201 | AAGUAGAAGAGCUAAAGAA |
| DB | 81 | SEQ ID NO 202 | AGUAGAAGAGCUAAAGAAA |
| DB | 82 | SEQ ID NO 203 | GUAGAAGAGCUAAAGAAAA |
| DB | 83 | SEQ ID NO 204 | UAGAAGAGCUAAAGAAAAA |
| DB | 84 | SEQ ID NO 205 | AGAAGAGCUAAAGAAAAAA |
| DB | 85 | SEQ ID NO 206 | GAAGAGCUAAAGAAAAAAU |
| DB | 86 | SEQ ID NO 207 | AAGAGCUAAAGAAAAAUA |
| DB | 87 | SEQ ID NO 208 | AGAGCUAAAGAAAAAUAC |
| DB | 88 | SEQ ID NO 209 | GAGCUAAAGAAAAAUACG |
| DB | 89 | SEQ ID NO 210 | AGCUAAAGAAAAAUACGG |
| DB | 90 | SEQ ID NO 211 | GCUAAAGAAAAAUACGGG |
| Luc | 1 | SEQ ID NO 212 | AUCCUCAUAAAGGCCAAGA |
| Luc | 2 | SEQ ID NO 213 | AGAUCCUCAUAAAGGCCAA |
| Luc | 3 | SEQ ID NO 214 | AGAGAUCCUCAUAAAGGCC |
| Luc | 4 | SEQ ID NO 215 | AGAGAGAUCCUCAUAAAGG |
| Luc | 5 | SEQ ID NO 216 | UCAGAGAGAUCCUCAUAAA |
| Luc | 6 | SEQ ID NO 217 | AAUCAGAGAGAUCCUCAUA |
| Luc | 7 | SEQ ID NO 218 | AAAAUCAGAGAGAUCCUCA |
| Luc | 8 | SEQ ID NO 219 | GAAAAAUCAGAGAGAUCCU |
| Luc | 9 | SEQ ID NO 220 | AAGAAAAAUCAGAGAGAUC |
| Luc | 10 | SEQ ID NO 221 | GCAAGAAAAAUCAGAGAGA |
| Luc | 11 | SEQ ID NO 222 | ACGCAAGAAAAAUCAGAGA |
| Luc | 12 | SEQ ID NO 223 | CGACGCAAGAAAAAUCAGA |
| Luc | 13 | SEQ ID NO 224 | CUCGACGCAAGAAAAAUCA |
| Luc | 14 | SEQ ID NO 225 | AACUCGACGCAAGAAAAAU |
| Luc | 15 | SEQ ID NO 226 | AAAACUCGACGCAAGAAAA |
| Luc | 16 | SEQ ID NO 227 | GGAAAACUCGACGCAAGAA |
| Luc | 17 | SEQ ID NO 228 | CCGGAAAACUCGACGCAAG |
| Luc | 18 | SEQ ID NO 229 | UACCGGAAAACUCGACGCA |
| Luc | 19 | SEQ ID NO 230 | CUUACCGGAAAACUCGACG |
| Luc | 20 | SEQ ID NO 231 | GUCUUACCGGAAAACUCGA |
| Luc | 21 | SEQ ID NO 232 | AGGUCUUACCGGAAAACUC |
| Luc | 22 | SEQ ID NO 233 | AAAGGUCUUACCGGAAAAC |
| Luc | 23 | SEQ ID NO 234 | CGAAAGGUCUUACCGGAAA |
| Luc | 24 | SEQ ID NO 235 | ACCGAAAGGUCUUACCGGA |
| Luc | 25 | SEQ ID NO 236 | GUACCGAAAGGUCUUACCG |
| Luc | 26 | SEQ ID NO 237 | AAGUACCGAAAGGUCUUAC |
| Luc | 27 | SEQ ID NO 238 | CGAAGUACCGAAAGGUCUU |
| Luc | 28 | SEQ ID NO 239 | GACGAAGUACCGAAAGGUC |
| Luc | 29 | SEQ ID NO 240 | UGGACGAAGUACCGAAAGG |
| Luc | 30 | SEQ ID NO 241 | UGUGGACGAAGUACCGAAA |
| Luc | 31 | SEQ ID NO 242 | UUUGUGGACGAAGUACCGA |
| Luc | 32 | SEQ ID NO 243 | UGUUUGUGGACGAAGUACC |
| Luc | 33 | SEQ ID NO 244 | UGUGUUUGUGGACGAAGUA |
| Luc | 34 | SEQ ID NO 245 | GUUGUGUUUGUGGACGAAG |
| Luc | 35 | SEQ ID NO 246 | GAGUUGUGUUUGUGGACGA |
| Luc | 36 | SEQ ID NO 247 | AGGAGUUGUGUUUGUGGAC |
| Luc | 37 | SEQ ID NO 248 | GGAGGAGUUGUGUUUGUGG |
| Luc | 38 | SEQ ID NO 249 | GCGGAGGAGUUGUGUUUGU |
| Luc | 39 | SEQ ID NO 250 | GCGCGGAGGAGUUGUGUUU |
| Luc | 40 | SEQ ID NO 251 | UUGCGCGGAGGAGUUGUGU |
| Luc | 41 | SEQ ID NO 252 | AGUUGCGCGGAGGAGUUGU |
| Luc | 42 | SEQ ID NO 253 | AAAGUUGCGCGGAGGAGUU |
| Luc | 43 | SEQ ID NO 254 | AAAAGUUGCGCGGAGGAG |
| Luc | 44 | SEQ ID NO 255 | CGAAAAGUUGCGCGGAGG |
| Luc | 45 | SEQ ID NO 256 | CGCGAAAAGUUGCGCGGA |
| Luc | 46 | SEQ ID NO 257 | ACCGCGAAAAGUUGCGCG |
| Luc | 47 | SEQ ID NO 258 | CAACCGCGAAAAGUUGCG |
| Luc | 48 | SEQ ID NO 259 | AACAACCGCGAAAAGUUG |
| Luc | 49 | SEQ ID NO 260 | GUAACAACCGCGAAAAGU |
| Luc | 50 | SEQ ID NO 261 | AAGUAACAACCGCGAAAAA |
| Luc | 51 | SEQ ID NO 262 | UCAAGUAACAACCGCGAAA |
| Luc | 52 | SEQ ID NO 263 | AGUCAAGUAACAACCGCGA |

TABLE IV-continued

| | | | |
|---|---|---|---|
| Luc | 53 | SEQ ID NO 264 | CCAGUCAAGUAACAACCGC |
| Luc | 54 | SEQ ID NO 265 | CGCCAGUCAAGUAACAACC |
| Luc | 55 | SEQ ID NO 266 | GUCGCCAGUCAAGUAACAA |
| Luc | 56 | SEQ ID NO 267 | ACGUCGCCAGUCAAGUAAC |
| Luc | 57 | SEQ ID NO 268 | UUACGUCGCCACUCAAGUA |
| Luc | 58 | SEQ ID NO 269 | GAUUACGUCGCCAGUCAAG |
| Luc | 59 | SEQ ID NO 270 | UGGAUUACGUCGCCAGUCA |
| Luc | 60 | SEQ ID NO 271 | CGUGGAUUACGUCGCCAGU |
| Luc | 61 | SEQ ID NO 272 | AUCGUGGAUUACGUCGCCA |
| Luc | 62 | SEQ ID NO 273 | AGAUCGUGGAUUACGUCGC |
| Luc | 63 | SEQ ID NO 274 | AGAGAUCGUGGAUUACGUC |
| Luc | 64 | SEQ ID NO 275 | AAAGAGAUCGUGGAUUACG |
| Luc | 65 | SEQ ID NO 276 | AAAAAGAGAUCGUGGAUUA |
| Luc | 66 | SEQ ID NO 277 | GGAAAAGAGAUCGUGGAU |
| Luc | 67 | SEQ ID NO 278 | ACGGAAAAGAGAUCGUGG |
| Luc | 68 | SEQ ID NO 279 | UGACGGAAAAGAGAUCGU |
| Luc | 69 | SEQ ID NO 280 | GAUGACGGAAAAGAGAUC |
| Luc | 70 | SEQ ID NO 281 | ACGAUGACGGAAAAAGAGA |
| Luc | 71 | SEQ ID NO 282 | AGACGAUGACGGAAAAAGA |
| Luc | 72 | SEQ ID NO 283 | AAAGACGAUGACGGAAAAA |
| Luc | 73 | SEQ ID NO 284 | GGAAAGACGAUGACGGAAA |
| Luc | 74 | SEQ ID NO 285 | ACGGAAAGACGAUGACGGA |
| Luc | 75 | SEQ ID NO 286 | GCACGGAAAGACGAUGACG |
| Luc | 76 | SEQ ID NO 287 | GAGCACGGAAAGACGAUGA |
| Luc | 77 | SEQ ID NO 288 | UGGAGCACGGAAAGACGAU |
| Luc | 78 | SEQ ID NO 289 | UUUGGACCACGGAAAGACG |
| Luc | 79 | SEQ ID NO 290 | GUUUUGGAGCACGGAAAGA |
| Luc | 80 | SEQ ID NO 291 | UUGUUUUGGAGCACGGAAA |
| Luc | 81 | SEQ ID NO 292 | UGUUGUUUUGGAGCACGGA |
| Luc | 82 | SEQ ID NO 293 | GUUGUUGUUUUGGAGCACG |
| Luc | 83 | SEQ ID NO 294 | CCGUUGUUGUUUUGGAGCA |
| Luc | 84 | SEQ ID NO 295 | CGCCGUUGUUGUUUUGGAG |
| Luc | 85 | SEQ ID NO 296 | GCCGCCGUUGUUGUUUUGG |
| Luc | 86 | SEQ ID NO 297 | CCGCCGCCGUUGUUGUUUU |
| Luc | 87 | SEQ ID NO 298 | UCCCGCCGCCGUUGUUGUU |
| Luc | 88 | SEQ ID NO 299 | CUUCCCGCCGCCGUUGUUG |
| Luc | 89 | SEQ ID NO 300 | AACUUCCCGCCGCCGUUGU |
| Luc | 90 | SEQ ID NO 301 | UGAACUUCCCGCCGCCGUU |

Example II

Validation of the Algorithm Using DBI, Luciferase, PLK, EGFR, and SEAP

Figures 10A, 10B, 10C, 10D, 10E, 10F:
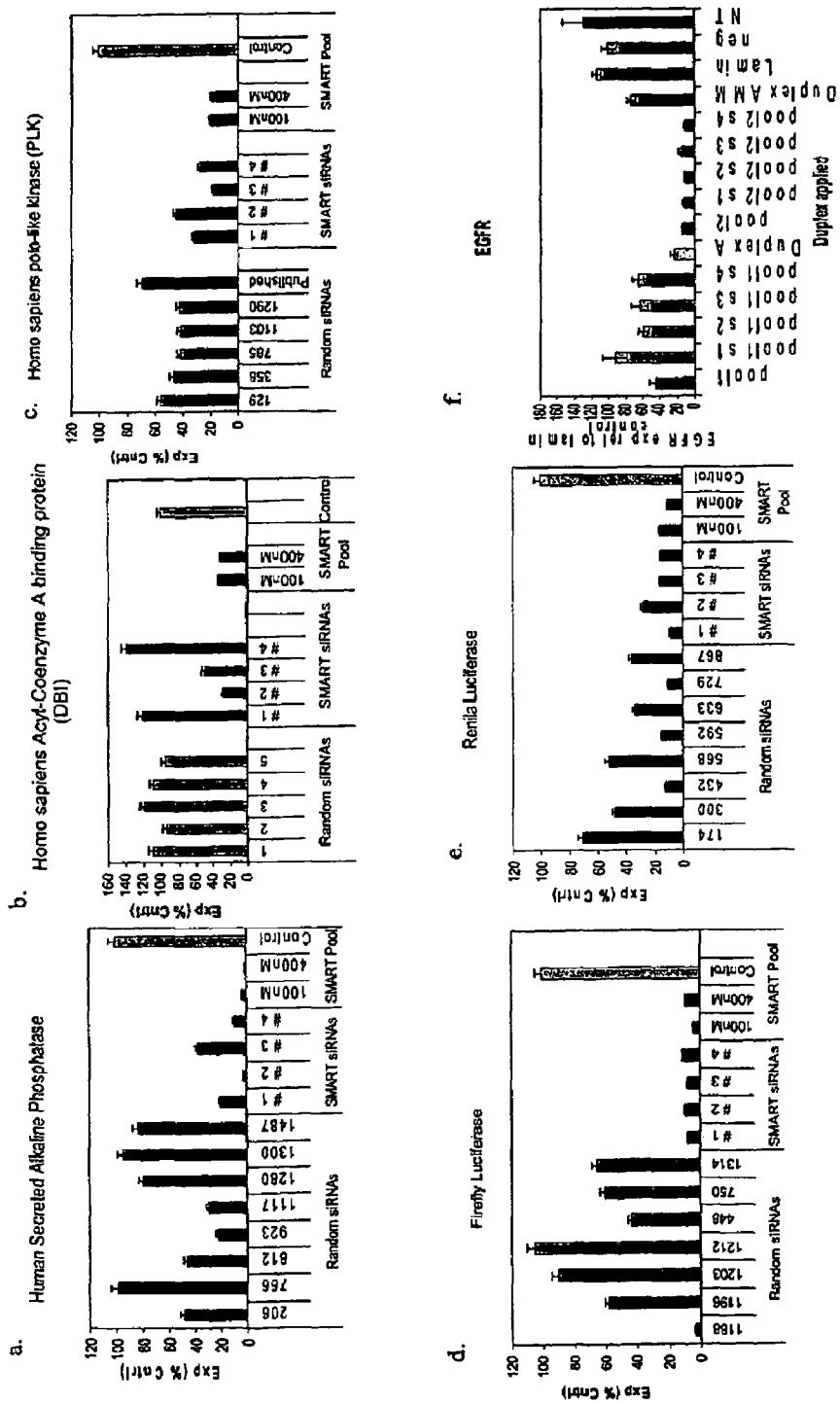
FIGS. 10A-E compare the RNAi of five different genes (SLAP, DBI, PLK, Firefly Luciferase, and Renila Luciferase) by varying numbers of randomly selected siRNA and four rationally designed (SMART-selected) siRNA chosen using the algorithm described in Formula VIII. In addition, RNAi induced by a pool of the four SMART-selected siRNA is reported at two different concentrations (100 and 400 nM). 10F is a comparison between a pool of randomly selected EGFR siRNA (Pool 1) and a pool of SMART selected EGFR siRNA (Pool 2). Pool 1, S1-S4 and Pool 2 S1-S4 represent the individual members that made up each respective pool. Note that numbers for random siRNAs represent the position of the 5' end of the sense strand of the duplex. The X-axis indicates the duplex that was applied. The Y-axis represents the % expression of the control(s).

The algorithm (Formula VIII) identified siRNAs for five genes, human DBI, firefly luciferase (fLuc), *renilla* luciferase (rLuc), human PLK, and human secreted alkaline phosphatase (SEAP). Four individual siRNAs were selected on the basis of their SMARTSCORES™, or siRNA rankings, derived by analysis of their sequence using Formula VIII (all of the siRNAs would be selected with Formula IX as well) and analyzed for their ability to silence their targets' expression. In addition to the scoring, a BLAST search was conducted for each siRNA. To minimize the potential for off-target silencing effects, only those target sequences with more than three mismatches against unrelated sequences were selected. Semizarov, et al (2003) Specificity of short interfering RNA determined through gene expression signatures. *Proc. Natl. Acad. Sci. USA* 100:6347. These duplexes were analyzed individually and in pools of 4 and compared with several siRNAs that were randomly selected. The functionality was measured a percentage of targeted gene knockdown as compared to controls. All siRNAs were transfected as described by the methods above at 100 nM concentration into HEK293 using Lipofectamine 2000. The level of the targeted gene expression was evaluated by B-DNA as described above and normalized to the non-specific control. FIG. 10 shows that the siRNAs selected by the algorithm disclosed herein were significantly more potent than randomly selected siRNAs. The algorithm increased the chances of identifying an F50 siRNA from 48% to 91%, and an F80 siRNA from 13% to 57%. In addition, pools of SMART siRNA silence the selected target better than randomly selected pools (see FIG. 10F).

Example III

Validation of the Algorithm Using Genes Involved in Clathrin-Dependant Endocytosis Components of clathrin-mediated endocytosis pathway are key to modulating intracellular signaling and play important roles in disease. Chromosomal rearrangements that result in fusion transcripts between the Mixed-Lineage Leukemia gene (MLL) and CALM (Clathrin assembly lymphoid myeloid leukemia gene) are believed to play a role in leukemogenesis. Similarly, disruptions in Rab7 and Rab9, as well as HIP1 (Huntingtin-interacting protein), genes that are believed to be involved in endocytosis, are potentially responsible for ailments resulting in lipid storage, and neuronal diseases, respectively. For these reasons, siRNA directed against clathrin and other genes involved in the clathrin-mediated endocytotic pathway are potentially important research and therapeutic tools.

siRNAs directed against genes involved in the clathrin-mediated endocytosis pathways were selected using Formula VIII. The targeted genes were clathrin heavy chain (CHC, accession # NM_004859), clathrin light chain A (CLCa, NM_001833), clathrin light chain B (CLCb, NM_001834), CALM (U45976), β2 subunit of AP-2 (β2, NM_001282), Eps15 (NM_001981), Eps15R (NM_021235), dynamin II (DYNII, NM_004945), Rab5a (BC001267), Rab5b (NM_002868), Rab5c (AF141304), and EEA.1 (XM_018197).

For each gene, four siRNAs duplexes with the highest scores were selected and a BLAST search was conducted for each of them using the Human EST database. In order to minimize the potential for off-target silencing effects, only those sequences with more than three mismatches against un-related sequences were used. All duplexes were synthesized at Dharmacon, Inc. as 21-mers with 3'-UU overhangs using a modified method of 2'-ACE chemistry Scaringe (2000) Advanced 5'-silyl-2'-orthoester approach to RNA oligonucleotide synthesis, *Methods Enzymol* 317:3 and the antisense strand was chemically phosphorylated to insure maximized activity.

HeLa cells were grown in Dulbecco's modified Eagle's medium (DMEM) containing 10% fetal bovine serum, antibiotics and glutamine. siRNA duplexes were resuspended in 1× siRNA Universal buffer (Dharmacon, Inc.) to 20 μM prior to transfection. HeLa cells in 12-well plates were transfected twice with 4 μl of 20 μM siRNA duplex in 3 μl Lipofectamine 2000 reagent (Invitrogen, Carlsbad, Calif., USA) at 24-hour intervals. For the transfections in which 2 or 3 siRNA duplexes were included, the amount of each duplex was decreased, so that the total amount was the same as in transfections with single siRNAs. Cells were plated into normal culture medium 12 hours prior to experiments, and protein levels were measured 2 or 4 days after the first transfection.

Equal amounts of lysates were resolved by electrophoresis, blotted, and stained with the antibody specific to targeted protein, as well as antibodies specific to unrelated proteins, PP1 phosphatase and Tsg101 (not shown). The cells were lysed in Triton X-100/glycerol solubilization buffer as described previously. Tebar, Bohlander, & Sorkin (1999) Clathrin Assembly Lymphoid Myeloid Leukemia (CALM) Protein: Localization in Endocytic-coated Pits, Interactions with Clathrin, and the Impact of Overexpression on Clathrin-mediated Traffic, *Mol. Biol. Cell* 10:2687. Cell lysates were electrophoresed, transferred to nitrocellulose membranes, and Western blotting was performed with several antibodies followed by detection using enhanced chemiluminescence system (Pierce, Inc). Several x-ray films were analyzed to determine the linear range of the chemiluminescence signals, and the quantifications were performed using densitometry and AlphaImager v5.5 software (Alpha Innotech Corporation). In experiments with Eps15R-targeted siRNAs, cell lysates were subjected to immunoprecipitation with Ab860, and Eps15R was detected in immunoprecipitates by Western blotting as described above.

The antibodies to assess the levels of each protein by Western blot were obtained from the following sources: monoclonal antibody to clathrin heavy chain (TD.1) was obtained from American Type Culture Collection (Rockville, Md., USA); polyclonal antibody to dynamin II was obtained from Affinity Bioreagents, Inc. (Golden, Colo., USA); monoclonal antibodies to EEA.1 and Rab5a were purchased from BD Transduction Laboratories (Los Angeles, Calif., USA); the monoclonal antibody to Tsg101 was purchased from Santa Cruz Biotechnology, Inc. (Santa Cruz, Calif., USA); the monoclonal antibody to GFP was from ZYMED Laboratories Inc. (South San Francisco, Calif., USA); the rabbit polyclonal antibodies Ab32 specific to α-adaptins and Ab20 to CALM were described previously Sorkin et al (1995) Stoichiometric Interaction of the Epidermal Growth Factor Receptor with the Clathrin-associated Protein Complex AP-2, *J. Biol. Chem.* 270:619, the polyclonal antibodies to clathrin light chains A and B were kindly provided by Dr. F. Brodsky (UCSF); monoclonal antibodies to PP1 (BD Transduction Laboratories) and α-Actinin (Chemicon) were kindly provided by Dr. M. Dell'Acqua (University of Colorado); Eps15 Ab577 and Eps15R Ab860 were kindly provided by Dr. P. P. Di Fiore (European Cancer Institute).

Figure 11:
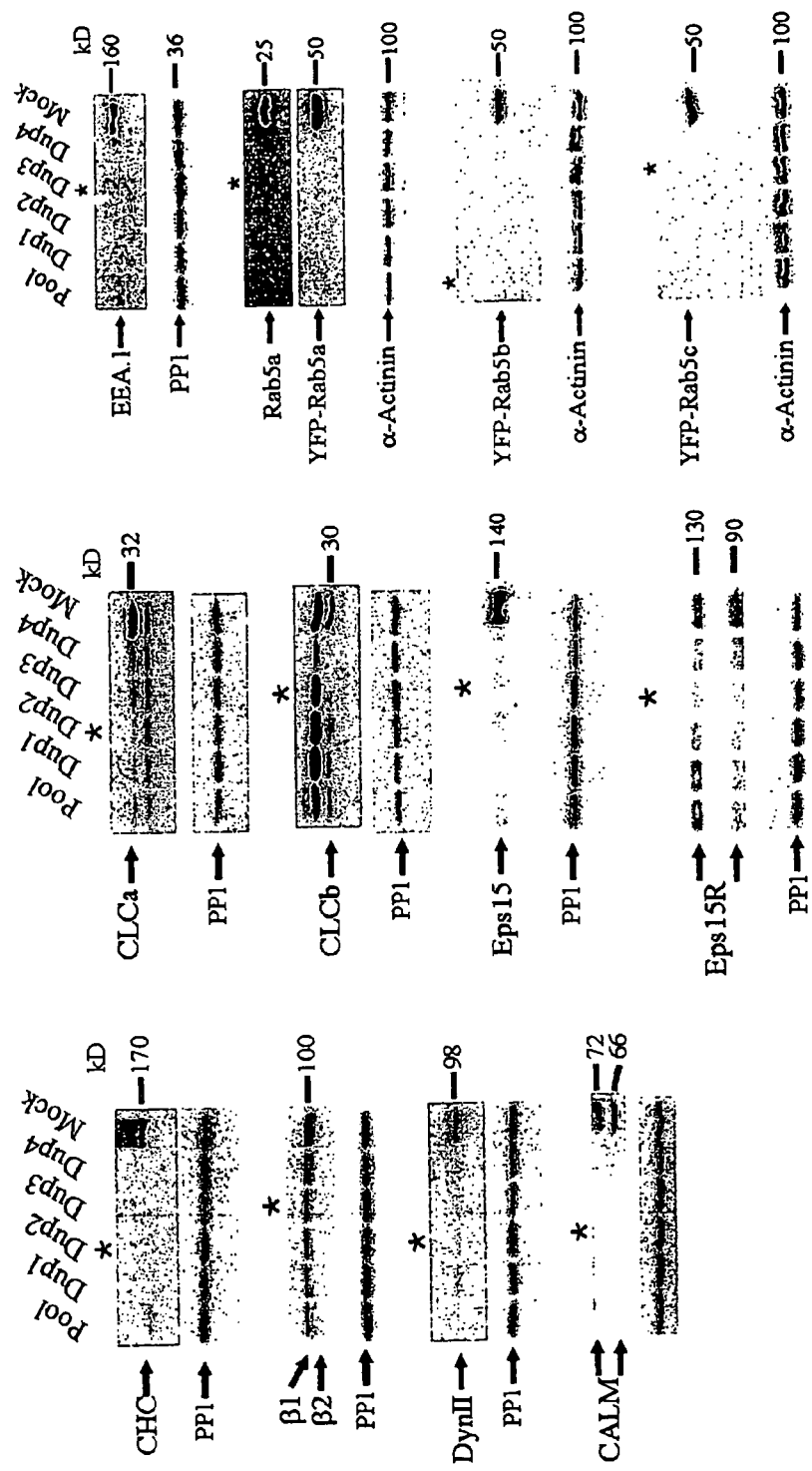
FIG. 11 shows the Western blot results from cells treated with siRNA directed against twelve different genes involved in the clathrin-dependent endocytosis pathway (CHC, DynII, CALM, CLCa, CLCb, Eps15, Eps15R, Rab5a, Rab5b, Rab5c, β2 subunit of AP-2 and EEA.1). SiRNA were selected using Formula VIII. "Pool" represents a mixture of duplexes 1-4. Total concentration of each siRNA in the pool is 25 nM. Total concentration=4×25=100 nM.

FIG. 11 demonstrates the in vivo functionality of 48 individual siRNAs, selected using Formula VIII (most of them will meet the criteria incorporated by Formula IX as well) targeting 12 genes. Various cell lines were transfected with siRNA duplexes (Dup1-4) or pools of siRNA duplexes (Pool), and the cells were lysed 3 days after transfection with the exception of CALM (2 days) and β2 (4 days).

Note a β1-adaptin band (part of AP-1 Golgi adaptor complex) that runs slightly slower than β2 adaptin. CALM has two splice variants, 66 and 72 kD. The full-length Eps15R (a doublet of ~130 kD) and several truncated spliced forms of ~100 kD and ~70 kD were detected in Eps15R immunoprecipitates (shown by arrows). The cells were lysed 3 days after transfection. Equal amounts of lysates were resolved by electrophoresis and blotted with the antibody specific to a targeted protein (GFP antibody for YFP fusion proteins) and the antibody specific to unrelated proteins PP1 phosphatase or α-actinin, and TSG101. The amount of protein in each specific band was normalized to the amount of non-specific proteins in each lane of the gel. Nearly all of them appear to be functional, which establishes that Formula VIII and IX can be used to predict siRNAs' functionality in general in a genome wide manner.

To generate the fusion of yellow fluorescent protein (YFP) with Rab5b or Rab5c (YFP-Rab5b or YFP-Rab5c), a DNA fragment encoding the full-length human Rab5b or Rab5c was obtained by PCR using Pfu polymerase (Stratagene) with a SacI restriction site introduced into the 5' end and a KpnI site into the 3' end and cloned into pEYFP-C1 vector (CLONTECH, Palo Alto, Calif., USA). GFP-CALM and YFP-Rab5a were described previously Tebar, Bohlander, & Sorkin (1999) Clathrin Assembly Lymphoid Myeloid Leukemia (CALM) Protein: Localization in Endocytic-coated Pits, Interactions with Clathrin, and the Impact of Overexpression on Clathrin-mediated Traffic, *Mol. Biol. Cell* 10:2687.

Example IV

Validation of the Algorithm Using Eg5, GADPH, ATE1, MEK2, MEK1, QB, LaminA/C, C-Myc, Human Cyclophilin, and Mouse Cyclophilin A number of genes have been identified as playing potentially important roles in disease etiology. Expression profiles of normal and diseased kidneys has implicated Edg5 in immunoglobulin A neuropathy, a common renal glomerular disease. Myc1, MEK1/2 and other related kinases have been associated with one or more cancers, while lamins have been implicated in muscular dystrophy and other diseases. For these reasons, siRNA directed against the genes encoding these classes of molecules would be important research and therapeutic tools.

Figure 12:
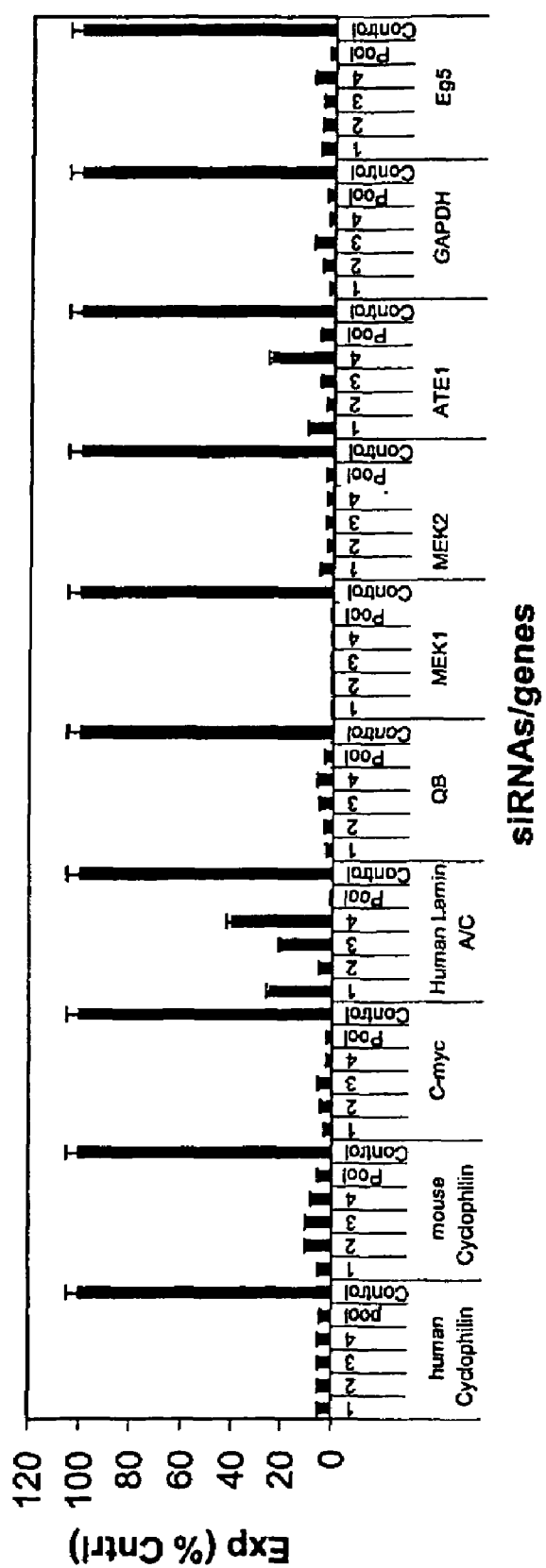
FIG. 12 is a representation of the gene silencing capabilities of rationally-selected siRNA directed against ten different genes (human and mouse cyclophilin, C-myc, human lamin A/C, QB (ubiquinol-cytochrome c reductase core protein I), MEK1 and MEK2, ATE1 (arginyl-tRNA protein transferase), GAPDH, and Eg5). The Y-axis is the percent expression of the control. Numbers 1, 2, 3 and 4 represent individual rationally selected siRNA. "Pool" represents a mixture of the four individual siRNA.

FIG. 12 illustrates four siRNAs targeting 10 different genes (Table V for sequence and accession number information) that were selected according to the Formula VIII and assayed as individuals and pools in HEK293 cells. The level of siRNA induced silencing was measured using the B-DNA assay. These studies demonstrated that thirty-six out of the forty individual SMART-selected siRNA tested are functional (90%) and all 10 pools are fully functional.

Example V

Validation of the Algorithm Using Bcl2

Bcl-2 is a ~25 kD, 205-239 amino acid, anti-apoptotic protein that contains considerable homology with other members of the BCL family including BCLX, MCL1, BAX, BAD, and BIK. The protein exists in at least two forms (Bcl2a, which has a hydrophobic tail for membrane anchorage, and Bcl2b, which lacks the hydrophobic tail) and is predominantly localized to the mitochondrial membrane. While Bcl2 expression is widely distributed, particular interest has focused on the expression of this molecule in B and T cells. Bcl2 expression is down-regulated in normal germinal center B cells yet in a high percentage of follicular lymphomas, Bcl2 expression has been observed to be elevated. Cytological studies have identified a common translocation ((14;18)(q32; q32)) amongst a high percentage (>70%) of these lymphomas. This genetic lesion places the Bcl2 gene in juxtaposition to immunoglobulin heavy chain gene (IgH) encoding sequences and is believed to enforce inappropriate levels of gene expression, and resistance to programmed cell death in the follicle center B cells. In other cases, hypomethylation of the Bcl2 promoter leads to enhanced expression and again, inhibition of apoptosis. In addition to cancer, dysregulated expression of Bcl-2 has been correlated with multiple sclerosis and various neurological diseases.

The correlation between Bcl-2 translocation and cancer makes this gene an attractive target for RNAi. Identification of siRNA directed against the bcl2 transcript (or Bcl2-IgH fusions) would further our understanding Bcl2 gene function and possibly provide a future therapeutic agent to battle diseases that result from altered expression or function of this gene.

In Silico Identification of Functional siRNA

To identify functional and hyperfunctional siRNA against the Bcl2 gene, the sequence for Bcl-2 was downloaded from the NCBI UNIGENE database and analyzed using the Formula VIII algorithm. As a result of these procedures, both the sequence and SMARTSCORES™, or siRNA rankings, of the Bcl2 siRNA were obtained and ranked according to their functionality. Subsequently, these sequences were BLAST'ed (database) to insure that the selected sequences were specific and contained minimal overlap with unrelated genes. The SMARTSCORES™, or siRNA rankings, for the top 10 Bcl-2 siRNA are identified in FIG. 13.

In Vivo Testing of Bcl-2 siRNA

Bcl-2 siRNAs having the top ten SMARTSCORES™, or siRNA rankings, were selected and tested in a functional assay to determine silencing efficiency. To accomplish this, each of the ten duplexes were synthesized using 2'-O-ACE chemistry and transfected at 100 nM concentrations into cells. Twenty-four hours later assays were performed on cell extracts to assess the degree of target silencing. Controls used in these experiments included mock transfected cells, and cells that were transfected with a non-specific siRNA duplex.

Figure 14:
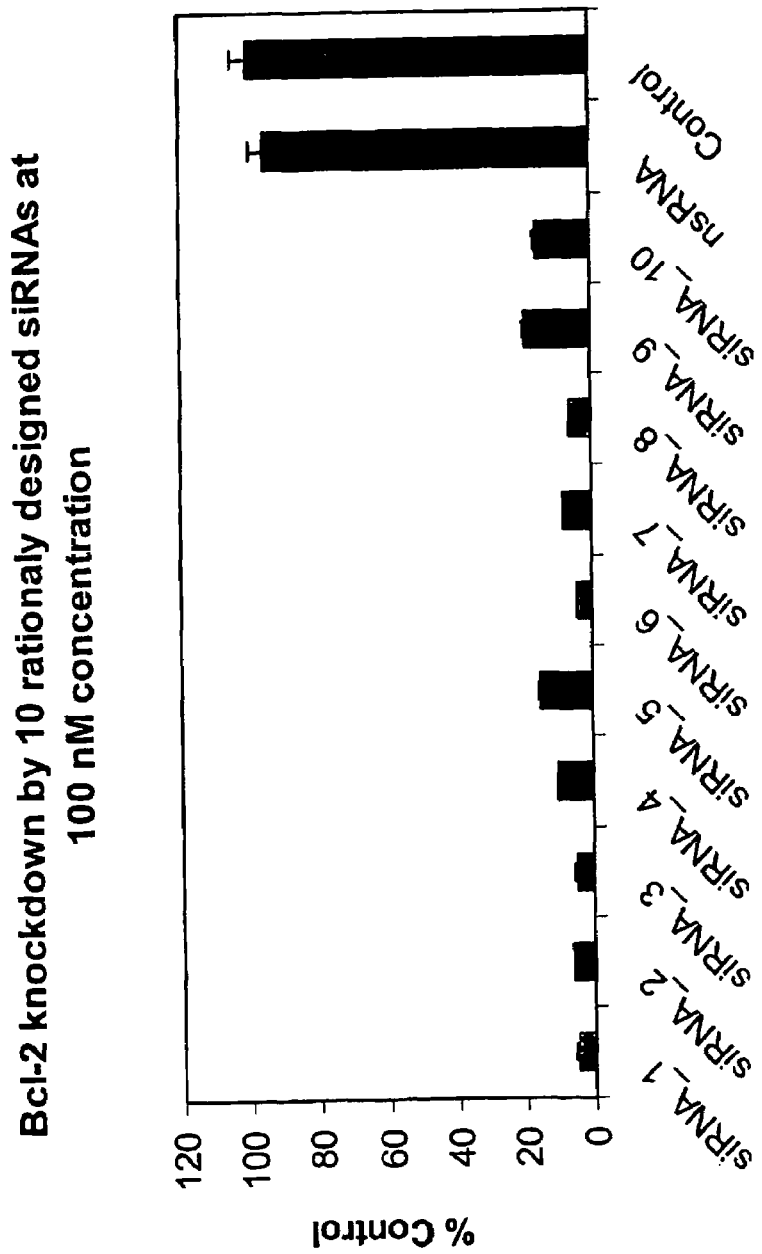
FIG. 14 is the knockdown by the top ten Bcl2 siRNAs at 100 nM concentrations. The Y-axis represents the amount of expression relative to the non-specific (ns) and transfection mixture control.

The results of these experiments are presented below (and in FIG. 14) and show that all ten of the selected siRNA induce 80% or better silencing of the Bcl2 message at 100 nM concentrations. These data verify that the algorithm successfully identified functional Bcl2 siRNA and provide a set of functional agents that can be used in experimental and therapeutic environments.

| siRNA 1 | GGGAGAUAGUGAUGAAGUA | SEQ ID NO 302 |
| siRNA 2 | GAAGUACAUCCAUUAUAAG | SEQ ID NO 303 |
| siRNA 3 | GUACGACAACCGGGAGAUA | SEQ ID NO 304 |
| siRNA 4 | AGAUAGUGAUGAAGUACAU | SEQ ID NO 305 |
| siRNA 5 | UGAAGACUCUGCUCAGUUU | SEQ ID NO 306 |
| siRNA 6 | GCAUGCGGCCUCUGUUUGA | SEQ ID NO 307 |
| siRNA 7 | UGCGGCCUCUGUUUGAUUU | SEQ ID NO 308 |
| siRNA 8 | GAGAUAGUGAUGAAGUACA | SEQ ID NO 309 |
| siRNA 9 | GGAGAUAGUGAUGAAGUAC | SEQ ID NO 310 |
| siRNA 10 | GAAGACUCUGCUCAGUUUG | SEQ ID NO 311 |

Bcl2 siRNA: Sense Strand, 5' to 3'

Example VI

Sequences Selected by the Algorithm

Sequences of the siRNAs selected using Formulas (Algorithms) VIII and IX with their corresponding ranking, which have been evaluated for the silencing activity in vivo in the present study (Formula VIII and IX, respectively).

TABLE V

| GENE NAME | ACCESSION NUMBER | SEQ ID NO | FTLLSEQTENCE | FORMULA VIII | FORMULA IX |
|---|---|---|---|---|---|
| CLTC | NM_004859 | 312 | GAAAGAAUCUGUAGAGAAA | 76 | 94.2 |
| CLTC | NM_004859 | 313 | GCAAUGAGCUGUUUGAAGA | 65 | 39.9 |
| CLTC | NM_004859 | 314 | UGACAAAGGUGGAUAAAUU | 57 | 38.2 |
| CLTC | NM_004859 | 315 | GGAAAUGGAUCUCUUUGAA | 54 | 49.4 |
| CLTA | NM_001833 | 316 | GGAAAGUAAUGGUCCAACA | 22 | 55.5 |
| CLTA | NM_001833 | 317 | AGACAGUUAUGCAGCUAUU | 4 | 22.9 |
| CLTA | NM_001833 | 318 | CCAAUUCUCGGAAGCAAGA | 1 | 17 |
| CLTA | NM_001833 | 319 | GAAAGUAAUGGUCCAACAG | -1 | -13 |
| CLTB | NM_001834 | 320 | GCGCCAGAGUGAACAAGUA | 17 | 57.5 |
| CLTB | NM_001834 | 321 | GAAGGUGGCCCAGCUAUGU | 15 | -8.6 |

TABLE V-continued

| GENE NAME | ACCESSION NUMBER | SEQ ID NO | FTLLSEQTENCE | FORMULA VIII | FORMULA IX |
|---|---|---|---|---|---|
| CLTB | NM_001834 | 322 | GGAACCAGCGCCAGAGUGA | 13 | 40.5 |
| CLTB | NM_001834 | 323 | GAGCGAGAUUGCAGGCAUA | 20 | 61.7 |
| CALM | U45976 | 324 | GUUAGUAUCUGAUGACUUG | 36 | -34.6 |
| CALM | U45976 | 325 | GAAAUGGAACCACUAAGAA | 33 | 46.1 |
| CALM | U45976 | 326 | GGAAAUGGAACCACUAAGA | 30 | 61.2 |
| CALM | U45976 | 327 | CAACUACACUUUCCAAUGC | 28 | 6.8 |
| EPS15 | NM_001981 | 328 | CCACCAAGAUUUCAUGAUA | 48 | 25.2 |
| EPS15 | NM_001981 | 329 | GAUCGGAACUCCAACAAGA | 43 | 49.3 |
| EPS15 | NM_001981 | 330 | AAACGGAGCUACAGAUUAU | 39 | 11.5 |
| EPS15 | NM_001981 | 331 | CCACACAGCAUUCUUGUAA | 33 | -23.6 |
| EPS15R | NM_021235 | 332 | GAAGUUACCUUGAGCAAUC | 48 | 33 |
| EPS15R | NM_021235 | 333 | GGACUUGGCCGAUCCAGAA | 27 | 33 |
| EPS15R | NM_021235 | 334 | GCACUUGGAUCGAGAUGAG | 20 | 1.3 |
| EPS15R | NM_021235 | 335 | CAAAGACCAAUUCGCGUUA | 17 | 27.7 |
| DNM2 | NM_004945 | 336 | CCGAAUCAAUCGCAUCUUC | 6 | -29.6 |
| DNM2 | NM_004945 | 337 | GACAUGAUCCUGCAGUUCA | 5 | -14 |
| DNM2 | NM_004945 | 338 | GAGCGAAUCGUCACCACUU | 5 | 24 |
| DNM2 | NM_004945 | 339 | CCUCCGAGCUGGCGUCUAC | -4 | -63.6 |
| ARF6 | AF93885 | 340 | UCACAUGGUUAACCUCUAA | 27 | -21.1 |
| ARF6 | AF93885 | 341 | GAUGAGGGACGCCAUAAUC | 7 | -38.4 |
| ARF6 | AF93885 | 342 | CCUCUAACUACAAAUCUUA | 4 | 16.9 |
| ARF6 | AF93885 | 343 | GGAAGGUGCUAUCCAAAAU | 4 | 11.5 |
| RAB5A | BC001267 | 344 | GCAAGCAAGUCCUAACAUU | 40 | 25.1 |
| RAB5A | BC001267 | 345 | GGAAGAGGAGUAGACCUUA | 17 | 50.1 |
| RAB5A | BC001267 | 346 | AGGAAUCAGUGUUGUAGUA | 16 | 11.5 |
| RAB5A | BC001267 | 347 | GAAGAGGAGUAGACCUUAC | 12 | 7 |
| RAB5B | NM_002868 | 348 | GAAAGUCAAGCCUGGUAUU | 14 | 18.1 |
| RAB5B | NM_002868 | 349 | AAAGUCAAGCCUGGUAUUA | 6 | -17.8 |
| RAB5B | NM_002868 | 350 | GCUAUGAACGUGAAUGAUC | 3 | -21.1 |
| RAB5B | NM_002868 | 351 | CAAGCCUGGUAUUACGUUU | -7 | -37.5 |
| RAB5C | AF141304 | 352 | GGAACAAGAUCUGUCAAUU | 38 | 51.9 |
| RAB5C | AF141304 | 353 | GCAAUGAACGUGAACGAAA | 29 | 43.7 |
| RAB5C | AF141304 | 354 | CAAUGAACGUGAACGAAAU | 18 | 43.3 |
| RAB5C | AF141304 | 355 | GGACAGGAGCGGUAUCACA | 6 | 18.2 |
| EEA1 | XM_018197 | 356 | AGACAGAGCUUGAGAAUAA | 67 | 64.1 |
| EEA1 | XM_018197 | 357 | GAGAAGAUCUUUAUGCAAA | 60 | 48.7 |
| EEA1 | XM_018197 | 358 | GAAGAGAAAUCAGCAGAUA | 58 | 45.7 |
| EEA1 | XM_018197 | 359 | GCAAGUAACUCAACUAACA | 56 | 72.3 |

TABLE V-continued

| GENE NAME | ACCESSION NUMBER | SEQ ID NO | FTLLSEQTENCE | FORMULA VIII | FORMULA IX |
|---|---|---|---|---|---|
| AP2B1 | NM_001282 | 360 | GAGCUAAUCUGCCACAUUG | 49 | -12.4 |
| AP2B1 | NM_001282 | 361 | GCAGAUGAGUUACUAGAAA | 44 | 48.9 |
| AP2B1 | NM_001282 | 362 | CAACUUAAUUGUCCAGAAA | 41 | 28.2 |
| AP2B1 | NM_001282 | 363 | CAACACAGGAUUCUGAUAA | 33 | -5.8 |
| PLK | NM_005030 | 364 | AGAUUGUGCCUAAGUCUCU | -35 | -3.4 |
| PLK | NM_005030 | 365 | AUGAAGAUCUGGAGGUGAA | 0 | -4.3 |
| PLK | NM_005030 | 366 | UUUGAGACUUCUUGCCUAA | 5 | -27.7 |
| PLK | NM_005030 | 367 | AGAUCACCCUCCUUAAAUA | 15 | 72.3 |
| GAPDH | NM_002046 | 368 | CAACGGAUUUGGUCGUAUU | 27 | -2.8 |
| GAPDH | NM_002046 | 369 | GAAAUCCCAUCACCAUCUU | 24 | 3.9 |
| GAPDH | NM_002046 | 370 | GACCUCAACUACAUGGUUU | 22 | -22.9 |
| GAPDH | NM_002046 | 371 | UGGUUUACAUGUUCCAAUA | 9 | 9.8 |
| c-Myc |  | 372 | GAAGAAAUCGAUGUUGUUU | 31 | -11.7 |
| c-Myc |  | 373 | ACACAAACUUGAACAGCUA | 22 | 51.3 |
| c-Myc |  | 374 | GGAAGAAAUCGAUGUUGUU | 18 | 26 |
| c-Myc |  | 375 | GAAACGACGAGAACAGUUG | 18 | -8.9 |
| MAP2K1 | NM_002755 | 376 | GCACAUGGAUGGAGGUUCU | 26 | 16 |
| MAP2K1 | NM_002755 | 377 | GCAGAGAGAGCAGAUUUGA | 16 | 0.4 |
| MAP2K1 | NM_002755 | 378 | GAGGUUCUCUGGAUCAAGU | 14 | 15.5 |
| MAP2K1 | NM_002755 | 379 | GAGCAGAUUUGAAGCAACU | 14 | 18.5 |
| MAP2K2 | NM_030662 | 380 | CAAAGACGAUGACUUCGAA | 37 | 26.4 |
| MAP2K2 | NM_030662 | 381 | GAUCAGCAUUUGCAUGGAA | 24 | -0.7 |
| MAP2K2 | NM_030662 | 382 | UCCAGGAGUUUGUCAAUAA | 17 | -4.5 |
| MAP2K2 | NM_030662 | 383 | GGAAGCUGAUCCACCUUGA | 16 | 59.2 |
| KNSL1(EG5) | NM_004523 | 384 | GCAGAAAUCUAAGGAUAUA | 53 | 35.8 |
| KNSL1(EG5) | NM_004523 | 385 | CAACAAGGAUGAAGUCUAU | 50 | 18.3 |
| KNSL1(EG5) | NM_004523 | 386 | CAGCAGAAAUCUAAGGAUA | 41 | 32.7 |
| KNSL1(EG5) | NM_004523 | 387 | CUAGAUGGCUUUCUCAGUA | 39 | 3.9 |
| CyclophilinA | NM_021130 | 388 | AGACAAGGUCCCAAAGACA | -16 | 58.1 |
| CyclophilinA | NM_021130 | 389 | GGAAUGGCAAGACCAGCAA | -6 | 36 |
| CyclophilinA | NM_021130 | 390 | AGAAUUAUUCCAGGGUUUA | -3 | 16.1 |
| CyclophilinA | NM_021130 | 391 | GCAGACAAGGUCCCAAAGA | 8 | 8.9 |
| LAMIN A/C | NM_170707 | 392 | AGAAGCAGCUUCAGGAUGA | 31 | 38.8 |
| LAMIN A/C | NM_170707 | 393 | GAGCUUGACUUCCAGAAGA | 33 | 22.4 |
| LAMIN A/C | NM_170707 | 394 | CCACCGAAGUUCACCCUAA | 21 | 27.5 |
| LAMIN A/C | NM_170707 | 395 | GAGAGAGCUCCUCCAUCA | 55 | 30.1 |
| CyclophilinB | M60857 | 396 | GAAAGAGCAUCUACGGUGA | 41 | 83.9 |
| CyclophilinB | M60857 | 397 | GAAAGGAUUUGGCUACAAA | 53 | 59.1 |

TABLE V-continued

| GENE NAME | ACCESSION NUMBER | SEQ ID NO | FTLLSEQTENCE | FORMULA VIII | FORMULA IX |
|---|---|---|---|---|---|
| CyclophilinB | M60857 | 398 | ACAGCAAAUUCCAUCGUGU | −20 | 28.8 |
| CyclophilinB | M60857 | 399 | GGAAAGACUGUUCCAAAAA | 2 | 27 |
| DBI1 | NM_020548 | 400 | CAACACGCCUCAUCCUCUA | 27 | −7.6 |
| DBI2 | NM_020548 | 401 | CAUGAAAGCUUACAUCAAC | 25 | −30.8 |
| DBI3 | NM_020548 | 402 | AAGAUGCCAUGAAAGCUUA | 17 | 22 |
| DBI4 | NM_020548 | 403 | GCACAUACCGCCUGAGUCU | 15 | 3.9 |
| rLUC1 | | 404 | GAUCAAAUCUGAAGAAGGA | 57 | 49.2 |
| rLUC2 | | 405 | GCCAAGAAGUUUCCUAAUA | 50 | 13.7 |
| rLUC3 | | 406 | CAGCAUAUCUUGAACCAUU | 41 | −2.2 |
| rLUC4 | | 407 | GAACAAAGGAAACGGAUGA | 39 | 29.2 |
| SeAP1 | NM_031313 | 408 | CGGAAACGGUCCAGGCUAU | 6 | 26.9 |
| SeAP2 | NM_031313 | 409 | GCUUCGAGCAGACAUGAUA | 4 | −11.2 |
| SeAP3 | NM_031313 | 410 | CCUACACGGUCCUCCUAUA | 4 | 4.9 |
| SeAP4 | NM_031313 | 411 | GCCAAGAACCUCAUCAUCU | 1 | −9.9 |
| fLUC1 | | 412 | GAUAUGGGCUGAAUACAAA | 54 | 40.4 |
| fLUC2 | | 413 | GCACUCUGAUUGACAAAUA | 47 | 54.7 |
| fLUC3 | | 414 | UGAAGUCUCUGAUUAAGUA | 46 | 34.5 |
| fLUC4 | | 415 | UCAGAGAGAUCCUCAUAAA | 40 | 11.4 |
| mCyclo_1 | NM_008907 | 416 | GCAAGAAGAUCACCAUUUC | 52 | 46.4 |
| mCyclo_2 | NM_008907 | 417 | GAGAGAAAUUUGAGGAUGA | 36 | 70.7 |
| mCyclo_3 | NM_008907 | 418 | GAAAGGAUUUGGCUAUAAG | 35 | −1.5 |
| mCyclo_4 | NM_008907 | 419 | GAAAGAAGGCAUGAACAUU | 27 | 10.3 |
| BCL2_1 | NM_000633 | 420 | GGGAGAUAGUGAUGAAGUA | 21 | 72 |
| BCL2_2 | NM_000633 | 421 | GAAGUACAUCCAUUAUAAG | 1 | 3.3 |
| BCL2_3 | NM_000633 | 422 | GUACGACAACCGGGAGAUA | 1 | 35.9 |
| BCL2_4 | NM_000633 | 423 | AGAUAGUGAUGAAGUACAU | −12 | 22.1 |
| BCL2_5 | NM_000633 | 424 | UGAAGACUCUGCUCAGUUU | 36 | 19.1 |
| BCL2_6 | NM_000633 | 425 | GCAUGCGGCCUCUGUUUGA | 5 | −9.7 |
| QB1 | NM_003365.1 | 426 | GCACACAGCUUACUACAUC | 52 | −4.8 |
| QB2 | NM_003365.1 | 427 | GAAAUGCCCUGGUAUCUCA | 49 | 22.1 |
| QB3 | NM_003365.1 | 428 | GAAGGAACGUGAUGUGAUC | 34 | 22.9 |
| QB4 | NM_003365.1 | 429 | GCACUACUCCUGUGUGUGA | 28 | 20.4 |
| ATE1-1 | NM_007041 | 430 | GAACCCAGCUGGAGAACUU | 45 | 15.5 |
| ATE1-2 | NM_007041 | 431 | GAUAUACAGUGUGAUCUUA | 40 | 12.2 |
| ATE1-3 | NM_007041 | 432 | GUACUACGAUCCUGAUUAU | 37 | 32.9 |
| ATE1-4 | NM_007041 | 433 | GUGCCGACCUUUACAAUUU | 35 | 18.2 |
| EGFR-1 | NM_005228 | 434 | GAAGGAAACUGAAUUCAAA | 68 | 79.4 |
| EGFR-1 | NM_005228 | 435 | GGAAAUAUGUACUACGAAA | 49 | 49.5 |

TABLE V-continued

| GENE NAME | ACCESSION NUMBER | SEQ ID NO | FTLLSEQTENCE | FORMULA VIII | FORMULA IX |
|---|---|---|---|---|---|
| EGFR-1 | NM_005228 | 436 | CCACAAAGCAGUGAAUUUA | 41 | 7.6 |
| EGFR-1 | NM_005228 | 437 | GUAACAAGCUCACGCAGUU | 40 | 25.9 |

Example VII

Genome-Wide Application of the Algorithm

The examples described above demonstrate that the algorithm(s) can successfully identify functional siRNA and that these duplexes can be used to induce the desirable phenotype of transcriptional knockdown or knockout. Each gene or family of genes in each organism plays an important role in maintaining physiological homeostasis and the algorithm can be used to develop functional, highly functional, or hyper-functional siRNA to each gene. To accomplish this for the human genome, the entire online NCBI REFSEQ database was accessed through ENTREZ (EFETCH). The database was processed through Formula VIII. For each gene the top 80-100 scores for siRNAs were obtained and BLAST'ed to insure that the selected sequences are specific in targeting the gene of choice. These sequences are provided on the compact disks in electronic form in parent application Ser. No. 10/714,333.

Many of the genes to which the described siRNA are directed play critical roles in disease etiology. For this reason, the siRNA listed in the compact disk may potentially act as therapeutic agents. A number of prophetic examples follow and should be understood in view of the siRNA that are identified on the compact disk. To isolate these siRNA, the appropriate message sequence for each gene is analyzed using one of the before mentioned formulas (preferably formula VIII) to identify potential siRNA targets. Subsequently these targets are BLAST'ed to eliminate homology with potentially off-targets.

The siRNA sequences listed above are presented in a 5'→3' sense strand direction. In addition, siRNA directed against the targets listed above as well as those directed against other targets and listed in the compact disk may be useful as therapeutic agents.

Example VIII

Evidence for the Benefits of Pooling

Evidence for the benefits of pooling have been demonstrated using the reporter gene, luciferase. Ninety siRNA duplexes were synthesized using Dharmacon proprietary ACE® chemistry against one of the standard reporter genes: firefly luciferase. The duplexes were designed to start two base pairs apart and to cover approximately 180 base pairs of the luciferase gene (see sequences in Table IV). Subsequently, the siRNA duplexes were co-transfected with a luciferase expression reporter plasmid into HEK293 cells using standard transfection protocols and luciferase activity was assayed at 24 and 48 hours.

Figure 15:
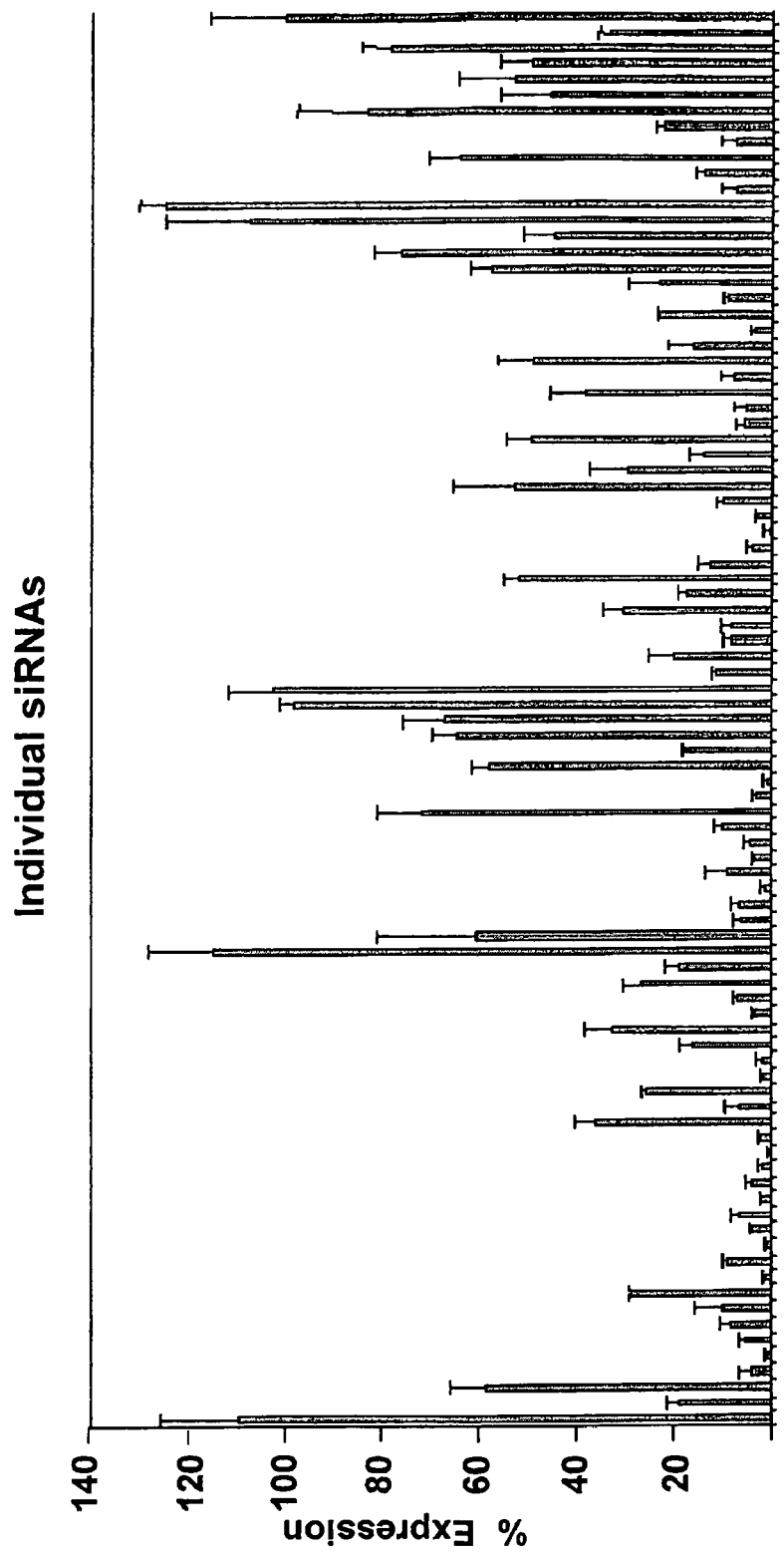
FIG. 15 represents a functional walk where siRNA beginning on every other base pair of a region of the luciferase gene are tested for the ability to silence the luciferase gene. The Y-axis represents the percent expression relative to a control. The X-axis represents the position of each individual siRNA. Reading from left to right across the X-axis, the position designations are 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, and Plasmid.

Transfection of individual siRNAs showed standard distribution of inhibitory effect. Some duplexes were active, while others were not. FIG. 15 represents a typical screen of ninety siRNA duplexes (SEQ ID NO 032-120) positioned two base pairs apart. As the figure suggests, the functionality of the siRNA duplex is determined more by a particular sequence of the oligonucleotide than by the relative oligonucleotide position within a gene or excessively sensitive part of the mRNA, which is important for traditional anti-sense technology.

Figure 16A:
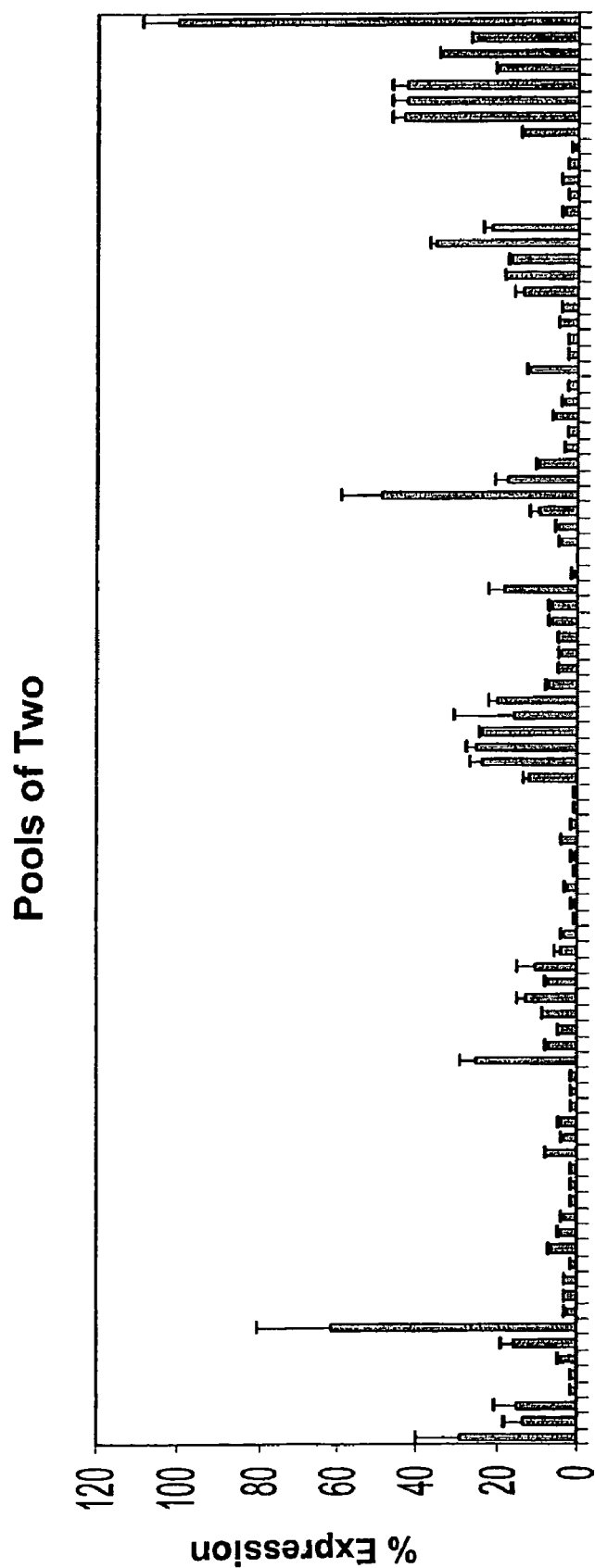
FIGS. 16A and 16B are histograms demonstrating the inhibition of target gene expression by pools of 2 (16A) and 3 (16B) siRNA duplexes taken from the walk described in FIG. 15. The Y-axis in each represents the percent expression relative to control. The X-axis in each represents the position of the first siRNA in paired pools, or trios of siRNAs. For instance, the first paired pool contains siRNAs 1 and 3. The second paired pool contains siRNAs 3 and 5. Pool 3 (of paired pools) contains siRNAs 5 and 7, and so on. For each of 16A and 16B, the X-axis from left to right designations are 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, and Plasmid.
Figure 16B:
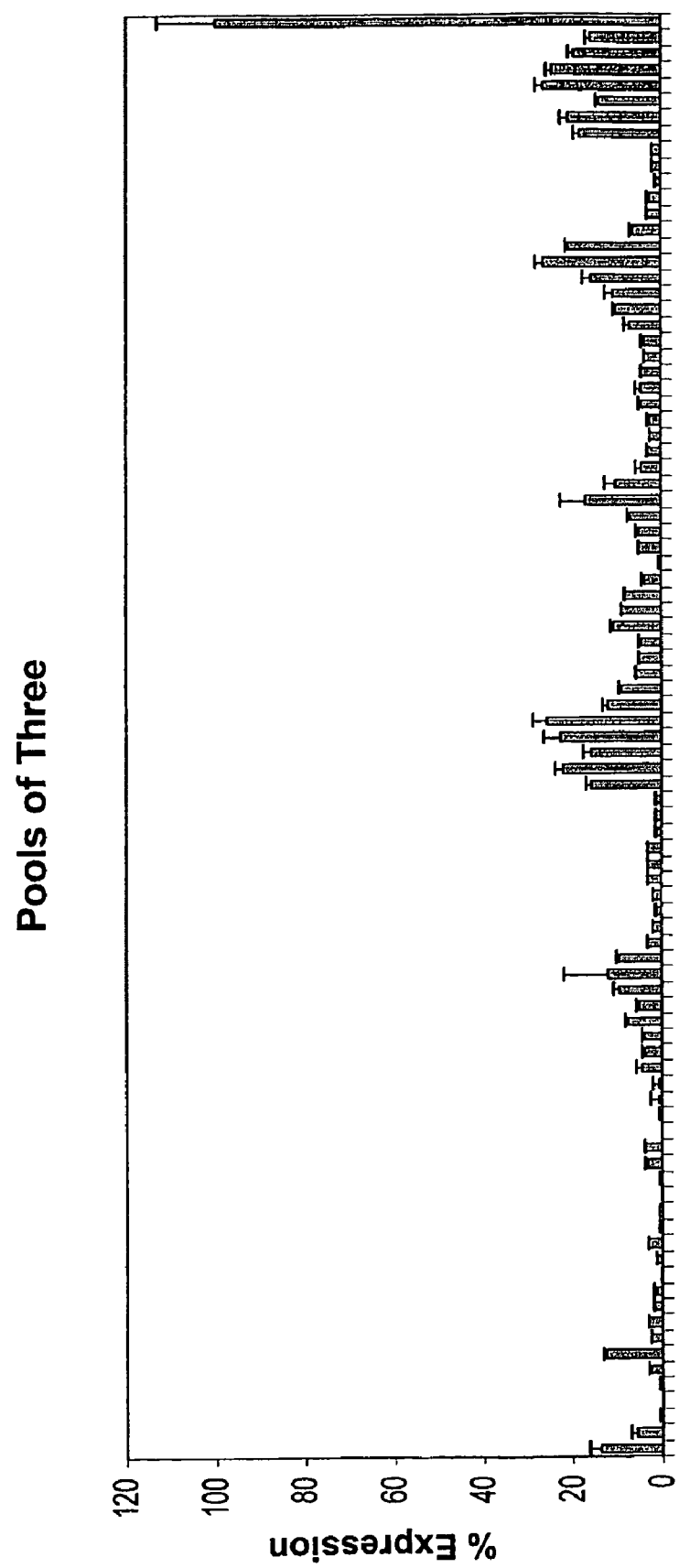
Figure 17A:
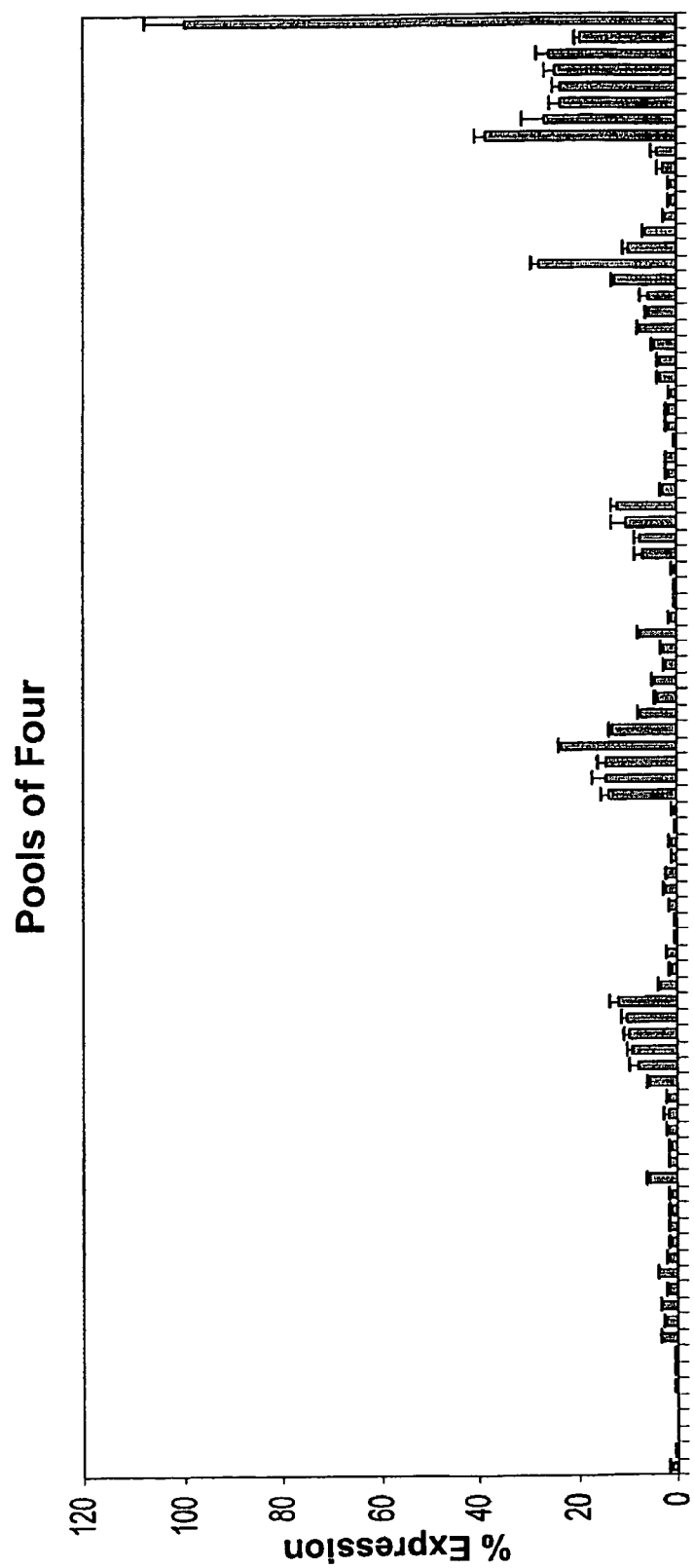
FIGS. 17A and 17B are histograms demonstrating the inhibition of target gene expression by pools of 4 (17A) and 5 (17B) siRNA duplexes. The Y-axis in each represents the percent expression relative to control. The X-axis in each represents the position of the first siRNA in each pool. For each of 17A and 17B, the X-axis from left to right is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, and Plasmid.
Figure 17B:
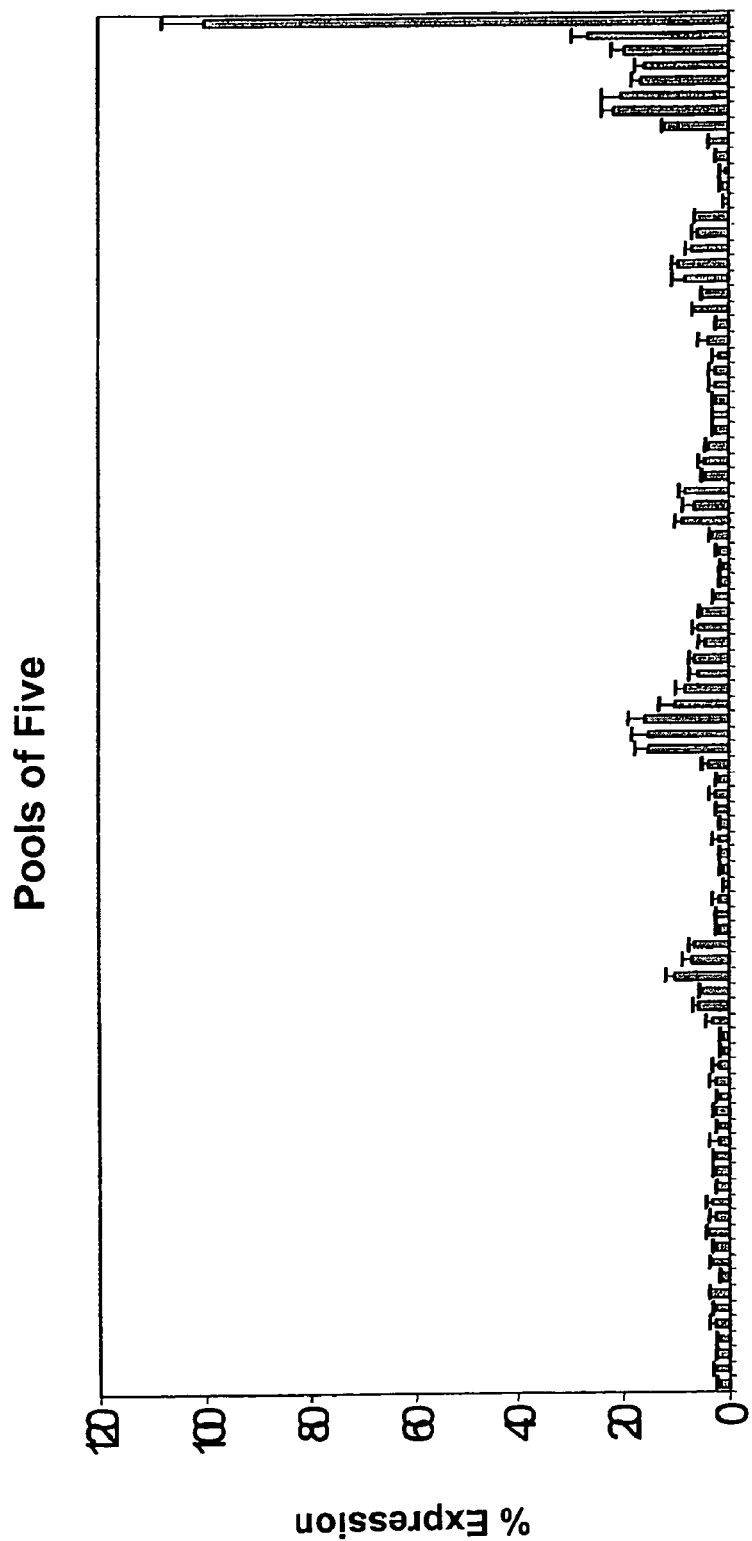
Figure 18A:
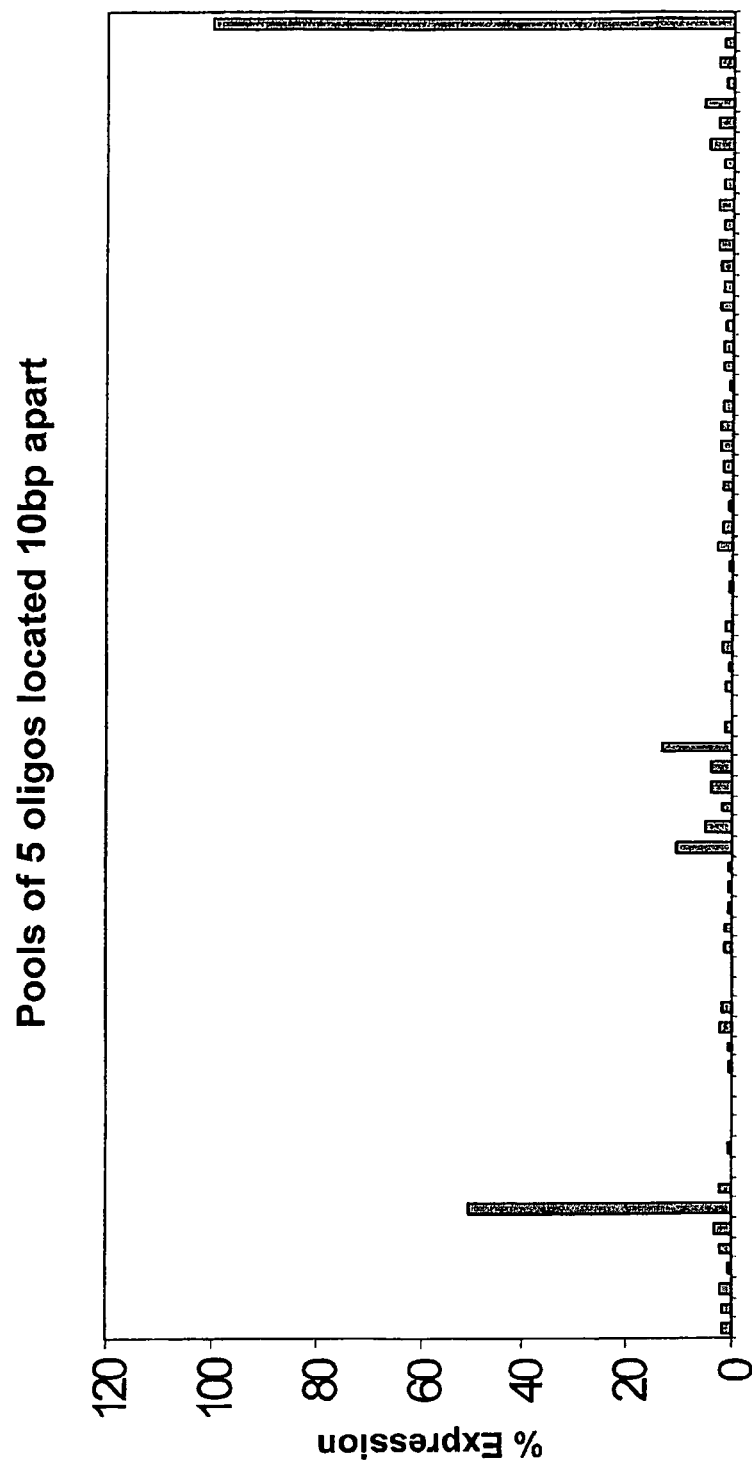
FIGS. 18A and 18B are histograms demonstrating the inhibition of target gene expression by siRNAs that are ten (18A) and twenty (18B) base pairs apart. The Y-axis represents the percent expression relative to a control. The X-axis represents the position of the first siRNA in each pool. For 18A, the X-axis from left to right designations are 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, and Plasmid. For 18B, the X-axis from left to right designations are 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, and Plasmid.
Figure 18B:
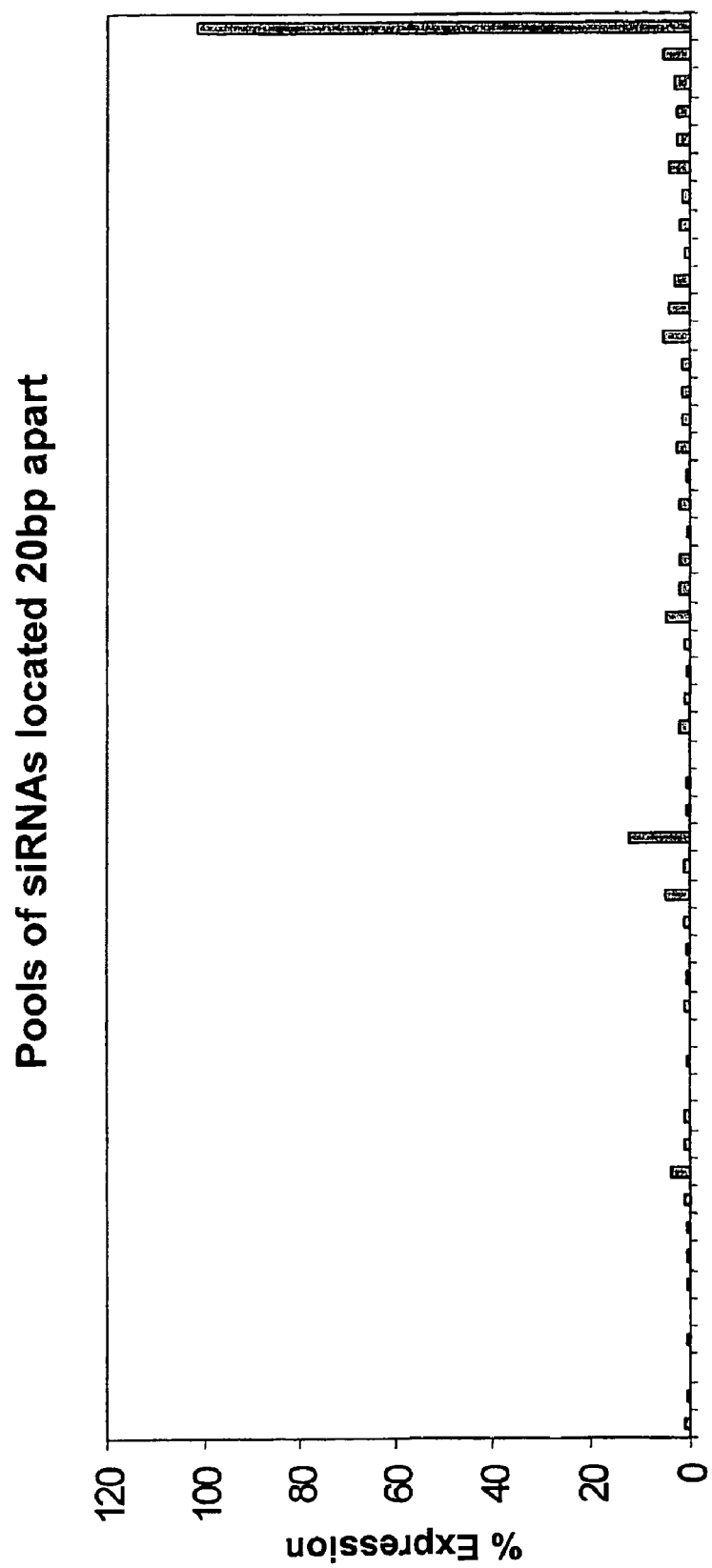

When two continuous oligonucleotides were pooled together, a significant increase in gene silencing activity was observed (see FIGS. 16A and 16B). A gradual increase in efficacy and the frequency of pools functionality was observed when the number of siRNAs increased to 3 and 4 (see FIGS. 16A, 16B, 17A, and 17B). Further, the relative positioning of the oligonucleotides within a pool did not determine whether a particular pool was functional (see FIGS. 18A and 18B, in which 100% of pools of oligonucleotides distanced by 2, 10 and 20 base pairs were functional).

However, relative positioning may nonetheless have an impact. An increased functionality may exist when the siRNA are positioned continuously head to toe (5' end of one directly adjacent to the 3' end of the others).

Figure 19:
FIG. 19 shows that pools of siRNAs (dark gray bar) work as well (or better) than the best siRNA in the pool (light gray bar). The Y-axis represents the percent expression relative to a control. The X-axis represents the position of the first siRNA in each pool. The X-axis from left to right designations are 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, and Plasmid.
Figure 20:
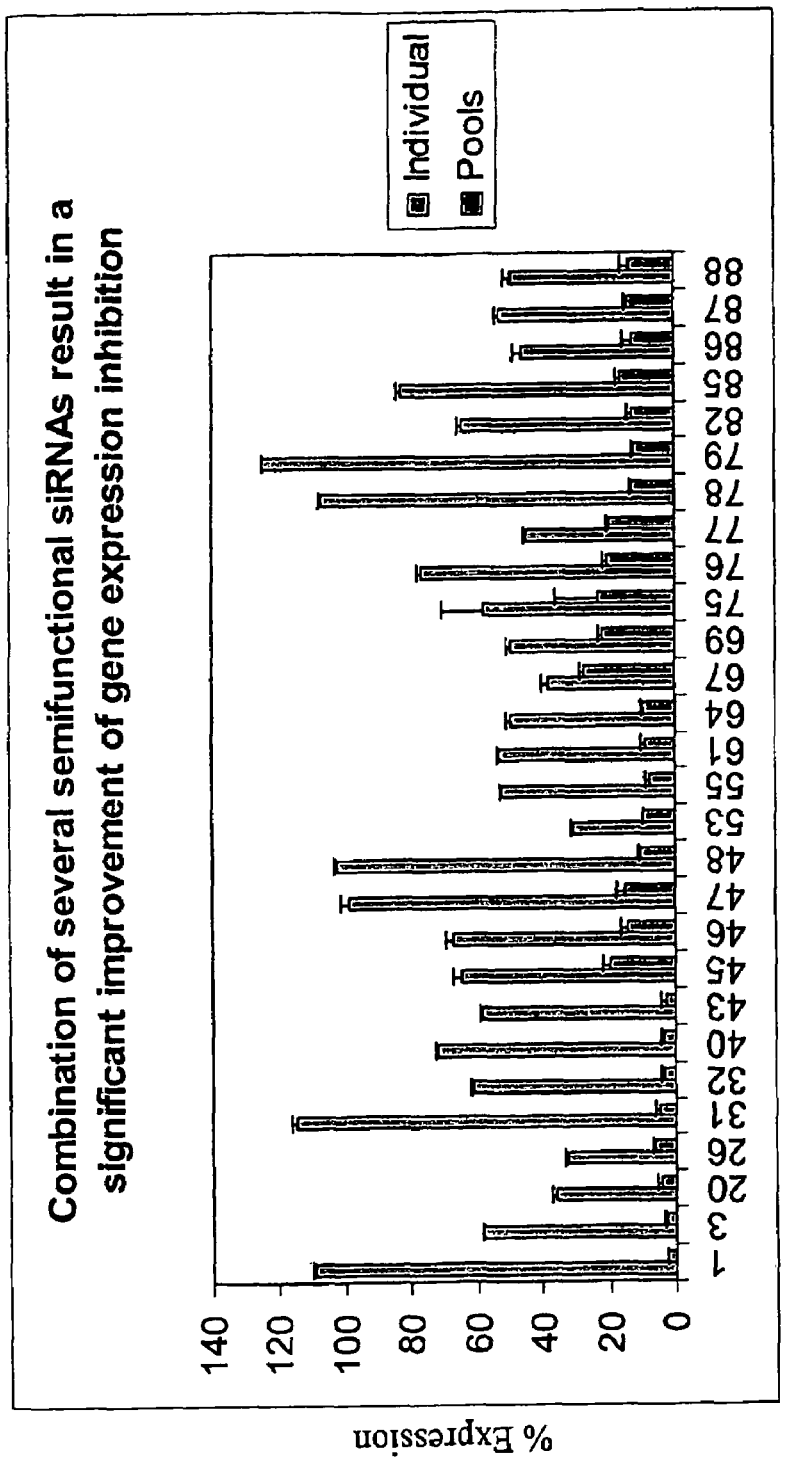
FIG. 20 shows that the combination of several semifunctional siRNAs (dark gray) result in a significant improvement of gene expression inhibition over individual (semi-functional; light gray) siRNA. The Y-axis represents the percent expression relative to a control.

Additionally, siRNA pools that were tested performed at least as well as the best oligonucleotide in the pool, under the experimental conditions whose results are depicted in FIG. 19. Moreover, when previously identified non-functional and marginally (semi) functional siRNA duplexes were pooled together in groups of five at a time, a significant functional cooperative action was observed (see FIG. 20). In fact, pools of semi-active oligonucleotides were 5 to 25 times more functional than the most potent oligonucleotide in the pool. Therefore, pooling several siRNA duplexes together does not interfere with the functionality of the most potent siRNAs within a pool, and pooling provides an unexpected significant increase in overall functionality

Example IX

Pooling Across Species

Figure 21:
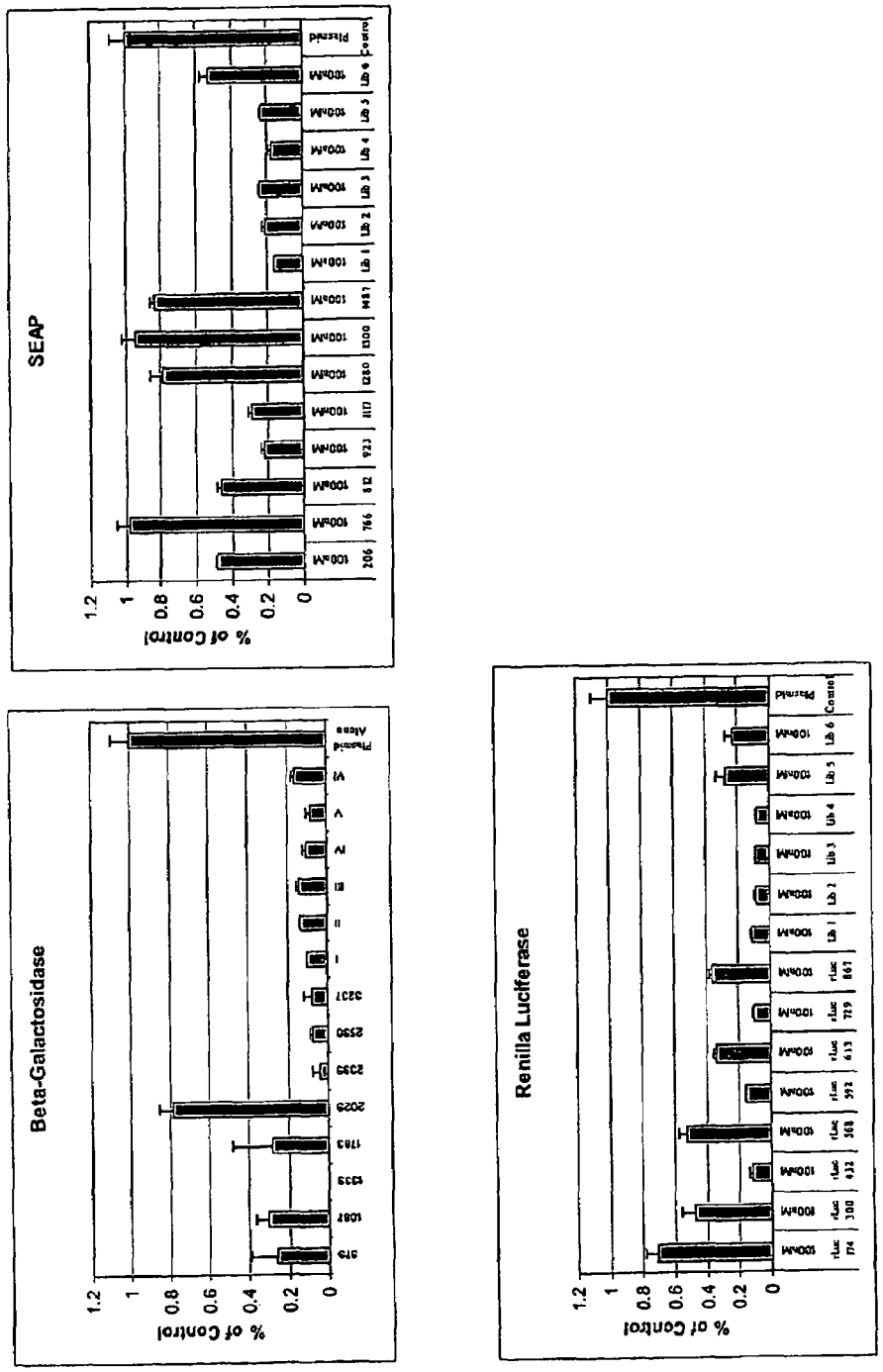
FIG. 21 shows both pools (Library, Lib) and individual siRNAs in inhibition of gene expression of Beta-Galactosidase, *Renilla* Luciferase and SEAP (alkaline phosphatase). Numbers on the X-axis indicate the position of the 5'-most nucleotide of the sense strand of the duplex. The Y-axis represents the percent expression of each gene relative to a control. Libraries contain siRNAs that begin at the following nucleotides: Seap: Lib 1: 206, 766, 812, 923, Lib 2: 1117, 1280, 1300, 1487, Lib 3: 206, 766, 812, 923, 1117, 1280, 1300, 1487, Lib 4: 206, 812, 1117, 1300, Lib 5: 766, 923, 1280, 1487, Lib 6: 206, 1487; Bgal: Lib 1: 979, 1339, 2029, 2590, Lib 2: 1087, 1783, 2399, 3257, Lib 3: 979, 1783, 2590, 3257, Lib 4: 979, 1087, 1339, 1783, 2029, 2399, 2590, 3257, Lib 5: 979, 1087, 1339, 1783, Lib 6: 2029, 2399, 2590, 3257; *Renilla*: Lib 1: 174, 300, 432, 568, Lib 2: 592, 633, 729, 867, Lib 3: 174, 300, 432, 568, 592, 633, 729, 867, Lib 4: 174, 432, 592, 729, Lib 5: 300, 568, 633, 867, Lib 6: 592, 568.

Experiments were performed on the following genes: β-galactosidase, *Renilla* luciferase, and Secreted alkaline phosphatase, which demonstrates the benefits of pooling (see FIG. 21). Approximately 50% of individual siRNAs designed to silence the above-specified genes were functional, while 100% of the pools that contain the same siRNA duplexes were functional.

Example X

Highly Functional siRNA

Pools of five siRNAs in which each two siRNAs overlap to 10-90% resulted in 98% functional entities (>80% silencing). Pools of siRNAs distributed throughout the mRNA that were evenly spaced, covering an approximate 20-2000 base pair range, were also functional. When the pools of siRNA were positioned continuously head to tail relative to mRNA sequences and mimicked the natural products of Dicer cleaved long double stranded RNA, 98% of the pools evidenced highly functional activity (>95% silencing).

Example XI

Human Cyclophyline

Table IV above lists the siRNA sequences for the human cyclophyline protein. A particularly functional siRNA may be selected by applying these sequences to any of Formula I to VII above.

Alternatively, one could pool 2, 3, 4, 5 or more of these sequences to create a kit for silencing a gene. Preferably, within the kit there would be at least one sequence that has a relatively high predicted functionality when any of Formulas I-VII is applied.

Example XII

Sample Pools of siRNAs and their Application to Human Disease

The genetic basis behind human disease is well documented and siRNA may be used as both research or diagnostic tools and therapeutic agents, either individually or in pools. Genes involved in signal transduction, the immune response, apoptosis, DNA repair, cell cycle control, and a variety of other physiological functions have clinical relevance and therapeutic agents that can modulate expression of these genes may alleviate some or all of the associated symptoms. In some instances, these genes can be described as a member of a family or class of genes and siRNA (randomly, conventionally, or rationally designed) can be directed against one or multiple members of the family to induce a desired result.

To identify rationally designed siRNA to each gene, the sequence was analyzed using Formula VIII to identify a SMARTpool containing the functional sequences. To confirm the activity of these sequences, the siRNA are introduced into a cell type of choice (e.g. HeLa cells, HEK293 cells) and the levels of the appropriate message are analyzed using one of several art proven techniques. siRNA having heightened levels of potency can be identified by testing each of the before mentioned duplexes at increasingly limiting concentrations. Similarly, siRNA having increased levels of longevity can be identified by introducing each duplex into cells and testing functionality at 24, 48, 72, 96, 120, 144, 168, and 192 hours after transfection. Agents that induce >95% silencing at sub-nanomolar concentrations and/or induce functional levels of silencing for >96 hours are considered hyperfunctional.

Example XIII

Validation of Multigene Knockout Using Rab5 and Eps

Two or more genes having similar, overlapping functions often leads to genetic redundancy. Mutations that knockout only one of, e.g., a pair of such genes (also referred to as homologs) results in little or no phenotype due to the fact that the remaining intact gene is capable of fulfilling the role of the disrupted counterpart. To fully understand the function of such genes in cellular physiology, it is often necessary to knockout or knockdown both homologs simultaneously. Unfortunately, concomitant knockdown of two or more genes is frequently difficult to achieve in higher organisms (e.g. mice) thus it is necessary to introduce new technologies dissect gene function. One such approach to knocking down multiple genes simultaneously is by using siRNA. For example, FIG. 11 showed that rationally designed siRNA directed against a number of genes involved in the clathrin-mediated endocytosis pathway resulted in significant levels of protein reduction (e.g. >80%). To determine the effects of gene knockdown on clathrin-related endocytosis, internalization assays were performed using epidermal growth factor and transferrin. Specifically, mouse receptor-grade EGF (Collaborative Research Inc.) and iron-saturated human transferrin (Sigma) were iodinated as described previously (Jiang, X., Huang, F., Marusyk, A. & Sorkin, A. (2003) *Mol Biol Cell* 14, 858-70). HeLa cells grown in 12-well dishes were incubated with $^{125}$I-EGF (1 ng/ml) or $^{125}$I-transferrin (1 µg/ml) in binding medium (DMEM, 0.1% bovine serum albumin) at 37° C., and the ratio of internalized and surface radioactivity was determined during 5-min time course to calculate specific internalization rate constant $k_e$ as described previously (Jiang, X et al.). The measurements of the uptakes of radiolabeled transferrin and EGF were performed using short time-course assays to avoid influence of the recycling on the uptake kinetics, and using low ligand concentration to avoid saturation of the clathrin-dependent pathway (for EGF Lund, K. A., Opresko, L. K., Strarbuck, C., Walsh, B. J. & Wiley, H. S. (1990) *J. Biol. Chem.* 265, 15713-13723).

Figure 22:
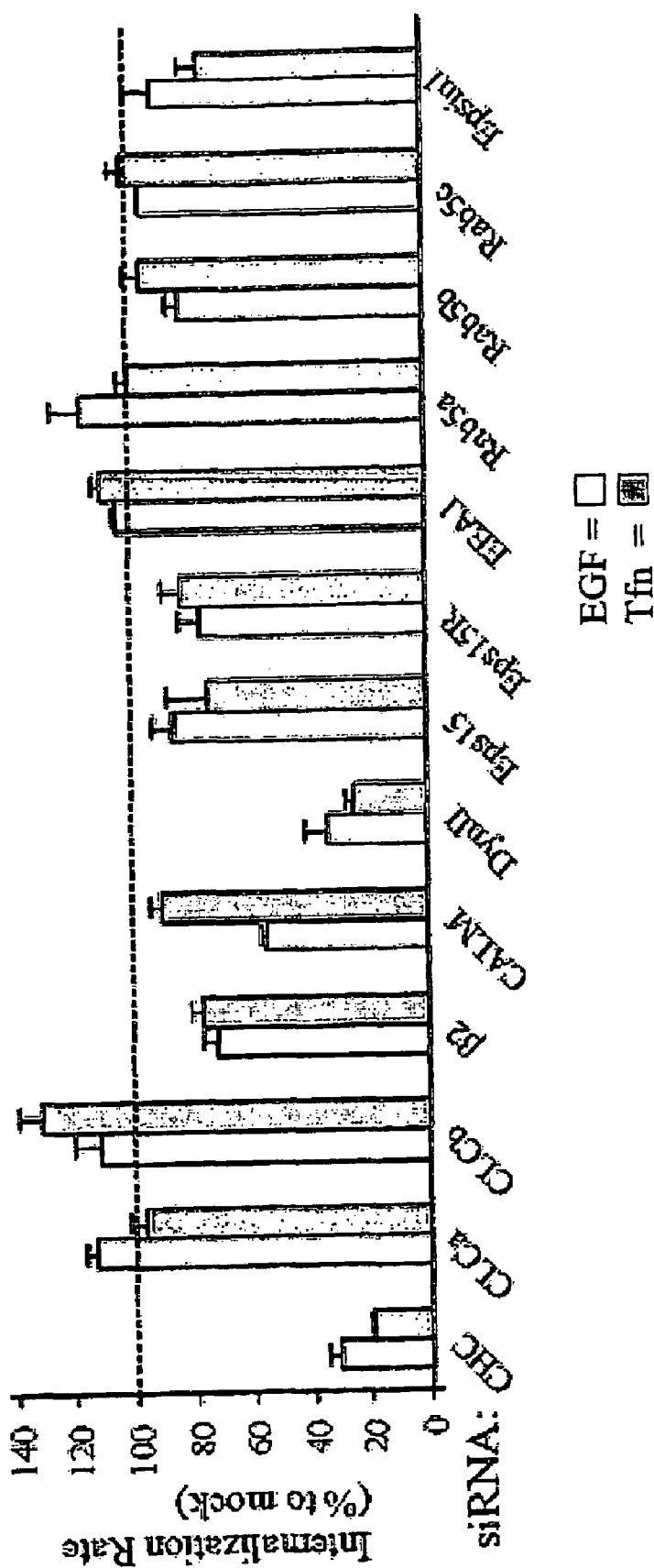
FIG. 22 shows the results of an EGFR and TfnR internalization assay when single gene knockdowns are performed. The Y-axis represents percent internalization relative to control.
Figure 23:
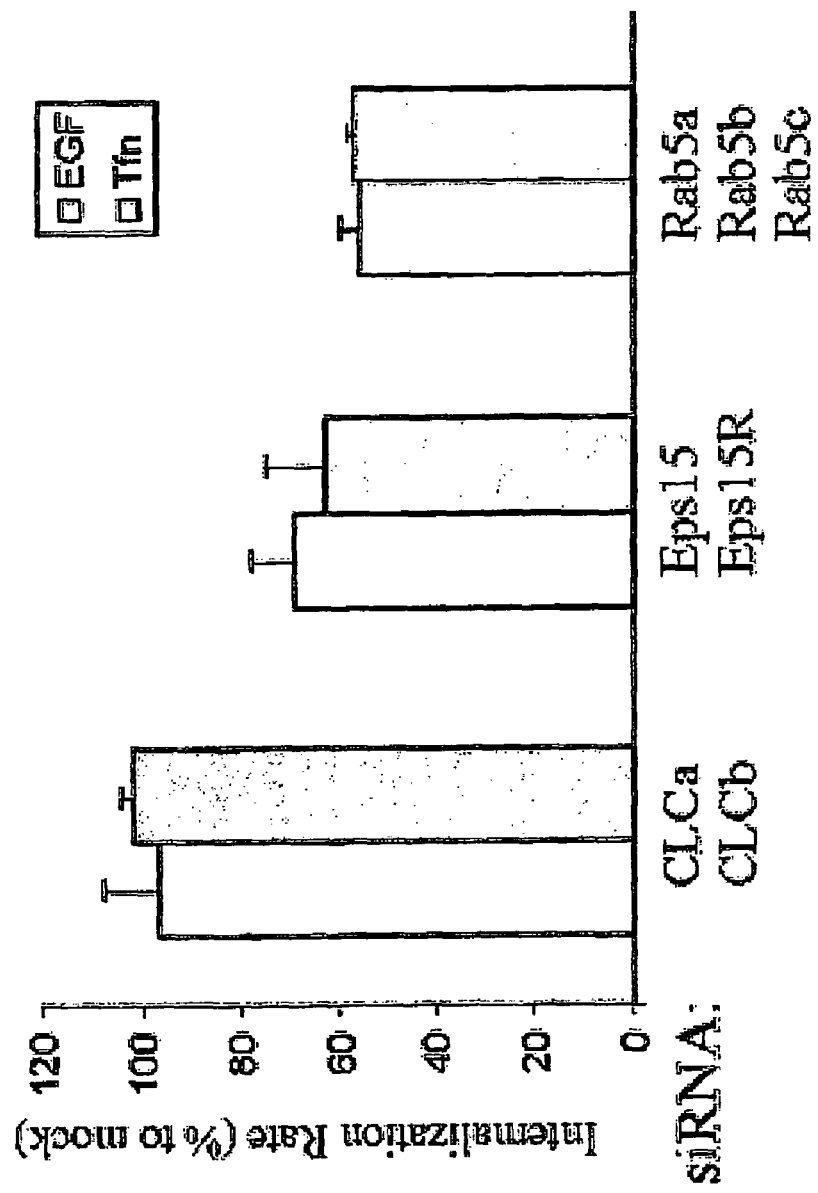
FIG. 23 shows the results of an EGFR and TfnR internalization assay when multiple genes are knocked down (e.g. Rab5a, b, c). The Y-axis represents the percent internalization relative to control.

The effects of knocking down Rab5a, 5b, 5c, Eps, or Eps 15R (individually) are shown in FIG. 22 and demonstrate that disruption of single genes has little or no effect on EGF or Tfn internalization. In contrast, simultaneous knock down of Rab5a, 5b, and 5c, or Eps and Eps 15R, leads to a distinct phenotype (note: total concentration of siRNA in these experiments remained constant with that in experiments in which a single siRNA was introduced, see FIG. 23). These experiments demonstrate the effectiveness of using rationally designed siRNA to knockdown multiple genes and validates the utility of these reagents to override genetic redundancy.

Example XIV

Validation of Multigene Targeting Using G6PD, GAPDH, PLK, and UQC

Figure 24:
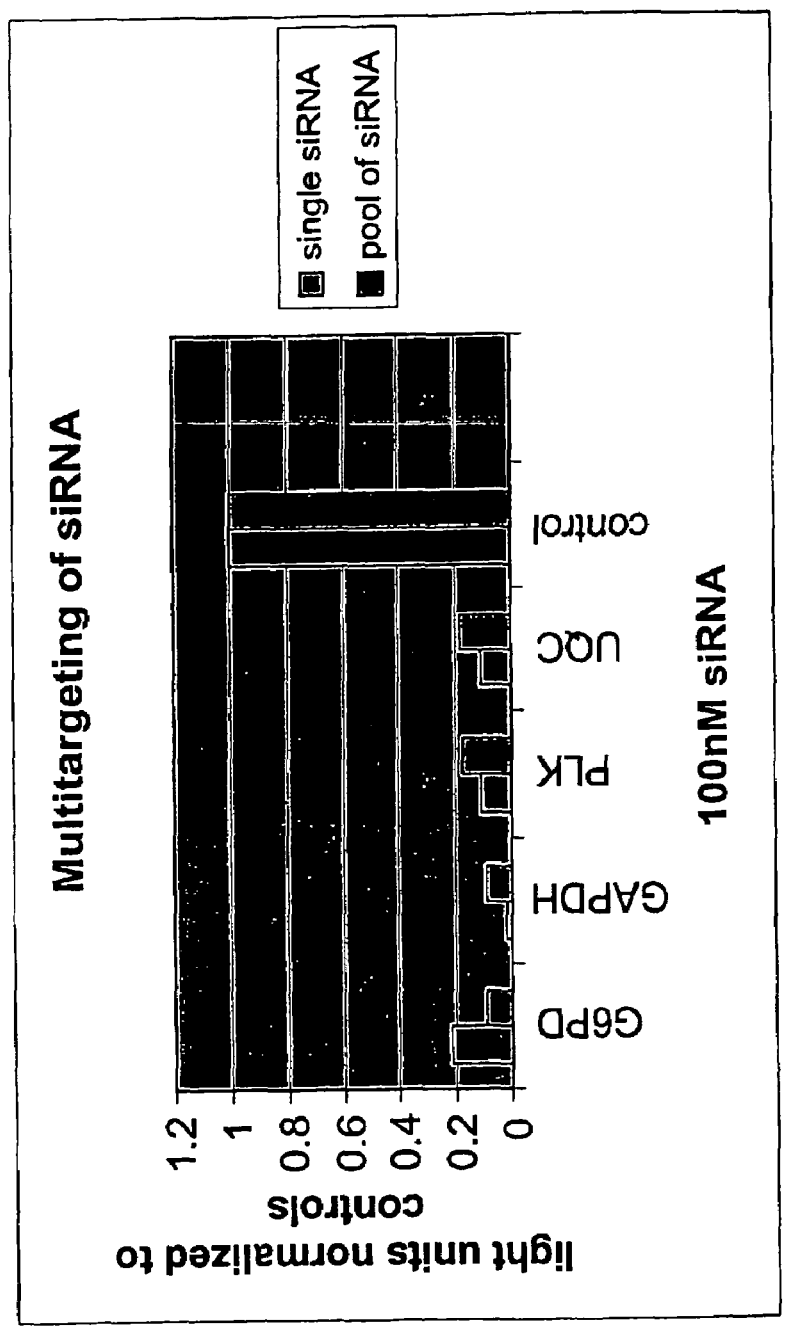
FIG. 24 shows the simultaneous knockdown of four different genes. siRNAs directed against G6PD, GAPDH, PLK, and UBQ were simultaneously introduced into cells. Twenty-four hours later, cultures were harvested and assayed for mRNA target levels for each of the four genes. A comparison is made between cells transfected with individual siRNAs vs. a pool of siRNAs directed against all four genes.

Further demonstration of the ability to knock down expression of multiple genes using rationally designed siRNA was performed using pools of siRNA directed against four separate genes. To achieve this, siRNA were transfected into cells (total siRNA concentration of 100 nM) and assayed twenty-four hours later by B-DNA. Results shown in FIG. 24 show that pools of rationally designed molecules are capable of simultaneously silencing four different genes.

Example XV

Validation of Multigene Knockouts as Demonstrated by Gene Expression Profiling, a Prophetic Example To further demonstrate the ability to concomitantly knock-down the expression of multiple gene targets, single siRNA or siRNA pools directed against a collection of genes (e.g. 4, 8, 16, or 23 different targets) are simultaneously transfected into cells and cultured for twenty-four hours. Subsequently, mRNA is harvested from treated (and untreated) cells and labeled with one of two fluorescent probes dyes (e.g. a red fluorescent probe for the treated cells, a green fluorescent probe for the control cells.). Equivalent amounts of labeled RNA from each sample is then mixed together and hybridized to sequences that have been linked to a solid support (e.g. a slide, "DNA CHIP"). Following hybridization, the slides are washed and analyzed to assess changes in the levels of target genes induced by siRNA.

Example XVI

Identifying Hyperfunctional siRNA

Identification of Hyperfunctional Bcl2 siRNA

Figure 25:
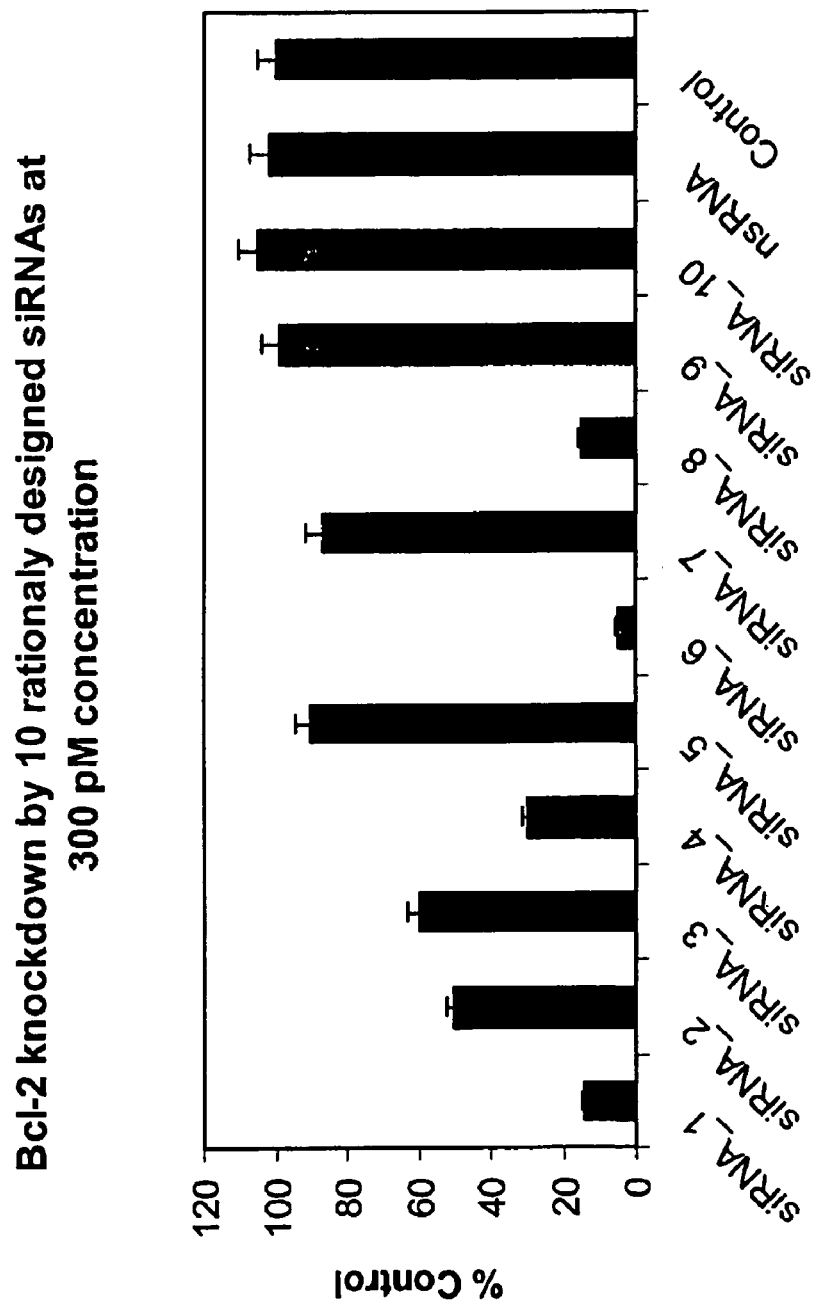
FIG. 25 shows the functionality of ten siRNAs at 0.3 nM concentrations.

The ten rationally designed Bcl2 siRNA (identified in FIGS. 13, 14) were tested to identify hyperpotent reagents. To accomplish this, each of the ten Bcl-2 siRNA were individually transfected into cells at a 300 µM (0.3 nM) concentrations. Twenty-four hours later, transcript levels were assessed by B-DNA assays and compared with relevant controls. As shown in FIG. 25, while the majority of Bcl-2 siRNA failed to induce functional levels of silencing at this concentration, siRNA 1 and 8 induced >80% silencing, and siRNA 6 exhibited greater than 90% silencing at this subnanomolar concentration.

Example XVII

Gene Silencing: Prophetic Example

Below is an example of how one might transfect a cell.

Select a cell line. The selection of a cell line is usually determined by the desired application. The most important feature to RNAi is the level of expression of the gene of interest. It is highly recommended to use cell lines for which siRNA transfection conditions have been specified and validated.

Plate the cells. Approximately 24 hours prior to transfection, plate the cells at the appropriate density so that they will be approximately 70-90% confluent, or approximately 1×10⁵ cells/ml at the time of transfection. Cell densities that are too low may lead to toxicity due to excess exposure and uptake of transfection reagent-siRNA complexes. Cell densities that are too high may lead to low transfection efficiencies and little or no silencing. Incubate the cells overnight. Standard incubation conditions for mammalian cells are 37° C. in 5% $CO_2$. Other cell types, such as insect cells, require different temperatures and $CO_2$ concentrations that are readily ascertainable by persons skilled in the art. Use conditions appropriate for the cell type of interest.

siRNA re-suspension. Add 20 µl siRNA universal buffer to each siRNA to generate a final concentration of 50 µM.

siRNA-lipid complex formation. Use RNase-free solutions and tubes. Using the following table, Table VI

TABLE VI

|  | 96-WELL | 24-WELL |
|---|---|---|
| MIXTURE 1 (TRANSIT-TKO-PLASMID DILUTION MIXTURE) | | |
| Opti-MEM | 9.3 µl | 46.5 µl |
| TransIT-TKO (1 µg/µl) | 0.5 µl | 2.5 µl |
| MIXTURE 1 FINAL VOLUME | 10.0 µl | 50.0 µl |
| MIXTURE 2 (SIRNA DILUTION MIXTURE) | | |
| Opti-MEM | 9.0 µl | 45.0 µl |
| siRNA (1 µM) | 1.0 µl | 5.0 µl |
| MIXTURE 2 FINAL VOLUME | 10.0 µl | 50.0 µl |
| MIXTURE 3 (SIRNA-TRANSFECTION REAGENT MIXTURE) | | |
| Mixture 1 | 10 µl | 50 µl |
| Mixture 2 | 10 µl | 50 µl |
| MIXTURE 3 FINAL VOLUME | 20 µl | 100 µl |

Incubate 20 minutes at room temperature

TABLE VI-continued

| MIXTURE 4 (MEDIA-SIRNA/TRANSFECTION REAGENT MIXTURE) | | |
|---|---|---|
| Mixture 3 | 20 µl | 100 µl |
| Complete media | 80 µl | 400 µl |
| MIXTURE 4 FINAL VOLUME | 100 µl | 500 µl |

Incubate 48 hours at 37° C.

Transfection. Create a Mixture 1 by combining the specified amounts of OPTI-MEM serum free media and transfection reagent in a sterile polystyrene tube. Create a Mixture 2 by combining specified amounts of each siRNA with OPTI-MEM media in sterile 1 ml tubes. Create a Mixture 3 by combining specified amounts of Mixture 1 and Mixture 2. Mix gently (do not vortex) and incubate at room temperature for 20 minutes. Create a Mixture 4 by combining specified amounts of Mixture 3 to complete media. Add appropriate volume to each cell culture well. Incubate cells with transfection reagent mixture for 24-72 hours at 37° C. This incubation time is flexible. The ratio of silencing will remain consistent at any point in the time period. Assay for gene silencing using an appropriate detection method such as RT-PCR, Western blot analysis, immunohistochemistry, phenotypic analysis, mass spectrometry, fluorescence, radioactive decay, or any other method that is now known or that comes to be known to persons skilled in the art and that from reading this disclosure would useful with the present invention. The optimal window for observing a knockdown phenotype is related to the mRNA turnover of the gene of interest, although 24-72 hours is standard. Final Volume reflects amount needed in each well for the desired cell culture format. When adjusting volumes for a Stock Mix, an additional 10% should be used to accommodate variability in pipetting, etc. Duplicate or triplicate assays should be carried out when possible.

Example XVIII siRNA Directed Against BCL2L1

The entire online NCBI REFSEQ database was accessed through ENTREZ (EFETCH). The database was processed through Formula VIII. For each gene the top 80-100 scores for siRNAs were obtained and BLAST'ed to insure that the selected sequences are specific in targeting the gene of choice. The selected sequences so obtained included the following 27 siRNAs directed against BLC2-like 1 (BCL2L1):

| | |
|---|---|
| AAAGUGCAGUUCAGUAAUA, | (SEQ ID NO 438) |
| GGAAAUGACCAGACACUGA, | (SEQ ID NO 439) |
| GGAUACAGCUGGAGUCAGU, | (SEQ ID NO 440) |
| GAGACUAGAUUGCCUUUGU, | (SEQ ID NO 441) |
| GAGCCCAUCCCUAUUAUAA, | (SEQ ID NO 442) |
| GGAGGGCCCUACCUGAUUG, | (SEQ ID NO 443) |
| GCUCUCUGCUGUACAUAUU, | (SEQ ID NO 444) |
| GGAGGCAGGCGACGAGUUU, | (SEQ ID NO 445) |
| AAAGGAGGCUGGCAGGUAU, | (SEQ ID NO 446) |
| CCAGAAAGGAGACUAGAUU, | (SEQ ID NO 447) |

| | | |
|---|---|---|
| GUUGAGCCCAUCCCUAUUA, | (SEQ ID NO 448) | |
| CAAAGGAGGCUGGCAGGUA, | (SEQ ID NO 449) | |
| GUCCAAAUGUCCUCCAGAA, | (SEQ ID NO 450) | |
| GGAGUCAGUUUAGUGAUGU, | (SEQ ID NO 451) | |
| GUUAAGCGUGUCUGUAUUU, | (SEQ ID NO 452) | |
| GUACAUAUUUGAGACUAGU, | (SEQ ID NO 453) | |
| GACAGCAUAUCAGAGCUUU, | (SEQ ID NO 454) | |
| GUGCAACCCUUACCCCUUA, | (SEQ ID NO 455) | |
| GGGUAGGGCUGACUAGAAG, | (SEQ ID NO 456) | |
| GCUUUGAACAGGAUACUUU, | (SEQ ID NO 457) | |
| CCUACAAGCUUUCCCAGAA, | (SEQ ID NO 458) | |
| GAAAGGGAGCUAUCAGGAA, | (SEQ ID NO 459) | |
| GAAUUUAUCACACUUCUGU, | (SEQ ID NO 460) | |
| GAGAAUCACUAACCAGAGA, | (SEQ ID NO 461) | |
| CCAGGGAGCUUGAAAGUUU, | (SEQ ID NO 462) | |
| CAACUGGGCCCAAGACAGA, and | (SEQ ID NO 463) | |
| AAGCGUGUCUGUAUUUAUG. | (SEQ ID NO 464) | |

While the invention has been described in connection with specific embodiments thereof, it will be understood that it is capable of further modifications and this application is intended to cover any variations, uses, or adaptations of the invention following, in general, the principles of the invention and including such departure from the present disclosure as come within known or customary practice within the art to which the invention pertains and as may be applied to the essential features hereinbefore set forth and as follows in the scope of the appended claims.

---

The invention claimed is:

1. An siRNA molecule, wherein said siRNA molecule consists of: (a) a sense region and an antisense region, wherein said sense region and said antisense region together form a duplex region comprising 19-30 base pairs and said antisense region comprises a sequence that is the complement of SEQ. ID NO. 453; and (b) either no overhang regions or at least one overhang region, wherein each overhang region is six or fewer bases in length.

2. The siRNA molecule of claim 1, wherein said antisense region and said sense region are each 19-25 nucleotides in length.

3. The siRNA molecule of claim 2, wherein said antisense region and said sense region are each 19 nucleotides in length.

4. The siRNA molecule of claim 1, wherein said antisense region is 100% complementary to a region of a target mRNA.

5. The siRNA molecule of claim 1, wherein said siRNA molecule has at least one overhang region.

6. The siRNA molecule of claim 1, wherein said siRNA molecule has no overhang regions.

7. The siRNA molecule of claim 2, wherein said siRNA molecule has at least one overhang region.

8. The siRNA molecule of claim 2, wherein said siRNA molecule has no overhang regions.

9. A chemically synthesized double stranded siRNA molecule, wherein:
   a. each strand of said double stranded siRNA molecule is between 19 and 30 nucleotides in length; and
   b. one strand of said double stranded siRNA molecule comprises a sequence that is the complement of SEQ. ID. NO. 453.

10. The chemically synthesized double stranded siRNA molecule of claim 9, wherein each strand of said siRNA molecule is 19-25 nucleotides in length.

11. The chemically synthesized double stranded siRNA molecule of claim 10, wherein each strand of said double stranded siRNA molecule is 19 nucleotides in length.

12. A pool of chemically synthesized double stranded siRNA molecules comprising a first chemically synthesized double stranded siRNA molecule and a second chemically synthesized double stranded siRNA molecule, wherein said first chemically synthesized double stranded siRNA molecule is the chemically synthesized double stranded siRNA molecule of claim 9, and wherein in the second chemically synthesized double stranded siRNA molecule each strand is between 19 and 30 nucleotides in length and one strand of said second chemically synthesized double stranded siRNA molecule comprises a sequence that is the complement of SEQ. ID. NO. 440.

13. The pool of chemically synthesized double stranded siRNA molecules of claim 12, wherein each strand of said first chemically synthesized double stranded siRNA molecule and said second chemically synthesized double stranded siRNA molecule is 19-25 nucleotides in length.

14. A pool of at least two siRNAs, wherein said pool comprises a first siRNA and a second siRNA, wherein
   (a) said first siRNA consists of: (i) duplex region of 19-30 base pairs that has first antisense region that comprises a sequence that is the complement of SEQ. ID. NO. 453; and (ii) either no overhang regions or at least one overhang region, wherein each overhang region is six or fewer bases in length; and
   (b) said second siRNA consists of: (i) a duplex region of 19-30 base pairs that has antisense region that comprises a sequence that is the complement of SEQ. ID. NO. 440; and (ii) either no overhang regions or at least one overhang region, wherein each overhang region is six or fewer bases in length.

15. The pool of claim 14, wherein at least one of said first siRNA and said second siRNA has no overhang regions.

16. The pool of claim 14, wherein said first siRNA and said second siRNA each have no overhang regions.

17. The pool of claim 15, wherein said duplex region of said first siRNA and said duplex region of said second siRNA are each 19-25 base pairs in length.

18. The pool of claim 16, wherein said duplex region of said first siRNA and said duplex region of said second siRNA are each 19-25 base pairs in length.

19. The pool of claim 17, wherein said duplex region of said first siRNA and said duplex region of said second siRNA are each 19 base pairs in length.

20. The pool of claim 18, wherein said duplex region of said first siRNA and said duplex region of said second siRNA are each 19 base pairs in length.

* * * * *

SEQUENCE LISTING

```
<160> NUMBER OF SEQ ID NOS: 464

<210> SEQ ID NO 1
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)...(2)
<223> OTHER INFORMATION: n is any nucleotide
<220> FEATURE:
<221> NAME/KEY: misc_feature
<222> LOCATION: (4)...(4)
<223> OTHER INFORMATION: n is any nucleotide
<220> FEATURE:
<221> NAME/KEY: misc_feature
<222> LOCATION: (6)...(9)
<223> OTHER INFORMATION: n is any nucleotide
<220> FEATURE:
<221> NAME/KEY: misc_feature
<222> LOCATION: (12)...(12)
<223> OTHER INFORMATION: n is any nucleotide
<220> FEATURE:
<221> NAME/KEY: misc_feature
<222> LOCATION: (15)...(18)
<223> OTHER INFORMATION: n is any nucleotide

<400> SEQUENCE: 1
nnanannnnu cnaannnna                                                 19

<210> SEQ ID NO 2
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)...(2)
<223> OTHER INFORMATION: n is any nucleotide
<220> FEATURE:
<221> NAME/KEY: misc_feature
<222> LOCATION: (4)...(4)
<223> OTHER INFORMATION: n is any nucleotide
```

```
<220> FEATURE:
<221> NAME/KEY: misc_feature
<222> LOCATION: (6)...(9)
<223> OTHER INFORMATION: n is any nucleotide
<220> FEATURE:
<221> NAME/KEY: misc_feature
<222> LOCATION: (12)...(12)
<223> OTHER INFORMATION: n is any nucleotide
<220> FEATURE:
<221> NAME/KEY: misc_feature
<222> LOCATION: (15)...(18)
<223> OTHER INFORMATION: n is any nucleotide

<400> SEQUENCE: 2
nnanannnnu gnaannnna                                            19

<210> SEQ ID NO 3
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)...(2)
<223> OTHER INFORMATION: n is any nucleotide
<220> FEATURE:
<221> NAME/KEY: misc_feature
<222> LOCATION: (4)...(4)
<223> OTHER INFORMATION: n is any nucleotide
<220> FEATURE:
<221> NAME/KEY: misc_feature
<222> LOCATION: (6)...(9)
<223> OTHER INFORMATION: n is any nucleotide
<220> FEATURE:
<221> NAME/KEY: misc_feature
<222> LOCATION: (12)...(12)
<223> OTHER INFORMATION: n is any nucleotide
<220> FEATURE:
<221> NAME/KEY: misc_feature
<222> LOCATION: (15)...(18)
<223> OTHER INFORMATION: n is any nucleotide

<400> SEQUENCE: 3
nnanannnnu unaannnna                                            19

<210> SEQ ID NO 4
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)...(2)
<223> OTHER INFORMATION: n is any nucleotide
<220> FEATURE:
<221> NAME/KEY: misc_feature
<222> LOCATION: (4)...(4)
<223> OTHER INFORMATION: n is any nucleotide
<220> FEATURE:
<221> NAME/KEY: misc_feature
<222> LOCATION: (6)...(9)
<223> OTHER INFORMATION: n is any nucleotide
<220> FEATURE:
<221> NAME/KEY: misc_feature
<222> LOCATION: (12)...(12)
<223> OTHER INFORMATION: n is any nucleotide
<220> FEATURE:
<221> NAME/KEY: misc_feature
<222> LOCATION: (15)...(18)
<223> OTHER INFORMATION: n is any nucleotide
```

<400> SEQUENCE: 4
nnanannnnu cncannnna					19

<210> SEQ ID NO 5
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)...(2)
<223> OTHER INFORMATION: n is any nucleotide
<220> FEATURE:
<221> NAME/KEY: misc_feature
<222> LOCATION: (4)...(4)
<223> OTHER INFORMATION: n is any nucleotide
<220> FEATURE:
<221> NAME/KEY: misc_feature
<222> LOCATION: (6)...(9)
<223> OTHER INFORMATION: n is any nucleotide
<220> FEATURE:
<221> NAME/KEY: misc_feature
<222> LOCATION: (12)...(12)
<223> OTHER INFORMATION: n is any nucleotide
<220> FEATURE:
<221> NAME/KEY: misc_feature
<222> LOCATION: (15)...(18)
<223> OTHER INFORMATION: n is any nucleotide

<400> SEQUENCE: 5
nnanannnnu gncannnna					19

<210> SEQ ID NO 6
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)...(2)
<223> OTHER INFORMATION: n is any nucleotide
<220> FEATURE:
<221> NAME/KEY: misc_feature
<222> LOCATION: (4)...(4)
<223> OTHER INFORMATION: n is any nucleotide
<220> FEATURE:
<221> NAME/KEY: misc_feature
<222> LOCATION: (6)...(9)
<223> OTHER INFORMATION: n is any nucleotide
<220> FEATURE:
<221> NAME/KEY: misc_feature
<222> LOCATION: (12)...(12)
<223> OTHER INFORMATION: n is any nucleotide
<220> FEATURE:
<221> NAME/KEY: misc_feature
<222> LOCATION: (15)...(18)
<223> OTHER INFORMATION: n is any nucleotide

<400> SEQUENCE: 6
nnanannnnu uncannnna					19

<210> SEQ ID NO 7
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)...(2)
<223> OTHER INFORMATION: n is any nucleotide

```
<220> FEATURE:
<221> NAME/KEY: misc_feature
<222> LOCATION: (4)...(4)
<223> OTHER INFORMATION: n is any nucleotide
<220> FEATURE:
<221> NAME/KEY: misc_feature
<222> LOCATION: (6)...(9)
<223> OTHER INFORMATION: n is any nucleotide
<220> FEATURE:
<221> NAME/KEY: misc_feature
<222> LOCATION: (12)...(12)
<223> OTHER INFORMATION: n is any nucleotide
<220> FEATURE:
<221> NAME/KEY: misc_feature
<222> LOCATION: (15)...(18)
<223> OTHER INFORMATION: n is any nucleotide

<400> SEQUENCE: 7
nnanannnnu cnuannnna                                               19

<210> SEQ ID NO 8
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)...(2)
<223> OTHER INFORMATION: n is any nucleotide
<220> FEATURE:
<221> NAME/KEY: misc_feature
<222> LOCATION: (4)...(4)
<223> OTHER INFORMATION: n is any nucleotide
<220> FEATURE:
<221> NAME/KEY: misc_feature
<222> LOCATION: (6)...(9)
<223> OTHER INFORMATION: n is any nucleotide
<220> FEATURE:
<221> NAME/KEY: misc_feature
<222> LOCATION: (12)...(12)
<223> OTHER INFORMATION: n is any nucleotide
<220> FEATURE:
<221> NAME/KEY: misc_feature
<222> LOCATION: (15)...(18)
<223> OTHER INFORMATION: n is any nucleotide

<400> SEQUENCE: 8
nnanannnnu gnuannnna                                               19

<210> SEQ ID NO 9
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)...(2)
<223> OTHER INFORMATION: n is any nucleotide
<220> FEATURE:
<221> NAME/KEY: misc_feature
<222> LOCATION: (4)...(4)
<223> OTHER INFORMATION: n is any nucleotide
<220> FEATURE:
<221> NAME/KEY: misc_feature
<222> LOCATION: (6)...(9)
<223> OTHER INFORMATION: n is any nucleotide
<220> FEATURE:
<221> NAME/KEY: misc_feature
<222> LOCATION: (12)...(12)
<223> OTHER INFORMATION: n is any nucleotide
```

```
<220> FEATURE:
<221> NAME/KEY: misc_feature
<222> LOCATION: (15)...(18)
<223> OTHER INFORMATION: n is any nucleotide

<400> SEQUENCE: 9
nnanannnnu unuannnna                                                    19

<210> SEQ ID NO 10
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)...(2)
<223> OTHER INFORMATION: n is any nucleotide
<220> FEATURE:
<221> NAME/KEY: misc_feature
<222> LOCATION: (4)...(4)
<223> OTHER INFORMATION: n is any nucleotide
<220> FEATURE:
<221> NAME/KEY: misc_feature
<222> LOCATION: (6)...(9)
<223> OTHER INFORMATION: n is any nucleotide
<220> FEATURE:
<221> NAME/KEY: misc_feature
<222> LOCATION: (12)...(12)
<223> OTHER INFORMATION: n is any nucleotide
<220> FEATURE:
<221> NAME/KEY: misc_feature
<222> LOCATION: (5)...(18)
<223> OTHER INFORMATION: n is any nucleotide

<400> SEQUENCE: 10
nnancnnnnu cnaannnna                                                    19

<210> SEQ ID NO 11
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)...(2)
<223> OTHER INFORMATION: n is any nucleotide
<220> FEATURE:
<221> NAME/KEY: misc_feature
<222> LOCATION: (4)...(4)
<223> OTHER INFORMATION: n is any nucleotide
<220> FEATURE:
<221> NAME/KEY: misc_feature
<222> LOCATION: (6)...(9)
<223> OTHER INFORMATION: n is any nucleotide
<220> FEATURE:
<221> NAME/KEY: misc_feature
<222> LOCATION: (12)...(12)
<223> OTHER INFORMATION: n is any nucleotide
<220> FEATURE:
<221> NAME/KEY: misc_feature
<222> LOCATION: (5)...(18)
<223> OTHER INFORMATION: n is any nucleotide

<400> SEQUENCE: 11
nnancnnnnu gnaannnna                                                    19

<210> SEQ ID NO 12
<211> LENGTH: 19
<212> TYPE: DNA
<213> ORGANISM: Artificial Sequence
```

```
<220> FEATURE:
<223> OTHER INFORMATION: Synthetic
<220> FEATURE:
<221> NAME/KEY: misc_feature
<222> LOCATION: (1)...(2)
<223> OTHER INFORMATION: n is any nucleotide
<220> FEATURE:
<221> NAME/KEY: misc_feature
<222> LOCATION: (4)...(4)
<223> OTHER INFORMATION: n is any nucleotide
<220> FEATURE:
<221> NAME/KEY: misc_feature
<222> LOCATION: (6)...(9)
<223> OTHER INFORMATION: n is any nucleotide
<220> FEATURE:
<221> NAME/KEY: misc_feature
<222> LOCATION: (12)...(12)
<223> OTHER INFORMATION: n is any nucleotide
<220> FEATURE:
<221> NAME/KEY: misc_feature
<222> LOCATION: (15)...(18)
<223> OTHER INFORMATION: n is any nucleotide

<400> SEQUENCE: 12
nnancnnnnu unaannnna                                              19

<210> SEQ ID NO 13
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)...(2)
<223> OTHER INFORMATION: n is any nucleotide
<220> FEATURE:
<221> NAME/KEY: misc_feature
<222> LOCATION: (4)...(4)
<223> OTHER INFORMATION: n is any nucleotide
<220> FEATURE:
<221> NAME/KEY: misc_feature
<222> LOCATION: (6)...(9)
<223> OTHER INFORMATION: n is any nucleotide
<220> FEATURE:
<221> NAME/KEY: misc_feature
<222> LOCATION: (12)...(12)
<223> OTHER INFORMATION: n is any nucleotide
<220> FEATURE:
<221> NAME/KEY: misc_feature
<222> LOCATION: (15)...(18)
<223> OTHER INFORMATION: n is any nucleotide

<400> SEQUENCE: 13
nnancnnnnu cncannnna                                              19

<210> SEQ ID NO 14
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)...(2)
<223> OTHER INFORMATION: n is any nucleotide
<220> FEATURE:
<221> NAME/KEY: misc_feature
<222> LOCATION: (4)...(4)
<223> OTHER INFORMATION: n is any nucleotide
<220> FEATURE:
<221> NAME/KEY: misc_feature
<222> LOCATION: (6)...(9)
<223> OTHER INFORMATION: n is any nucleotide
```

```
<220> FEATURE:
<221> NAME/KEY: misc_feature
<222> LOCATION: (12)...(12)
<223> OTHER INFORMATION: n is any nucleotide
<220> FEATURE:
<221> NAME/KEY: misc_feature
<222> LOCATION: (15)...(18)
<223> OTHER INFORMATION: n is any nucleotide

<400> SEQUENCE: 14
nnancnnnnu gncannnna                                                 19

<210> SEQ ID NO 15
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)...(2)
<223> OTHER INFORMATION: n is any nucleotide
<220> FEATURE:
<221> NAME/KEY: misc_feature
<222> LOCATION: (4)...(4)
<223> OTHER INFORMATION: n is any nucleotide
<220> FEATURE:
<221> NAME/KEY: misc_feature
<222> LOCATION: (6)...(9)
<223> OTHER INFORMATION: n is any nucleotide
<220> FEATURE:
<221> NAME/KEY: misc_feature
<222> LOCATION: (12)...(2)
<223> OTHER INFORMATION: n is any nucleotide
<220> FEATURE:
<221> NAME/KEY: misc_feature
<222> LOCATION: (15)...(18)
<223> OTHER INFORMATION: n is any nucleotide

<400> SEQUENCE: 15
nnancnnnnu uncannnna                                                 19

<210> SEQ ID NO 16
<211> LENGTH: 18
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)...(1)
<223> OTHER INFORMATION: n is any nucleotide
<220> FEATURE:
<221> NAME/KEY: misc_feature
<222> LOCATION: (3)...(3)
<223> OTHER INFORMATION: n is any nucleotide
<220> FEATURE:
<221> NAME/KEY: misc_feature
<222> LOCATION: (5)...(8)
<223> OTHER INFORMATION: n is any nucleotide
<220> FEATURE:
<221> NAME/KEY: misc_feature
<222> LOCATION: (11)...(11)
<223> OTHER INFORMATION: n is any nucleotide
<220> FEATURE:
<221> NAME/KEY: misc_feature
<222> LOCATION: (14)...(7)
<223> OTHER INFORMATION: n is any nucleotide

<400> SEQUENCE: 16
nancnnnnuc nuannnna                                                  18
```

```
<210> SEQ ID NO 17
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)...(2)
<223> OTHER INFORMATION: n is any nucleotide
<220> FEATURE:
<221> NAME/KEY: misc_feature
<222> LOCATION: (4)...(4)
<223> OTHER INFORMATION: n is any nucleotide
<220> FEATURE:
<221> NAME/KEY: misc_feature
<222> LOCATION: (6)...(90)
<223> OTHER INFORMATION: n is any nucleotide
<220> FEATURE:
<221> NAME/KEY: misc_feature
<222> LOCATION: (12)...(12)
<223> OTHER INFORMATION: n is any nucleotide
<220> FEATURE:
<221> NAME/KEY: misc_feature
<222> LOCATION: (15)...(18)
<223> OTHER INFORMATION: n is any nucleotide

<400> SEQUENCE: 17
nnancnnnnu gnuannna                                                19

<210> SEQ ID NO 18
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)...(2)
<223> OTHER INFORMATION: n is any nucleotide
<220> FEATURE:
<221> NAME/KEY: misc_feature
<222> LOCATION: (4)...(4)
<223> OTHER INFORMATION: n is any nucleotide
<220> FEATURE:
<221> NAME/KEY: misc_feature
<222> LOCATION: (6)...(9)
<223> OTHER INFORMATION: n is any nucleotide
<220> FEATURE:
<221> NAME/KEY: misc_feature
<222> LOCATION: (12)...(12)
<223> OTHER INFORMATION: n is any nucleotide
<220> FEATURE:
<221> NAME/KEY: misc_feature
<222> LOCATION: (15)...(18)
<223> OTHER INFORMATION: n is any nucleotide

<400> SEQUENCE: 18
nnancnnnnu unuannna                                                19

<210> SEQ ID NO 19
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)...(2)
<223> OTHER INFORMATION: n is any nucleotide
<220> FEATURE:
<221> NAME/KEY: misc_feature
<222> LOCATION: (4)...(4)
<223> OTHER INFORMATION: n is any nucleotide
```

```
<220> FEATURE:
<221> NAME/KEY: misc_feature
<222> LOCATION: (6)...(9)
<223> OTHER INFORMATION: n is any nucleotide
<220> FEATURE:
<221> NAME/KEY: misc_feature
<222> LOCATION: (12)...(12)
<223> OTHER INFORMATION: n is any nucleotide
<220> FEATURE:
<221> NAME/KEY: misc_feature
<222> LOCATION: (15)...(18)
<223> OTHER INFORMATION: n is any nucleotide

<400> SEQUENCE: 19
nnangnnnnu cnaannnna                                                19

<210> SEQ ID NO 20
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)...(2)
<223> OTHER INFORMATION: n is any nucleotide
<220> FEATURE:
<221> NAME/KEY: misc_feature
<222> LOCATION: (4)...(4)
<223> OTHER INFORMATION: n is any nucleotide
<220> FEATURE:
<221> NAME/KEY: misc_feature
<222> LOCATION: (6)...(9)
<223> OTHER INFORMATION: n is any nucleotide
<220> FEATURE:
<221> NAME/KEY: misc_feature
<222> LOCATION: (12)...(12)
<223> OTHER INFORMATION: n is any nucleotide
<220> FEATURE:
<221> NAME/KEY: misc_feature
<222> LOCATION: (15)...(18)
<223> OTHER INFORMATION: n is any nucleotide

<400> SEQUENCE: 20
nnangnnnnu gnaannnna                                                19

<210> SEQ ID NO 21
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)...(2)
<223> OTHER INFORMATION: n is any nucleotide
<220> FEATURE:
<221> NAME/KEY: misc_feature
<222> LOCATION: (4)...(4)
<223> OTHER INFORMATION: n is any nucleotide
<220> FEATURE:
<221> NAME/KEY: misc_feature
<222> LOCATION: (6)...(9)
<223> OTHER INFORMATION: n is any nucleotide
<220> FEATURE:
<221> NAME/KEY: misc_feature
<222> LOCATION: (12)...(12)
<223> OTHER INFORMATION: n is any nucleotide
<220> FEATURE:
<221> NAME/KEY: misc_feature
<222> LOCATION: (15)...(18)
<223> OTHER INFORMATION: n is any nucleotide
```

```
<400> SEQUENCE: 21
nnangnnnnu unaannnna                                                    19

<210> SEQ ID NO 22
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)...(2)
<223> OTHER INFORMATION: n is any nucleotide
<220> FEATURE:
<221> NAME/KEY: misc_feature
<222> LOCATION: (4)...(4)
<223> OTHER INFORMATION: n is any nucleotide
<220> FEATURE:
<221> NAME/KEY: misc_feature
<222> LOCATION: (6)...(9)
<223> OTHER INFORMATION: n is any nucleotide
<220> FEATURE:
<221> NAME/KEY: misc_feature
<222> LOCATION: (12)...(12)
<223> OTHER INFORMATION: n is any nucleotide
<220> FEATURE:
<221> NAME/KEY: misc_feature
<222> LOCATION: (15)...(18)
<223> OTHER INFORMATION: n is any nucleotide

<400> SEQUENCE: 22
nnangnnnnu cncannnna                                                    19

<210> SEQ ID NO 23
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)...(2)
<223> OTHER INFORMATION: n is any nucleotide
<220> FEATURE:
<221> NAME/KEY: misc_feature
<222> LOCATION: (4)...(4)
<223> OTHER INFORMATION: n is any nucleotide
<220> FEATURE:
<221> NAME/KEY: misc_feature
<222> LOCATION: (6)...(9)
<223> OTHER INFORMATION: n is any nucleotide
<220> FEATURE:
<221> NAME/KEY: misc_feature
<222> LOCATION: (12)...(12)
<223> OTHER INFORMATION: n is any nucleotide
<220> FEATURE:
<221> NAME/KEY: misc_feature
<222> LOCATION: (15)...(18)
<223> OTHER INFORMATION: n is any nucleotide

<400> SEQUENCE: 23
nnangnnnnu gncannnna                                                    19

<210> SEQ ID NO 24
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)...(2)
<223> OTHER INFORMATION: n is any nucleotide
```

```
<220> FEATURE:
<221> NAME/KEY: misc_feature
<222> LOCATION: (4)...(4)
<223> OTHER INFORMATION: n is any nucleotide
<220> FEATURE:
<221> NAME/KEY: misc_feature
<222> LOCATION: (6)...(9)
<223> OTHER INFORMATION: n is any nucleotide
<220> FEATURE:
<221> NAME/KEY: misc_feature
<222> LOCATION: (12)...(12)
<223> OTHER INFORMATION: n is any nucleotide
<220> FEATURE:
<221> NAME/KEY: misc_feature
<222> LOCATION: (15)...(18)
<223> OTHER INFORMATION: n is any nucleotide

<400> SEQUENCE: 24
nnangnnnnu uncannnna                                                19

<210> SEQ ID NO 25
<211> LENGTH: 18
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)...(1)
<223> OTHER INFORMATION: n is any nucleotide
<220> FEATURE:
<221> NAME/KEY: misc_feature
<222> LOCATION: (3)...(3)
<223> OTHER INFORMATION: n is any nucleotide
<220> FEATURE:
<221> NAME/KEY: misc_feature
<222> LOCATION: (5)...(8)
<223> OTHER INFORMATION: n is any nucleotide
<220> FEATURE:
<221> NAME/KEY: misc_feature
<222> LOCATION: (11)...(11)
<223> OTHER INFORMATION: n is any nucleotide
<220> FEATURE:
<221> NAME/KEY: misc_feature
<222> LOCATION: (14)...(17)
<223> OTHER INFORMATION: n is any nucleotide

<400> SEQUENCE: 25
nangnnnnuc nuannnna                                                 18

<210> SEQ ID NO 26
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)...(2)
<223> OTHER INFORMATION: n is any nucleotide
<220> FEATURE:
<221> NAME/KEY: misc_feature
<222> LOCATION: (4)...(4)
<223> OTHER INFORMATION: n is any nucleotide
<220> FEATURE:
<221> NAME/KEY: misc_feature
<222> LOCATION: (6)...(90)
<223> OTHER INFORMATION: n is any nucleotide
<220> FEATURE:
<221> NAME/KEY: misc_feature
<222> LOCATION: (12)...(12)
<223> OTHER INFORMATION: n is any nucleotide
```

```
<220> FEATURE:
<221> NAME/KEY: misc_feature
<222> LOCATION: (15)...(18)
<223> OTHER INFORMATION: n is any nucleotide

<400> SEQUENCE: 26
nnangnnnnu gnuannnna                                                    19

<210> SEQ ID NO 27
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)...(2)
<223> OTHER INFORMATION: n is any nucleotide
<220> FEATURE:
<221> NAME/KEY: misc_feature
<222> LOCATION: (4)...(4)
<223> OTHER INFORMATION: n is any nucleotide
<220> FEATURE:
<221> NAME/KEY: misc_feature
<222> LOCATION: (6)...(9)
<223> OTHER INFORMATION: n is any nucleotide
<220> FEATURE:
<221> NAME/KEY: misc_feature
<222> LOCATION: (12)...(12)
<223> OTHER INFORMATION: n is any nucleotide
<220> FEATURE:
<221> NAME/KEY: misc_feature
<222> LOCATION: (15)...(8)
<223> OTHER INFORMATION: n is any nucleotide

<400> SEQUENCE: 27
nnangnnnnn unuannnna                                                    19

<210> SEQ ID NO 28
<211> LENGTH: 22
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)...(5)
<223> OTHER INFORMATION: n is any nucleotide
<220> FEATURE:
<221> NAME/KEY: misc_feature
<222> LOCATION: (7)...(7)
<223> OTHER INFORMATION: n is any nucleotide
<220> FEATURE:
<221> NAME/KEY: misc_feature
<222> LOCATION: (9)...(2)
<223> OTHER INFORMATION: n is any nucleotide
<220> FEATURE:
<221> NAME/KEY: misc_feature
<222> LOCATION: (15)...(15)
<223> OTHER INFORMATION: n is any nucleotide
<220> FEATURE:
<221> NAME/KEY: misc_feature
<222> LOCATION: (18)...(24)
<223> OTHER INFORMATION: n is any nucleotide

<400> SEQUENCE: 28
gucnnanann nnucnaannn na                                                22

<210> SEQ ID NO 29
<211> LENGTH: 208
<212> TYPE: DNA
<213> ORGANISM: homo sapiens
```

<220> FEATURE:
<223> OTHER INFORMATION: Synthetic

<400> SEQUENCE: 29

| | | | | | |
|---|---|---|---|---|---|
| gttccaaaaa | cagtggataa | ttttgtggcc | ttagctacag | gagagaaagg | atttggctac | 60 |
| aaaaacagca | aattccatcg | tgtaatcaag | gacttcatga | tccagggcgg | agacttcacc | 120 |
| aggggagatg | gcacaggagg | aaagagcatc | tacggtgagc | gcttccccga | tgagaacttc | 180 |
| aaactgaagc | actacgggcc | tggctggg | | | | 208 |

<210> SEQ ID NO 30
<211> LENGTH: 200
<212> TYPE: DNA
<213> ORGANISM: photinus pyralis
<220> FEATURE:
<223> OTHER INFORMATION: Synthetic

<400> SEQUENCE: 30

| | | | | | |
|---|---|---|---|---|---|
| tgaacttccc | gccgccgttg | ttgttttgga | gcacggaaag | acgatgacgg | aaaaagagat | 60 |
| cgtggattac | gtcgccagtc | aagtaacaac | cgcgaaaaag | ttgcgcggag | gagttgtgtt | 120 |
| tgtggacgaa | gtaccgaaag | gtcttaccgg | aaaactcgac | gcaagaaaaa | tcagagagat | 180 |
| cctcataaag | gccaagaagg | | | | | 200 |

<210> SEQ ID NO 31
<211> LENGTH: 108
<212> TYPE: DNA
<213> ORGANISM: homo sapiens
<220> FEATURE:
<223> OTHER INFORMATION: Synthetic

<400> SEQUENCE: 31

| | | | | | |
|---|---|---|---|---|---|
| acgggcaagg | ccaagtggga | tgcctggaat | gagctgaaag | ggacttccaa | ggaagatgcc | 60 |
| atgaaagctt | acatcaacaa | agtagaagag | ctaaagaaaa | aatacggg | | 108 |

<210> SEQ ID NO 32
<211> LENGTH: 19
<212> TYPE: RNA
<213> ORGANISM: Artificial Sequence
<220> FEATURE:
<223> OTHER INFORMATION: Synthetic

<400> SEQUENCE: 32
guuccaaaaa caguggaua                                                     19

<210> SEQ ID NO 33
<211> LENGTH: 19
<212> TYPE: RNA
<213> ORGANISM: Artificial Sequence
<220> FEATURE:
<223> OTHER INFORMATION: Synthetic

<400> SEQUENCE: 33
uccaaaaaca guggauaau                                                     19

<210> SEQ ID NO 34
<211> LENGTH: 19
<212> TYPE: RNA
<213> ORGANISM: Artificial Sequence
<220> FEATURE:
<223> OTHER INFORMATION: Synthetic

```
<400> SEQUENCE: 34
caaaaacagu ggauaauuu                                              19

<210> SEQ ID NO 35
<211> LENGTH: 19
<212> TYPE: RNA
<213> ORGANISM: Artificial Sequence
<220> FEATURE:
<223> OTHER INFORMATION: Synthetic

<400> SEQUENCE: 35
aaaacagugg auaauuuug                                              19

<210> SEQ ID NO 36
<211> LENGTH: 19
<212> TYPE: RNA
<213> ORGANISM: Artificial Sequence
<220> FEATURE:
<223> OTHER INFORMATION: Synthetic

<400> SEQUENCE: 36
aacaguggau aauuuugug                                              19

<210> SEQ ID NO 37
<211> LENGTH: 19
<212> TYPE: RNA
<213> ORGANISM: Artificial Sequence
<220> FEATURE:
<223> OTHER INFORMATION: Synthetic

<400> SEQUENCE: 37
caguggauaa uuuuguggc                                              19

<210> SEQ ID NO 38
<211> LENGTH: 19
<212> TYPE: RNA
<213> ORGANISM: Artificial Sequence
<220> FEATURE:
<223> OTHER INFORMATION: Synthetic

<400> SEQUENCE: 38
guggauaauu uuguggccu                                              19

<210> SEQ ID NO 39
<211> LENGTH: 19
<212> TYPE: RNA
<213> ORGANISM: Artificial Sequence
<220> FEATURE:
<223> OTHER INFORMATION: Synthetic

<400> SEQUENCE: 39
ggauaauuuu guggccuua                                              19

<210> SEQ ID NO 40
<211> LENGTH: 19
<212> TYPE: RNA
<213> ORGANISM: Artificial Sequence
<220> FEATURE:
<223> OTHER INFORMATION: Synthetic

<400> SEQUENCE: 40
auaauuuugu ggccuuagc                                              19
```

```
<210> SEQ ID NO 41
<211> LENGTH: 19
<212> TYPE: RNA
<213> ORGANISM: Artificial Sequence
<220> FEATURE:
<223> OTHER INFORMATION: Synthetic

<400> SEQUENCE: 41
aauuuugugg ccuuagcua                                                  19

<210> SEQ ID NO 42
<211> LENGTH: 19
<212> TYPE: RNA
<213> ORGANISM: Artificial Sequence
<220> FEATURE:
<223> OTHER INFORMATION: Synthetic

<400> SEQUENCE: 42
uuuuguggcc uuagcuaca                                                  19

<210> SEQ ID NO 43
<211> LENGTH: 19
<212> TYPE: RNA
<213> ORGANISM: Artificial Sequence
<220> FEATURE:
<223> OTHER INFORMATION: Synthetic

<400> SEQUENCE: 43
uuguggccuu agcuacagg                                                  19

<210> SEQ ID NO 44
<211> LENGTH: 19
<212> TYPE: RNA
<213> ORGANISM: Artificial Sequence
<220> FEATURE:
<223> OTHER INFORMATION: Synthetic

<400> SEQUENCE: 44
guggccuuag cuacaggag                                                  19

<210> SEQ ID NO 45
<211> LENGTH: 19
<212> TYPE: RNA
<213> ORGANISM: Artificial Sequence
<220> FEATURE:
<223> OTHER INFORMATION: Synthetic

<400> SEQUENCE: 45
ggccuuagcu acaggagag                                                  19

<210> SEQ ID NO 46
<211> LENGTH: 19
<212> TYPE: RNA
<213> ORGANISM: Artificial Sequence
<220> FEATURE:
<223> OTHER INFORMATION: Synthetic

<400> SEQUENCE: 46
ccuuagcuac aggagagaa                                                  19

<210> SEQ ID NO 47
<211> LENGTH: 19
<212> TYPE: RNA
<213> ORGANISM: Artificial Sequence
<220> FEATURE:
<223> OTHER INFORMATION: Synthetic
```

```
<400> SEQUENCE: 47
uuagcuacag gagagaaag                                                19

<210> SEQ ID NO 48
<211> LENGTH: 19
<212> TYPE: RNA
<213> ORGANISM: Artificial Sequence
<220> FEATURE:
<223> OTHER INFORMATION: Synthetic

<400> SEQUENCE: 48
agcuacagga gagaaagga                                                19

<210> SEQ ID NO 49
<211> LENGTH: 19
<212> TYPE: RNA
<213> ORGANISM: Artificial Sequence
<220> FEATURE:
<223> OTHER INFORMATION: Synthetic

<400> SEQUENCE: 49
cuacaggaga gaaaggauu                                                19

<210> SEQ ID NO 50
<211> LENGTH: 19
<212> TYPE: RNA
<213> ORGANISM: Artificial Sequence
<220> FEATURE:
<223> OTHER INFORMATION: Synthetic

<400> SEQUENCE: 50
acaggagaga aaggauuug                                                19

<210> SEQ ID NO 51
<211> LENGTH: 19
<212> TYPE: RNA
<213> ORGANISM: Artificial Sequence
<220> FEATURE:
<223> OTHER INFORMATION: Synthetic

<400> SEQUENCE: 51
aggagagaaa ggauuuggc                                                19

<210> SEQ ID NO 52
<211> LENGTH: 19
<212> TYPE: RNA
<213> ORGANISM: Artificial Sequence
<220> FEATURE:
<223> OTHER INFORMATION: Synthetic

<400> SEQUENCE: 52
gagagaaagg auuuggcua                                                19

<210> SEQ ID NO 53
<211> LENGTH: 19
<212> TYPE: RNA
<213> ORGANISM: Artificial Sequence
<220> FEATURE:
<223> OTHER INFORMATION: Synthetic

<400> SEQUENCE: 53
gagaaaggau uuggcuaca                                                19
```

<210> SEQ ID NO 54
<211> LENGTH: 19
<212> TYPE: RNA
<213> ORGANISM: Artificial Sequence
<220> FEATURE:
<223> OTHER INFORMATION: Synthetic

<400> SEQUENCE: 54
gaaaggauuu ggcuacaaa                                                19

<210> SEQ ID NO 55
<211> LENGTH: 19
<212> TYPE: RNA
<213> ORGANISM: Artificial Sequence
<220> FEATURE:
<223> OTHER INFORMATION: Synthetic

<400> SEQUENCE: 55
aaggauuugg cuacaaaa                                                 19

<210> SEQ ID NO 56
<211> LENGTH: 19
<212> TYPE: RNA
<213> ORGANISM: Artificial Sequence
<220> FEATURE:
<223> OTHER INFORMATION: Synthetic

<400> SEQUENCE: 56
ggauuuggcu acaaaaaca                                                19

<210> SEQ ID NO 57
<211> LENGTH: 19
<212> TYPE: RNA
<213> ORGANISM: Artificial Sequence
<220> FEATURE:
<223> OTHER INFORMATION: Synthetic

<400> SEQUENCE: 57
auuuggcuac aaaacagc                                                 19

<210> SEQ ID NO 58
<211> LENGTH: 19
<212> TYPE: RNA
<213> ORGANISM: Artificial Sequence
<220> FEATURE:
<223> OTHER INFORMATION: Synthetic

<400> SEQUENCE: 58
uuggcuacaa aaacagcaa                                                19

<210> SEQ ID NO 59
<211> LENGTH: 19
<212> TYPE: RNA
<213> ORGANISM: Artificial Sequence
<220> FEATURE:
<223> OTHER INFORMATION: Synthetic

<400> SEQUENCE: 59
ggcuacaaaa acagcaaau                                                19

<210> SEQ ID NO 60
<211> LENGTH: 19
<212> TYPE: RNA
<213> ORGANISM: Artificial Sequence
<220> FEATURE:
<223> OTHER INFORMATION: Synthetic

```
<400> SEQUENCE: 60
cuacaaaaac agcaaauuc                                                19

<210> SEQ ID NO 61
<211> LENGTH: 19
<212> TYPE: RNA
<213> ORGANISM: Artificial Sequence
<220> FEATURE:
<223> OTHER INFORMATION: Synthetic

<400> SEQUENCE: 61
acaaaaacag caaauucca                                                19

<210> SEQ ID NO 62
<211> LENGTH: 19
<212> TYPE: RNA
<213> ORGANISM: Artificial Sequence
<220> FEATURE:
<223> OTHER INFORMATION: Synthetic

<400> SEQUENCE: 62
aaaaacagca aauuccauc                                                19

<210> SEQ ID NO 63
<211> LENGTH: 19
<212> TYPE: RNA
<213> ORGANISM: Artificial Sequence
<220> FEATURE:
<223> OTHER INFORMATION: Synthetic

<400> SEQUENCE: 63
aaacagcaaa uuccaucgu                                                19

<210> SEQ ID NO 64
<211> LENGTH: 19
<212> TYPE: RNA
<213> ORGANISM: Artificial Sequence
<220> FEATURE:
<223> OTHER INFORMATION: Synthetic

<400> SEQUENCE: 64
acagcaaauu ccaucgugu                                                19

<210> SEQ ID NO 65
<211> LENGTH: 19
<212> TYPE: RNA
<213> ORGANISM: Artificial Sequence
<220> FEATURE:
<223> OTHER INFORMATION: Synthetic

<400> SEQUENCE: 65
agcaaauucc aucguguaa                                                19

<210> SEQ ID NO 66
<211> LENGTH: 19
<212> TYPE: RNA
<213> ORGANISM: Artificial Sequence
<220> FEATURE:
<223> OTHER INFORMATION: Synthetic

<400> SEQUENCE: 66
caaauuccau cguguaauc                                                19
```

```
<210> SEQ ID NO 67
<211> LENGTH: 19
<212> TYPE: RNA
<213> ORGANISM: Artificial Sequence
<220> FEATURE:
<223> OTHER INFORMATION: Synthetic

<400> SEQUENCE: 67
aauuccaucg uguaaucaa                                               19

<210> SEQ ID NO 68
<211> LENGTH: 19
<212> TYPE: RNA
<213> ORGANISM: Artificial Sequence
<220> FEATURE:
<223> OTHER INFORMATION: Synthetic

<400> SEQUENCE: 68
uuccaucgug uaaucaagg                                               19

<210> SEQ ID NO 69
<211> LENGTH: 19
<212> TYPE: RNA
<213> ORGANISM: Artificial Sequence
<220> FEATURE:
<223> OTHER INFORMATION: Synthetic

<400> SEQUENCE: 69 ccaucguguaa aucaaggac                                              19

<210> SEQ ID NO 70
<211> LENGTH: 19
<212> TYPE: RNA
<213> ORGANISM: Artificial Sequence
<220> FEATURE:
<223> OTHER INFORMATION: Synthetic

<400> SEQUENCE: 70
aucguguaau caaggacuu                                               19

<210> SEQ ID NO 71
<211> LENGTH: 19
<212> TYPE: RNA
<213> ORGANISM: Artificial Sequence
<220> FEATURE:
<223> OTHER INFORMATION: Synthetic

<400> SEQUENCE: 71
cguguaauca aggacuuca                                               19

<210> SEQ ID NO 72
<211> LENGTH: 19
<212> TYPE: RNA
<213> ORGANISM: Artificial Sequence
<220> FEATURE:
<223> OTHER INFORMATION: Synthetic

<400> SEQUENCE: 72
uguaaucaag gacuucaug                                               19

<210> SEQ ID NO 73
<211> LENGTH: 19
<212> TYPE: RNA
<213> ORGANISM: Artificial Sequence
<220> FEATURE:
<223> OTHER INFORMATION: Synthetic
```

<400> SEQUENCE: 73
uaaucaagga cuucaugau					19

<210> SEQ ID NO 74
<211> LENGTH: 19
<212> TYPE: RNA
<213> ORGANISM: Artificial Sequence
<220> FEATURE:
<223> OTHER INFORMATION: Synthetic

<400> SEQUENCE: 74
aucaaggacu ucaugaucc					19

<210> SEQ ID NO 75
<211> LENGTH: 19
<212> TYPE: RNA
<213> ORGANISM: Artificial Sequence
<220> FEATURE:
<223> OTHER INFORMATION: Synthetic

<400> SEQUENCE: 75
caaggacuuc augauccag					19

<210> SEQ ID NO 76
<211> LENGTH: 19
<212> TYPE: RNA
<213> ORGANISM: Artificial Sequence
<220> FEATURE:
<223> OTHER INFORMATION: Synthetic

<400> SEQUENCE: 76
aggacuucau gauccaggg					19

<210> SEQ ID NO 77
<211> LENGTH: 19
<212> TYPE: RNA
<213> ORGANISM: Artificial Sequence
<220> FEATURE:
<223> OTHER INFORMATION: Synthetic

<400> SEQUENCE: 77
gacuucauga uccagggcg					19

<210> SEQ ID NO 78
<211> LENGTH: 19
<212> TYPE: RNA
<213> ORGANISM: Artificial Sequence
<220> FEATURE:
<223> OTHER INFORMATION: Synthetic

<400> SEQUENCE: 78
cuucaugauc cagggcgga					19

<210> SEQ ID NO 79
<211> LENGTH: 19
<212> TYPE: RNA
<213> ORGANISM: Artificial Sequence
<220> FEATURE:
<223> OTHER INFORMATION: Synthetic

<400> SEQUENCE: 79
ucaugaucca gggcggaga					19

```
<210> SEQ ID NO 80
<211> LENGTH: 19
<212> TYPE: RNA
<213> ORGANISM: Artificial Sequence
<220> FEATURE:
<223> OTHER INFORMATION: Synthetic

<400> SEQUENCE: 80
augauccagg gcggagacu                                                      19

<210> SEQ ID NO 81
<211> LENGTH: 19
<212> TYPE: RNA
<213> ORGANISM: Artificial Sequence
<220> FEATURE:
<223> OTHER INFORMATION: Synthetic

<400> SEQUENCE: 81
gauccagggc ggagacuuc                                                      19

<210> SEQ ID NO 82
<211> LENGTH: 19
<212> TYPE: RNA
<213> ORGANISM: Artificial Sequence
<220> FEATURE:
<223> OTHER INFORMATION: Synthetic

<400> SEQUENCE: 82
uccagggcgg agacuucac                                                      19

<210> SEQ ID NO 83
<211> LENGTH: 19
<212> TYPE: RNA
<213> ORGANISM: Artificial Sequence
<220> FEATURE:
<223> OTHER INFORMATION: Synthetic

<400> SEQUENCE: 83
cagggcggag acuucacca                                                      19

<210> SEQ ID NO 84
<211> LENGTH: 19
<212> TYPE: RNA
<213> ORGANISM: Artificial Sequence
<220> FEATURE:
<223> OTHER INFORMATION: Synthetic

<400> SEQUENCE: 84
gggcggagac uucaccagg                                                      19

<210> SEQ ID NO 85
<211> LENGTH: 19
<212> TYPE: RNA
<213> ORGANISM: Artificial Sequence
<220> FEATURE:
<223> OTHER INFORMATION: Synthetic

<400> SEQUENCE: 85
gcggagacuu caccagggg                                                      19

<210> SEQ ID NO 86
<211> LENGTH: 19
<212> TYPE: RNA
<213> ORGANISM: Artificial Sequence
<220> FEATURE:
<223> OTHER INFORMATION: Synthetic
```

```
<400> SEQUENCE: 86
ggagacuuca ccaggggag                                                  19

<210> SEQ ID NO 87
<211> LENGTH: 19
<212> TYPE: RNA
<213> ORGANISM: Artificial Sequence
<220> FEATURE:
<223> OTHER INFORMATION: Synthetic

<400> SEQUENCE: 87
agacuucacc agggagau                                                   19

<210> SEQ ID NO 88
<211> LENGTH: 19
<212> TYPE: RNA
<213> ORGANISM: Artificial Sequence
<220> FEATURE:
<223> OTHER INFORMATION: Synthetic

<400> SEQUENCE: 88
acuucaccag gggagaugg                                                  19

<210> SEQ ID NO 89
<211> LENGTH: 19
<212> TYPE: RNA
<213> ORGANISM: Artificial Sequence
<220> FEATURE:
<223> OTHER INFORMATION: Synthetic

<400> SEQUENCE: 89
uucaccaggg gagauggca                                                  19

<210> SEQ ID NO 90
<211> LENGTH: 19
<212> TYPE: RNA
<213> ORGANISM: Artificial Sequence
<220> FEATURE:
<223> OTHER INFORMATION: Synthetic

<400> SEQUENCE: 90
caccagggga gauggcaca                                                  19

<210> SEQ ID NO 91
<211> LENGTH: 19
<212> TYPE: RNA
<213> ORGANISM: Artificial Sequence
<220> FEATURE:
<223> OTHER INFORMATION: Synthetic

<400> SEQUENCE: 91
ccaggggaga uggcacagg                                                  19

<210> SEQ ID NO 92
<211> LENGTH: 19
<212> TYPE: RNA
<213> ORGANISM: Artificial Sequence
<220> FEATURE:
<223> OTHER INFORMATION: Synthetic

<400> SEQUENCE: 92
aggggagaug gcacaggag                                                  19
```

```
<210> SEQ ID NO 93
<211> LENGTH: 19
<212> TYPE: RNA
<213> ORGANISM: Artificial Sequence
<220> FEATURE:
<223> OTHER INFORMATION: Synthetic

<400> SEQUENCE: 93
gggagauggc acaggagga                                                19

<210> SEQ ID NO 94
<211> LENGTH: 19
<212> TYPE: RNA
<213> ORGANISM: Artificial Sequence
<220> FEATURE:
<223> OTHER INFORMATION: Synthetic

<400> SEQUENCE: 94
gagauggcac aggaggaaa                                                19

<210> SEQ ID NO 95
<211> LENGTH: 19
<212> TYPE: RNA
<213> ORGANISM: Artificial Sequence
<220> FEATURE:
<223> OTHER INFORMATION: Synthetic

<400> SEQUENCE: 95
gauggcacag gaggaaaga                                                19

<210> SEQ ID NO 96
<211> LENGTH: 19
<212> TYPE: RNA
<213> ORGANISM: Artificial Sequence
<220> FEATURE:
<223> OTHER INFORMATION: Synthetic

<400> SEQUENCE: 96
uggcacagga ggaaagagc                                                19

<210> SEQ ID NO 97
<211> LENGTH: 19
<212> TYPE: RNA
<213> ORGANISM: Artificial Sequence
<220> FEATURE:
<223> OTHER INFORMATION: Synthetic

<400> SEQUENCE: 97
gcacaggagg aaagagcau                                                19

<210> SEQ ID NO 98
<211> LENGTH: 19
<212> TYPE: RNA
<213> ORGANISM: Artificial Sequence
<220> FEATURE:
<223> OTHER INFORMATION: Synthetic

<400> SEQUENCE: 98
acaggaggaa agagcaucu                                                19

<210> SEQ ID NO 99
<211> LENGTH: 19
<212> TYPE: RNA
<213> ORGANISM: Artificial Sequence
<220> FEATURE:
<223> OTHER INFORMATION: Synthetic
```

```
<400> SEQUENCE: 99
aggaggaaag agcaucuac                                                   19

<210> SEQ ID NO 100
<211> LENGTH: 19
<212> TYPE: RNA
<213> ORGANISM: Artificial Sequence
<220> FEATURE:
<223> OTHER INFORMATION: Synthetic

<400> SEQUENCE: 100
gaggaaagag caucuacgg                                                   19

<210> SEQ ID NO 101
<211> LENGTH: 19
<212> TYPE: RNA
<213> ORGANISM: Artificial Sequence
<220> FEATURE:
<223> OTHER INFORMATION: Synthetic

<400> SEQUENCE: 101
ggaaagagca ucuacggug                                                   19

<210> SEQ ID NO 102
<211> LENGTH: 19
<212> TYPE: RNA
<213> ORGANISM: Artificial Sequence
<220> FEATURE:
<223> OTHER INFORMATION: Synthetic

<400> SEQUENCE: 102
aaagagcauc uacggugag                                                   19

<210> SEQ ID NO 103
<211> LENGTH: 19
<212> TYPE: RNA
<213> ORGANISM: Artificial Sequence
<220> FEATURE:
<223> OTHER INFORMATION: Synthetic

<400> SEQUENCE: 103
agagcaucua cggugagcg                                                   19

<210> SEQ ID NO 104
<211> LENGTH: 19
<212> TYPE: RNA
<213> ORGANISM: Artificial Sequence
<220> FEATURE:
<223> OTHER INFORMATION: Synthetic

<400> SEQUENCE: 104
agcaucuacg gugagcgcu                                                   19

<210> SEQ ID NO 105
<211> LENGTH: 19
<212> TYPE: RNA
<213> ORGANISM: Artificial Sequence
<220> FEATURE:
<223> OTHER INFORMATION: Synthetic

<400> SEQUENCE: 105
caucuacggu gagcgcuuc                                                   19
```

```
<210> SEQ ID NO 106
<211> LENGTH: 19
<212> TYPE: RNA
<213> ORGANISM: Artificial Sequence
<220> FEATURE:
<223> OTHER INFORMATION: Synthetic

<400> SEQUENCE: 106
ucuacgguga gcgcuuccc                                                    19

<210> SEQ ID NO 107
<211> LENGTH: 19
<212> TYPE: RNA
<213> ORGANISM: Artificial Sequence
<220> FEATURE:
<223> OTHER INFORMATION: Synthetic

<400> SEQUENCE: 107
uacggugagc gcuuccccg                                                    19

<210> SEQ ID NO 108
<211> LENGTH: 19
<212> TYPE: RNA
<213> ORGANISM: Artificial Sequence
<220> FEATURE:
<223> OTHER INFORMATION: Synthetic

<400> SEQUENCE: 108
cggugagcgc uuccccgau                                                    19

<210> SEQ ID NO 109
<211> LENGTH: 19
<212> TYPE: RNA
<213> ORGANISM: Artificial Sequence
<220> FEATURE:
<223> OTHER INFORMATION: Synthetic

<400> SEQUENCE: 109
gugagcgcuu ccccgauga                                                    19

<210> SEQ ID NO 110
<211> LENGTH: 19
<212> TYPE: RNA
<213> ORGANISM: Artificial Sequence
<220> FEATURE:
<223> OTHER INFORMATION: Synthetic

<400> SEQUENCE: 110
gagcgcuucc ccgaugaga                                                    19

<210> SEQ ID NO 111
<211> LENGTH: 19
<212> TYPE: RNA
<213> ORGANISM: Artificial Sequence
<220> FEATURE:
<223> OTHER INFORMATION: Synthetic

<400> SEQUENCE: 111 gcgcuuccc gaugagaac                                                     19

<210> SEQ ID NO 112
<211> LENGTH: 19
<212> TYPE: RNA
<213> ORGANISM: Artificial Sequence
<220> FEATURE:
<223> OTHER INFORMATION: Synthetic
```

<400> SEQUENCE: 112 gcuucccga ugagaacuu                                                19

<210> SEQ ID NO 113
<211> LENGTH: 19
<212> TYPE: RNA
<213> ORGANISM: Artificial Sequence
<220> FEATURE:
<223> OTHER INFORMATION: Synthetic

<400> SEQUENCE: 113
uuccccgaug agaacuuca                                               19

<210> SEQ ID NO 114
<211> LENGTH: 19
<212> TYPE: RNA
<213> ORGANISM: Artificial Sequence
<220> FEATURE:
<223> OTHER INFORMATION: Synthetic

<400> SEQUENCE: 114
ccccgaugag aacuucaaa                                               19

<210> SEQ ID NO 115
<211> LENGTH: 19
<212> TYPE: RNA
<213> ORGANISM: Artificial Sequence
<220> FEATURE:
<223> OTHER INFORMATION: Synthetic

<400> SEQUENCE: 115
ccgaugagaa cuucaaacu                                               19

<210> SEQ ID NO 116
<211> LENGTH: 19
<212> TYPE: RNA
<213> ORGANISM: Artificial Sequence
<220> FEATURE:
<223> OTHER INFORMATION: Synthetic

<400> SEQUENCE: 116
gaugagaacu ucaaacuga                                               19

<210> SEQ ID NO 117
<211> LENGTH: 19
<212> TYPE: RNA
<213> ORGANISM: Artificial Sequence
<220> FEATURE:
<223> OTHER INFORMATION: Synthetic

<400> SEQUENCE: 117
ugagaacuuc aaacugaag                                               19

<210> SEQ ID NO 118
<211> LENGTH: 19
<212> TYPE: RNA
<213> ORGANISM: Artificial Sequence
<220> FEATURE:
<223> OTHER INFORMATION: Synthetic

<400> SEQUENCE: 118
agaacuucaa acugaagca                                               19

```
<210> SEQ ID NO 119
<211> LENGTH: 19
<212> TYPE: RNA
<213> ORGANISM: Artificial Sequence
<220> FEATURE:
<223> OTHER INFORMATION: Synthetic

<400> SEQUENCE: 119
aacuucaaac ugaagcacu                                                  19

<210> SEQ ID NO 120
<211> LENGTH: 19
<212> TYPE: RNA
<213> ORGANISM: Artificial Sequence
<220> FEATURE:
<223> OTHER INFORMATION: Synthetic

<400> SEQUENCE: 120
cuucaaacug aagcacuac                                                  19

<210> SEQ ID NO 121
<211> LENGTH: 19
<212> TYPE: RNA
<213> ORGANISM: Artificial Sequence
<220> FEATURE:
<223> OTHER INFORMATION: Synthetic

<400> SEQUENCE: 121
ucaaacugaa gcacuacgg                                                  19

<210> SEQ ID NO 122
<211> LENGTH: 19
<212> TYPE: RNA
<213> ORGANISM: Artificial Sequence
<220> FEATURE:
<223> OTHER INFORMATION: Synthetic

<400> SEQUENCE: 122
acgggcaagg ccaaguggg                                                  19

<210> SEQ ID NO 123
<211> LENGTH: 19
<212> TYPE: RNA
<213> ORGANISM: Artificial Sequence
<220> FEATURE:
<223> OTHER INFORMATION: Synthetic

<400> SEQUENCE: 123
cgggcaaggc caaguggga                                                  19

<210> SEQ ID NO 124
<211> LENGTH: 19
<212> TYPE: RNA
<213> ORGANISM: Artificial Sequence
<220> FEATURE:
<223> OTHER INFORMATION: Synthetic

<400> SEQUENCE: 124
gggcaaggcc aagugggau                                                  19

<210> SEQ ID NO 125
<211> LENGTH: 19
<212> TYPE: RNA
<213> ORGANISM: Artificial Sequence
<220> FEATURE:
<223> OTHER INFORMATION: Synthetic
```

```
<400> SEQUENCE: 125
ggcaaggcca agugggaug                                                    19

<210> SEQ ID NO 126
<211> LENGTH: 19
<212> TYPE: RNA
<213> ORGANISM: Artificial Sequence
<220> FEATURE:
<223> OTHER INFORMATION: Synthetic

<400> SEQUENCE: 126
gcaaggccaa gugggaugc                                                    19

<210> SEQ ID NO 127
<211> LENGTH: 19
<212> TYPE: RNA
<213> ORGANISM: Artificial Sequence
<220> FEATURE:
<223> OTHER INFORMATION: Synthetic

<400> SEQUENCE: 127
caaggccaag ugggaugcc                                                    19

<210> SEQ ID NO 128
<211> LENGTH: 19
<212> TYPE: RNA
<213> ORGANISM: Artificial Sequence
<220> FEATURE:
<223> OTHER INFORMATION: Synthetic

<400> SEQUENCE: 128
aaggccaagu gggaugccu                                                    19

<210> SEQ ID NO 129
<211> LENGTH: 19
<212> TYPE: RNA
<213> ORGANISM: Artificial Sequence
<220> FEATURE:
<223> OTHER INFORMATION: Synthetic

<400> SEQUENCE: 129
aggccaagug ggaugccug                                                    19

<210> SEQ ID NO 130
<211> LENGTH: 19
<212> TYPE: RNA
<213> ORGANISM: Artificial Sequence
<220> FEATURE:
<223> OTHER INFORMATION: Synthetic

<400> SEQUENCE: 130
ggccaagugg gaugccugg                                                    19

<210> SEQ ID NO 131
<211> LENGTH: 19
<212> TYPE: RNA
<213> ORGANISM: Artificial Sequence
<220> FEATURE:
<223> OTHER INFORMATION: Synthetic

<400> SEQUENCE: 131
gccaaguggg augccugga                                                    19
```

```
<210> SEQ ID NO 132
<211> LENGTH: 19
<212> TYPE: RNA
<213> ORGANISM: Artificial Sequence
<220> FEATURE:
<223> OTHER INFORMATION: Synthetic

<400> SEQUENCE: 132
ccaaguggga ugccuggaa                                               19

<210> SEQ ID NO 133
<211> LENGTH: 19
<212> TYPE: RNA
<213> ORGANISM: Artificial Sequence
<220> FEATURE:
<223> OTHER INFORMATION: Synthetic

<400> SEQUENCE: 133
caagugggau gccuggaau                                               19

<210> SEQ ID NO 134
<211> LENGTH: 19
<212> TYPE: RNA
<213> ORGANISM: Artificial Sequence
<220> FEATURE:
<223> OTHER INFORMATION: Synthetic

<400> SEQUENCE: 134
aagugggaug ccuggaaug                                               19

<210> SEQ ID NO 135
<211> LENGTH: 19
<212> TYPE: RNA
<213> ORGANISM: Artificial Sequence
<220> FEATURE:
<223> OTHER INFORMATION: Synthetic

<400> SEQUENCE: 135
agugggaugc cuggaauga                                               19

<210> SEQ ID NO 136
<211> LENGTH: 19
<212> TYPE: RNA
<213> ORGANISM: Artificial Sequence
<220> FEATURE:
<223> OTHER INFORMATION: Synthetic

<400> SEQUENCE: 136
gugggaugcc uggaaugag                                               19

<210> SEQ ID NO 137
<211> LENGTH: 19
<212> TYPE: RNA
<213> ORGANISM: Artificial Sequence
<220> FEATURE:
<223> OTHER INFORMATION: Synthetic

<400> SEQUENCE: 137
ugggaugccu ggaaugagc                                               19

<210> SEQ ID NO 138
<211> LENGTH: 19
<212> TYPE: RNA
<213> ORGANISM: Artificial Sequence
<220> FEATURE:
<223> OTHER INFORMATION: Synthetic
```

```
<400> SEQUENCE: 138
gggaugccug gaaugagcu                                                    19

<210> SEQ ID NO 139
<211> LENGTH: 19
<212> TYPE: RNA
<213> ORGANISM: Artificial Sequence
<220> FEATURE:
<223> OTHER INFORMATION: Synthetic

<400> SEQUENCE: 139
ggaugccugg aaugagcug                                                    19

<210> SEQ ID NO 140
<211> LENGTH: 19
<212> TYPE: RNA
<213> ORGANISM: Artificial Sequence
<220> FEATURE:
<223> OTHER INFORMATION: Synthetic

<400> SEQUENCE: 140
gaugccugga augagcuga                                                    19

<210> SEQ ID NO 141
<211> LENGTH: 19
<212> TYPE: RNA
<213> ORGANISM: Artificial Sequence
<220> FEATURE:
<223> OTHER INFORMATION: Synthetic

<400> SEQUENCE: 141
augccuggaa ugagcugaa                                                    19

<210> SEQ ID NO 142
<211> LENGTH: 19
<212> TYPE: RNA
<213> ORGANISM: Artificial Sequence
<220> FEATURE:
<223> OTHER INFORMATION: Synthetic

<400> SEQUENCE: 142
ugccuggaau gagcugaaa                                                    19

<210> SEQ ID NO 143
<211> LENGTH: 19
<212> TYPE: RNA
<213> ORGANISM: Artificial Sequence
<220> FEATURE:
<223> OTHER INFORMATION: Synthetic

<400> SEQUENCE: 143
gccuggaaug agcugaaag                                                    19

<210> SEQ ID NO 144
<211> LENGTH: 19
<212> TYPE: RNA
<213> ORGANISM: Artificial Sequence
<220> FEATURE:
<223> OTHER INFORMATION: Synthetic

<400> SEQUENCE: 144
ccuggaauga gcugaaagg                                                    19
```

```
<210> SEQ ID NO 145
<211> LENGTH: 19
<212> TYPE: RNA
<213> ORGANISM: Artificial Sequence
<220> FEATURE:
<223> OTHER INFORMATION: Synthetic

<400> SEQUENCE: 145
cuggaaugag cugaaaggg                                                19

<210> SEQ ID NO 146
<211> LENGTH: 19
<212> TYPE: RNA
<213> ORGANISM: Artificial Sequence
<220> FEATURE:
<223> OTHER INFORMATION: Synthetic

<400> SEQUENCE: 146
uggaaugagc ugaaaggga                                                19

<210> SEQ ID NO 147
<211> LENGTH: 19
<212> TYPE: RNA
<213> ORGANISM: Artificial Sequence
<220> FEATURE:
<223> OTHER INFORMATION: Synthetic

<400> SEQUENCE: 147
ggaaugagcu gaaagggac                                                19

<210> SEQ ID NO 148
<211> LENGTH: 19
<212> TYPE: RNA
<213> ORGANISM: Artificial Sequence
<220> FEATURE:
<223> OTHER INFORMATION: Synthetic

<400> SEQUENCE: 148
gaaugagcug aaagggacu                                                19

<210> SEQ ID NO 149
<211> LENGTH: 19
<212> TYPE: RNA
<213> ORGANISM: Artificial Sequence
<220> FEATURE:
<223> OTHER INFORMATION: Synthetic

<400> SEQUENCE: 149
aaugagcuga aagggacuu                                                19

<210> SEQ ID NO 150
<211> LENGTH: 19
<212> TYPE: RNA
<213> ORGANISM: Artificial Sequence
<220> FEATURE:
<223> OTHER INFORMATION: Synthetic

<400> SEQUENCE: 150
augagcugaa agggacuuc                                                19

<210> SEQ ID NO 151
<211> LENGTH: 19
<212> TYPE: RNA
<213> ORGANISM: Artificial Sequence
<220> FEATURE:
<223> OTHER INFORMATION: Synthetic
```

```
<400> SEQUENCE: 151
ugagcugaaa gggacuucc                                                19

<210> SEQ ID NO 152
<211> LENGTH: 19
<212> TYPE: RNA
<213> ORGANISM: Artificial Sequence
<220> FEATURE:
<223> OTHER INFORMATION: Synthetic

<400> SEQUENCE: 152
gagcugaaag ggacuucca                                                19

<210> SEQ ID NO 153
<211> LENGTH: 19
<212> TYPE: RNA
<213> ORGANISM: Artificial Sequence
<220> FEATURE:
<223> OTHER INFORMATION: Synthetic

<400> SEQUENCE: 153
agcugaaagg gacuuccaa                                                19

<210> SEQ ID NO 154
<211> LENGTH: 19
<212> TYPE: RNA
<213> ORGANISM: Artificial Sequence
<220> FEATURE:
<223> OTHER INFORMATION: Synthetic

<400> SEQUENCE: 154
gcugaaaggg acuuccaag                                                19

<210> SEQ ID NO 155
<211> LENGTH: 19
<212> TYPE: RNA
<213> ORGANISM: Artificial Sequence
<220> FEATURE:
<223> OTHER INFORMATION: Synthetic

<400> SEQUENCE: 155
cugaaaggga cuuccaagg                                                19

<210> SEQ ID NO 156
<211> LENGTH: 19
<212> TYPE: RNA
<213> ORGANISM: Artificial Sequence
<220> FEATURE:
<223> OTHER INFORMATION: Synthetic

<400> SEQUENCE: 156
ugaaagggac uuccaagga                                                19

<210> SEQ ID NO 157
<211> LENGTH: 19
<212> TYPE: RNA
<213> ORGANISM: Artificial Sequence
<220> FEATURE:
<223> OTHER INFORMATION: Synthetic

<400> SEQUENCE: 157
gaaagggacu uccaaggaa                                                19
```

```
<210> SEQ ID NO 158
<211> LENGTH: 19
<212> TYPE: RNA
<213> ORGANISM: Artificial Sequence
<220> FEATURE:
<223> OTHER INFORMATION: Synthetic

<400> SEQUENCE: 158
aaagggacuu ccaaggaag                                              19

<210> SEQ ID NO 159
<211> LENGTH: 19
<212> TYPE: RNA
<213> ORGANISM: Artificial Sequence
<220> FEATURE:
<223> OTHER INFORMATION: Synthetic

<400> SEQUENCE: 159
aagggacuuc caaggaaga                                              19

<210> SEQ ID NO 160
<211> LENGTH: 19
<212> TYPE: RNA
<213> ORGANISM: Artificial Sequence
<220> FEATURE:
<223> OTHER INFORMATION: Synthetic

<400> SEQUENCE: 160
agggacuucc aaggaagau                                              19

<210> SEQ ID NO 161
<211> LENGTH: 19
<212> TYPE: RNA
<213> ORGANISM: Artificial Sequence
<220> FEATURE:
<223> OTHER INFORMATION: Synthetic

<400> SEQUENCE: 161
gggacuucca aggaagaug                                              19

<210> SEQ ID NO 162
<211> LENGTH: 19
<212> TYPE: RNA
<213> ORGANISM: Artificial Sequence
<220> FEATURE:
<223> OTHER INFORMATION: Synthetic

<400> SEQUENCE: 162
ggacuuccaa ggaagaugc                                              19

<210> SEQ ID NO 163
<211> LENGTH: 19
<212> TYPE: RNA
<213> ORGANISM: Artificial Sequence
<220> FEATURE:
<223> OTHER INFORMATION: Synthetic

<400> SEQUENCE: 163
gacuuccaag gaagaugcc                                              19

<210> SEQ ID NO 164
<211> LENGTH: 19
<212> TYPE: RNA
<213> ORGANISM: Artificial Sequence
<220> FEATURE:
<223> OTHER INFORMATION: Synthetic
```

```
<400> SEQUENCE: 164
acuuccaagg aagaugcca                                          19

<210> SEQ ID NO 165
<211> LENGTH: 19
<212> TYPE: RNA
<213> ORGANISM: Artificial Sequence
<220> FEATURE:
<223> OTHER INFORMATION: Synthetic

<400> SEQUENCE: 165
cuuccaagga agaugccau                                          19

<210> SEQ ID NO 166
<211> LENGTH: 19
<212> TYPE: RNA
<213> ORGANISM: Artificial Sequence
<220> FEATURE:
<223> OTHER INFORMATION: Synthetic

<400> SEQUENCE: 166
uuccaaggaa gaugccaug                                          19

<210> SEQ ID NO 167
<211> LENGTH: 19
<212> TYPE: RNA
<213> ORGANISM: Artificial Sequence
<220> FEATURE:
<223> OTHER INFORMATION: Synthetic

<400> SEQUENCE: 167
uccaaggaag augccauga                                          19

<210> SEQ ID NO 168
<211> LENGTH: 19
<212> TYPE: RNA
<213> ORGANISM: Artificial Sequence
<220> FEATURE:
<223> OTHER INFORMATION: Synthetic

<400> SEQUENCE: 168
ccaaggaaga ugccaugaa                                          19

<210> SEQ ID NO 169
<211> LENGTH: 19
<212> TYPE: RNA
<213> ORGANISM: Artificial Sequence
<220> FEATURE:
<223> OTHER INFORMATION: Synthetic

<400> SEQUENCE: 169
caaggaagau gccaugaaa                                          19

<210> SEQ ID NO 170
<211> LENGTH: 19
<212> TYPE: RNA
<213> ORGANISM: Artificial Sequence
<220> FEATURE:
<223> OTHER INFORMATION: Synthetic

<400> SEQUENCE: 170
aaggaagaug ccaugaaag                                          19
```

```
<210> SEQ ID NO 171
<211> LENGTH: 19
<212> TYPE: RNA
<213> ORGANISM: Artificial Sequence
<220> FEATURE:
<223> OTHER INFORMATION: Synthetic

<400> SEQUENCE: 171
aggaagaugc caugaaagc                                                   19

<210> SEQ ID NO 172
<211> LENGTH: 19
<212> TYPE: RNA
<213> ORGANISM: Artificial Sequence
<220> FEATURE:
<223> OTHER INFORMATION: Synthetic

<400> SEQUENCE: 172
ggaagaugcc augaaagcu                                                   19

<210> SEQ ID NO 173
<211> LENGTH: 19
<212> TYPE: RNA
<213> ORGANISM: Artificial Sequence
<220> FEATURE:
<223> OTHER INFORMATION: Synthetic

<400> SEQUENCE: 173
gaagaugcca ugaaagcuu                                                   19

<210> SEQ ID NO 174
<211> LENGTH: 19
<212> TYPE: RNA
<213> ORGANISM: Artificial Sequence
<220> FEATURE:
<223> OTHER INFORMATION: Synthetic

<400> SEQUENCE: 174
aagaugccau gaaagcuua                                                   19

<210> SEQ ID NO 175
<211> LENGTH: 19
<212> TYPE: RNA
<213> ORGANISM: Artificial Sequence
<220> FEATURE:
<223> OTHER INFORMATION: Synthetic

<400> SEQUENCE: 175
agaugccaug aaagcuuac                                                   19

<210> SEQ ID NO 176
<211> LENGTH: 19
<212> TYPE: RNA
<213> ORGANISM: Artificial Sequence
<220> FEATURE:
<223> OTHER INFORMATION: Synthetic

<400> SEQUENCE: 176
gaugccauga aagcuuaca                                                   19

<210> SEQ ID NO 177
<211> LENGTH: 19
<212> TYPE: RNA
<213> ORGANISM: Artificial Sequence
<220> FEATURE:
<223> OTHER INFORMATION: Synthetic
```

```
<400> SEQUENCE: 177
augccaugaa agcuuacau                                              19

<210> SEQ ID NO 178
<211> LENGTH: 19
<212> TYPE: RNA
<213> ORGANISM: Artificial Sequence
<220> FEATURE:
<223> OTHER INFORMATION: Synthetic

<400> SEQUENCE: 178
ugccaugaaa gcuuacauc                                              19

<210> SEQ ID NO 179
<211> LENGTH: 19
<212> TYPE: RNA
<213> ORGANISM: Artificial Sequence
<220> FEATURE:
<223> OTHER INFORMATION: Synthetic

<400> SEQUENCE: 179
gccaugaaag cuuacauca                                              19

<210> SEQ ID NO 180
<211> LENGTH: 19
<212> TYPE: RNA
<213> ORGANISM: Artificial Sequence
<220> FEATURE:
<223> OTHER INFORMATION: Synthetic

<400> SEQUENCE: 180
ccaugaaagc uuacaucaa                                              19

<210> SEQ ID NO 181
<211> LENGTH: 19
<212> TYPE: RNA
<213> ORGANISM: Artificial Sequence
<220> FEATURE:
<223> OTHER INFORMATION: Synthetic

<400> SEQUENCE: 181
caugaaagcu uacaucaac                                              19

<210> SEQ ID NO 182
<211> LENGTH: 19
<212> TYPE: RNA
<213> ORGANISM: Artificial Sequence
<220> FEATURE:
<223> OTHER INFORMATION: Synthetic

<400> SEQUENCE: 182
augaaagcuu acaucaaca                                              19

<210> SEQ ID NO 183
<211> LENGTH: 19
<212> TYPE: RNA
<213> ORGANISM: Artificial Sequence
<220> FEATURE:
<223> OTHER INFORMATION: Synthetic

<400> SEQUENCE: 183
ugaaagcuua caucaacaa                                              19
```

```
<210> SEQ ID NO 184
<211> LENGTH: 19
<212> TYPE: RNA
<213> ORGANISM: Artificial Sequence
<220> FEATURE:
<223> OTHER INFORMATION: Synthetic

<400> SEQUENCE: 184
gaaagcuuac aucaacaaa                                                    19

<210> SEQ ID NO 185
<211> LENGTH: 19
<212> TYPE: RNA
<213> ORGANISM: Artificial Sequence
<220> FEATURE:
<223> OTHER INFORMATION: Synthetic

<400> SEQUENCE: 185
aaagcuuaca ucaacaaag                                                    19

<210> SEQ ID NO 186
<211> LENGTH: 19
<212> TYPE: RNA
<213> ORGANISM: Artificial Sequence
<220> FEATURE:
<223> OTHER INFORMATION: Synthetic

<400> SEQUENCE: 186
aagcuuacau caacaaagu                                                    19

<210> SEQ ID NO 187
<211> LENGTH: 19
<212> TYPE: RNA
<213> ORGANISM: Artificial Sequence
<220> FEATURE:
<223> OTHER INFORMATION: Synthetic

<400> SEQUENCE: 187
agcuuacauc aacaaagua                                                    19

<210> SEQ ID NO 188
<211> LENGTH: 19
<212> TYPE: RNA
<213> ORGANISM: Artificial Sequence
<220> FEATURE:
<223> OTHER INFORMATION: Synthetic

<400> SEQUENCE: 188
gcuuacauca acaaaguag                                                    19

<210> SEQ ID NO 189
<211> LENGTH: 19
<212> TYPE: RNA
<213> ORGANISM: Artificial Sequence
<220> FEATURE:
<223> OTHER INFORMATION: Synthetic

<400> SEQUENCE: 189
cuuacaucaa caaaguaga                                                    19

<210> SEQ ID NO 190
<211> LENGTH: 19
<212> TYPE: RNA
<213> ORGANISM: Artificial Sequence
<220> FEATURE:
<223> OTHER INFORMATION: Synthetic
```

```
<400> SEQUENCE: 190
uuacaucaac aaaguagaa                                            19

<210> SEQ ID NO 191
<211> LENGTH: 19
<212> TYPE: RNA
<213> ORGANISM: Artificial Sequence
<220> FEATURE:
<223> OTHER INFORMATION: Synthetic

<400> SEQUENCE: 191
uacaucaaca aaguagaag                                            19

<210> SEQ ID NO 192
<211> LENGTH: 19
<212> TYPE: RNA
<213> ORGANISM: Artificial Sequence
<220> FEATURE:
<223> OTHER INFORMATION: Synthetic

<400> SEQUENCE: 192
acaucaacaa aguagaaga                                            19

<210> SEQ ID NO 193
<211> LENGTH: 19
<212> TYPE: RNA
<213> ORGANISM: Artificial Sequence
<220> FEATURE:
<223> OTHER INFORMATION: Synthetic

<400> SEQUENCE: 193
caucaacaaa guagaagag                                            19

<210> SEQ ID NO 194
<211> LENGTH: 19
<212> TYPE: RNA
<213> ORGANISM: Artificial Sequence
<220> FEATURE:
<223> OTHER INFORMATION: Synthetic

<400> SEQUENCE: 194
aucaacaaag uagaagagc                                            19

<210> SEQ ID NO 195
<211> LENGTH: 19
<212> TYPE: RNA
<213> ORGANISM: Artificial Sequence
<220> FEATURE:
<223> OTHER INFORMATION: Synthetic

<400> SEQUENCE: 195
ucaacaaagu agaagagcu                                            19

<210> SEQ ID NO 196
<211> LENGTH: 19
<212> TYPE: RNA
<213> ORGANISM: Artificial Sequence
<220> FEATURE:
<223> OTHER INFORMATION: Synthetic

<400> SEQUENCE: 196
caacaaagua gaagagcua                                            19
```

```
<210> SEQ ID NO 197
<211> LENGTH: 19
<212> TYPE: RNA
<213> ORGANISM: Artificial Sequence
<220> FEATURE:
<223> OTHER INFORMATION: Synthetic

<400> SEQUENCE: 197
aacaaaguag aagagcuaa                                                19

<210> SEQ ID NO 198
<211> LENGTH: 19
<212> TYPE: RNA
<213> ORGANISM: Artificial Sequence
<220> FEATURE:
<223> OTHER INFORMATION: Synthetic

<400> SEQUENCE: 198
acaaaguaga agagcuaaa                                                19

<210> SEQ ID NO 199
<211> LENGTH: 19
<212> TYPE: RNA
<213> ORGANISM: Artificial Sequence
<220> FEATURE:
<223> OTHER INFORMATION: Synthetic

<400> SEQUENCE: 199
caaaguagaa gagcuaaag                                                19

<210> SEQ ID NO 200
<211> LENGTH: 19
<212> TYPE: RNA
<213> ORGANISM: Artificial Sequence
<220> FEATURE:
<223> OTHER INFORMATION: Synthetic

<400> SEQUENCE: 200
aaaguagaag agcuaaaga                                                19

<210> SEQ ID NO 201
<211> LENGTH: 19
<212> TYPE: RNA
<213> ORGANISM: Artificial Sequence
<220> FEATURE:
<223> OTHER INFORMATION: Synthetic

<400> SEQUENCE: 201
aaguagaaga gcuaaagaa                                                19

<210> SEQ ID NO 202
<211> LENGTH: 19
<212> TYPE: RNA
<213> ORGANISM: Artificial Sequence
<220> FEATURE:
<223> OTHER INFORMATION: Synthetic

<400> SEQUENCE: 202
aguagaagag cuaaagaaa                                                19

<210> SEQ ID NO 203
<211> LENGTH: 19
<212> TYPE: RNA
<213> ORGANISM: Artificial Sequence
<220> FEATURE:
<223> OTHER INFORMATION: Synthetic
```

```
<400> SEQUENCE: 203
guagaagagc uaagaaaa                                               19

<210> SEQ ID NO 204
<211> LENGTH: 19
<212> TYPE: RNA
<213> ORGANISM: Artificial Sequence
<220> FEATURE:
<223> OTHER INFORMATION: Synthetic

<400> SEQUENCE: 204
uagaagagcu aagaaaaa                                               19

<210> SEQ ID NO 205
<211> LENGTH: 19
<212> TYPE: RNA
<213> ORGANISM: Artificial Sequence
<220> FEATURE:
<223> OTHER INFORMATION: Synthetic

<400> SEQUENCE: 205
agaagagcua agaaaaaa                                               19

<210> SEQ ID NO 206
<211> LENGTH: 19
<212> TYPE: RNA
<213> ORGANISM: Artificial Sequence
<220> FEATURE:
<223> OTHER INFORMATION: Synthetic

<400> SEQUENCE: 206
gaagagcuaa agaaaaaau                                              19

<210> SEQ ID NO 207
<211> LENGTH: 19
<212> TYPE: RNA
<213> ORGANISM: Artificial Sequence
<220> FEATURE:
<223> OTHER INFORMATION: Synthetic

<400> SEQUENCE: 207
aagagcuaaa gaaaaaaua                                              19

<210> SEQ ID NO 208
<211> LENGTH: 19
<212> TYPE: RNA
<213> ORGANISM: Artificial Sequence
<220> FEATURE:
<223> OTHER INFORMATION: Synthetic

<400> SEQUENCE: 208
agagcuaaag aaaaauac                                               19

<210> SEQ ID NO 209
<211> LENGTH: 19
<212> TYPE: RNA
<213> ORGANISM: Artificial Sequence
<220> FEATURE:
<223> OTHER INFORMATION: Synthetic

<400> SEQUENCE: 209
gagcuaaaga aaaauacg                                               19
```

```
<210> SEQ ID NO 210
<211> LENGTH: 19
<212> TYPE: RNA
<213> ORGANISM: Artificial Sequence
<220> FEATURE:
<223> OTHER INFORMATION: Synthetic

<400> SEQUENCE: 210
agcuaaagaa aaaauacgg                                                19

<210> SEQ ID NO 211
<211> LENGTH: 19
<212> TYPE: RNA
<213> ORGANISM: Artificial Sequence
<220> FEATURE:
<223> OTHER INFORMATION: Synthetic

<400> SEQUENCE: 211
gcuaaagaaa aaauacggg                                                19

<210> SEQ ID NO 212
<211> LENGTH: 19
<212> TYPE: RNA
<213> ORGANISM: Artificial Sequence
<220> FEATURE:
<223> OTHER INFORMATION: Synthetic

<400> SEQUENCE: 212
auccucauaa aggccaaga                                                19

<210> SEQ ID NO 213
<211> LENGTH: 19
<212> TYPE: RNA
<213> ORGANISM: Artificial Sequence
<220> FEATURE:
<223> OTHER INFORMATION: Synthetic

<400> SEQUENCE: 213
agauccucau aaaggccaa                                                19

<210> SEQ ID NO 214
<211> LENGTH: 19
<212> TYPE: RNA
<213> ORGANISM: Artificial Sequence
<220> FEATURE:
<223> OTHER INFORMATION: Synthetic

<400> SEQUENCE: 214
agagauccuc auaaaggcc                                                19

<210> SEQ ID NO 215
<211> LENGTH: 19
<212> TYPE: RNA
<213> ORGANISM: Artificial Sequence
<220> FEATURE:
<223> OTHER INFORMATION: Synthetic

<400> SEQUENCE: 215
agagagaucc ucauaaagg                                                19

<210> SEQ ID NO 216
<211> LENGTH: 19
<212> TYPE: RNA
<213> ORGANISM: Artificial Sequence
<220> FEATURE:
<223> OTHER INFORMATION: Synthetic
```

<400> SEQUENCE: 216
ucagagagau ccucauaaa                                                    19

<210> SEQ ID NO 217
<211> LENGTH: 19
<212> TYPE: RNA
<213> ORGANISM: Artificial Sequence
<220> FEATURE:
<223> OTHER INFORMATION: Synthetic

<400> SEQUENCE: 217
aaucagagag auccucaua                                                    19

<210> SEQ ID NO 218
<211> LENGTH: 19
<212> TYPE: RNA
<213> ORGANISM: Artificial Sequence
<220> FEATURE:
<223> OTHER INFORMATION: Synthetic

<400> SEQUENCE: 218
aaaaucagag agauccuca                                                    19

<210> SEQ ID NO 219
<211> LENGTH: 19
<212> TYPE: RNA
<213> ORGANISM: Artificial Sequence
<220> FEATURE:
<223> OTHER INFORMATION: Synthetic

<400> SEQUENCE: 219 gaaaaucag agagauccu                                                     19

<210> SEQ ID NO 220
<211> LENGTH: 19
<212> TYPE: RNA
<213> ORGANISM: Artificial Sequence
<220> FEATURE:
<223> OTHER INFORMATION: Synthetic

<400> SEQUENCE: 220
aagaaaaauc agagagauc                                                    19

<210> SEQ ID NO 221
<211> LENGTH: 19
<212> TYPE: RNA
<213> ORGANISM: Artificial Sequence
<220> FEATURE:
<223> OTHER INFORMATION: Synthetic

<400> SEQUENCE: 221
gcaagaaaaa ucagagaga                                                    19

<210> SEQ ID NO 222
<211> LENGTH: 19
<212> TYPE: RNA
<213> ORGANISM: Artificial Sequence
<220> FEATURE:
<223> OTHER INFORMATION: Synthetic

<400> SEQUENCE: 222
acgcaagaaa aaucagaga                                                    19

```
<210> SEQ ID NO 223
<211> LENGTH: 19
<212> TYPE: RNA
<213> ORGANISM: Artificial Sequence
<220> FEATURE:
<223> OTHER INFORMATION: Synthetic

<400> SEQUENCE: 223
cgacgcaaga aaaucaga                                                   19

<210> SEQ ID NO 224
<211> LENGTH: 19
<212> TYPE: RNA
<213> ORGANISM: Artificial Sequence
<220> FEATURE:
<223> OTHER INFORMATION: Synthetic

<400> SEQUENCE: 224
cucgacgcaa gaaaaauca                                                  19

<210> SEQ ID NO 225
<211> LENGTH: 19
<212> TYPE: RNA
<213> ORGANISM: Artificial Sequence
<220> FEATURE:
<223> OTHER INFORMATION: Synthetic

<400> SEQUENCE: 225
aacucgacgc aagaaaaau                                                  19

<210> SEQ ID NO 226
<211> LENGTH: 19
<212> TYPE: RNA
<213> ORGANISM: Artificial Sequence
<220> FEATURE:
<223> OTHER INFORMATION: Synthetic

<400> SEQUENCE: 226
aaaacucgac gcaagaaaa                                                  19

<210> SEQ ID NO 227
<211> LENGTH: 19
<212> TYPE: RNA
<213> ORGANISM: Artificial Sequence
<220> FEATURE:
<223> OTHER INFORMATION: Synthetic

<400> SEQUENCE: 227
ggaaaacucg acgcaagaa                                                  19

<210> SEQ ID NO 228
<211> LENGTH: 19
<212> TYPE: RNA
<213> ORGANISM: Artificial Sequence
<220> FEATURE:
<223> OTHER INFORMATION: Synthetic

<400> SEQUENCE: 228
ccggaaaacu cgacgcaag                                                  19

<210> SEQ ID NO 229
<211> LENGTH: 19
<212> TYPE: RNA
<213> ORGANISM: Artificial Sequence
<220> FEATURE:
<223> OTHER INFORMATION: Synthetic
```

```
<400> SEQUENCE: 229
uaccggaaaa cucgacgca                                                19

<210> SEQ ID NO 230
<211> LENGTH: 19
<212> TYPE: RNA
<213> ORGANISM: Artificial Sequence
<220> FEATURE:
<223> OTHER INFORMATION: Synthetic

<400> SEQUENCE: 230
cuuaccggaa aacucgacg                                                19

<210> SEQ ID NO 231
<211> LENGTH: 19
<212> TYPE: RNA
<213> ORGANISM: Artificial Sequence
<220> FEATURE:
<223> OTHER INFORMATION: Synthetic

<400> SEQUENCE: 231
gucuuaccgg aaaacucga                                                19

<210> SEQ ID NO 232
<211> LENGTH: 19
<212> TYPE: RNA
<213> ORGANISM: Artificial Sequence
<220> FEATURE:
<223> OTHER INFORMATION: Synthetic

<400> SEQUENCE: 232
aggucuuacc ggaaaacuc                                                19

<210> SEQ ID NO 233
<211> LENGTH: 19
<212> TYPE: RNA
<213> ORGANISM: Artificial Sequence
<220> FEATURE:
<223> OTHER INFORMATION: Synthetic

<400> SEQUENCE: 233
aaaggucuua ccggaaaac                                                19

<210> SEQ ID NO 234
<211> LENGTH: 19
<212> TYPE: RNA
<213> ORGANISM: Artificial Sequence
<220> FEATURE:
<223> OTHER INFORMATION: Synthetic

<400> SEQUENCE: 234
cgaaaggucu uaccggaaa                                                19

<210> SEQ ID NO 235
<211> LENGTH: 19
<212> TYPE: RNA
<213> ORGANISM: Artificial Sequence
<220> FEATURE:
<223> OTHER INFORMATION: Synthetic

<400> SEQUENCE: 235
accgaaaggu cuuaccgga                                                19
```

```
<210> SEQ ID NO 236
<211> LENGTH: 19
<212> TYPE: RNA
<213> ORGANISM: Artificial Sequence
<220> FEATURE:
<223> OTHER INFORMATION: Synthetic

<400> SEQUENCE: 236
guaccgaaag gucuuaccg                                                  19

<210> SEQ ID NO 237
<211> LENGTH: 19
<212> TYPE: RNA
<213> ORGANISM: Artificial Sequence
<220> FEATURE:
<223> OTHER INFORMATION: Synthetic

<400> SEQUENCE: 237
aaguaccgaa aggucuuac                                                  19

<210> SEQ ID NO 238
<211> LENGTH: 19
<212> TYPE: RNA
<213> ORGANISM: Artificial Sequence
<220> FEATURE:
<223> OTHER INFORMATION: Synthetic

<400> SEQUENCE: 238
cgaaguaccg aaaggucuu                                                  19

<210> SEQ ID NO 239
<211> LENGTH: 19
<212> TYPE: RNA
<213> ORGANISM: Artificial Sequence
<220> FEATURE:
<223> OTHER INFORMATION: Synthetic

<400> SEQUENCE: 239
gacgaaguac cgaaagguc                                                  19

<210> SEQ ID NO 240
<211> LENGTH: 19
<212> TYPE: RNA
<213> ORGANISM: Artificial Sequence
<220> FEATURE:
<223> OTHER INFORMATION: Synthetic

<400> SEQUENCE: 240
uggacgaagu accgaaagg                                                  19

<210> SEQ ID NO 241
<211> LENGTH: 19
<212> TYPE: RNA
<213> ORGANISM: Artificial Sequence
<220> FEATURE:
<223> OTHER INFORMATION: Synthetic

<400> SEQUENCE: 241
uguggacgaa guaccgaaa                                                  19

<210> SEQ ID NO 242
<211> LENGTH: 19
<212> TYPE: RNA
<213> ORGANISM: Artificial Sequence
<220> FEATURE:
<223> OTHER INFORMATION: Synthetic
```

```
<400> SEQUENCE: 242
uuuguggacg aaguaccga                                          19

<210> SEQ ID NO 243
<211> LENGTH: 19
<212> TYPE: RNA
<213> ORGANISM: Artificial Sequence
<220> FEATURE:
<223> OTHER INFORMATION: Synthetic

<400> SEQUENCE: 243
uguuugugga cgaaguacc                                          19

<210> SEQ ID NO 244
<211> LENGTH: 19
<212> TYPE: RNA
<213> ORGANISM: Artificial Sequence
<220> FEATURE:
<223> OTHER INFORMATION: Synthetic

<400> SEQUENCE: 244
uguguuugug gacgaagua                                          19

<210> SEQ ID NO 245
<211> LENGTH: 19
<212> TYPE: RNA
<213> ORGANISM: Artificial Sequence
<220> FEATURE:
<223> OTHER INFORMATION: Synthetic

<400> SEQUENCE: 245
guuguguuug uggacgaag                                          19

<210> SEQ ID NO 246
<211> LENGTH: 19
<212> TYPE: RNA
<213> ORGANISM: Artificial Sequence
<220> FEATURE:
<223> OTHER INFORMATION: Synthetic

<400> SEQUENCE: 246
gaguuguguu uguggacga                                          19

<210> SEQ ID NO 247
<211> LENGTH: 19
<212> TYPE: RNA
<213> ORGANISM: Artificial Sequence
<220> FEATURE:
<223> OTHER INFORMATION: Synthetic

<400> SEQUENCE: 247
aggaguugug uuuguggac                                          19

<210> SEQ ID NO 248
<211> LENGTH: 19
<212> TYPE: RNA
<213> ORGANISM: Artificial Sequence
<220> FEATURE:
<223> OTHER INFORMATION: Synthetic

<400> SEQUENCE: 248
ggaggaguug uguuugugg                                          19
```

```
<210> SEQ ID NO 249
<211> LENGTH: 19
<212> TYPE: RNA
<213> ORGANISM: Artificial Sequence
<220> FEATURE:
<223> OTHER INFORMATION: Synthetic

<400> SEQUENCE: 249
gcggaggagu uguguuugu                                               19

<210> SEQ ID NO 250
<211> LENGTH: 19
<212> TYPE: RNA
<213> ORGANISM: Artificial Sequence
<220> FEATURE:
<223> OTHER INFORMATION: Synthetic

<400> SEQUENCE: 250
gcgcggagga guuguguuu                                               19

<210> SEQ ID NO 251
<211> LENGTH: 19
<212> TYPE: RNA
<213> ORGANISM: Artificial Sequence
<220> FEATURE:
<223> OTHER INFORMATION: Synthetic

<400> SEQUENCE: 251
uugcgcggag gaguugugu                                               19

<210> SEQ ID NO 252
<211> LENGTH: 19
<212> TYPE: RNA
<213> ORGANISM: Artificial Sequence
<220> FEATURE:
<223> OTHER INFORMATION: Synthetic

<400> SEQUENCE: 252
aguugcgcgg aggaguugu                                               19

<210> SEQ ID NO 253
<211> LENGTH: 19
<212> TYPE: RNA
<213> ORGANISM: Artificial Sequence
<220> FEATURE:
<223> OTHER INFORMATION: Synthetic

<400> SEQUENCE: 253
aaaguugcgc ggaggaguu                                               19

<210> SEQ ID NO 254
<211> LENGTH: 19
<212> TYPE: RNA
<213> ORGANISM: Artificial Sequence
<220> FEATURE:
<223> OTHER INFORMATION: Synthetic

<400> SEQUENCE: 254
aaaaaguugc gcggaggag                                               19

<210> SEQ ID NO 255
<211> LENGTH: 19
<212> TYPE: RNA
<213> ORGANISM: Artificial Sequence
<220> FEATURE:
<223> OTHER INFORMATION: Synthetic
```

<400> SEQUENCE: 255
cgaaaaaguu gcgcggagg                                                      19

<210> SEQ ID NO 256
<211> LENGTH: 19
<212> TYPE: RNA
<213> ORGANISM: Artificial Sequence
<220> FEATURE:
<223> OTHER INFORMATION: Synthetic

<400> SEQUENCE: 256
cgcgaaaaag uugcgcgga                                                      19

<210> SEQ ID NO 257
<211> LENGTH: 19
<212> TYPE: RNA
<213> ORGANISM: Artificial Sequence
<220> FEATURE:
<223> OTHER INFORMATION: Synthetic

<400> SEQUENCE: 257
accgcgaaaa aguugcgcg                                                      19

<210> SEQ ID NO 258
<211> LENGTH: 19
<212> TYPE: RNA
<213> ORGANISM: Artificial Sequence
<220> FEATURE:
<223> OTHER INFORMATION: Synthetic

<400> SEQUENCE: 258
caaccgcgaa aaaguugcg                                                      19

<210> SEQ ID NO 259
<211> LENGTH: 19
<212> TYPE: RNA
<213> ORGANISM: Artificial Sequence
<220> FEATURE:
<223> OTHER INFORMATION: Synthetic

<400> SEQUENCE: 259
aacaaccgcg aaaaaguug                                                      19

<210> SEQ ID NO 260
<211> LENGTH: 19
<212> TYPE: RNA
<213> ORGANISM: Artificial Sequence
<220> FEATURE:
<223> OTHER INFORMATION: Synthetic

<400> SEQUENCE: 260
guaacaaccg cgaaaaagu                                                      19

<210> SEQ ID NO 261
<211> LENGTH: 19
<212> TYPE: RNA
<213> ORGANISM: Artificial Sequence
<220> FEATURE:
<223> OTHER INFORMATION: Synthetic

<400> SEQUENCE: 261
aaguaacaac cgcgaaaaa                                                      19

```
<210> SEQ ID NO 262
<211> LENGTH: 19
<212> TYPE: RNA
<213> ORGANISM: Artificial Sequence
<220> FEATURE:
<223> OTHER INFORMATION: Synthetic

<400> SEQUENCE: 262
ucaaguaaca accgcgaaa                                                    19

<210> SEQ ID NO 263
<211> LENGTH: 19
<212> TYPE: RNA
<213> ORGANISM: Artificial Sequence
<220> FEATURE:
<223> OTHER INFORMATION: Synthetic

<400> SEQUENCE: 263
agucaaguaa caaccgcga                                                    19

<210> SEQ ID NO 264
<211> LENGTH: 19
<212> TYPE: RNA
<213> ORGANISM: Artificial Sequence
<220> FEATURE:
<223> OTHER INFORMATION: Synthetic

<400> SEQUENCE: 264
ccagucaagu aacaaccgc                                                    19

<210> SEQ ID NO 265
<211> LENGTH: 19
<212> TYPE: RNA
<213> ORGANISM: Artificial Sequence
<220> FEATURE:
<223> OTHER INFORMATION: Synthetic

<400> SEQUENCE: 265
cgccagucaa guaacaacc                                                    19

<210> SEQ ID NO 266
<211> LENGTH: 19
<212> TYPE: RNA
<213> ORGANISM: Artificial Sequence
<220> FEATURE:
<223> OTHER INFORMATION: Synthetic

<400> SEQUENCE: 266
gucgccaguc aaguaacaa                                                    19

<210> SEQ ID NO 267
<211> LENGTH: 19
<212> TYPE: RNA
<213> ORGANISM: Artificial Sequence
<220> FEATURE:
<223> OTHER INFORMATION: Synthetic

<400> SEQUENCE: 267
acgucgccag ucaaguaac                                                    19

<210> SEQ ID NO 268
<211> LENGTH: 19
<212> TYPE: RNA
<213> ORGANISM: Artificial Sequence
<220> FEATURE:
<223> OTHER INFORMATION: Synthetic
```

-continued

<400> SEQUENCE: 268
uuacgucgcc agucaagua                                            19

<210> SEQ ID NO 269
<211> LENGTH: 19
<212> TYPE: RNA
<213> ORGANISM: Artificial Sequence
<220> FEATURE:
<223> OTHER INFORMATION: Synthetic

<400> SEQUENCE: 269
gauuacgucg ccagucaag                                            19

<210> SEQ ID NO 270
<211> LENGTH: 19
<212> TYPE: RNA
<213> ORGANISM: Artificial Sequence
<220> FEATURE:
<223> OTHER INFORMATION: Synthetic

<400> SEQUENCE: 270
uggauuacgu cgccaguca                                            19

<210> SEQ ID NO 271
<211> LENGTH: 19
<212> TYPE: RNA
<213> ORGANISM: Artificial Sequence
<220> FEATURE:
<223> OTHER INFORMATION: Synthetic

<400> SEQUENCE: 271
cguggauuac gucgccagu                                            19

<210> SEQ ID NO 272
<211> LENGTH: 19
<212> TYPE: RNA
<213> ORGANISM: Artificial Sequence
<220> FEATURE:
<223> OTHER INFORMATION: Synthetic

<400> SEQUENCE: 272
aucguggauu acgucgcca                                            19

<210> SEQ ID NO 273
<211> LENGTH: 19
<212> TYPE: RNA
<213> ORGANISM: Artificial Sequence
<220> FEATURE:
<223> OTHER INFORMATION: Synthetic

<400> SEQUENCE: 273
agaucgugga uuacgucgc                                            19

<210> SEQ ID NO 274
<211> LENGTH: 19
<212> TYPE: RNA
<213> ORGANISM: Artificial Sequence
<220> FEATURE:
<223> OTHER INFORMATION: Synthetic

<400> SEQUENCE: 274
agagaucgug gauuacguc                                            19

```
<210> SEQ ID NO 275
<211> LENGTH: 19
<212> TYPE: RNA
<213> ORGANISM: Artificial Sequence
<220> FEATURE:
<223> OTHER INFORMATION: Synthetic

<400> SEQUENCE: 275
aaagagaucg uggauuacg                                                  19

<210> SEQ ID NO 276
<211> LENGTH: 19
<212> TYPE: RNA
<213> ORGANISM: Artificial Sequence
<220> FEATURE:
<223> OTHER INFORMATION: Synthetic

<400> SEQUENCE: 276
aaaaagagau cguggauua                                                  19

<210> SEQ ID NO 277
<211> LENGTH: 19
<212> TYPE: RNA
<213> ORGANISM: Artificial Sequence
<220> FEATURE:
<223> OTHER INFORMATION: Synthetic

<400> SEQUENCE: 277
ggaaaaagag aucguggau                                                  19

<210> SEQ ID NO 278
<211> LENGTH: 19
<212> TYPE: RNA
<213> ORGANISM: Artificial Sequence
<220> FEATURE:
<223> OTHER INFORMATION: Synthetic

<400> SEQUENCE: 278
acggaaaaag agaucgugg                                                  19

<210> SEQ ID NO 279
<211> LENGTH: 19
<212> TYPE: RNA
<213> ORGANISM: Artificial Sequence
<220> FEATURE:
<223> OTHER INFORMATION: Synthetic

<400> SEQUENCE: 279
ugacggaaaa agagaucgu                                                  19

<210> SEQ ID NO 280
<211> LENGTH: 19
<212> TYPE: RNA
<213> ORGANISM: Artificial Sequence
<220> FEATURE:
<223> OTHER INFORMATION: Synthetic

<400> SEQUENCE: 280
gaugacggaa aaagagauc                                                  19

<210> SEQ ID NO 281
<211> LENGTH: 19
<212> TYPE: RNA
<213> ORGANISM: Artificial Sequence
<220> FEATURE:
<223> OTHER INFORMATION: Synthetic
```

```
<400> SEQUENCE: 281
acgaugacgg aaaaagaga                                              19

<210> SEQ ID NO 282
<211> LENGTH: 19
<212> TYPE: RNA
<213> ORGANISM: Artificial Sequence
<220> FEATURE:
<223> OTHER INFORMATION: Synthetic

<400> SEQUENCE: 282
agacgaugac ggaaaaaga                                              19

<210> SEQ ID NO 283
<211> LENGTH: 19
<212> TYPE: RNA
<213> ORGANISM: Artificial Sequence
<220> FEATURE:
<223> OTHER INFORMATION: Synthetic

<400> SEQUENCE: 283
aaagacgaug acggaaaaa                                              19

<210> SEQ ID NO 284
<211> LENGTH: 19
<212> TYPE: RNA
<213> ORGANISM: Artificial Sequence
<220> FEATURE:
<223> OTHER INFORMATION: Synthetic

<400> SEQUENCE: 284
ggaaagacga ugacggaaa                                              19

<210> SEQ ID NO 285
<211> LENGTH: 19
<212> TYPE: RNA
<213> ORGANISM: Artificial Sequence
<220> FEATURE:
<223> OTHER INFORMATION: Synthetic

<400> SEQUENCE: 285
acggaaagac gaugacgga                                              19

<210> SEQ ID NO 286
<211> LENGTH: 19
<212> TYPE: RNA
<213> ORGANISM: Artificial Sequence
<220> FEATURE:
<223> OTHER INFORMATION: Synthetic

<400> SEQUENCE: 286
gcacggaaag acgaugacg                                              19

<210> SEQ ID NO 287
<211> LENGTH: 19
<212> TYPE: RNA
<213> ORGANISM: Artificial Sequence
<220> FEATURE:
<223> OTHER INFORMATION: Synthetic

<400> SEQUENCE: 287
gagcacggaa agacgauga                                              19
```

```
<210> SEQ ID NO 288
<211> LENGTH: 19
<212> TYPE: RNA
<213> ORGANISM: Artificial Sequence
<220> FEATURE:
<223> OTHER INFORMATION: Synthetic

<400> SEQUENCE: 288
uggagcacgg aaagacgau                                               19

<210> SEQ ID NO 289
<211> LENGTH: 19
<212> TYPE: RNA
<213> ORGANISM: Artificial Sequence
<220> FEATURE:
<223> OTHER INFORMATION: Synthetic

<400> SEQUENCE: 289
uuuggagcac ggaaagacg                                               19

<210> SEQ ID NO 290
<211> LENGTH: 19
<212> TYPE: RNA
<213> ORGANISM: Artificial Sequence
<220> FEATURE:
<223> OTHER INFORMATION: Synthetic

<400> SEQUENCE: 290 guuuggagc acggaaaga                                                19

<210> SEQ ID NO 291
<211> LENGTH: 19
<212> TYPE: RNA
<213> ORGANISM: Artificial Sequence
<220> FEATURE:
<223> OTHER INFORMATION: Synthetic

<400> SEQUENCE: 291
uuguuuugga gcacggaaa                                               19

<210> SEQ ID NO 292
<211> LENGTH: 19
<212> TYPE: RNA
<213> ORGANISM: Artificial Sequence
<220> FEATURE:
<223> OTHER INFORMATION: Synthetic

<400> SEQUENCE: 292 uguuguuug gagcacgga                                                19

<210> SEQ ID NO 293
<211> LENGTH: 19
<212> TYPE: RNA
<213> ORGANISM: Artificial Sequence
<220> FEATURE:
<223> OTHER INFORMATION: Synthetic

<400> SEQUENCE: 293
guuguuguuu uggagcacg                                               19

<210> SEQ ID NO 294
<211> LENGTH: 19
<212> TYPE: RNA
<213> ORGANISM: Artificial Sequence
<220> FEATURE:
<223> OTHER INFORMATION: Synthetic
```

```
<400> SEQUENCE: 294
ccguuguugu uuuggagca                                                19

<210> SEQ ID NO 295
<211> LENGTH: 19
<212> TYPE: RNA
<213> ORGANISM: Artificial Sequence
<220> FEATURE:
<223> OTHER INFORMATION: Synthetic

<400> SEQUENCE: 295
cgccguuguu guuuggag                                                 19

<210> SEQ ID NO 296
<211> LENGTH: 19
<212> TYPE: RNA
<213> ORGANISM: Artificial Sequence
<220> FEATURE:
<223> OTHER INFORMATION: Synthetic

<400> SEQUENCE: 296
gccgccguug uuguuuugg                                                19

<210> SEQ ID NO 297
<211> LENGTH: 19
<212> TYPE: RNA
<213> ORGANISM: Artificial Sequence
<220> FEATURE:
<223> OTHER INFORMATION: Synthetic

<400> SEQUENCE: 297
ccgccgccgu uguuguuuu                                                19

<210> SEQ ID NO 298
<211> LENGTH: 19
<212> TYPE: RNA
<213> ORGANISM: Artificial Sequence
<220> FEATURE:
<223> OTHER INFORMATION: Synthetic

<400> SEQUENCE: 298
ucccgccgcc guuguuguu                                                19

<210> SEQ ID NO 299
<211> LENGTH: 19
<212> TYPE: RNA
<213> ORGANISM: Artificial Sequence
<220> FEATURE:
<223> OTHER INFORMATION: Synthetic

<400> SEQUENCE: 299
cuucccgccg ccguuguug                                                19

<210> SEQ ID NO 300
<211> LENGTH: 19
<212> TYPE: RNA
<213> ORGANISM: Artificial Sequence
<220> FEATURE:
<223> OTHER INFORMATION: Synthetic

<400> SEQUENCE: 300
aacuucccgc cgccguugu                                                19
```

```
<210> SEQ ID NO 301
<211> LENGTH: 19
<212> TYPE: RNA
<213> ORGANISM: Artificial Sequence
<220> FEATURE:
<223> OTHER INFORMATION: Synthetic

<400> SEQUENCE: 301
ugaacuuccc gccgccguu                                                  19

<210> SEQ ID NO 302
<211> LENGTH: 19
<212> TYPE: RNA
<213> ORGANISM: Artificial Sequence
<220> FEATURE:
<223> OTHER INFORMATION: Synthetic

<400> SEQUENCE: 302
gggagauagu gaugaagua                                                  19

<210> SEQ ID NO 303
<211> LENGTH: 19
<212> TYPE: RNA
<213> ORGANISM: Artificial Sequence
<220> FEATURE:
<223> OTHER INFORMATION: Synthetic

<400> SEQUENCE: 303
gaaguacauc cauuauaag                                                  19

<210> SEQ ID NO 304
<211> LENGTH: 19
<212> TYPE: RNA
<213> ORGANISM: Artificial Sequence
<220> FEATURE:
<223> OTHER INFORMATION: Synthetic

<400> SEQUENCE: 304
guacgacaac cgggagaua                                                  19

<210> SEQ ID NO 305
<211> LENGTH: 19
<212> TYPE: RNA
<213> ORGANISM: Artificial Sequence
<220> FEATURE:
<223> OTHER INFORMATION: Synthetic

<400> SEQUENCE: 305
agauagugau gaaguacau                                                  19

<210> SEQ ID NO 306
<211> LENGTH: 19
<212> TYPE: RNA
<213> ORGANISM: Artificial Sequence
<220> FEATURE:
<223> OTHER INFORMATION: Synthetic

<400> SEQUENCE: 306
ugaagacucu gcucaguuu                                                  19

<210> SEQ ID NO 307
<211> LENGTH: 19
<212> TYPE: RNA
<213> ORGANISM: Artificial Sequence
<220> FEATURE:
<223> OTHER INFORMATION: Synthetic
```

```
<400> SEQUENCE: 307
gcaugcggcc ucuguuuga                                                19

<210> SEQ ID NO 308
<211> LENGTH: 19
<212> TYPE: RNA
<213> ORGANISM: Artificial Sequence
<220> FEATURE:
<223> OTHER INFORMATION: Synthetic

<400> SEQUENCE: 308
ugcggccucu guuugauuu                                                19

<210> SEQ ID NO 309
<211> LENGTH: 19
<212> TYPE: RNA
<213> ORGANISM: Artificial Sequence
<220> FEATURE:
<223> OTHER INFORMATION: Synthetic

<400> SEQUENCE: 309
gagauaguga ugaaguaca                                                19

<210> SEQ ID NO 310
<211> LENGTH: 19
<212> TYPE: RNA
<213> ORGANISM: Artificial Sequence
<220> FEATURE:
<223> OTHER INFORMATION: Synthetic

<400> SEQUENCE: 310
ggagauagug augaaguac                                                19

<210> SEQ ID NO 311
<211> LENGTH: 19
<212> TYPE: RNA
<213> ORGANISM: Artificial Sequence
<220> FEATURE:
<223> OTHER INFORMATION: Synthetic

<400> SEQUENCE: 311
gaagacucug cucaguuug                                                19

<210> SEQ ID NO 312
<211> LENGTH: 19
<212> TYPE: RNA
<213> ORGANISM: Artificial Sequence
<220> FEATURE:
<223> OTHER INFORMATION: Synthetic

<400> SEQUENCE: 312
gaaagaaucu guagagaaa                                                19

<210> SEQ ID NO 313
<211> LENGTH: 19
<212> TYPE: RNA
<213> ORGANISM: Artificial Sequence
<220> FEATURE:
<223> OTHER INFORMATION: Synthetic

<400> SEQUENCE: 313
gcaaugagcu guuugaaga                                                19
```

```
<210> SEQ ID NO 314
<211> LENGTH: 19
<212> TYPE: RNA
<213> ORGANISM: Artificial Sequence
<220> FEATURE:
<223> OTHER INFORMATION: Synthetic

<400> SEQUENCE: 314
ugacaaaggu ggauaaauu                                                    19

<210> SEQ ID NO 315
<211> LENGTH: 19
<212> TYPE: RNA
<213> ORGANISM: Artificial Sequence
<220> FEATURE:
<223> OTHER INFORMATION: Synthetic

<400> SEQUENCE: 315
ggaaauggau cucuuugaa                                                    19

<210> SEQ ID NO 316
<211> LENGTH: 19
<212> TYPE: RNA
<213> ORGANISM: Artificial Sequence
<220> FEATURE:
<223> OTHER INFORMATION: Synthetic

<400> SEQUENCE: 316
ggaaaguaau gguccaaca                                                    19

<210> SEQ ID NO 317
<211> LENGTH: 19
<212> TYPE: RNA
<213> ORGANISM: Artificial Sequence
<220> FEATURE:
<223> OTHER INFORMATION: Synthetic

<400> SEQUENCE: 317
agacaguuau gcagcuauu                                                    19

<210> SEQ ID NO 318
<211> LENGTH: 19
<212> TYPE: RNA
<213> ORGANISM: Artificial Sequence
<220> FEATURE:
<223> OTHER INFORMATION: Synthetic

<400> SEQUENCE: 318
ccaauucucg gaagcaaga                                                    19

<210> SEQ ID NO 319
<211> LENGTH: 19
<212> TYPE: RNA
<213> ORGANISM: Artificial Sequence
<220> FEATURE:
<223> OTHER INFORMATION: Synthetic

<400> SEQUENCE: 319
gaaaguaaug guccaacag                                                    19

<210> SEQ ID NO 320
<211> LENGTH: 19
<212> TYPE: RNA
<213> ORGANISM: Artificial Sequence
<220> FEATURE:
<223> OTHER INFORMATION: Synthetic
```

```
<400> SEQUENCE: 320
gcgccagagu gaacaagua                                              19

<210> SEQ ID NO 321
<211> LENGTH: 19
<212> TYPE: RNA
<213> ORGANISM: Artificial Sequence
<220> FEATURE:
<223> OTHER INFORMATION: Synthetic

<400> SEQUENCE: 321
gaagguggcc cagcuaugu                                              19

<210> SEQ ID NO 322
<211> LENGTH: 19
<212> TYPE: RNA
<213> ORGANISM: Artificial Sequence
<220> FEATURE:
<223> OTHER INFORMATION: Synthetic

<400> SEQUENCE: 322
ggaaccagcg ccagaguga                                              19

<210> SEQ ID NO 323
<211> LENGTH: 19
<212> TYPE: RNA
<213> ORGANISM: Artificial Sequence
<220> FEATURE:
<223> OTHER INFORMATION: Synthetic

<400> SEQUENCE: 323
gagcgagauu gcaggcaua                                              19

<210> SEQ ID NO 324
<211> LENGTH: 19
<212> TYPE: RNA
<213> ORGANISM: Artificial Sequence
<220> FEATURE:
<223> OTHER INFORMATION: Synthetic

<400> SEQUENCE: 324
guuaguaucu gaugacuug                                              19

<210> SEQ ID NO 325
<211> LENGTH: 19
<212> TYPE: RNA
<213> ORGANISM: Artificial Sequence
<220> FEATURE:
<223> OTHER INFORMATION: Synthetic

<400> SEQUENCE: 325
gaaauggaac cacuaagaa                                              19

<210> SEQ ID NO 326
<211> LENGTH: 19
<212> TYPE: RNA
<213> ORGANISM: Artificial Sequence
<220> FEATURE:
<223> OTHER INFORMATION: Synthetic

<400> SEQUENCE: 326
ggaaauggaa ccacuaaga                                              19
```

```
<210> SEQ ID NO 327
<211> LENGTH: 19
<212> TYPE: RNA
<213> ORGANISM: Artificial Sequence
<220> FEATURE:
<223> OTHER INFORMATION: Synthetic

<400> SEQUENCE: 327
caacuacacu uuccaaugc                                                  19

<210> SEQ ID NO 328
<211> LENGTH: 19
<212> TYPE: RNA
<213> ORGANISM: Artificial Sequence
<220> FEATURE:
<223> OTHER INFORMATION: Synthetic

<400> SEQUENCE: 328
ccaccaagau uucaugaua                                                  19

<210> SEQ ID NO 329
<211> LENGTH: 19
<212> TYPE: RNA
<213> ORGANISM: Artificial Sequence
<220> FEATURE:
<223> OTHER INFORMATION: Synthetic

<400> SEQUENCE: 329
gaucggaacu ccaacaaga                                                  19

<210> SEQ ID NO 330
<211> LENGTH: 19
<212> TYPE: RNA
<213> ORGANISM: Artificial Sequence
<220> FEATURE:
<223> OTHER INFORMATION: Synthetic

<400> SEQUENCE: 330
aaacggagcu acagauuau                                                  19

<210> SEQ ID NO 331
<211> LENGTH: 19
<212> TYPE: RNA
<213> ORGANISM: Artificial Sequence
<220> FEATURE:
<223> OTHER INFORMATION: Synthetic

<400> SEQUENCE: 331
ccacacagca uucuuguaa                                                  19

<210> SEQ ID NO 332
<211> LENGTH: 19
<212> TYPE: RNA
<213> ORGANISM: Artificial Sequence
<220> FEATURE:
<223> OTHER INFORMATION: Synthetic

<400> SEQUENCE: 332
gaaguuaccu ugagcaauc                                                  19

<210> SEQ ID NO 333
<211> LENGTH: 19
<212> TYPE: RNA
<213> ORGANISM: Artificial Sequence
<220> FEATURE:
<223> OTHER INFORMATION: Synthetic
```

```
<400> SEQUENCE: 333
ggacuuggcc gauccagaa                                            19

<210> SEQ ID NO 334
<211> LENGTH: 19
<212> TYPE: RNA
<213> ORGANISM: Artificial Sequence
<220> FEATURE:
<223> OTHER INFORMATION: Synthetic

<400> SEQUENCE: 334
gcacuuggau cgagaugag                                            19

<210> SEQ ID NO 335
<211> LENGTH: 19
<212> TYPE: RNA
<213> ORGANISM: Artificial Sequence
<220> FEATURE:
<223> OTHER INFORMATION: Synthetic

<400> SEQUENCE: 335
caaagaccaa uucgcguua                                            19

<210> SEQ ID NO 336
<211> LENGTH: 19
<212> TYPE: RNA
<213> ORGANISM: Artificial Sequence
<220> FEATURE:
<223> OTHER INFORMATION: Synthetic

<400> SEQUENCE: 336
ccgaaucaau cgcaucuuc                                            19

<210> SEQ ID NO 337
<211> LENGTH: 19
<212> TYPE: RNA
<213> ORGANISM: Artificial Sequence
<220> FEATURE:
<223> OTHER INFORMATION: Synthetic

<400> SEQUENCE: 337
gacaugaucc ugcaguuca                                            19

<210> SEQ ID NO 338
<211> LENGTH: 19
<212> TYPE: RNA
<213> ORGANISM: Artificial Sequence
<220> FEATURE:
<223> OTHER INFORMATION: Synthetic

<400> SEQUENCE: 338
gagcgaaucg ucaccacuu                                            19

<210> SEQ ID NO 339
<211> LENGTH: 19
<212> TYPE: RNA
<213> ORGANISM: Artificial Sequence
<220> FEATURE:
<223> OTHER INFORMATION: Synthetic

<400> SEQUENCE: 339
ccuccgagcu ggcgucuac                                            19
```

```
<210> SEQ ID NO 340
<211> LENGTH: 19
<212> TYPE: RNA
<213> ORGANISM: Artificial Sequence
<220> FEATURE:
<223> OTHER INFORMATION: Synthetic

<400> SEQUENCE: 340
ucacaugguu aaccucuaa                                                19

<210> SEQ ID NO 341
<211> LENGTH: 19
<212> TYPE: RNA
<213> ORGANISM: Artificial Sequence
<220> FEATURE:
<223> OTHER INFORMATION: Synthetic

<400> SEQUENCE: 341
gaugagggac gccauaauc                                                19

<210> SEQ ID NO 342
<211> LENGTH: 19
<212> TYPE: RNA
<213> ORGANISM: Artificial Sequence
<220> FEATURE:
<223> OTHER INFORMATION: Synthetic

<400> SEQUENCE: 342
ccucuaacua caaaucuua                                                19

<210> SEQ ID NO 343
<211> LENGTH: 19
<212> TYPE: RNA
<213> ORGANISM: Artificial Sequence
<220> FEATURE:
<223> OTHER INFORMATION: Synthetic

<400> SEQUENCE: 343
ggaaggugcu auccaaaau                                                19

<210> SEQ ID NO 344
<211> LENGTH: 19
<212> TYPE: RNA
<213> ORGANISM: Artificial Sequence
<220> FEATURE:
<223> OTHER INFORMATION: Synthetic

<400> SEQUENCE: 344
gcaagcaagu ccuaacauu                                                19

<210> SEQ ID NO 345
<211> LENGTH: 19
<212> TYPE: RNA
<213> ORGANISM: Artificial Sequence
<220> FEATURE:
<223> OTHER INFORMATION: Synthetic

<400> SEQUENCE: 345
ggaagaggag uagaccuua                                                19

<210> SEQ ID NO 346
<211> LENGTH: 19
<212> TYPE: RNA
<213> ORGANISM: Artificial Sequence
<220> FEATURE:
<223> OTHER INFORMATION: Synthetic
```

```
<400> SEQUENCE: 346
aggaaucagu guuguagua                                                19

<210> SEQ ID NO 347
<211> LENGTH: 19
<212> TYPE: RNA
<213> ORGANISM: Artificial Sequence
<220> FEATURE:
<223> OTHER INFORMATION: Synthetic

<400> SEQUENCE: 347
gaagaggagu agaccuuac                                                19

<210> SEQ ID NO 348
<211> LENGTH: 19
<212> TYPE: RNA
<213> ORGANISM: Artificial Sequence
<220> FEATURE:
<223> OTHER INFORMATION: Synthetic

<400> SEQUENCE: 348
gaaagucaag ccugguauu                                                19

<210> SEQ ID NO 349
<211> LENGTH: 19
<212> TYPE: RNA
<213> ORGANISM: Artificial Sequence
<220> FEATURE:
<223> OTHER INFORMATION: Synthetic

<400> SEQUENCE: 349
aaagucaagc cugguauua                                                19

<210> SEQ ID NO 350
<211> LENGTH: 19
<212> TYPE: RNA
<213> ORGANISM: Artificial Sequence
<220> FEATURE:
<223> OTHER INFORMATION: Synthetic

<400> SEQUENCE: 350
gcuaugaacg ugaaugauc                                                19

<210> SEQ ID NO 351
<211> LENGTH: 19
<212> TYPE: RNA
<213> ORGANISM: Artificial Sequence
<220> FEATURE:
<223> OTHER INFORMATION: Synthetic

<400> SEQUENCE: 351
caagccuggu auuacguuu                                                19

<210> SEQ ID NO 352
<211> LENGTH: 19
<212> TYPE: RNA
<213> ORGANISM: Artificial Sequence
<220> FEATURE:
<223> OTHER INFORMATION: Synthetic

<400> SEQUENCE: 352
ggaacaagau cugucaauu                                                19
```

```
<210> SEQ ID NO 353
<211> LENGTH: 19
<212> TYPE: RNA
<213> ORGANISM: Artificial Sequence
<220> FEATURE:
<223> OTHER INFORMATION: Synthetic

<400> SEQUENCE: 353
gcaaugaacg ugaacgaaa                                            19

<210> SEQ ID NO 354
<211> LENGTH: 19
<212> TYPE: RNA
<213> ORGANISM: Artificial Sequence
<220> FEATURE:
<223> OTHER INFORMATION: Synthetic

<400> SEQUENCE: 354
caaugaacgu gaacgaaau                                            19

<210> SEQ ID NO 355
<211> LENGTH: 19
<212> TYPE: RNA
<213> ORGANISM: Artificial Sequence
<220> FEATURE:
<223> OTHER INFORMATION: Synthetic

<400> SEQUENCE: 355
ggacaggagc gguaucaca                                            19

<210> SEQ ID NO 356
<211> LENGTH: 19
<212> TYPE: RNA
<213> ORGANISM: Artificial Sequence
<220> FEATURE:
<223> OTHER INFORMATION: Synthetic

<400> SEQUENCE: 356
agacagagcu ugagaauaa                                            19

<210> SEQ ID NO 357
<211> LENGTH: 19
<212> TYPE: RNA
<213> ORGANISM: Artificial Sequence
<220> FEATURE:
<223> OTHER INFORMATION: Synthetic

<400> SEQUENCE: 357
gagaagaucu uuaugcaaa                                            19

<210> SEQ ID NO 358
<211> LENGTH: 19
<212> TYPE: RNA
<213> ORGANISM: Artificial Sequence
<220> FEATURE:
<223> OTHER INFORMATION: Synthetic

<400> SEQUENCE: 358
gaagagaaau cagcagaua                                            19

<210> SEQ ID NO 359
<211> LENGTH: 19
<212> TYPE: RNA
<213> ORGANISM: Artificial Sequence
<220> FEATURE:
<223> OTHER INFORMATION: Synthetic
```

```
<400> SEQUENCE: 359
gcaaguaacu caacuaaca                                          19

<210> SEQ ID NO 360
<211> LENGTH: 19
<212> TYPE: RNA
<213> ORGANISM: Artificial Sequence
<220> FEATURE:
<223> OTHER INFORMATION: Synthetic

<400> SEQUENCE: 360
gagcuaaucu gccacauug                                          19

<210> SEQ ID NO 361
<211> LENGTH: 19
<212> TYPE: RNA
<213> ORGANISM: Artificial Sequence
<220> FEATURE:
<223> OTHER INFORMATION: Synthetic

<400> SEQUENCE: 361
gcagaugagu uacuagaaa                                          19

<210> SEQ ID NO 362
<211> LENGTH: 19
<212> TYPE: RNA
<213> ORGANISM: Artificial Sequence
<220> FEATURE:
<223> OTHER INFORMATION: Synthetic

<400> SEQUENCE: 362
caacuuaauu guccagaaa                                          19

<210> SEQ ID NO 363
<211> LENGTH: 19
<212> TYPE: RNA
<213> ORGANISM: Artificial Sequence
<220> FEATURE:
<223> OTHER INFORMATION: Synthetic

<400> SEQUENCE: 363
caacacagga uucugauaa                                          19

<210> SEQ ID NO 364
<211> LENGTH: 19
<212> TYPE: RNA
<213> ORGANISM: Artificial Sequence
<220> FEATURE:
<223> OTHER INFORMATION: Synthetic

<400> SEQUENCE: 364
agauugugcc uaagucucu                                          19

<210> SEQ ID NO 365
<211> LENGTH: 19
<212> TYPE: RNA
<213> ORGANISM: Artificial Sequence
<220> FEATURE:
<223> OTHER INFORMATION: Synthetic

<400> SEQUENCE: 365
augaagaucu ggaggugaa                                          19
```

```
<210> SEQ ID NO 366
<211> LENGTH: 19
<212> TYPE: RNA
<213> ORGANISM: Artificial Sequence
<220> FEATURE:
<223> OTHER INFORMATION: Synthetic

<400> SEQUENCE: 366
uuugagacuu cuugccuaa                                                19

<210> SEQ ID NO 367
<211> LENGTH: 19
<212> TYPE: RNA
<213> ORGANISM: Artificial Sequence
<220> FEATURE:
<223> OTHER INFORMATION: Synthetic

<400> SEQUENCE: 367
agaucacccu ccuuaaaua                                                19

<210> SEQ ID NO 368
<211> LENGTH: 19
<212> TYPE: RNA
<213> ORGANISM: Artificial Sequence
<220> FEATURE:
<223> OTHER INFORMATION: Synthetic

<400> SEQUENCE: 368
caacggauuu ggucguauu                                                19

<210> SEQ ID NO 369
<211> LENGTH: 19
<212> TYPE: RNA
<213> ORGANISM: Artificial Sequence
<220> FEATURE:
<223> OTHER INFORMATION: Synthetic

<400> SEQUENCE: 369
gaaaucccau caccaucuu                                                19

<210> SEQ ID NO 370
<211> LENGTH: 19
<212> TYPE: RNA
<213> ORGANISM: Artificial Sequence
<220> FEATURE:
<223> OTHER INFORMATION: Synthetic

<400> SEQUENCE: 370
gaccucaacu acaugguuu                                                19

<210> SEQ ID NO 371
<211> LENGTH: 19
<212> TYPE: RNA
<213> ORGANISM: Artificial Sequence
<220> FEATURE:
<223> OTHER INFORMATION: Synthetic

<400> SEQUENCE: 371
ugguuuacau guuccaaua                                                19

<210> SEQ ID NO 372
<211> LENGTH: 19
<212> TYPE: RNA
<213> ORGANISM: Artificial Sequence
<220> FEATURE:
<223> OTHER INFORMATION: Synthetic
```

```
<400> SEQUENCE: 372
gaagaaaucg auguuguuu                                               19

<210> SEQ ID NO 373
<211> LENGTH: 19
<212> TYPE: RNA
<213> ORGANISM: Artificial Sequence
<220> FEATURE:
<223> OTHER INFORMATION: Synthetic

<400> SEQUENCE: 373
acacaaacuu gaacagcua                                               19

<210> SEQ ID NO 374
<211> LENGTH: 19
<212> TYPE: RNA
<213> ORGANISM: Artificial Sequence
<220> FEATURE:
<223> OTHER INFORMATION: Synthetic

<400> SEQUENCE: 374
ggaagaaauc gauguuguu                                               19

<210> SEQ ID NO 375
<211> LENGTH: 19
<212> TYPE: RNA
<213> ORGANISM: Artificial Sequence
<220> FEATURE:
<223> OTHER INFORMATION: Synthetic

<400> SEQUENCE: 375
gaaacgacga gaacaguug                                               19

<210> SEQ ID NO 376
<211> LENGTH: 19
<212> TYPE: RNA
<213> ORGANISM: Artificial Sequence
<220> FEATURE:
<223> OTHER INFORMATION: Synthetic

<400> SEQUENCE: 376
gcacauggau ggagguucu                                               19

<210> SEQ ID NO 377
<211> LENGTH: 19
<212> TYPE: RNA
<213> ORGANISM: Artificial Sequence
<220> FEATURE:
<223> OTHER INFORMATION: Synthetic

<400> SEQUENCE: 377
gcagagagag cagauuuga                                               19

<210> SEQ ID NO 378
<211> LENGTH: 19
<212> TYPE: RNA
<213> ORGANISM: Artificial Sequence
<220> FEATURE:
<223> OTHER INFORMATION: Synthetic

<400> SEQUENCE: 378
gagguucucu ggaucaagu                                               19
```

```
<210> SEQ ID NO 379
<211> LENGTH: 19
<212> TYPE: RNA
<213> ORGANISM: Artificial Sequence
<220> FEATURE:
<223> OTHER INFORMATION: Synthetic

<400> SEQUENCE: 379
gagcagauuu gaagcaacu                                                  19

<210> SEQ ID NO 380
<211> LENGTH: 19
<212> TYPE: RNA
<213> ORGANISM: Artificial Sequence
<220> FEATURE:
<223> OTHER INFORMATION: Synthetic

<400> SEQUENCE: 380
caaagacgau gacuucgaa                                                  19

<210> SEQ ID NO 381
<211> LENGTH: 19
<212> TYPE: RNA
<213> ORGANISM: Artificial Sequence
<220> FEATURE:
<223> OTHER INFORMATION: Synthetic

<400> SEQUENCE: 381
gaucagcauu ugcauggaa                                                  19

<210> SEQ ID NO 382
<211> LENGTH: 19
<212> TYPE: RNA
<213> ORGANISM: Artificial Sequence
<220> FEATURE:
<223> OTHER INFORMATION: Synthetic

<400> SEQUENCE: 382
uccaggaguu ugucaauaa                                                  19

<210> SEQ ID NO 383
<211> LENGTH: 19
<212> TYPE: RNA
<213> ORGANISM: Artificial Sequence
<220> FEATURE:
<223> OTHER INFORMATION: Synthetic

<400> SEQUENCE: 383
ggaagcugau ccaccuuga                                                  19

<210> SEQ ID NO 384
<211> LENGTH: 19
<212> TYPE: RNA
<213> ORGANISM: Artificial Sequence
<220> FEATURE:
<223> OTHER INFORMATION: Synthetic

<400> SEQUENCE: 384
gcagaaaucu aaggauaua                                                  19

<210> SEQ ID NO 385
<211> LENGTH: 19
<212> TYPE: RNA
<213> ORGANISM: Artificial Sequence
<220> FEATURE:
<223> OTHER INFORMATION: Synthetic
```

<400> SEQUENCE: 385
caacaaggau gaagucuau                                                19

<210> SEQ ID NO 386
<211> LENGTH: 19
<212> TYPE: RNA
<213> ORGANISM: Artificial Sequence
<220> FEATURE:
<223> OTHER INFORMATION: Synthetic

<400> SEQUENCE: 386
cagcagaaau cuaaggaua                                                19

<210> SEQ ID NO 387
<211> LENGTH: 19
<212> TYPE: RNA
<213> ORGANISM: Artificial Sequence
<220> FEATURE:
<223> OTHER INFORMATION: Synthetic

<400> SEQUENCE: 387
cuagauggcu uucucagua                                                19

<210> SEQ ID NO 388
<211> LENGTH: 19
<212> TYPE: RNA
<213> ORGANISM: Artificial Sequence
<220> FEATURE:
<223> OTHER INFORMATION: Synthetic

<400> SEQUENCE: 388
agacaagguc ccaaagaca                                                19

<210> SEQ ID NO 389
<211> LENGTH: 19
<212> TYPE: RNA
<213> ORGANISM: Artificial Sequence
<220> FEATURE:
<223> OTHER INFORMATION: Synthetic

<400> SEQUENCE: 389
ggaauggcaa gaccagcaa                                                19

<210> SEQ ID NO 390
<211> LENGTH: 19
<212> TYPE: RNA
<213> ORGANISM: Artificial Sequence
<220> FEATURE:
<223> OTHER INFORMATION: Synthetic

<400> SEQUENCE: 390
agaauuauuc caggguuua                                                19

<210> SEQ ID NO 391
<211> LENGTH: 19
<212> TYPE: RNA
<213> ORGANISM: Artificial Sequence
<220> FEATURE:
<223> OTHER INFORMATION: Synthetic

<400> SEQUENCE: 391
gcagacaagg ucccaaaga                                                19

```
<210> SEQ ID NO 392
<211> LENGTH: 19
<212> TYPE: RNA
<213> ORGANISM: Artificial Sequence
<220> FEATURE:
<223> OTHER INFORMATION: Synthetic

<400> SEQUENCE: 392
agaagcagcu ucaggauga                                               19

<210> SEQ ID NO 393
<211> LENGTH: 19
<212> TYPE: RNA
<213> ORGANISM: Artificial Sequence
<220> FEATURE:
<223> OTHER INFORMATION: Synthetic

<400> SEQUENCE: 393
gagcuugacu uccagaaga                                               19

<210> SEQ ID NO 394
<211> LENGTH: 19
<212> TYPE: RNA
<213> ORGANISM: Artificial Sequence
<220> FEATURE:
<223> OTHER INFORMATION: Synthetic

<400> SEQUENCE: 394
ccaccgaagu ucacccuaa                                               19

<210> SEQ ID NO 395
<211> LENGTH: 19
<212> TYPE: RNA
<213> ORGANISM: Artificial Sequence
<220> FEATURE:
<223> OTHER INFORMATION: Synthetic

<400> SEQUENCE: 395
gagaagagcu ccuccauca                                               19

<210> SEQ ID NO 396
<211> LENGTH: 19
<212> TYPE: RNA
<213> ORGANISM: Artificial Sequence
<220> FEATURE:
<223> OTHER INFORMATION: Synthetic

<400> SEQUENCE: 396
gaaagagcau cuacgguga                                               19

<210> SEQ ID NO 397
<211> LENGTH: 19
<212> TYPE: RNA
<213> ORGANISM: Artificial Sequence
<220> FEATURE:
<223> OTHER INFORMATION: Synthetic

<400> SEQUENCE: 397
gaaaggauuu ggcuacaaa                                               19

<210> SEQ ID NO 398
<211> LENGTH: 19
<212> TYPE: RNA
<213> ORGANISM: Artificial Sequence
<220> FEATURE:
<223> OTHER INFORMATION: Synthetic
```

```
<400> SEQUENCE: 398
acagcaaauu ccaucgugu                                                    19

<210> SEQ ID NO 399
<211> LENGTH: 19
<212> TYPE: RNA
<213> ORGANISM: Artificial Sequence
<220> FEATURE:
<223> OTHER INFORMATION: Synthetic

<400> SEQUENCE: 399
ggaaagacug uuccaaaaa                                                    19

<210> SEQ ID NO 400
<211> LENGTH: 19
<212> TYPE: RNA
<213> ORGANISM: Artificial Sequence
<220> FEATURE:
<223> OTHER INFORMATION: Synthetic

<400> SEQUENCE: 400
caacacgccu cauccucua                                                    19

<210> SEQ ID NO 401
<211> LENGTH: 19
<212> TYPE: RNA
<213> ORGANISM: Artificial Sequence
<220> FEATURE:
<223> OTHER INFORMATION: Synthetic

<400> SEQUENCE: 401
caugaaagcu uacaucaac                                                    19

<210> SEQ ID NO 402
<211> LENGTH: 19
<212> TYPE: RNA
<213> ORGANISM: Artificial Sequence
<220> FEATURE:
<223> OTHER INFORMATION: Synthetic

<400> SEQUENCE: 402
aagaugccau gaaagcuua                                                    19

<210> SEQ ID NO 403
<211> LENGTH: 19
<212> TYPE: RNA
<213> ORGANISM: Artificial Sequence
<220> FEATURE:
<223> OTHER INFORMATION: Synthetic

<400> SEQUENCE: 403
gcacauaccg ccugagucu                                                    19

<210> SEQ ID NO 404
<211> LENGTH: 19
<212> TYPE: RNA
<213> ORGANISM: Artificial Sequence
<220> FEATURE:
<223> OTHER INFORMATION: Synthetic

<400> SEQUENCE: 404
gaucaaaucu gaagaagga                                                    19
```

```
<210> SEQ ID NO 405
<211> LENGTH: 19
<212> TYPE: RNA
<213> ORGANISM: Artificial Sequence
<220> FEATURE:
<223> OTHER INFORMATION: Synthetic

<400> SEQUENCE: 405
gccaagaagu uccuaaua                                            19

<210> SEQ ID NO 406
<211> LENGTH: 19
<212> TYPE: RNA
<213> ORGANISM: Artificial Sequence
<220> FEATURE:
<223> OTHER INFORMATION: Synthetic

<400> SEQUENCE: 406
cagcauaucu ugaaccauu                                           19

<210> SEQ ID NO 407
<211> LENGTH: 19
<212> TYPE: RNA
<213> ORGANISM: Artificial Sequence
<220> FEATURE:
<223> OTHER INFORMATION: Synthetic

<400> SEQUENCE: 407
gaacaaagga aacggauga                                           19

<210> SEQ ID NO 408
<211> LENGTH: 19
<212> TYPE: RNA
<213> ORGANISM: Artificial Sequence
<220> FEATURE:
<223> OTHER INFORMATION: Synthetic

<400> SEQUENCE: 408
cggaaacggu ccaggcuau                                           19

<210> SEQ ID NO 409
<211> LENGTH: 19
<212> TYPE: RNA
<213> ORGANISM: Artificial Sequence
<220> FEATURE:
<223> OTHER INFORMATION: Synthetic

<400> SEQUENCE: 409
gcuucgagca gacaugaua                                           19

<210> SEQ ID NO 410
<211> LENGTH: 19
<212> TYPE: RNA
<213> ORGANISM: Artificial Sequence
<220> FEATURE:
<223> OTHER INFORMATION: Synthetic

<400> SEQUENCE: 410
ccuacacggu ccuccuaua                                           19

<210> SEQ ID NO 411
<211> LENGTH: 19
<212> TYPE: RNA
<213> ORGANISM: Artificial Sequence
<220> FEATURE:
<223> OTHER INFORMATION: Synthetic
```

```
<400> SEQUENCE: 411
gccaagaacc ucaucaucu                                              19

<210> SEQ ID NO 412
<211> LENGTH: 19
<212> TYPE: RNA
<213> ORGANISM: Artificial Sequence
<220> FEATURE:
<223> OTHER INFORMATION: Synthetic

<400> SEQUENCE: 412
gauaugggcu gaauacaaa                                              19

<210> SEQ ID NO 413
<211> LENGTH: 19
<212> TYPE: RNA
<213> ORGANISM: Artificial Sequence
<220> FEATURE:
<223> OTHER INFORMATION: Synthetic

<400> SEQUENCE: 413
gcacucugau ugacaaaua                                              19

<210> SEQ ID NO 414
<211> LENGTH: 19
<212> TYPE: RNA
<213> ORGANISM: Artificial Sequence
<220> FEATURE:
<223> OTHER INFORMATION: Synthetic

<400> SEQUENCE: 414
ugaagucucu gauuaagua                                              19

<210> SEQ ID NO 415
<211> LENGTH: 19
<212> TYPE: RNA
<213> ORGANISM: Artificial Sequence
<220> FEATURE:
<223> OTHER INFORMATION: Synthetic

<400> SEQUENCE: 415
ucagagagau ccucauaaa                                              19

<210> SEQ ID NO 416
<211> LENGTH: 19
<212> TYPE: RNA
<213> ORGANISM: Artificial Sequence
<220> FEATURE:
<223> OTHER INFORMATION: Synthetic

<400> SEQUENCE: 416
gcaagaagau caccauuuc                                              19

<210> SEQ ID NO 417
<211> LENGTH: 19
<212> TYPE: RNA
<213> ORGANISM: Artificial Sequence
<220> FEATURE:
<223> OTHER INFORMATION: Synthetic

<400> SEQUENCE: 417
gagagaaauu ugaggauga                                              19
```

```
<210> SEQ ID NO 418
<211> LENGTH: 19
<212> TYPE: RNA
<213> ORGANISM: Artificial Sequence
<220> FEATURE:
<223> OTHER INFORMATION: Synthetic

<400> SEQUENCE: 418
gaaaggauuu ggcuauaag                                              19

<210> SEQ ID NO 419
<211> LENGTH: 19
<212> TYPE: RNA
<213> ORGANISM: Artificial Sequence
<220> FEATURE:
<223> OTHER INFORMATION: Synthetic

<400> SEQUENCE: 419
gaaagaaggc augaacauu                                              19

<210> SEQ ID NO 420
<211> LENGTH: 19
<212> TYPE: RNA
<213> ORGANISM: Artificial Sequence
<220> FEATURE:
<223> OTHER INFORMATION: Synthetic

<400> SEQUENCE: 420
gggagauagu gaugaagua                                              19

<210> SEQ ID NO 421
<211> LENGTH: 19
<212> TYPE: RNA
<213> ORGANISM: Artificial Sequence
<220> FEATURE:
<223> OTHER INFORMATION: Synthetic

<400> SEQUENCE: 421
gaaguacauc cauuauaag                                              19

<210> SEQ ID NO 422
<211> LENGTH: 19
<212> TYPE: RNA
<213> ORGANISM: Artificial Sequence
<220> FEATURE:
<223> OTHER INFORMATION: Synthetic

<400> SEQUENCE: 422
guacgacaac cgggagaua                                              19

<210> SEQ ID NO 423
<211> LENGTH: 19
<212> TYPE: RNA
<213> ORGANISM: Artificial Sequence
<220> FEATURE:
<223> OTHER INFORMATION: Synthetic

<400> SEQUENCE: 423
agauagugau gaaguacau                                              19

<210> SEQ ID NO 424
<211> LENGTH: 19
<212> TYPE: RNA
<213> ORGANISM: Artificial Sequence
<220> FEATURE:
<223> OTHER INFORMATION: Synthetic
```

```
<400> SEQUENCE: 424
ugaagacucu gcucaguuu                                                 19

<210> SEQ ID NO 425
<211> LENGTH: 19
<212> TYPE: RNA
<213> ORGANISM: Artificial Sequence
<220> FEATURE:
<223> OTHER INFORMATION: Synthetic

<400> SEQUENCE: 425
gcaugcggcc ucuguuuga                                                 19

<210> SEQ ID NO 426
<211> LENGTH: 19
<212> TYPE: RNA
<213> ORGANISM: Artificial Sequence
<220> FEATURE:
<223> OTHER INFORMATION: Synthetic

<400> SEQUENCE: 426
gcacacagcu uacuacauc                                                 19

<210> SEQ ID NO 427
<211> LENGTH: 19
<212> TYPE: RNA
<213> ORGANISM: Artificial Sequence
<220> FEATURE:
<223> OTHER INFORMATION: Synthetic

<400> SEQUENCE: 427
gaaaugcccu gguaucuca                                                 19

<210> SEQ ID NO 428
<211> LENGTH: 19
<212> TYPE: RNA
<213> ORGANISM: Artificial Sequence
<220> FEATURE:
<223> OTHER INFORMATION: Synthetic

<400> SEQUENCE: 428
gaaggaacgu gaugugauc                                                 19

<210> SEQ ID NO 429
<211> LENGTH: 19
<212> TYPE: RNA
<213> ORGANISM: Artificial Sequence
<220> FEATURE:
<223> OTHER INFORMATION: Synthetic

<400> SEQUENCE: 429
gcacuacucc uguguguga                                                 19

<210> SEQ ID NO 430
<211> LENGTH: 19
<212> TYPE: RNA
<213> ORGANISM: Artificial Sequence
<220> FEATURE:
<223> OTHER INFORMATION: Synthetic

<400> SEQUENCE: 430
gaacccagcu ggagaacuu                                                 19
```

```
<210> SEQ ID NO 431
<211> LENGTH: 19
<212> TYPE: RNA
<213> ORGANISM: Artificial Sequence
<220> FEATURE:
<223> OTHER INFORMATION: Synthetic

<400> SEQUENCE: 431
gauauacagu gugaucuua                                               19

<210> SEQ ID NO 432
<211> LENGTH: 19
<212> TYPE: RNA
<213> ORGANISM: Artificial Sequence
<220> FEATURE:
<223> OTHER INFORMATION: Synthetic

<400> SEQUENCE: 432
guacuacgau ccugauuau                                               19

<210> SEQ ID NO 433
<211> LENGTH: 19
<212> TYPE: RNA
<213> ORGANISM: Artificial Sequence
<220> FEATURE:
<223> OTHER INFORMATION: Synthetic

<400> SEQUENCE: 433
gugccgaccu uuacaauuu                                               19

<210> SEQ ID NO 434
<211> LENGTH: 19
<212> TYPE: RNA
<213> ORGANISM: Artificial Sequence
<220> FEATURE:
<223> OTHER INFORMATION: Synthetic

<400> SEQUENCE: 434
gaaggaaacu gaauucaaa                                               19

<210> SEQ ID NO 435
<211> LENGTH: 19
<212> TYPE: RNA
<213> ORGANISM: Artificial Sequence
<220> FEATURE:
<223> OTHER INFORMATION: Synthetic

<400> SEQUENCE: 435
ggaaauaugu acuacgaaa                                               19

<210> SEQ ID NO 436
<211> LENGTH: 19
<212> TYPE: RNA
<213> ORGANISM: Artificial Sequence
<220> FEATURE:
<223> OTHER INFORMATION: Synthetic

<400> SEQUENCE: 436
ccacaaagca gugaauuua                                               19

<210> SEQ ID NO 437
<211> LENGTH: 19
<212> TYPE: RNA
<213> ORGANISM: Artificial Sequence
<220> FEATURE:
<223> OTHER INFORMATION: Synthetic
```

```
<400> SEQUENCE: 437
guaacaagcu cacgcaguu                                                  19

<210> SEQ ID NO 438
<211> LENGTH: 19
<212> TYPE: RNA
<213> ORGANISM: Artificial Sequence
<220> FEATURE:
<223> OTHER INFORMATION: Synthetic

<400> SEQUENCE: 438
aaagugcagu ucaguaaua                                                  19

<210> SEQ ID NO 439
<211> LENGTH: 19
<212> TYPE: RNA
<213> ORGANISM: Artificial Sequence
<220> FEATURE:
<223> OTHER INFORMATION: Synthetic

<400> SEQUENCE: 439
ggaaaugacc agacacuga                                                  19

<210> SEQ ID NO 440
<211> LENGTH: 19
<212> TYPE: RNA
<213> ORGANISM: Artificial Sequence
<220> FEATURE:
<223> OTHER INFORMATION: Synthetic

<400> SEQUENCE: 440
ggauacagcu ggagucagu                                                  19

<210> SEQ ID NO 441
<211> LENGTH: 19
<212> TYPE: RNA
<213> ORGANISM: Artificial Sequence
<220> FEATURE:
<223> OTHER INFORMATION: Synthetic

<400> SEQUENCE: 441
gagacuagau ugccuuugu                                                  19

<210> SEQ ID NO 442
<211> LENGTH: 19
<212> TYPE: RNA
<213> ORGANISM: Artificial Sequence
<220> FEATURE:
<223> OTHER INFORMATION: Synthetic

<400> SEQUENCE: 442
gagcccaucc cuauuauaa                                                  19

<210> SEQ ID NO 443
<211> LENGTH: 19
<212> TYPE: RNA
<213> ORGANISM: Artificial Sequence
<220> FEATURE:
<223> OTHER INFORMATION: Synthetic

<400> SEQUENCE: 443
ggagggcccu accugauug                                                  19
```

```
<210> SEQ ID NO 444
<211> LENGTH: 19
<212> TYPE: RNA
<213> ORGANISM: Artificial Sequence
<220> FEATURE:
<223> OTHER INFORMATION: Synthetic

<400> SEQUENCE: 444
gcucucugcu guacauauu                                                  19

<210> SEQ ID NO 445
<211> LENGTH: 19
<212> TYPE: RNA
<213> ORGANISM: Artificial Sequence
<220> FEATURE:
<223> OTHER INFORMATION: Synthetic

<400> SEQUENCE: 445
ggaggcaggc gacgaguuu                                                  19

<210> SEQ ID NO 446
<211> LENGTH: 19
<212> TYPE: RNA
<213> ORGANISM: Artificial Sequence
<220> FEATURE:
<223> OTHER INFORMATION: Synthetic

<400> SEQUENCE: 446
aaaggaggcu ggcagguau                                                  19

<210> SEQ ID NO 447
<211> LENGTH: 19
<212> TYPE: RNA
<213> ORGANISM: Artificial Sequence
<220> FEATURE:
<223> OTHER INFORMATION: Synthetic

<400> SEQUENCE: 447
ccagaaagga gacuagauu                                                  19

<210> SEQ ID NO 448
<211> LENGTH: 19
<212> TYPE: RNA
<213> ORGANISM: Artificial Sequence
<220> FEATURE:
<223> OTHER INFORMATION: Synthetic

<400> SEQUENCE: 448
guugagccca ucccuauua                                                  19

<210> SEQ ID NO 449
<211> LENGTH: 19
<212> TYPE: RNA
<213> ORGANISM: Artificial Sequence
<220> FEATURE:
<223> OTHER INFORMATION: Synthetic

<400> SEQUENCE: 449
caaaggaggc uggcaggua                                                  19

<210> SEQ ID NO 450
<211> LENGTH: 19
<212> TYPE: RNA
<213> ORGANISM: Artificial Sequence
<220> FEATURE:
<223> OTHER INFORMATION: Synthetic
```

```
<400> SEQUENCE: 450
guccaaaugu ccuccagaa                                                 19

<210> SEQ ID NO 451
<211> LENGTH: 19
<212> TYPE: RNA
<213> ORGANISM: Artificial Sequence
<220> FEATURE:
<223> OTHER INFORMATION: Synthetic

<400> SEQUENCE: 451
ggagucaguu uagugaugu                                                 19

<210> SEQ ID NO 452
<211> LENGTH: 19
<212> TYPE: RNA
<213> ORGANISM: Artificial Sequence
<220> FEATURE:
<223> OTHER INFORMATION: Synthetic

<400> SEQUENCE: 452
guuaagcgug ucuguauuu                                                 19

<210> SEQ ID NO 453
<211> LENGTH: 19
<212> TYPE: RNA
<213> ORGANISM: Artificial Sequence
<220> FEATURE:
<223> OTHER INFORMATION: Synthetic

<400> SEQUENCE: 453
guacauauuu gagacuagu                                                 19

<210> SEQ ID NO 454
<211> LENGTH: 19
<212> TYPE: RNA
<213> ORGANISM: Artificial Sequence
<220> FEATURE:
<223> OTHER INFORMATION: Synthetic

<400> SEQUENCE: 454
gacagcauau cagagcuuu                                                 19

<210> SEQ ID NO 455
<211> LENGTH: 19
<212> TYPE: RNA
<213> ORGANISM: Artificial Sequence
<220> FEATURE:
<223> OTHER INFORMATION: Synthetic

<400> SEQUENCE: 455
gugcaacccu uaccccuua                                                 19

<210> SEQ ID NO 456
<211> LENGTH: 19
<212> TYPE: RNA
<213> ORGANISM: Artificial Sequence
<220> FEATURE:
<223> OTHER INFORMATION: Synthetic

<400> SEQUENCE: 456
ggguagggcu gacuagaag                                                 19
```

```
<210> SEQ ID NO 457
<211> LENGTH: 19
<212> TYPE: RNA
<213> ORGANISM: Artificial Sequence
<220> FEATURE:
<223> OTHER INFORMATION: Synthetic

<400> SEQUENCE: 457 gcuugaaca ggauacuuu                                                   19

<210> SEQ ID NO 458
<211> LENGTH: 19
<212> TYPE: RNA
<213> ORGANISM: Artificial Sequence
<220> FEATURE:
<223> OTHER INFORMATION: Synthetic

<400> SEQUENCE: 458
ccuacaagcu uucccagaa                                                  19

<210> SEQ ID NO 459
<211> LENGTH: 19
<212> TYPE: RNA
<213> ORGANISM: Artificial Sequence
<220> FEATURE:
<223> OTHER INFORMATION: Synthetic

<400> SEQUENCE: 459
gaaagggagc uaucaggaa                                                  19

<210> SEQ ID NO 460
<211> LENGTH: 19
<212> TYPE: RNA
<213> ORGANISM: Artificial Sequence
<220> FEATURE:
<223> OTHER INFORMATION: Synthetic

<400> SEQUENCE: 460
gaauuuauca cacuucugu                                                  19

<210> SEQ ID NO 461
<211> LENGTH: 19
<212> TYPE: RNA
<213> ORGANISM: Artificial Sequence
<220> FEATURE:
<223> OTHER INFORMATION: Synthetic

<400> SEQUENCE: 461
gagaaucacu aaccagaga                                                  19

<210> SEQ ID NO 462
<211> LENGTH: 19
<212> TYPE: RNA
<213> ORGANISM: Artificial Sequence
<220> FEATURE:
<223> OTHER INFORMATION: Synthetic

<400> SEQUENCE: 462
ccagggagcu ugaaaguuu                                                  19

<210> SEQ ID NO 463
<211> LENGTH: 19
<212> TYPE: RNA
<213> ORGANISM: Artificial Sequence
<220> FEATURE:
<223> OTHER INFORMATION: Synthetic
```

-continued

```
<400> SEQUENCE: 463
caacugggcc caagacaga                                                    19

<210> SEQ ID NO 464
<211> LENGTH: 19
<212> TYPE: RNA
<213> ORGANISM: Artificial Sequence
<220> FEATURE:
<223> OTHER INFORMATION: Synthetic

<400> SEQUENCE: 464
aagcgugucu guauuuaug                                                    19
```